US012668586B2

(12) United States Patent
Wang et al.

(10) Patent No.: US 12,668,586 B2
(45) Date of Patent: Jun. 30, 2026

(54) AHR INHIBITOR, USE THEREOF, AND PREPARATION METHOD THEREFOR

(71) Applicant: CHONGQING PHARSCIN INNOBIO CO., LTD., Chongqing (CN)

(72) Inventors: Yuxun Wang, Boston, MA (US); Xiaohui Liu, Salt Lake City, UT (US); Zhicheng Jiang, Chongqing (CN); Jichao Wu, Chongqing (CN); Xiaoquan Wu, Chongqing (CN); Qi Huang, Chongqing (CN); Shengyong Yang, Chongqing (CN)

(73) Assignee: CHONGQING PHARSCIN INNOBIO CO., LTD., Chongqing (CN)

( * ) Notice: Subject to any disclaimer, the term of this patent is extended or adjusted under 35 U.S.C. 154(b) by 0 days.

(21) Appl. No.: 18/692,791

(22) PCT Filed: Sep. 13, 2022

(86) PCT No.: PCT/CN2022/118454
§ 371 (c)(1),
(2) Date: Mar. 15, 2024

(87) PCT Pub. No.: WO2023/040830
PCT Pub. Date: Mar. 23, 2023

(65) Prior Publication Data
US 2024/0327386 A1 Oct. 3, 2024

(30) Foreign Application Priority Data

Sep. 18, 2021 (CN) .......................... 202111110412.7
May 23, 2022 (CN) .......................... 202210571711.9

(51) Int. Cl.
*C07D 401/12* (2006.01)
*A61K 31/506* (2006.01)
*C07D 401/14* (2006.01)
*C07D 403/04* (2006.01)
*C07D 403/12* (2006.01)
*C07D 403/14* (2006.01)
*C07D 405/14* (2006.01)
*C07D 413/14* (2006.01)
*C07D 471/04* (2006.01)

(52) U.S. Cl.
CPC .......... *C07D 403/04* (2013.01); *A61K 31/506* (2013.01); *C07D 401/12* (2013.01); *C07D 401/14* (2013.01); *C07D 403/14* (2013.01); *C07D 405/14* (2013.01); *C07D 413/14* (2013.01); *C07D 471/04* (2013.01)

(58) Field of Classification Search
CPC .. C07D 401/12; C07D 401/14; C07D 403/12; C07D 403/14; C07D 413/14
See application file for complete search history.

(56) References Cited

U.S. PATENT DOCUMENTS

2020/0031805 A1 1/2020 Deuschle et al.

FOREIGN PATENT DOCUMENTS

| | | | |
|---|---|---|---|
| CN | 102271682 | A | 12/2011 |
| CN | 103442712 | A | 12/2013 |
| CN | 108341813 | A | 7/2018 |
| CN | 111217802 | A | 6/2020 |
| CN | 113214138 | A | 8/2021 |
| CN | 113372347 | A | 9/2021 |
| CN | 114456178 | A | 5/2022 |
| EP | 1644338 | A | 10/2004 |
| WO | 2005113514 | A2 | 12/2005 |
| WO | 2010051188 | A1 | 5/2010 |
| WO | 2014049488 | A1 | 4/2014 |
| WO | 2014053533 | A1 | 4/2014 |
| WO | 2016069780 | A1 | 5/2016 |
| WO | 2018195397 | A2 | 10/2018 |
| WO | 2019101641 | A1 | 5/2019 |
| WO | 2019101647 | A2 | 5/2019 |
| WO | 2021102288 | A1 | 5/2021 |

OTHER PUBLICATIONS

RN 860787-58-2 in STNext Registry,2005.*
Shuanglong Jin, et al., "Design, synthesis and biological evaluation of phenylsulfonamide-based IDO1 inhibitors" Journal of China Pharmaceutical University, vol. 49(1): 34-38 (2018).
Xiaofei Yin, et al., "Aryl hydrocarbon receptor and tumor development and progression" Chinese Journal of Cancer Biotherapy, vol. 18, No. 2 (2011).
Shuai Meng, et al., "Recent progress in the study of Hsp90 inhibitors" China Journal of Antibiotics, vol. 36(4):241-248 (2011).
Chenyu Tian, et al., "Identification of triazolopyridine derivatives as a new class of AhR agonists and evaluation of anti-psoriasis effect in a mouse model" European Journal of Medicinal Chemistry, DOI: 10.1016/j.ejmech.2022.114122 (2022).
Lihui Wang, et al., "Synthesis and properties of small-molecule photovoltaicmaterial based on fluorene benzothiadiazole" Journal of Dalian University of Technology, vol. 54(5) (2014).

(Continued)

*Primary Examiner* — Brian E McDowell
(74) *Attorney, Agent, or Firm* — Squire Patton Boggs (US) LLP

(57) ABSTRACT

The present disclosure relates to a compound having an AhR inhibitory effect as shown in FIG. (I), and a use thereof and a preparation method thereof.

(I)

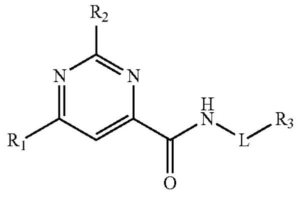

7 Claims, No Drawings

(56) References Cited

OTHER PUBLICATIONS

Zhang Guo, et al., "Discovery of 5-((1H-indazol-3-yl) methylene)-2-thioxoimidazolidin-4-one derivatives as a new class of AHR agonists with anti-psoriasis activity in a mouse model" Bioorganic and Medicinal Chemistry Letters, DOI: 10.1016/j.bmcl.2023.129383 (2023).

Notification to Grant Patent Right for Invention issued in Chinese Application No. 202210571711.9 on Jul. 7, 2023.

International Search Report for International Application PCT/CN2022/118454, dated Dec. 5, 2022.

Sun, et al., "Switchable assembly of substituted pyrimidines and 2H-imidazoles via Cu(I)-catalysed ring expansion of 2 methoxyl-2H-azirines," Org. Chem. Front., Apr. 20, 2022, 9, 3006-3011 DOI https://doi.org/10.1039/D2QO00341D.

* cited by examiner

AHR INHIBITOR, USE THEREOF, AND PREPARATION METHOD THEREFOR

CROSS-REFERENCE TO RELATED APPLICATIONS

This application is a National Stage application of International Application No. PCT/CN2022/118454, filed Sep. 13, 2022, which claims the benefit of Chinese Patent Application No. 202111110412.7, filed Sep. 18, 2021, and Chinese Patent Application No. 202210571711.9, filed May 23, 2022. The entire contents of the above-identified applications are hereby fully incorporated herein by reference.

TECHNICAL FIELD

The present disclosure relates to the field of medicine, in particular to a compound having an AhR inhibitory effect, a use thereof, and a preparation method therefor.

BACKGROUND

Aryl hydrocarbon receptor (AhR) is a transcription factor activated by a ligand and is a member of a basic helix-loop-helix/Per-ARNT-Sim (bHLH-PAS) family. AhR exists extensively in living organisms, and bodies of mammals, amphibians, reptiles, and birds contain AhR proteins. Various cells in the human body express AhR.

Functional domains of an AhR protein consist of three parts: a bHLH domain, a PAS domain, and a domain rich in glutamic acid. The bHLH domain is located at an N-terminal of the AhR protein to assist in binding of AhR to a promoter region of a target gene and protein dimerization; the PAS domain assists in the protein dimerization by connecting to an AhR nuclear transporter (ARNT) and binding to a ligand to form a protein complex; and a C-terminal region is the domain rich in glutamate, which plays a role in recruitment and transcriptional activation.

In an inactive form, AhR usually forms a multi-protein complex with a heat shock protein 90 (Hsp90), p23, an X-related protein 2 (XAP2), and an AhR-related protein 9 (ARA9) in a cytoplasm. A classic signaling pathway shows that, when AhR binds to a ligand and is activated, a conformational change occurs therein to expose a nuclear localization signal sequence, a receptor-ligand complex translocates to a nucleus to form a heterodimer with ARNT within the nucleus, and the AhR/ARNT complex binds to a heterologous biological response element of a target gene promoter (core sequence: 5'-TNGCGTG-3') to promote expression of a target gene. The target gene includes cytochrome P450 enzymes (CYP1A1, CYP1A2, CYPiB1), glutathione S-transferase, guanosine diphosphate glucuronate glycosyltransferase, NAD(P)H dependent quinone oxidoreductase-1, aldehyde dehydrogenase 3A1, anti-breast cancer protein genes, etc. Accordingly, AhR participates in many important physiological processes, such as regulation of cell cycle and proliferation, immune response, circadian rhythm, tumor induction, expression of genes related to lipid metabolism, etc.

AhR shows different biological effects by binding to exogenous or endogenous ligands with different structural properties. The exogenous ligands mainly include polycyclic aromatic hydrocarbons (PAHs), polychlorinated biphenyls (PCBs), natural compounds, small molecules, etc. The endogenous ligands include tryptophan metabolites, heme metabolites, arachidonic acid metabolites, etc. On the one hand, AhR can be activated by ligands to improve downstream gene expression levels of CYP1A1 and the like, increase phase I or phase II exogenous metabolic enzymes of target gene expression products, and promote body's metabolism of exogenous toxins, thereby protecting the body from the influence of exogenous substances, for example, an AhR receptor agonist MCDF (6-methyl-1,3,8-trichlorodiphenylfuran) can induce the expression of target gene CYP1A1 and enhance its metabolism, thereby inhibiting the proliferation of estrogen receptor negative breast cancer tumor cells. On the other hand, AhR can indirectly intervene in interaction between AhR and other tumor related signaling pathways, such as AhR-ER, AhR mitogen activated protein kinases (MAPKs), etc. and play a role in tumor development, for example, DIM (3,3'-indole methane) is a beneficial dietary ingredient, which can strongly inhibit ER-α expression and estrogen signaling pathways through AhR dependent pathways to reduce the onset risk of human breast cancer.

In recent years, AhR has received much attention in the field of immunity. A balance between Treg and Th17 cells is manifested as effective immune response and autoantigen tolerance in chronic infection or autoimmunity. Use of different ligands to activate AhR can purposefully induce the differentiation of Treg and Th17 cells, thereby exhibiting a bidirectional effect of AhR immune enhancement or inhibition. TCDD can activate AhR to induce the differentiation of Th0 cells into Treg cells, thereby alleviating experimental autoimmune encephalomyelitis (EAE), while FICZ activates AhR to promote the differentiation of Th0 cells into Th17 cells, thereby exacerbating EAE. Therefore, different degrees of inhibition or activation of AhR based on the diversity of AhR ligands can play different roles in the fields of tumors and immunity.

TCDD is one of the exogenous ligands of AhR, and the relationship between AhR and immunity initially derives from studies on TCDD related signaling pathways. TCDD induced AhR pathways have inhibitory effects on T cells and dendritic cells, resulting in strong immune suppression. AhR is highly expressed and continuously activated in various types of tumors, such as colon cancer, gastric cancer, prostate cancer, ovarian cancer, and melanoma. Increasing studies indicate that AhR promotes the occurrence, progression, infiltration, and metastasis of cancer cells. Deeper studies found that tryptophan metabolite, kynurenine, is an important endogenous AhR ligand. Tryptophan-2,3-dioxygenase (TDO2) metabolizes tryptophan into kynurenine in various types of tumors such as gliomas. The kynurenine has a strong inhibitory effect on anti-tumor immune response, thereby promoting the survival and movement of tumor cells. The strong immune inhibitory effect of the kynurenine is mediated by AhR. In addition, the activation of AhR can also enhance the mobility, infiltration, and drug resistance of triple negative breast cancer cells. The inhibition of AhR can overcome the drug resistance of melanoma to BRAF inhibitors. AhR can mediate tobacco induced PD-L1 expression, which is associated with immune response of tumors. AhR inhibitors have significant anti-tumor activity and exhibit synergistic effects with anti-PD-L1 or anti-PD-1 antibodies in mouse models of lung cancer, colon cancer, and fibrosarcoma. Combinations of AhR inhibitors and anti-PD-L1 antibodies can increase the infiltration of T cells and the expression of IFN γ and TNF α. The AhR inhibitors can also relieve immune inhibition caused by kynurenine induced Treg and macrophages, thereby achieving immune anticancer effects. Glioma is the most common primary central nervous system tumor. Due to the lack of clear boundaries with normal brain tissues, it is difficult to completely excise the glioma in surgeries. Meanwhile, the glioma is insensitive to radiotherapy, chemotherapy, and targeted therapy, and is prone to recurrence. About 70% of gliomas have isocitrate dehydrogenase (IDH) mutations. Recent studies show that IDH mutated glioma cells release tumorigenic (R)-2-hydroxyglutaric acid (R-2-HG), which interferes with the amino acid metabolism of "cell scavenger" macrophages and activates immune system regulatory molecules AHR, so that the macrophages produce an immune inhibitory response to inhibit the immune system and the activity of T cells. Small molecule AHR inhibitors can effectively prolong the lifespan of IDH mutant tumor mice. In summary, AhR is an important cancer target and tumor immune target, and AhR inhibitors have great potential as anticancer drugs.

Recent studies show that AhR is a host factor of Zika virus, and Zika virus infection can induce kynurenine production to activate AhR. The activation of AhR can limit the production of type I interferon to inhibit the antiviral immunity of hosts. Therefore, AhR can serve as a target for antiviral therapy. Studies found that AhR inhibitors effectively inhibit replication of Zika virus and dengue virus and alleviate pathological changes caused by viruses. Further studies also found that COVID-19 infection can also activate AhR, and the activation of AhR signaling pathways can interfere with the regeneration activity of pulmonary epithelial basal cells. Therefore, AhR inhibitors also have the potential to treat COVID-19 infection.

SUMMARY

The present disclosure aims to provide a compound having an AhR inhibitory effect or a pharmaceutically acceptable salt thereof.

The present disclosure relates to a compound represented by formula (I) or a pharmaceutically acceptable salt thereof:

(I)

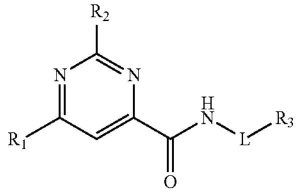

wherein, $R_1$ is selected from 5- to 10-membered aryl or 5- to 10-membered heteroaryl, and the 5- to 10-membered aryl or 5- to 10-membered heteroaryl is optionally substituted by one or two $R_{11}$.

Preferably, $R_1$ is selected from 5- to 7-membered aryl or 5- to 7-membered heteroaryl containing one or two atoms selected from N or O, and the 5- to 7-membered aryl or 5- to 7-membered heteroaryl containing one or two atoms selected from N or O is optionally substituted by one or two $R_{11}$.

Preferably, $R_1$ is selected from phenyl, pyridyl, pyrazolyl, or isoxazolyl, and the phenyl, pyridyl, pyrazolyl, or isoxazolyl is optionally substituted by one or two $R_{11}$.

Preferably, $R_1$ is selected from phenyl, pyridyl, or pyrazolyl, and the phenyl, pyridyl, or pyrazolyl is optionally substituted by one or two $R_{11}$.

$R_{11}$ is selected from halogen, cyano, hydroxyl, carboxyl, $C_{1-3}$ amido, $C_{1-6}$ alkyl, $C_{1-6}$ alkoxy, or $C_{3-6}$ cycloalkyl, wherein the $C_{1-6}$ alkyl, $C_{1-6}$ alkoxy, or $C_{3-6}$ cycloalkyl is optionally substituted by one or more halogens or hydroxyls.

Preferably, $R_{11}$ is selected from halogen, cyano, $C_{1-3}$ alkyl, or $C_{1-3}$ alkoxy, wherein the $C_{1-3}$ alkyl or $C_{1-3}$ alkoxy is optionally substituted by one or more fluorines.

Preferably, $R_{11}$ is selected from fluorine, chlorine, cyano, $C_{1-3}$ alkyl, or $C_{1-3}$ alkoxy, wherein the $C_{1-3}$ alkyl or $C_{1-3}$ alkoxy is optionally substituted by one, two, or three fluorines.

Preferably, $R_{11}$ is selected from fluorine, chlorine, cyano, methyl, trifluoromethyl, or trifluoromethoxy. Preferably, $R_1$ is selected from phenyl, pyridyl, or pyrazolyl, and the phenyl, pyridyl, or pyrazolyl is optionally substituted by one or two substituents selected from fluorine, chlorine, cyano, methyl, trifluoromethyl, or trifluoromethoxy.

Preferably, $R_1$ is selected from

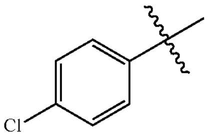 , 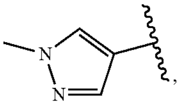 ,
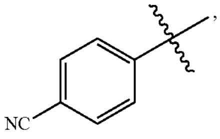 , 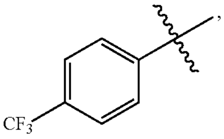 ,
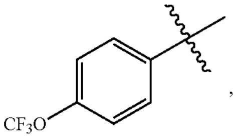 , 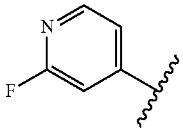 ,
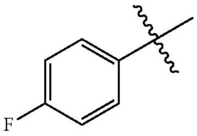 , or 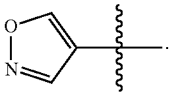 .

Preferably, $R_1$ is selected from

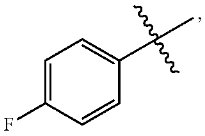 , 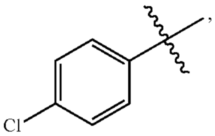 ,
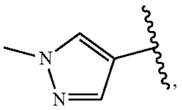 , 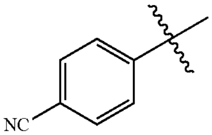 ,
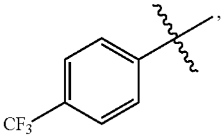 , 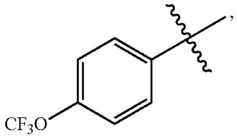 , or
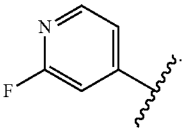 .

$R_2$ is selected from $C_{3-6}$ cycloalkyl, 3- to 6-membered heterocyclic alkyl, 5- to 10-membered aryl, or 5- to 10-membered heteroaryl, and the $C_{3-6}$ cycloalkyl, 3- to 6-membered heterocyclic alkyl, 5- to 10-membered aryl, or 5- to 10-membered heteroaryl is optionally substituted by one or more $R_{21}$. Preferably, $R_2$ is selected from 5- to 7-membered aryl or 5- to 7-membered heteroaryl containing one or two atoms selected from N or O, and the 5- to 7-membered aryl or 5- to 7-membered heteroaryl containing one or two atoms selected from N or O is optionally substituted by one or two $R_{21}$.

Preferably, $R_2$ is selected from phenyl, pyrazolyl, pyridyl, isoxazolyl, or pyrimidyl, and the phenyl, pyrazolyl, pyridyl, isoxazolyl, or pyrimidyl is optionally substituted by one or two $R_{21}$.

$R_{21}$ is selected from cyano, amino, halogen, hydroxyl, carboxyl, $C_{1-6}$ alkoxy, $C_{1-6}$ alkyl, or $C_{3-6}$ cycloalkyl, wherein the $C_{1-6}$ alkoxy, $C_{1-6}$ alkyl, or $C_{3-6}$ cycloalkyl is optionally substituted by one or more halogens, hydroxyls, or $C_{1-3}$ alkyls.

Preferably, $R_{21}$ is selected from cyano, amino, fluorine, chlorine, $C_{1-6}$ alkoxy, $C_{1-3}$ alkyl, or $C_{3-6}$ cycloalkyl, wherein the $C_{1-6}$ alkoxy, $C_{1-3}$ alkyl, or $C_{3-6}$ cycloalkyl is optionally substituted by one, two, or three halogens or $C_{1-3}$ alkyls.

Preferably, $R_{21}$ is selected from cyano, amino, fluorine, chlorine, methyl, methoxy, or cyclopropyl.

Preferably, $R_2$ is selected from phenyl, pyrazolyl, pyridyl, isoxazolyl, or pyrimidyl, and the phenyl, pyrazolyl, pyridyl, isoxazolyl, or pyrimidyl is optionally substituted by one or two substituents selected from cyano, amino, fluorine, chlorine, methyl, methoxy, or cyclopropyl.

Preferably, $R_2$ is selected from

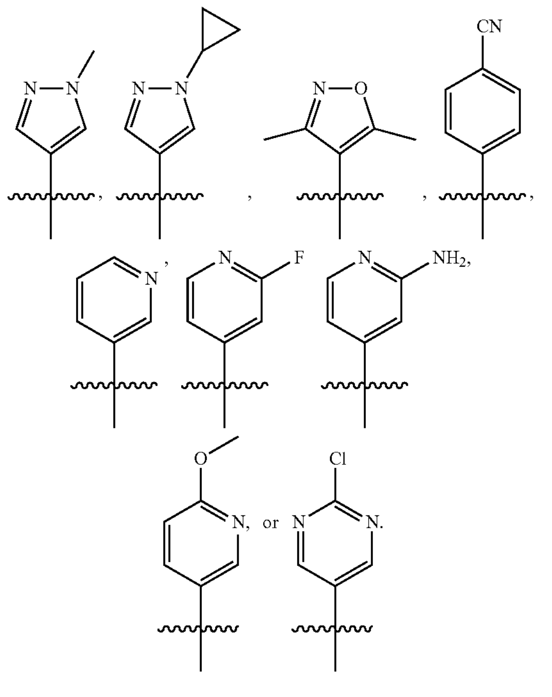

L is selected from $-(CH_2)_n-$, wherein one or more hydrogens on $CH_2$ are substituted by $R_L$.

n is an integer selected from 0-6; preferably, n is an integer selected from 0-3; and preferably, n is selected from 0, 1, or 2.

$R_L$ is selected from $C_{1-6}$ alkyl, $C_{1-6}$ alkoxy, $C_{3-6}$ cycloalkyl, hydroxyl, carboxyl, amino, cyano, or halogen, wherein the $C_{1-6}$ alkyl, $C_{1-6}$ alkoxy, or $C_{3-6}$ cycloalkyl is optionally substituted by one, two, or three halogens or hydroxyls; or two $R_L$ connected to the same carbon atom are connected to form $C_{3-6}$ cycloalkyl or 3- to 6-membered heterocyclic alkyl, and the $C_{3-6}$ cycloalkyl or 3- to 6-membered heterocyclic alkyl is optionally substituted by one, two, or three halogens or hydroxyls.

Preferably, $R_L$ is selected from methylene, methyl, ethyl, or cyclopropyl, or two methylenes connected to the same carbon atom are connected to form cyclopropyl.

Preferably, L is selected from $-(CH_2)_n-$, and n is selected from 0, 1, or 2, wherein one or more hydrogens on $CH_2$ are substituted by methyl, ethyl, or cyclopropyl, or two methyls connected to the same carbon atom are connected to form cyclopropyl. Preferably, L is selected from a single bond, $-CH(CH_3)-$, $-CH_2CH_2-$, $-CH(CH_2CH_3)-$,

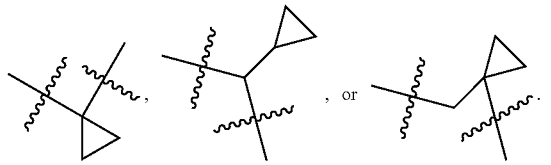 [SMILES: *C1(*)CC1 ; *C(*)C1CC1 ; *CC1(*)CC1]

$R_3$ is selected from 5- to 10-membered aryl, 5- to 10-membered heteroaryl, 5- to 10-membered heterocyclic alkyl, 9- to 12-membered partially unsaturated bicyclic carbocyclic group, or 9- to 12-membered partially unsaturated bicyclic heterocyclic group, and the 5- to 10-membered aryl, 5- to 10-membered heteroaryl, 5- to 10-membered heterocyclic alkyl, 9- to 12-membered partially unsaturated bicyclic carbocyclic group, or 9- to 12-membered partially unsaturated bicyclic heterocyclic group is optionally substituted by one or more $R_{31}$.

Preferably, $R_3$ is selected from 5- to 10-membered aryl, 5- to 10-membered heteroaryl, 9- to 12-membered partially unsaturated bicyclic carbocyclic group, or 9- to 12-membered partially unsaturated bicyclic heterocyclic group, and the 5- to 10-membered aryl, 5- to 10-membered heteroaryl, 9- to 12-membered partially unsaturated bicyclic carbocyclic group, or 9- to 12-membered partially unsaturated bicyclic heterocyclic group is optionally substituted by one or more $R_{31}$.

Preferably, $R_3$ is selected from phenyl, 5- to 10-membered heteroaryl containing 1-3 atoms independently selected from N or 0, 5- to 10-membered heterocyclic alkyl containing 1-2 N atoms, 9- to 12-membered benzocycloalkyl, or 9- to 12-membered partially unsaturated bicyclic heterocyclic group containing 1-2 atoms independently selected from N, O, or S, and the phenyl, 5- to 10-membered heteroaryl containing 1-3 atoms independently selected from N or 0, 5- to 10-membered heterocyclic alkyl containing 1-2 N atoms, 9- to 12-membered benzocycloalkyl, or 9- to 12-membered partially unsaturated bicyclic heterocyclic group containing 1-2 atoms independently selected from N, O, or S is optionally substituted by one or more $R_{31}$.

Preferably, $R_3$ is selected from phenyl, 5- to 10-membered heteroaryl containing 1-3 atoms independently selected from N or 0, 9- to 12-membered benzocycloalkyl, or 9- to 12-membered partially unsaturated bicyclic heterocycle containing 1-2 atoms independently selected from N, O, or S, and the phenyl, 5- to 10-membered heteroaryl containing 1-3 atoms independently selected from N or 0, 9- to 12-membered benzocycloalkyl, or 9- to 12-membered partially unsaturated bicyclic heterocycle containing 1-2 atoms independently selected from N, O, or S is optionally substituted by one or more $R_{31}$.

Preferably, $R_3$ is selected from phenyl, pyridocyclopentyl, benzocyclopentyl, benzocyclohexyl, pyridyl, indolyl, pyrimidyl, pyrazolyl, benzodioxycyclopentyl (benzodioxymethylene), triazolopyridyl, tetrahydroquinolyl, indazolyl, piperidyl, or benzimidazolyl, and the phenyl, pyridocyclopentyl, benzocyclopentyl, benzocyclohexyl, pyridyl, indolyl, pyrimidyl, pyrazolyl, benzodioxycyclopentyl, triazolopyridyl, tetrahydroquinolyl, indazolyl, piperidyl, or benzimidazolyl is optionally substituted by one, two, or three $R_{31}$.

Preferably, $R_3$ is selected from phenyl, pyridocyclopentyl, benzocyclopentyl, pyridyl, indolyl, pyrimidyl, pyrazolyl, benzodioxycyclopentyl, triazolopyridyl, or tetrahydroquinolyl, and the phenyl, pyridocyclopentyl, benzocyclopentyl, pyridyl, indolyl, pyrimidyl, pyrazolyl, benzodioxycyclopentyl, triazolopyridyl, or tetrahydroquinolyl is optionally substituted by one, two, or three $R_{31}$.

Preferably, $R_{31}$ is selected from halogen, hydroxyl, cyano, $C_{1-3}$ alkyl, $C_{1-3}$ alkoxy, $C_{1-5}$ amido, $C_{1-5}$ acyl, or —$C_{1-3}$ alkyl-C(O)$NH_2$, and the $C_{1-3}$ alkyl, $C_{1-3}$ alkoxy, $C_{1-5}$ amido, $C_{1-5}$ acyl, or —$C_{1-3}$ alkyl-C(O)$NH_2$ is optionally substituted by one or more $C_{1-3}$ alkyls, halogens, hydroxyls, cyanos, trifluoromethyls, or $C_{3-6}$ cycloalkyls.

$R_{31}$ is selected from halogen, hydroxyl, cyano, $C_{1-3}$ alkyl, $C_{1-3}$ alkoxy, or $C_{1-5}$ amido, and the $C_{1-3}$ alkyl, $C_{1-3}$ alkoxy, or $C_{1-5}$ amido is optionally substituted by one or more $C_{1-3}$ alkyls, halogens, or hydroxyls.

Preferably, $R_{31}$ is selected from halogen, hydroxyl, cyano, $C_{1-3}$ alkyl, $C_{1-3}$ alkoxy, $C_{1-3}$ amido, $C_{1-3}$ acyl, or —$C_{1-3}$ alkyl-C(O)$NH_2$, and the $C_{1-3}$ alkyl, $C_{1-3}$ alkoxy, $C_{1-3}$ amido, $C_{1-3}$ acyl, or —$C_{1-3}$ alkyl-C(O)$NH_2$ is optionally substituted by one, two, or three $C_{1-3}$ alkyls, halogens, hydroxyls, cyanos, trifluoromethyls, or cyclopropyls.

Preferably, $R_{31}$ is selected from fluorine, chlorine, methyl, methoxy, trifluoromethyl, trifluoroethyl, hydroxyl, cyano, ethylcyano,

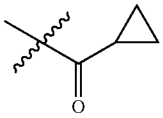
,
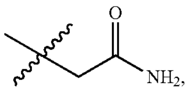
,
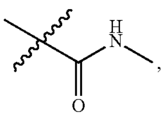
, or
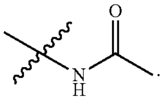
.

Preferably, $R_{31}$ is selected from halogen, hydroxyl, cyano, $C_{1-3}$ alkyl, $C_{1-3}$ alkoxy, or $C_{1-3}$ amido, wherein the $C_{1-3}$ alkyl, $C_{1-3}$ alkoxy, or $C_{1-3}$ amido is optionally substituted by one, two, or three $C_{1-3}$ alkyls, halogens, or hydroxyls.

Preferably, $R_3$ is selected from phenyl, pyridocyclopentyl, benzocyclopentyl, benzocyclohexyl, pyridyl, indolyl, pyrimidyl, pyrazolyl, benzodioxycyclopentyl, triazolopyridyl, tetrahydroquinolyl, indazolyl, piperidyl, or benzimidazolyl, and the phenyl, pyridocyclopentyl, benzocyclopentyl, benzocyclohexyl, pyridyl, indolyl, pyrimidyl, pyrazolyl, benzodioxycyclopentyl, triazolopyridyl, tetrahydroquinolyl, indazolyl, piperidyl, or benzimidazolyl is optionally substituted by one, two, or three substituents selected from fluorine, chlorine, methyl, methoxy, trifluoromethyl, trifluoroethyl, hydroxyl, cyano, ethylcyano,

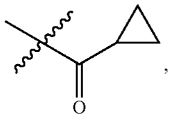
,
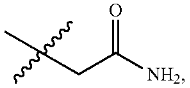
,
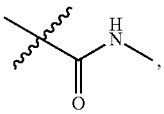
, or
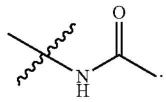
.

Preferably, $R_3$ is selected from

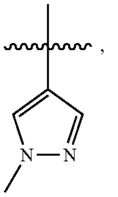
,
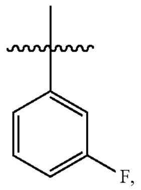
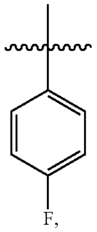
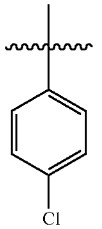
,
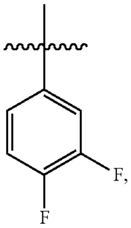
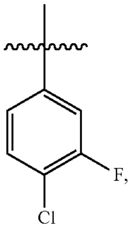
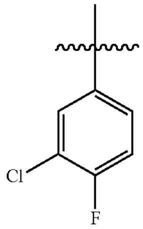
,
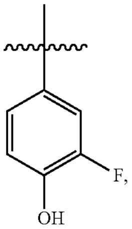
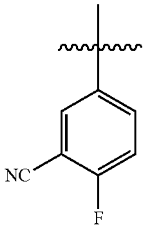
,
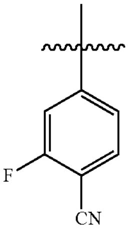
,
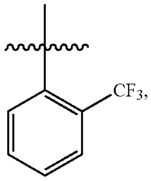
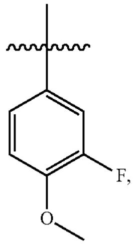
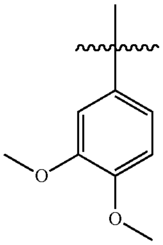
,
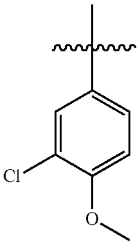
,
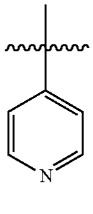
, -continued
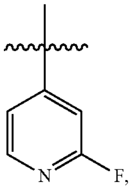
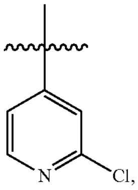
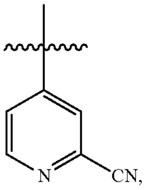
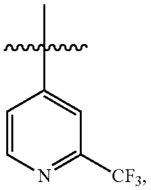
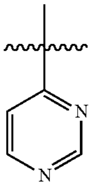
,
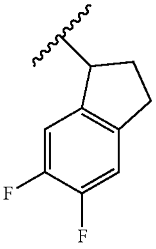
,
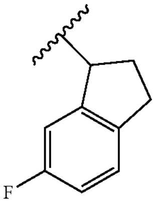
,
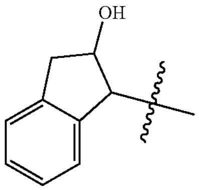
,
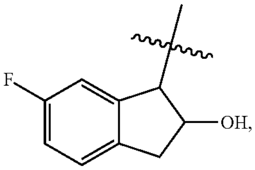
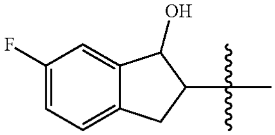
,
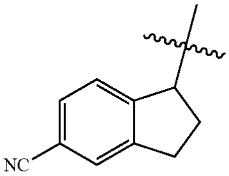
,
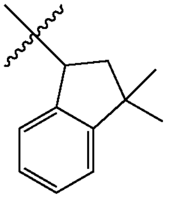
,
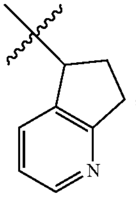
,
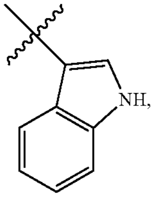
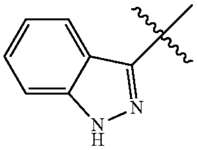
,
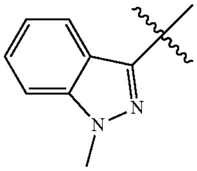
,
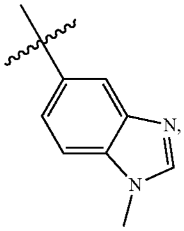
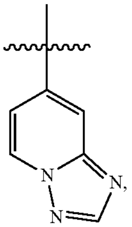
-continued
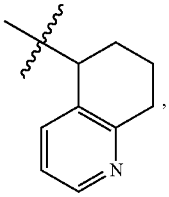
,
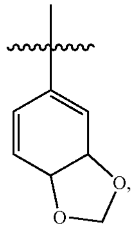
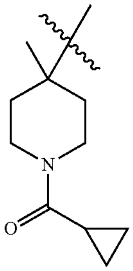
,
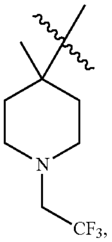
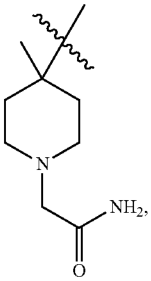
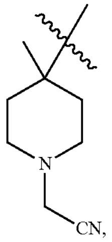
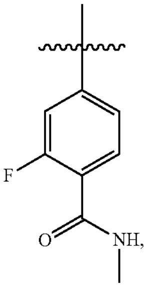
or
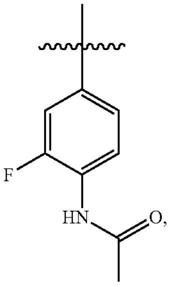
or
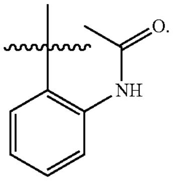
Preferably, $R_3$ is selected from
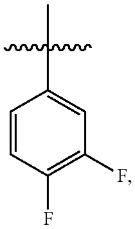
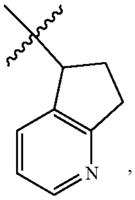
,
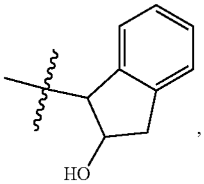
, -continued
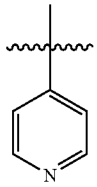, 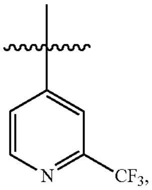, 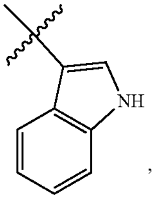,
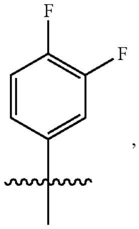, 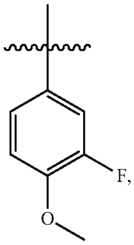, 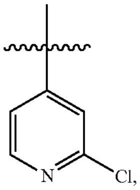, 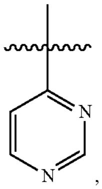,
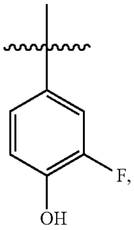, 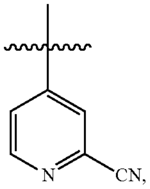, 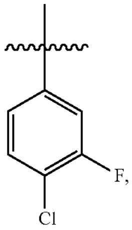, 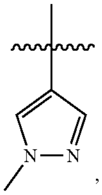,
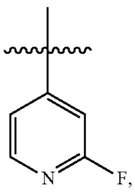, 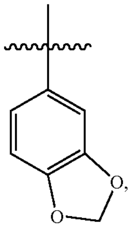, 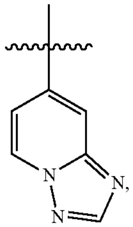, 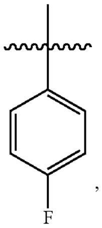,
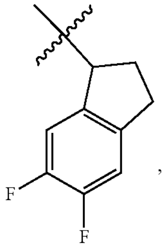, 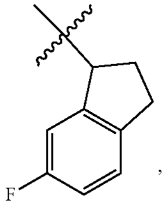, 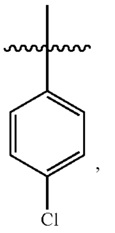,
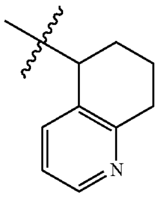, 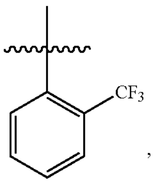, 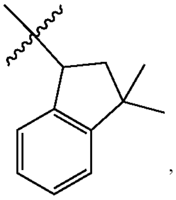,
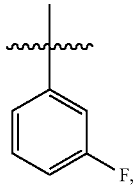, 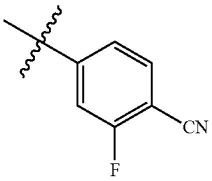, 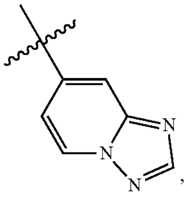,
-continued
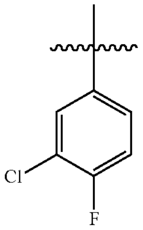, 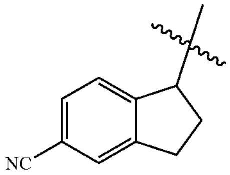, 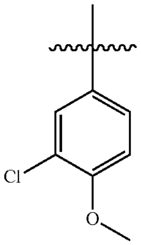,
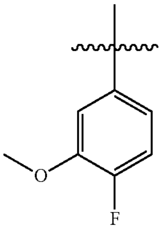, 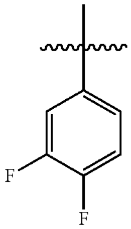, 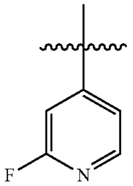,
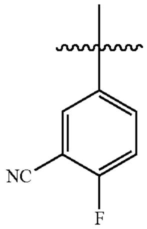, 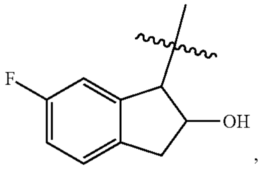,
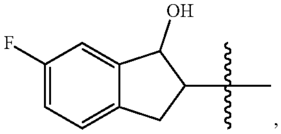, 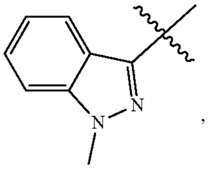,
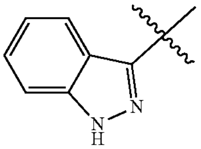, 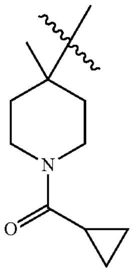, 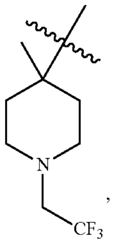,
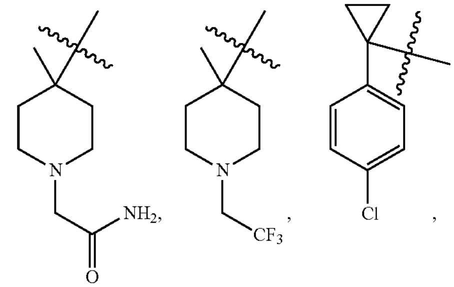
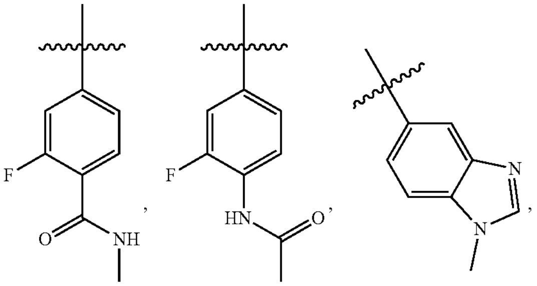

-continued
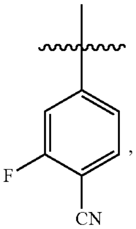, or 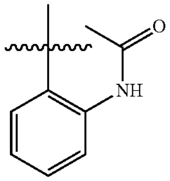.
Preferably, -L-$R_3$ is selected from
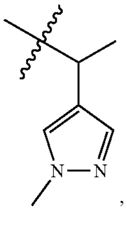, 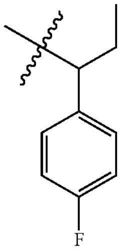, 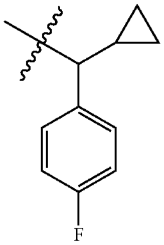,
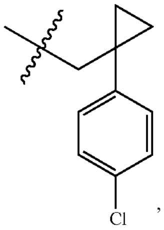, 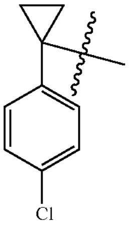, 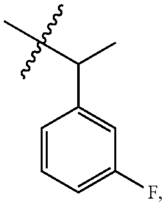
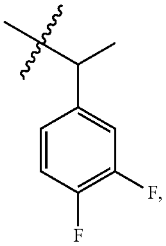 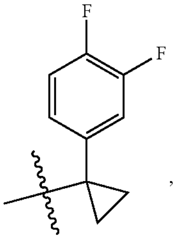, 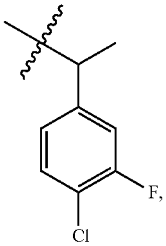
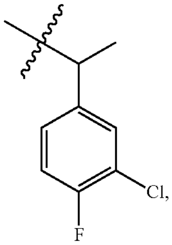 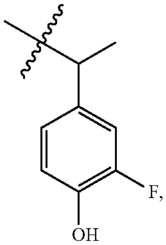 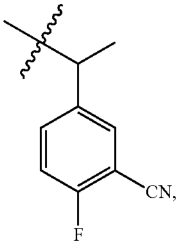
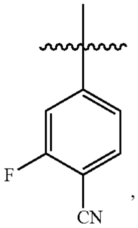, 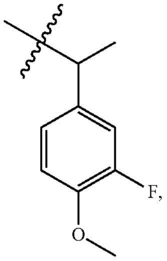 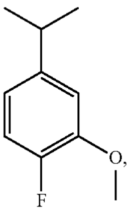
-continued
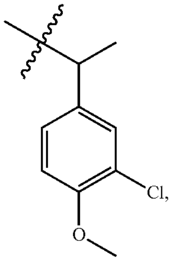 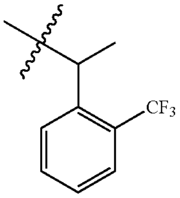, 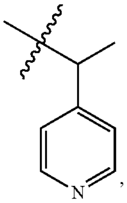
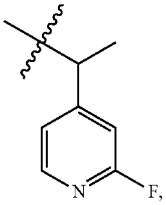 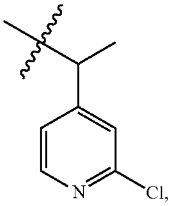 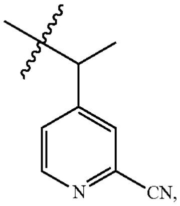
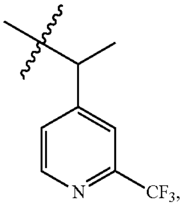 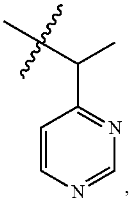, 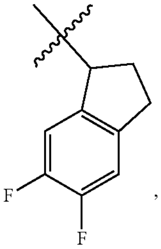,
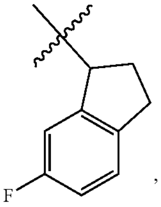, 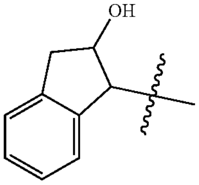, 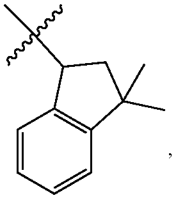,
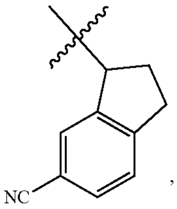, 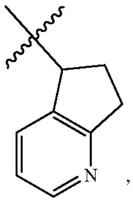, 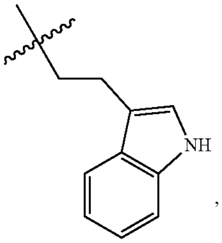,
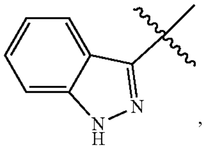, 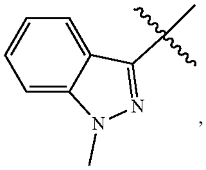,
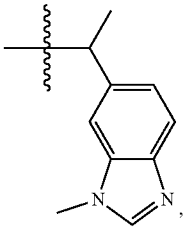 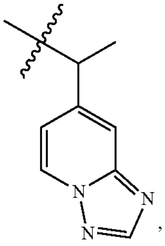, 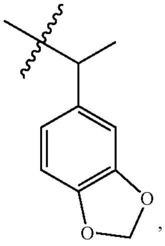, -continued
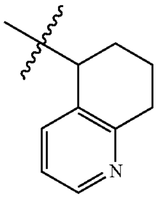, 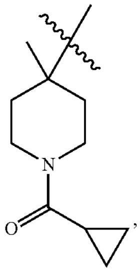 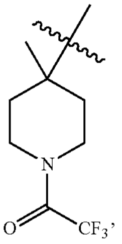
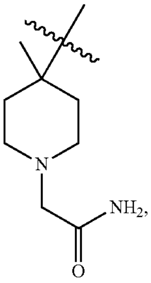 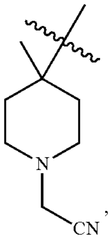 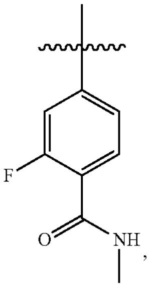 or
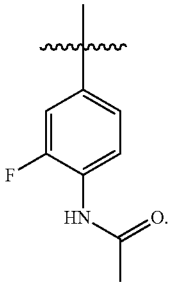
Preferably, -L-$R_3$ is selected from
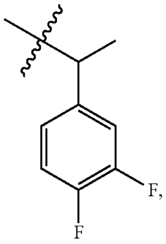 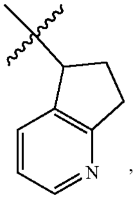, 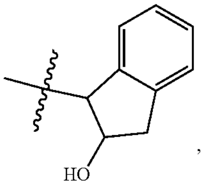,
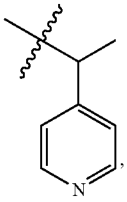 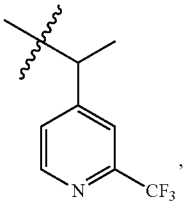, 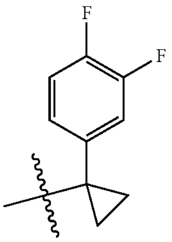,
-continued
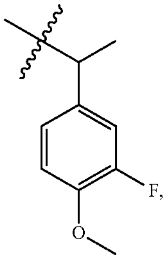 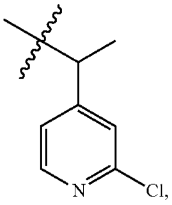 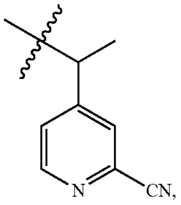
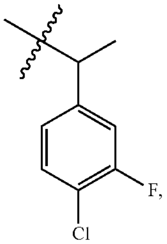 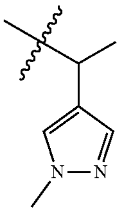, 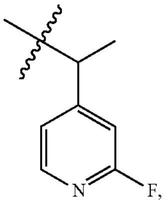
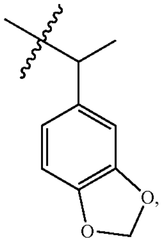 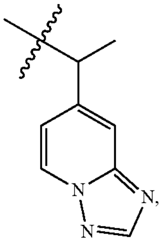 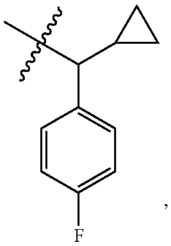,
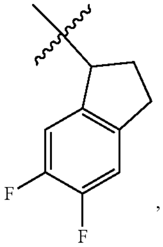, 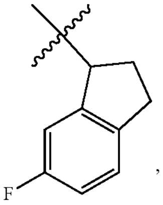, 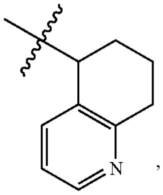,
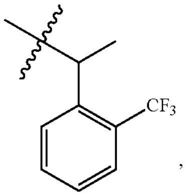, 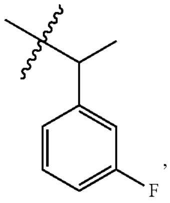,
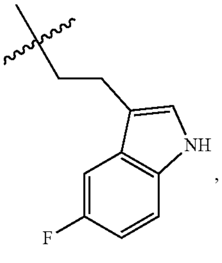, 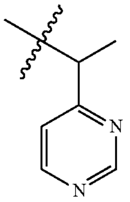, 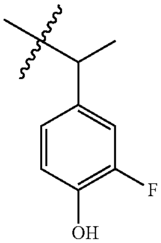,
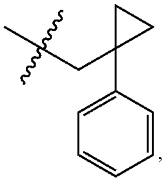, or 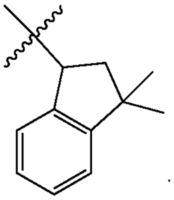.

In an aspect of the present disclosure, a compound represented by formula (Ia) or a pharmaceutically acceptable salt thereof is involved, which has the following structure:

(Ia)

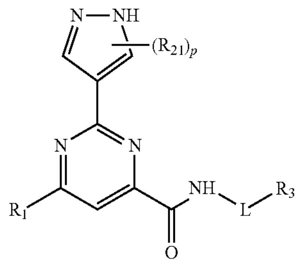

wherein $R_1$, $R_3$, $R_{11}$, $R_{21}$, $R_{31}$, L, and $R_L$ have definitions as described in formula (I) above, and p is an integer selected from 0-3. Preferably, p is selected from 0, 1, or 2.

In an aspect of the present disclosure, a compound represented by formula (Ib) or a pharmaceutically acceptable salt thereof is provided, which has the following structure:

(Ib)

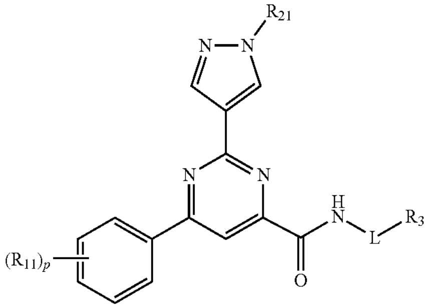

wherein $R_3$, $R_{11}$, $R_{21}$, $R_{31}$, L, and $R_L$ have definitions described in formula (I) or formula (Ia) above.

p is an integer selected from 0-3; preferably, p is selected from 0, 1, or 2. In an aspect of the present disclosure, a compound represented by formula (Ic) or a pharmaceutically acceptable salt thereof is provided, which has the following structure:

(Ic)

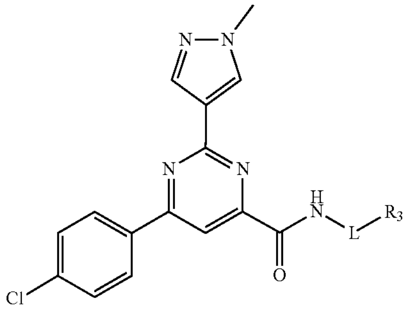

wherein $R_3$, $R_{31}$, L, and $R_L$ have definitions described in formula (I).

In an aspect of the present disclosure, a compound represented by formula (II) or a pharmaceutically acceptable salt thereof is provided, which has the following structure:

(II)

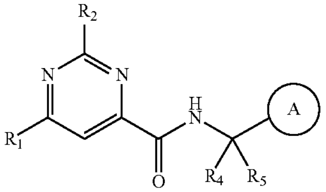

wherein $R_1$, $R_2$, $R_{11}$, and $R_{21}$ have definitions described in formula (I).

$R_4$ and $R_5$ are independently selected from hydrogen, $C_{1-3}$ alkyl, or $C_{3-6}$ cycloalkyl; or $R_4$ and $R_5$ are connected to form $C_{3-6}$ cycloalkyl.

Preferably, $R_4$ is hydrogen, $R_5$ is selected from $C_{1-3}$ alkyl or $C_{3-6}$ cycloalkyl.

Preferably, $R_4$ is hydrogen, $R_5$ is selected from methyl, ethyl, or cyclopropyl.

Preferably, $R_4$ and $R_5$ are connected to form cyclopropyl.

Ring A is selected from 5- to 10-membered aryl, 5- to 10-membered heteroaryl, 5- to 10-membered heterocyclic alkyl, or 9- to 12-membered partially unsaturated bicyclic heterocyclic group, and the 5- to 10-membered aryl, 5- to 10-membered heteroaryl, 5- to 10-membered heterocyclic alkyl, or 9- to 12-membered partially unsaturated bicyclic heterocyclic group is optionally substituted by one or more $R_{31}$.

Ring A is selected from 5- to 10-membered aryl, 5- to 10-membered heteroaryl, or 9- to 12-membered partially unsaturated bicyclic heterocyclic group, and the 5- to 10-membered aryl, 5- to 10-membered heteroaryl, or 9- to 12-membered partially unsaturated bicyclic heterocyclic group is optionally substituted by one or more $R_{31}$.

Preferably, ring A is selected from phenyl, 5- to 10-membered heteroaryl containing 1-3 atoms independently selected from N or 0, 5- to 10-membered heterocyclic alkyl containing 1-2 N atoms, or 9- to 12-membered partially unsaturated bicyclic heterocyclic group containing 1-2 atoms independently selected from N, O, or S, and the phenyl, 5- to 10-membered heteroaryl containing 1-3 atoms independently selected from N or 0, 5- to 10-membered heterocyclic alkyl containing 1-2 N atoms, or 9- to 12-membered partially unsaturated bicyclic heterocyclic group containing 1-2 atoms independently selected from N, O, or S is optionally substituted by one or more $R_{31}$.

Preferably, ring A is selected from phenyl, 5- to 10-membered heteroaryl containing 1-3 atoms independently selected from N or 0, or 9- to 12-membered partially unsaturated bicyclic heterocyclic group containing 1-2 atoms independently selected from N, O, or S, and the phenyl, 5- to 10-membered heteroaryl containing 1-3 atoms independently selected from N or 0, or 9- to 12-membered partially unsaturated bicyclic heterocyclic group containing 1-2 atoms independently selected from N, O, or S is optionally substituted by one or more $R_{31}$.

Preferably, ring A is selected from phenyl, pyridyl, indolyl, pyrimidyl, pyrazolyl, benzodioxycyclopentyl, triazolopyridyl, tetrahydroquinolyl, pyridylcyclopentyl, benzocyclopentyl, indazolyl, piperidyl, or benzimidazolyl, and the phenyl, pyridyl, indolyl, pyrimidyl, pyrazolyl, benzodioxycyclopentyl, triazolopyridyl, tetrahydroquinolyl, pyridylcyclopentyl, benzocyclopentyl, indazolyl, piperidyl, or benzimidazolyl is optionally substituted by one, two, or three $R_{31}$.

Preferably, ring A is selected from phenyl, pyridyl, indolyl, pyrimidyl, pyrazolyl, benzodioxycyclopentyl, or triazolopyridyl, and the phenyl, pyridyl, indolyl, pyrimidyl, pyrazolyl, benzodioxycyclopentyl, or triazolopyridyl is optionally substituted by one, two, or three $R_{31}$.

Preferably, ring A is selected from phenyl,

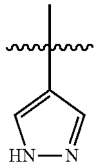 , 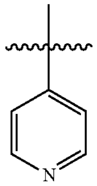 , 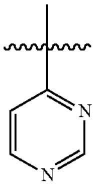 , 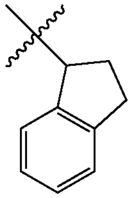 , 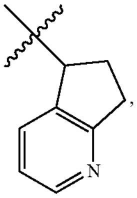 , 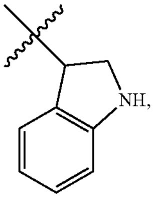 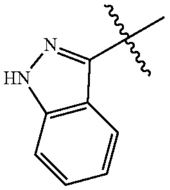 , 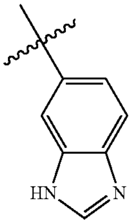 , 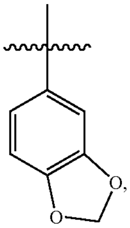 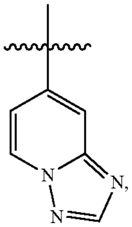 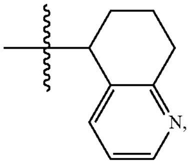 or 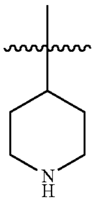 , and the phenyl,

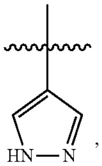 , 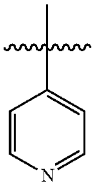 , 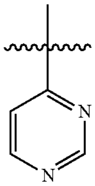 , 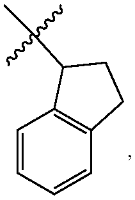 , 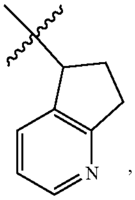 , 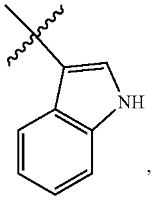 , 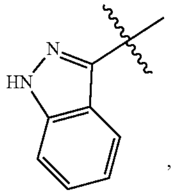 , -continued

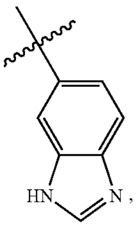 , 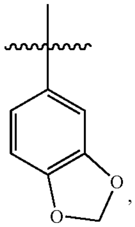 , 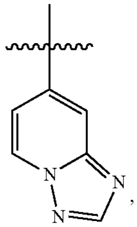 , 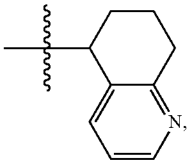 or 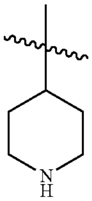

is optionally substituted by one, two, or three $R_{31}$.

$R_{31}$ is selected from halogen, hydroxyl, cyano, $C_{1-3}$ alkyl, $C_{1-3}$ alkoxy, $C_{1-3}$ amido, $C_{1-3}$ acyl, or —$C_{1-3}$ alkyl-C(O)$NH_2$, and the $C_{1-3}$ alkyl, $C_{1-3}$ alkoxy, $C_{1-3}$ amido, $C_{1-3}$ acyl, or —$C_{1-3}$ alkyl-C(O)$NH_2$ is optionally substituted by one, two, or three $C_{1-3}$ alkyls, halogens, hydroxyls, cyanos, or cyclopropyls;

Preferably, $R_{31}$ is selected from fluorine, chlorine, methyl, methoxy, trifluoromethyl, trifluoroethyl, hydroxyl, cyano, ethylcyano,

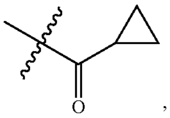 , 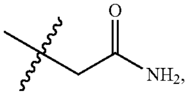 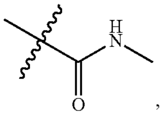 , and 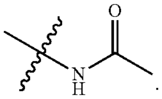 .

Preferably, ring A is selected from phenyl,

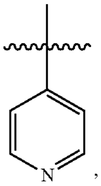 , 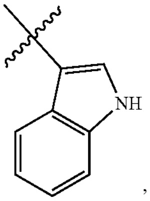 , 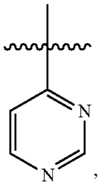 , 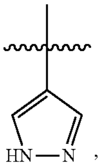 , 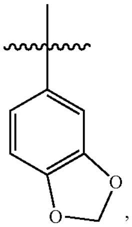 , or 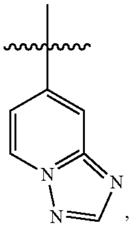 , and the phenyl,
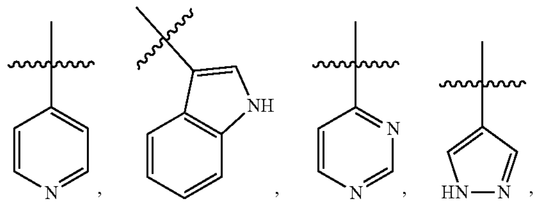
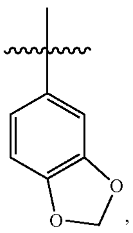
or
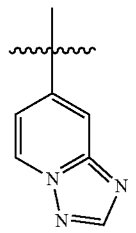
is optionally substituted by one, two, or three $R_{31}$.
Preferably, ring A is selected from
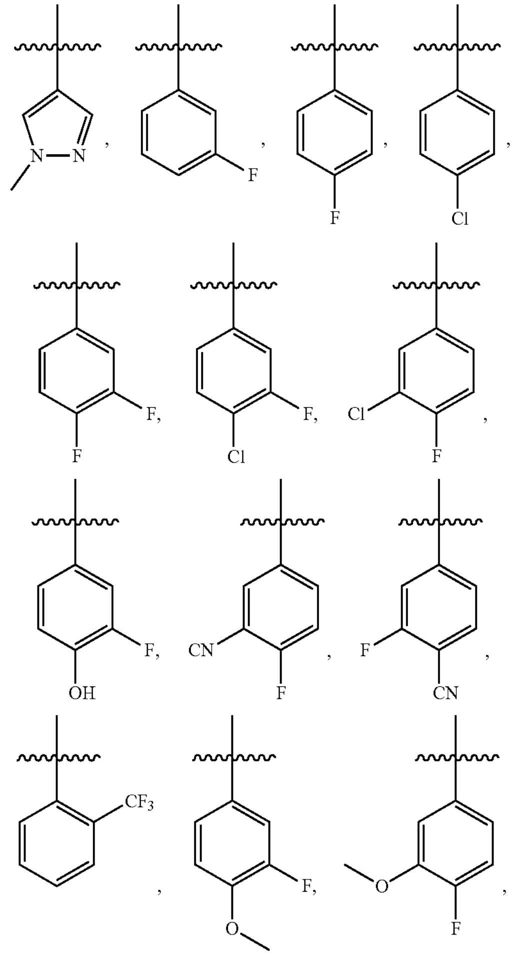
-continued
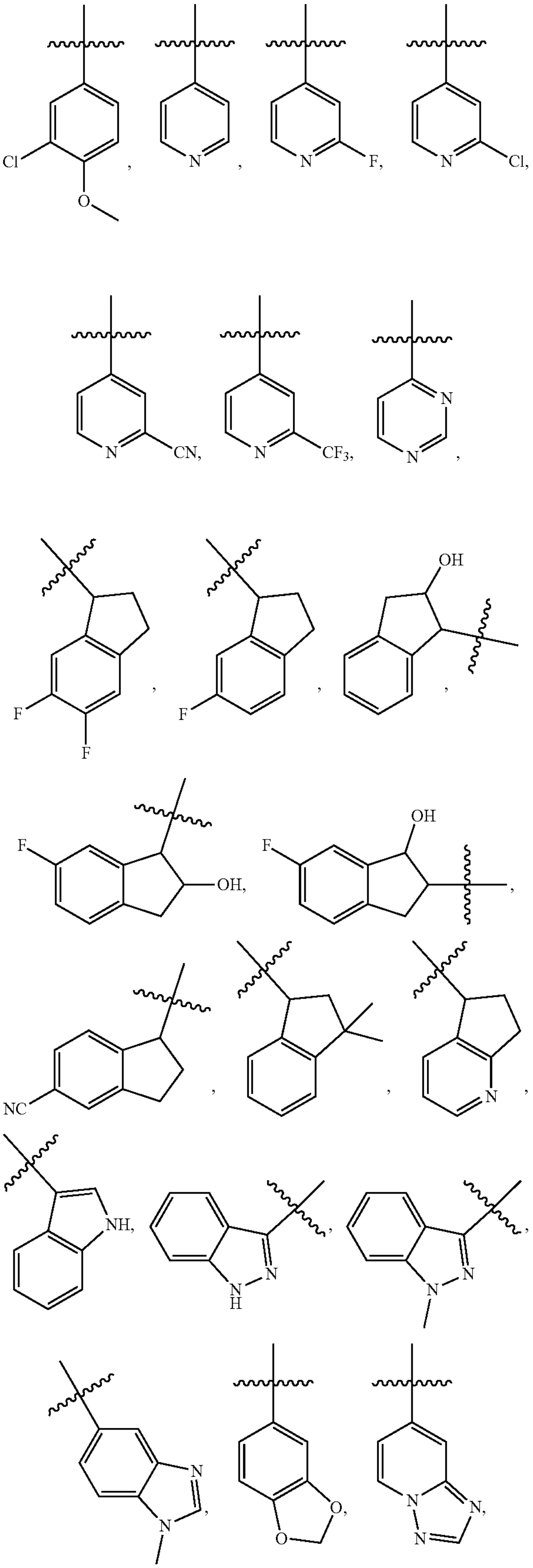

-continued
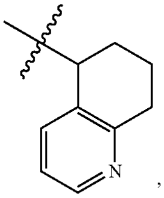
,
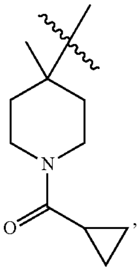
,
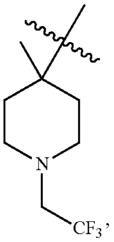
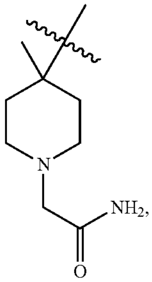
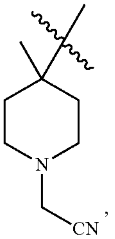
,
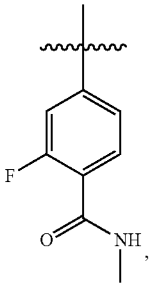
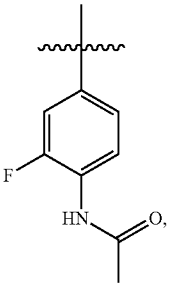
or
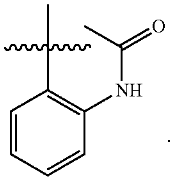
.
Preferably, ring A is selected from
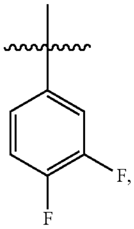
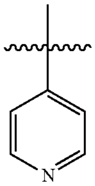
,
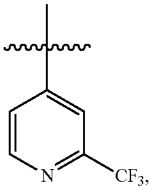
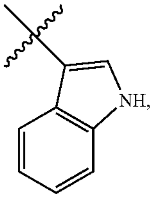
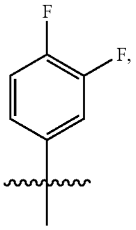
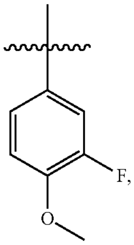
-continued
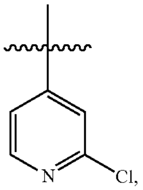
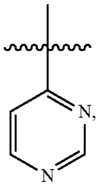
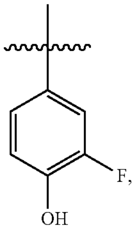
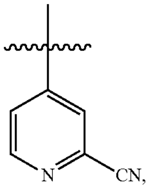
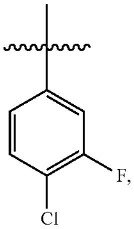
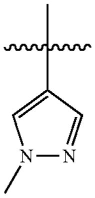
,
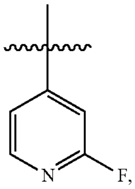
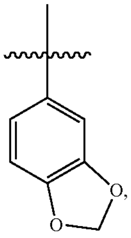
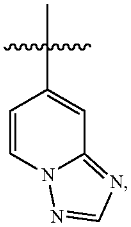
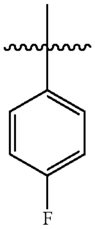
,
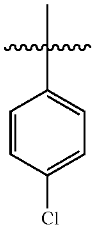
,
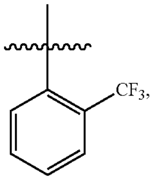
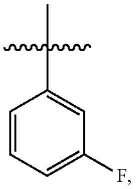
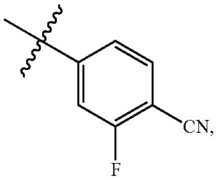
or
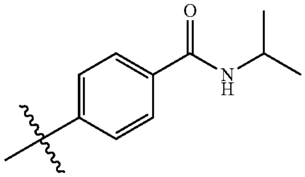
.
In an aspect of the present disclosure, a compound represented by formula (III) or a pharmaceutically acceptable salt thereof is involved, which has the following structure:

(III)

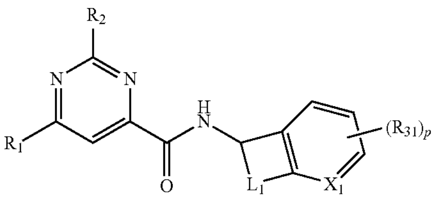

wherein $R_1$, $R_2$, $R_{31}$, and p have definitions described in formula (I) or formula (Ia) above.

$X_1$ is CH or N;

$L_1$ is selected from $-(CH_2)_m-$, wherein one or more hydrogens on $CH_2$ are substituted by $R_{LL}$;

m is an integer selected from 1-3; preferably, n is selected from 2 or 3;

$R_{LL}$ is selected from $C_{1-3}$ alkyl, cyano, hydroxyl, carboxyl, or halogen;

Preferably, $R_{LL}$ is selected from methyl or hydroxyl.

The present disclosure relates to the following compounds or pharmaceutically acceptable salts thereof:

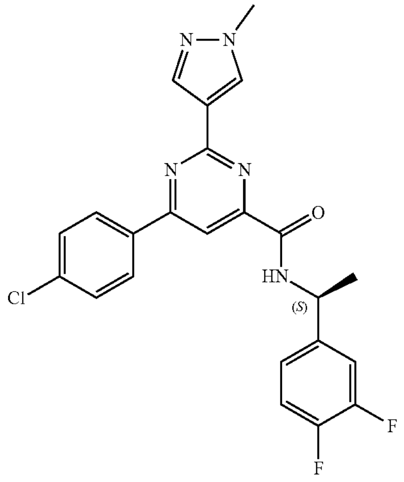

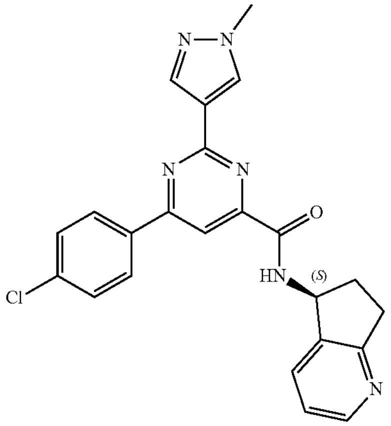

-continued

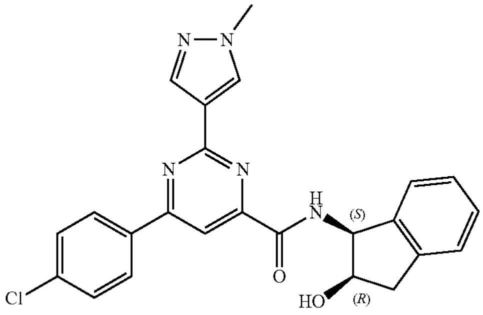

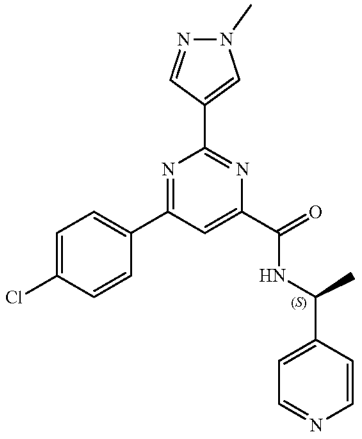

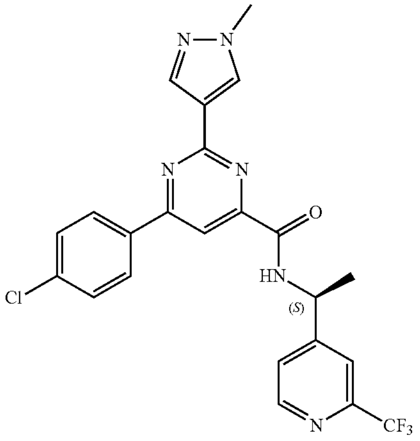

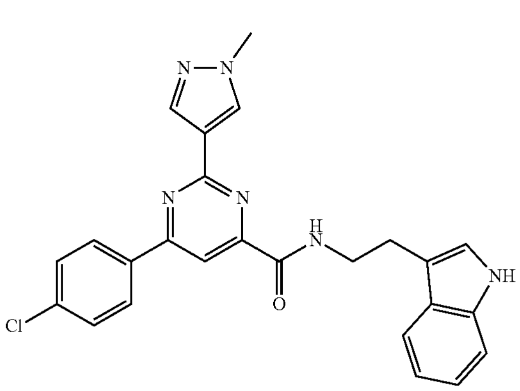

-continued
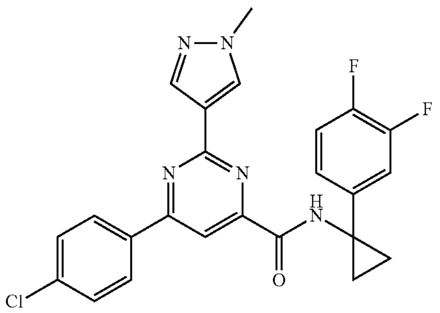
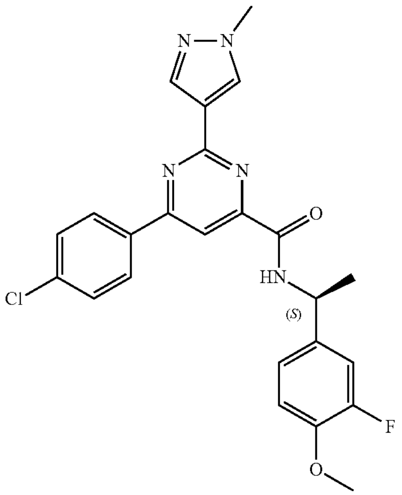
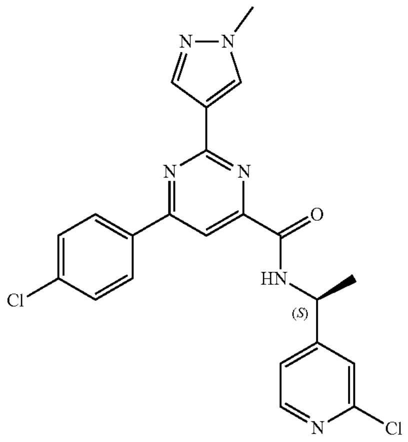
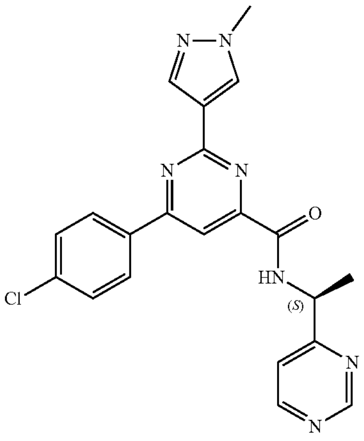
-continued
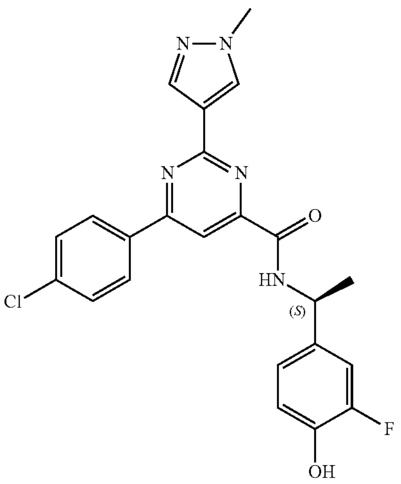
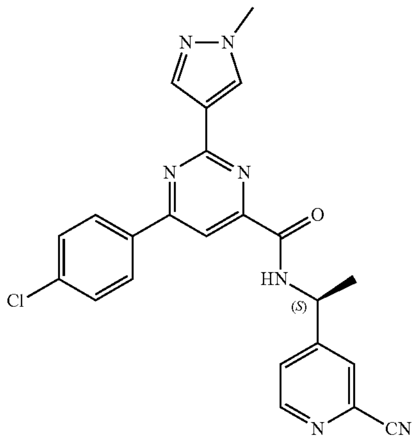
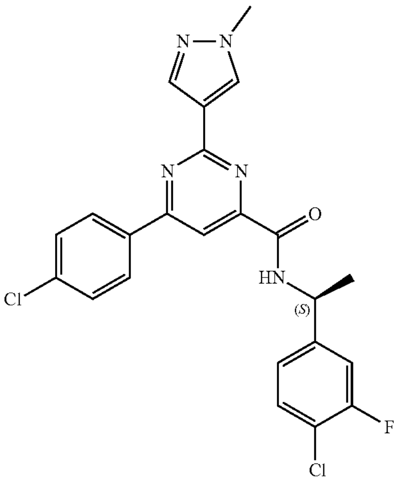

-continued
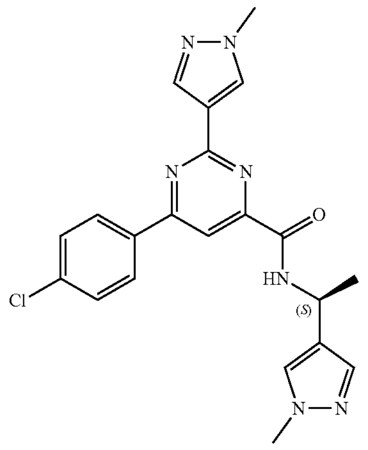
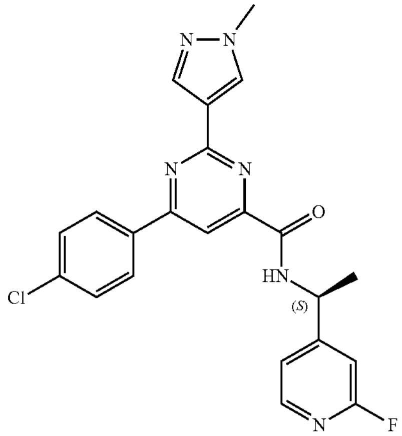
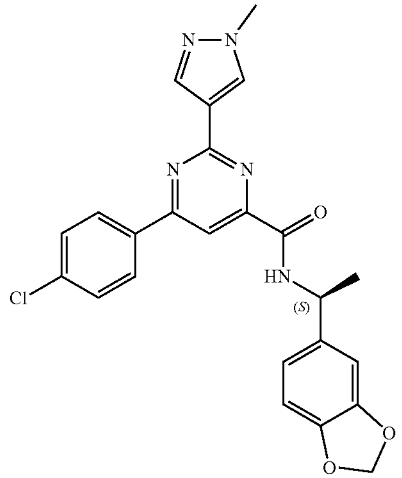
-continued
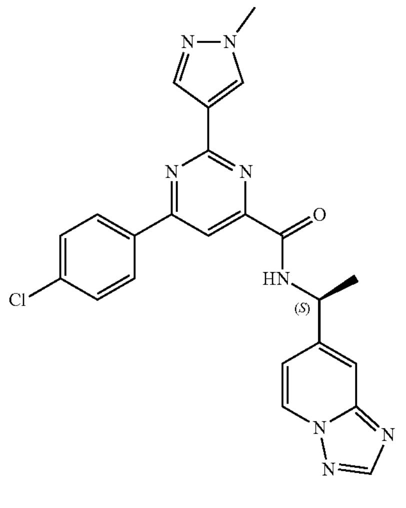
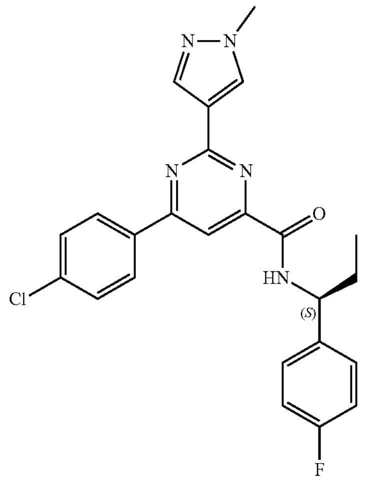
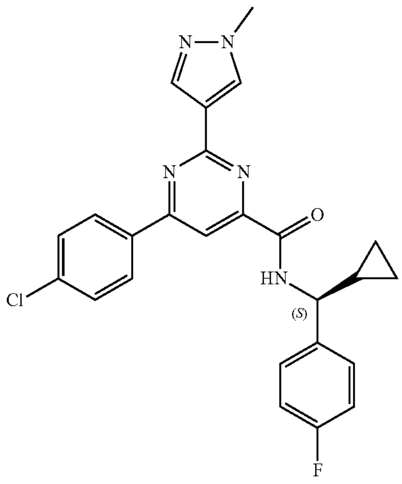

-continued
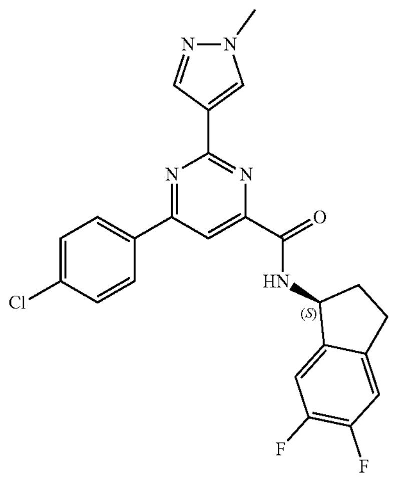
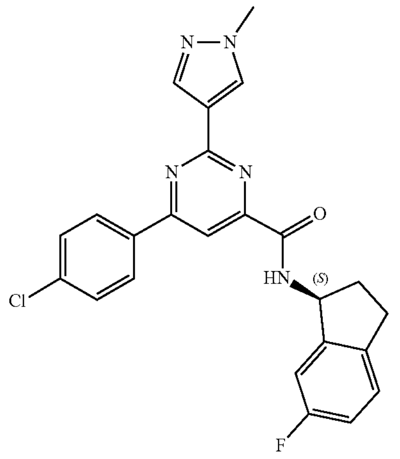
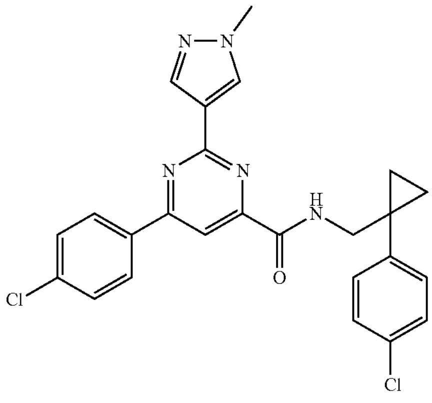
-continued
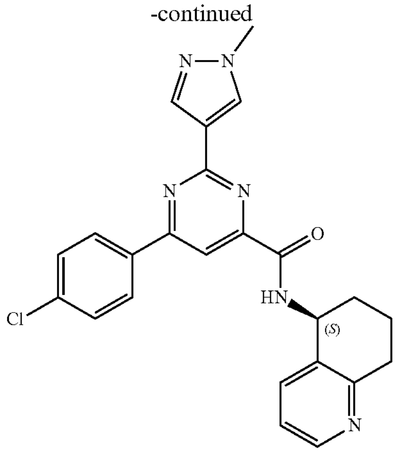
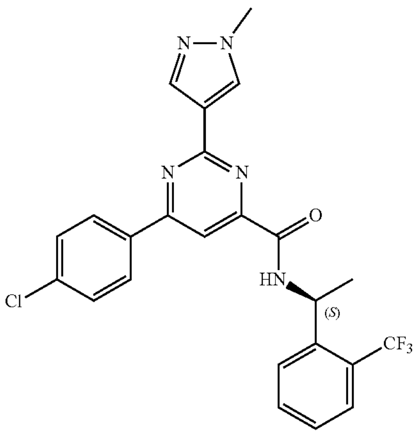
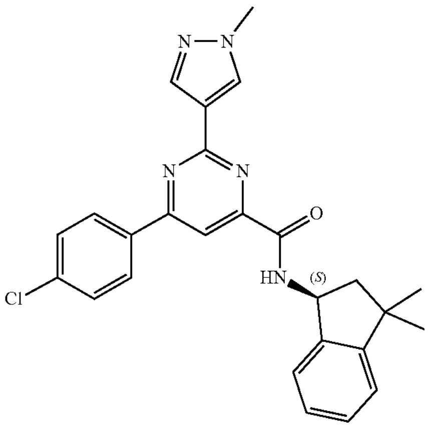
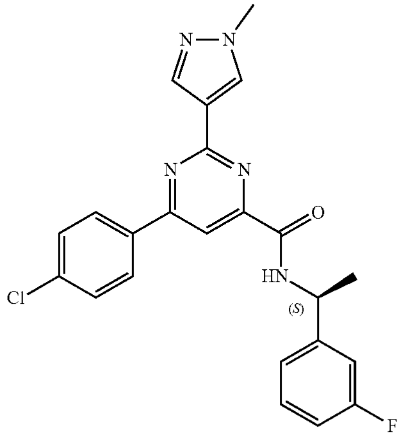

-continued
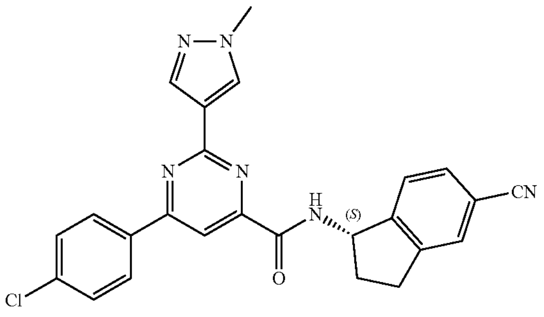
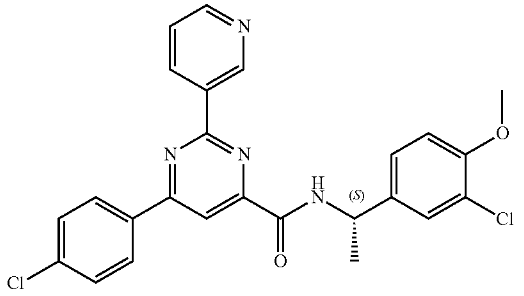
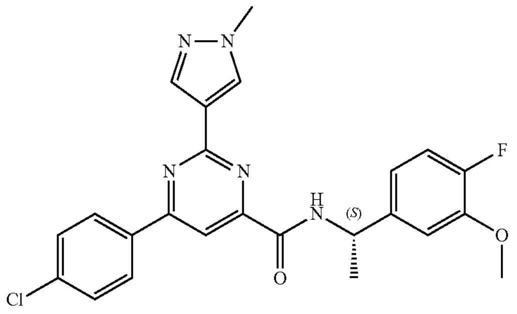
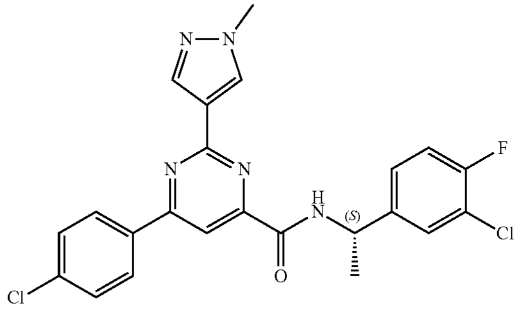
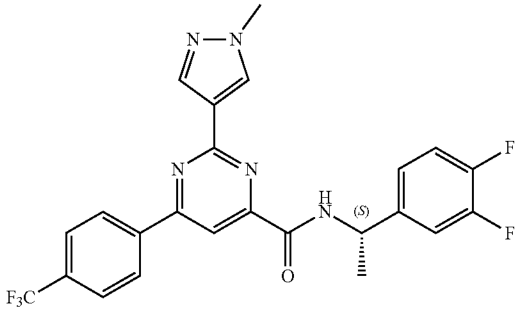
-continued
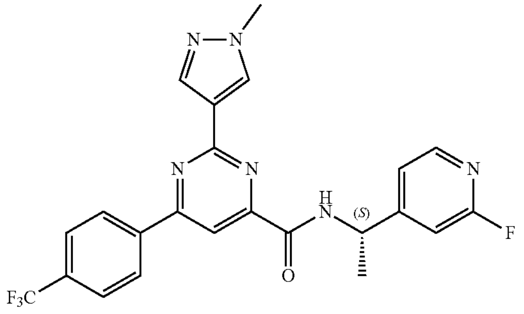
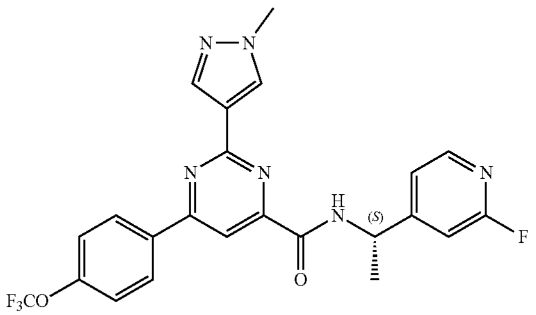
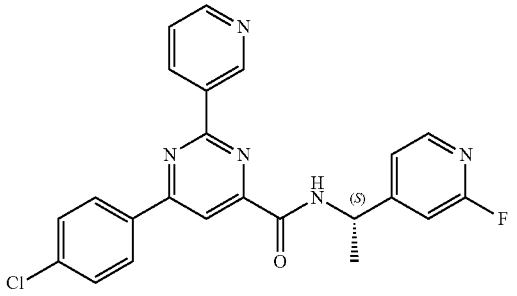
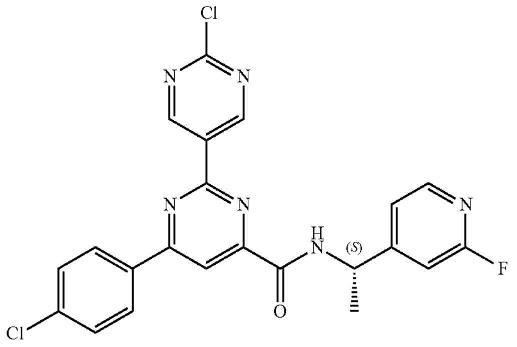
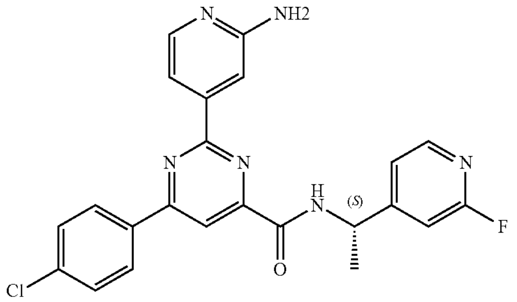

-continued
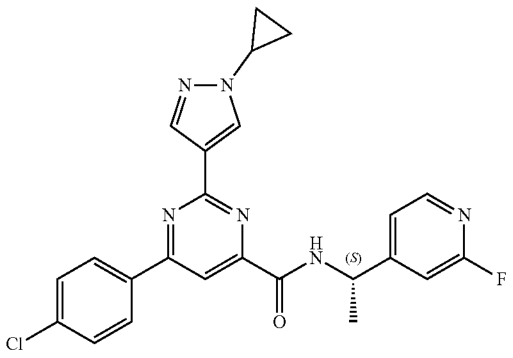
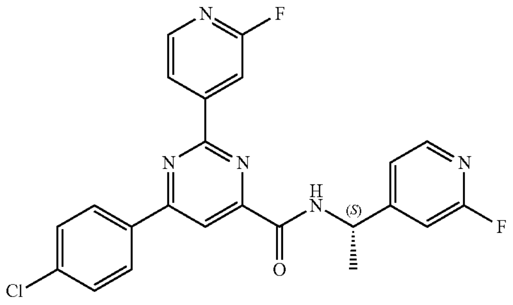
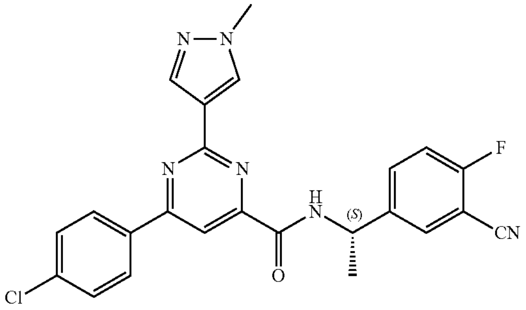
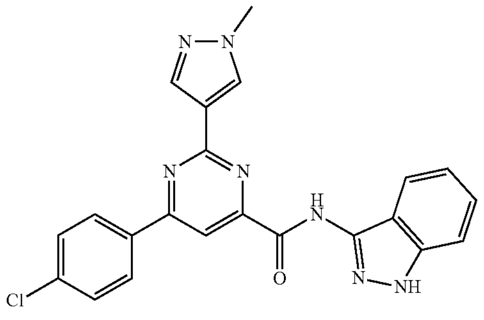
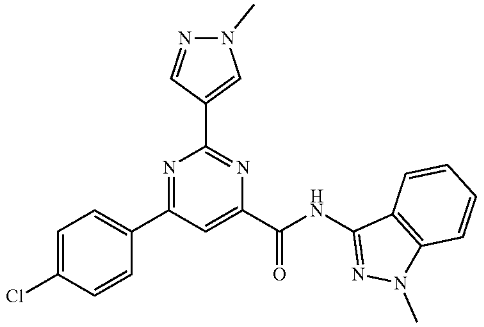
-continued
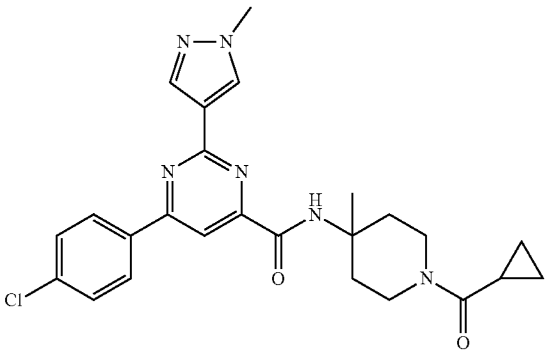
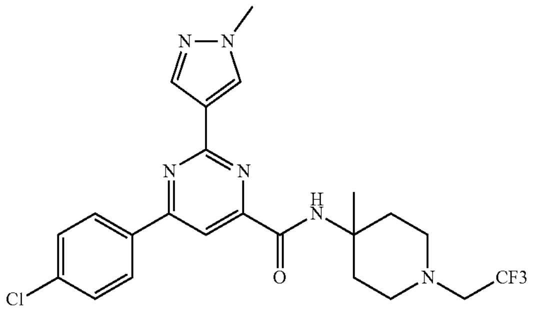
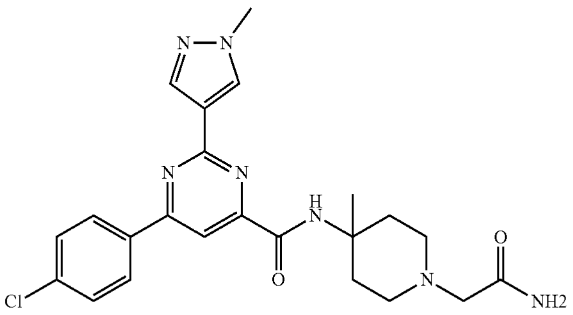
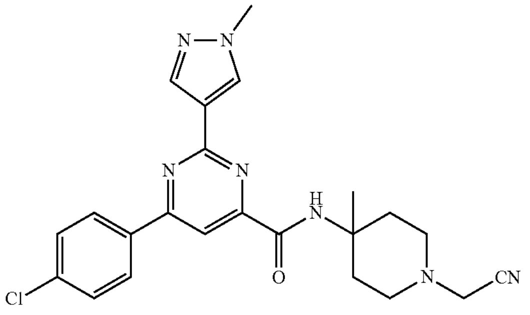
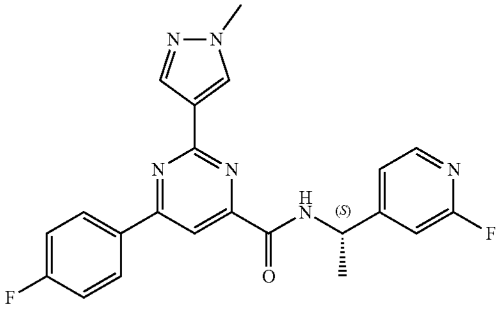

-continued
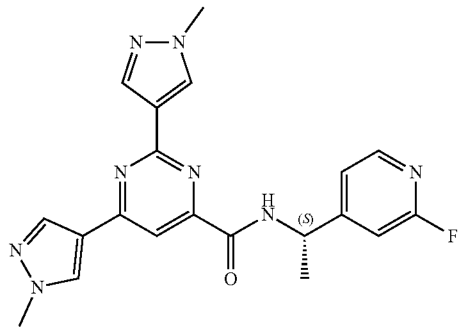
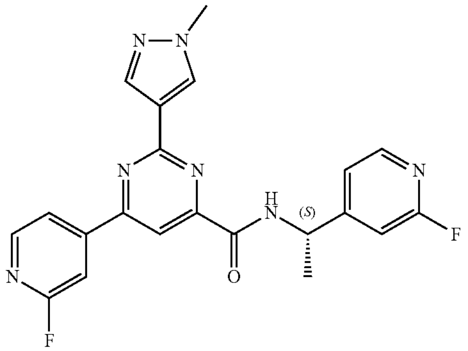
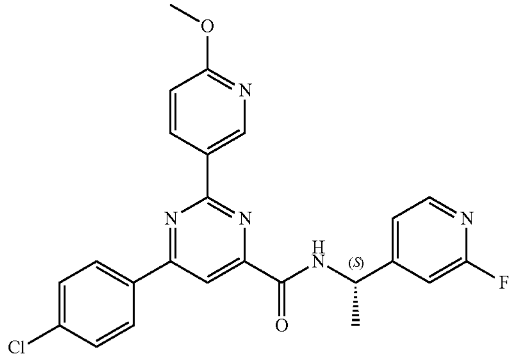
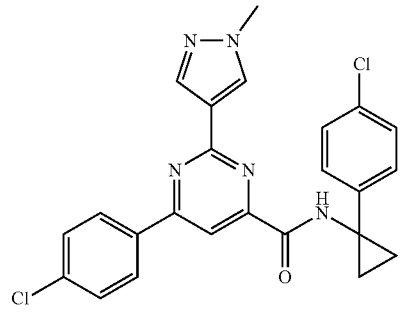
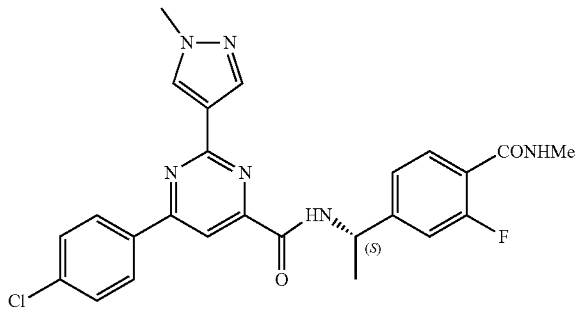
-continued
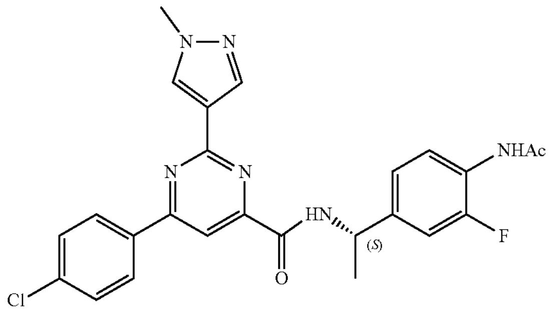
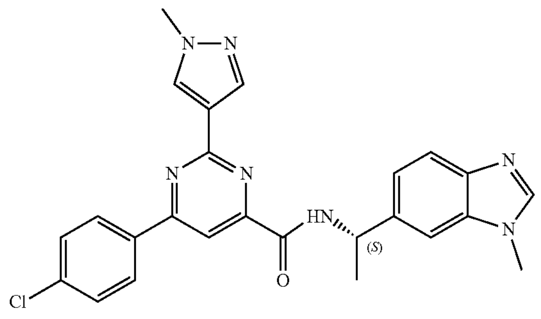
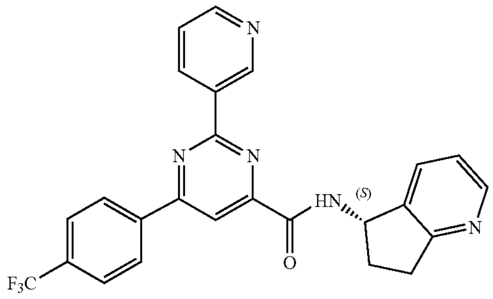
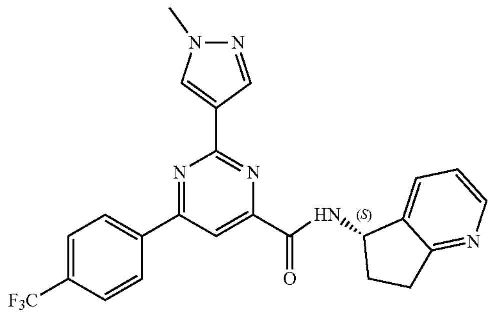
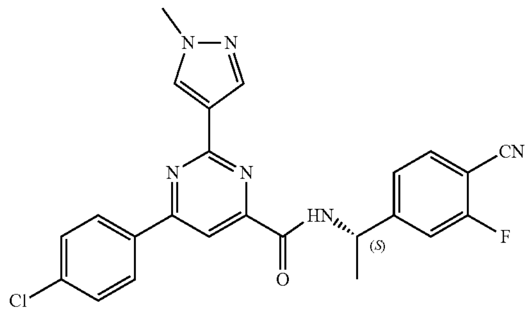

-continued

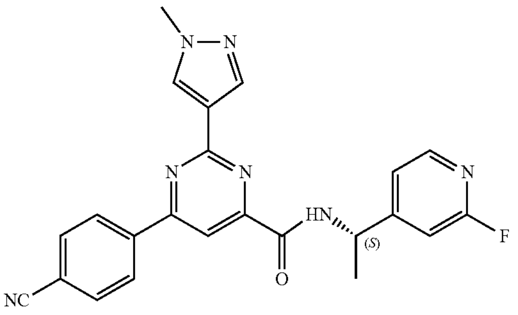

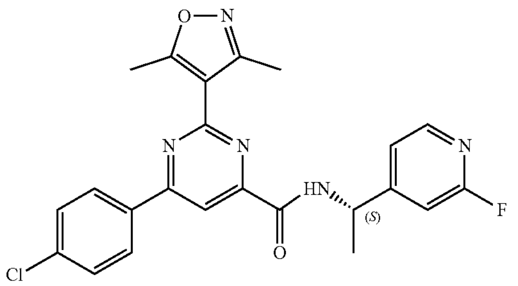

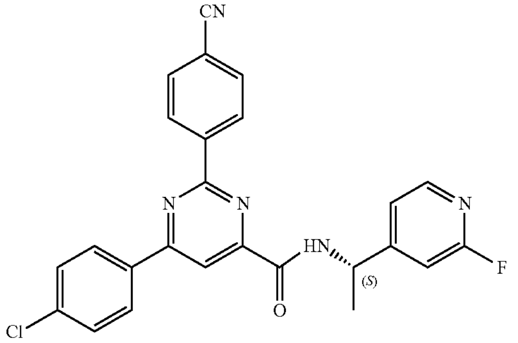

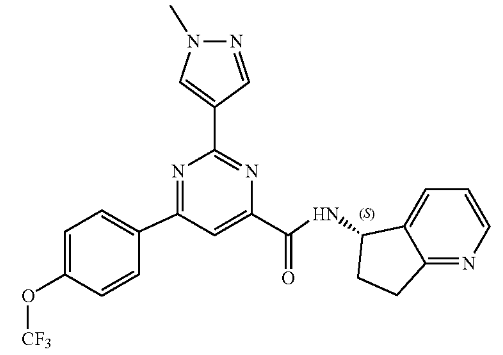

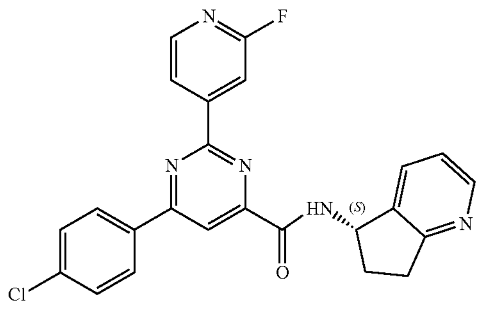

-continued

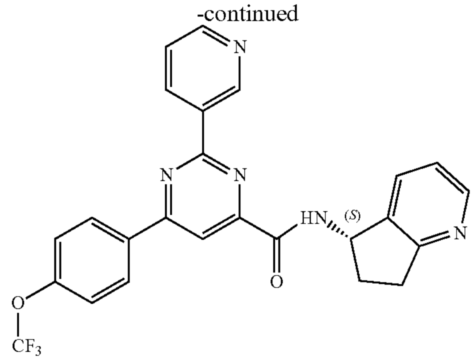

.

In an aspect of the present disclosure, the compound of formula (I) or pharmaceutically acceptable salt thereof includes any or a combination of hydrochloride, hydrobromate, sulfate, phosphate, carbonate, acetate, propionate, methanesulfonate, lactate, benzenesulfonate, p-toluenesulfonate, succinate, maleate, fumarate, tartrate, citrate, or malate.

In an aspect of the present disclosure, a preparation method for the compound represented by formula (I) includes one step or an optional combination selected from the following steps:

(1) connecting boronic acid-$R_1$ to chlorine at pyrimidine site No. 6 in 2,6-dichloropyrimidine-4-carboxylic acid through Suzuki coupling reaction;

(2) connecting boronic acid-$R_2$ to chlorine at pyrimidine site No. 2 in the 2,6-dichloropyrimidine-4-carboxylic acid through Suzuki coupling reaction; and (3) connecting $NH_2$—$R_3$ to carboxylic acid at pyrimidine site No. 4 in the 2,6-dichloropyrimidine-4-carboxylic acid through condensation reaction;

wherein $R_1$, $R_2$, and $R_3$ are defined as formula (I) above.

The present disclosure relates to a pharmaceutical composition containing the above compound or pharmaceutically acceptable salt thereof and pharmaceutically acceptable excipients.

The present disclosure relates to a use of the above compound or pharmaceutically acceptable salt thereof or the pharmaceutical composition in preparation of a drug for treating an AhR mediated disease in a patient.

In an embodiment, the AhR mediated disease includes cancers, inflammatory diseases, and infectious diseases.

Preferably, the infectious diseases are viral infectious diseases.

Preferably, the cancers include colon cancer, gastric cancer, prostate cancer, ovarian cancer, lung cancer, melanoma, glioma, and fibrosarcoma.

Preferably, the viral infections include COVID-19, Zika virus, and dengue virus infection.

The present disclosure relates to a use of the above compound or pharmaceutically acceptable salt thereof or pharmaceutical composition in preparation of an AhR inhibitor.

The present disclosure relates to a method for inhibiting AhR in a patient in need, including administering, to the patient, the above compound or pharmaceutically acceptable salt thereof.

The present disclosure relates to a method for inhibiting AhR in a biological sample, including contact of the biological sample with the above compound or pharmaceutically acceptable salt thereof or pharmaceutical composition.

The present disclosure relates to a method for treating an AhR mediated disease in a patient in need, including administering, to the patient, the above compound or pharmaceutically acceptable salt thereof.

Preferably, the AhR mediated disease includes but is not limited to cancers, inflammatory diseases, and infectious diseases, such as viral infection COVID-19, Zika virus, and dengue virus infection.

Another aspect of the present disclosure provides a use of an AhR inhibitor containing any of the aforementioned compounds or pharmaceutically acceptable salts thereof or pharmaceutical compositions in treatment of cancers.

Preferably, the cancers include colon cancer, gastric cancer, prostate cancer, ovarian cancer, lung cancer, colon cancer, melanoma, glioma, and fibrosarcoma. Another aspect of the present disclosure provides a use of an AhR inhibitor containing any of the aforementioned compounds or pharmaceutically acceptable salts thereof or pharmaceutical compositions in treatment of inflammatory diseases.

Another aspect of the present disclosure provides a use of an AhR inhibitor containing any of the aforementioned compounds or pharmaceutically acceptable salts thereof or pharmaceutical compositions in treatment of infectious diseases.

Preferably, the infectious diseases are viral infectious diseases.

Preferably, the viral infections include COVID-19, Zika virus, and dengue virus infection.

DETAILED DESCRIPTION

Based on the above content of the present disclosure, various other forms of modifications, replacements, or changes may be made in accordance with common technical knowledge and customary means in the art, without departing from the basic technical idea of the present disclosure.

I. Definition

The term "include" or its transformations such as "included" or "including" will be understood to include the stated elements or components throughout the specification and claims, and does not exclude other elements or components, unless otherwise expressly stated.

Compounds in the present disclosure may be asymmetric, for example, having one or more stereoisomers. Unless otherwise specified, all stereoisomers include enantiomers and diastereoisomers. The compounds containing asymmetric carbon atoms in the present disclosure may be isolated in an optically active pure form or racemic form. The optically active pure form may be split from racemic mixtures or synthesized using chiral raw materials or chiral reagents. Racemes, diastereoisomers, and enantiomers are all included within the scope of the present disclosure.

The compounds in the present disclosure further include tautomeric forms. The tautomeric form originates from exchange of a single bond with adjacent double bonds accompanied by migration of a proton.

The term "optional" or "optionally" indicates that a subsequently described event or situation may or may not occur, including the occurrence and non-occurrence of the event or situation.

A numerical range herein refers to all integers within a given range. For example, "$C_{1-6}$" indicates that a group may have 1 carbon atom, 2 carbon atoms, 3 carbon atoms, 4 carbon atoms, 5 carbon atoms, or 6 carbon atoms; and "$C_3$-6" indicates that a group may have 3 carbon atoms, 4 carbon atoms, 5 carbon atoms, or 6 carbon atoms.

The term "substituted by" or "substituted via" indicates that a specific atom or any one or more hydrogen atoms on a group are substituted by a substituent(s), as long as the valence state of the specific atom or group is normal and the substituted compound is stable. When the substituent is a ketone group (i.e., =O), it means that two hydrogen atoms are substituted. Unless otherwise specified, the type and number of substituents may be arbitrary on the basis of chemical feasibility.

In the present disclosure, when any variable (such as $R_n$) appears more than once in the composition or structure of a compound, its definition in each case is independent. Therefore, for example, if a group is substituted by 1-5 Rs, the group may be optionally substituted by up to 5 Rs, and the R has an independent option in each case. In addition, combinations of substituents and/or variants thereof are allowed only if such combinations produce stable compounds.

The term "alkyl" refers to a saturated aliphatic hydrocarbon group, which is a linear or branched group containing 1 to 20 carbon atoms, preferably an alkyl group containing 1 to 8 carbon atoms, more preferably an alkyl group containing 1 to 6 carbon atoms, and most preferably an alkyl group containing 1 to 3 carbon atoms. Non-limiting examples include methyl, ethyl, n-propyl, isopropyl, n-butyl, isobutyl, tert-butyl, sec-butyl, n-amyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 2,2-diethylhexyl, 2,2-diethylhexyl, and various branched isomers. More preferably, the alkyl is lower alkyl containing 1 to 6 carbon atoms. Non-limiting embodiments include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl may be substituted or unsubstituted. When substituted, the alkyl may be substituted at any available connection point. The substituent is preferably one or more of the following groups, independently selected from alkyl, alkenyl, alkynyl, alkoxy, alkylthio, alkylamino, halogen, sulfydryl, hydroxyl, nitro, cyano, cycloalkyl, heterocyclic alkyl, aryl, heteroaryl, cycloalkoxy, heterocyclic alkoxy, cycloalkylthio, heterocyclic alkylthio, oxy, carboxyl, or carboxylate group, and preferably methyl, ethyl, isopropyl, tert-butyl, halogenated alkyl, deuterated alkyl, alkoxy substituted alkyl, and hydroxyl substituted alkyl are preferred.

The term "alkenyl" refers to an alkyl group, as defined above, including at least two carbon atoms and at least one carbon-carbon double bond, such as vinyl, 1-propenyl, 2-propenyl, and 1-, 2-, or 3-butenyl. The alkenyl may be substituted or unsubstituted. When the alkenyl is substituted, the substituent is preferably one or more of the following groups, independently selected from alkyl, alkenyl, alkynyl, alkoxy, alkylthio, alkylamino, halogen, sulfydryl, hydroxyl, nitro, cyano, cycloalkyl, heterocyclic alkyl, aryl, heteroaryl, cycloalkoxy, heterocyclic alkoxy, cycloalkylthio, or heterocyclic alkylthio.

The term “cycloalkyl” refers to a saturated monocyclic alkane substituent, and a cycloalkyl ring contains at least 3 carbon atoms, preferably 3 to 12 carbon atoms, and more preferably 3 to 6 carbon atoms. Non-limiting examples of the cycloalkyl include cyclopropyl, cyclobutyl, cyclopentyl, cyclohexyl, etc.

The term “heterocyclic group” or “heterocyclic alkyl” refers to a saturated monocyclic hydrocarbon substituent, wherein one or more ring atoms are heteroatoms selected from nitrogen, oxygen, or S(O)m (wherein m is an integer from 0 to 2), but do not include ring portions of —O—O—, —O—S—, or —S—S—, and the remaining ring atoms are carbon. Non-limiting examples of the heterocyclic group include pyrrolyl, imidazolyl, tetrahydrofuryl, tetrahydrothienyl, dihydroimidazolyl, dihydrofuryl, dihydropyrazolyl, dihydropyrrolyl, piperidinyl, piperazinyl, morpholinyl, thiomorpholinyl, etc., and preferably pyrrolidyl, morpholinyl, piperidinyl, cycloheptyl, 1,4-diazocycloheptyl, and piperazinyl.

The heterocyclic group may be optionally substituted or unsubstituted. When the heterocyclic group is substituted, the substituent is preferably one or more of the following groups, independently selected from alkyl, alkenyl, alkynyl, alkoxy, alkylthio, alkylamino, halogen, sulfydryl, cyano, nitro, chloro, cycloalkyl, heterocyclic alkyl, aryl, heteroaryl, cycloalkoxy, heterocyclic alkoxy, cycloalkylthio, heterocyclic alkylthio, oxy, carboxyl, or carboxylate group.

The term “aryl” refers to 6- to 14-membered all-carbon monocyclic or fused polycyclic (i.e., ring sharing adjacent carbon atom pairs) groups with conjugated a electron systems, preferably 6 to 12-membered, such as phenyl and naphthyl. Phenyl is preferred. The aryl ring may be condensed onto a heteroaryl, heterocyclic, or cycloalkyl group, and includes benzo 5- to 10-membered heteroaryl, benzo 3- to 8-membered cycloalkyl, and benzo 3- to 8-membered heteroalkyl, and preferably benzo 5- to 6-membered heteroaryl, benzo 3- to 6-membered cycloalkyl, and benzo 3 to 6-membered heteroalkyl, wherein the heterocyclic group is a heterocyclic group containing 1-3 nitrogen atoms, oxygen atoms, or sulfur atoms; or the aryl ring further includes a ternary nitrogen-containing fused ring containing a benzene ring.

The aryl may be substituted or unsubstituted. When the aryl is substituted, the substituent is preferably one or more of the following groups, independently selected from alkyl, alkenyl, alkynyl, alkoxy, alkylthio, alkylamino, halogen, sulfydryl, hydrogen, nitro, cyano, cycloalkyl, heterocyclic alkyl, aryl, heteroaryl, cycloalkoxy, heterocyclic alkoxy, cycloalkylthio, heterocyclic alkylthio, carboxyl, or carboxylate group.

The term “heteroaryl” refers to a heteroaromatic system containing heteroatoms and carbon atoms, wherein the heteroatoms are selected from oxygen, sulfur, and nitrogen. The heteroaryl is preferably 5-membered or 6-membered, such as imidazolyl, furyl, thienyl, thiazolyl, pyrazolyl, pyrrolyl, triazolyl, tetrazolyl, pyridyl, pyrimidyl, thiadiazolyl, pyrazinyl, etc.; preferably triazolyl, thienyl, imidazolyl, pyrazolyl, oxazolyl, pyrimidyl, or thiazolyl; and more preferably pyrazolyl, pyrrolyl, and oxazolyl.

The heteroaryl may be optionally substituted or unsubstituted. When the heteroaryl is substituted, the substituent is preferably one or more of the following groups, independently selected from alkyl, alkenyl, alkynyl, alkoxy, alkylthio, alkylamino, halogen, sulfydryl, hydrogen, nitro, cyano, cycloalkyl, heterocyclic alkyl, aryl, heteroaryl, cycloalkoxy, heterocyclic alkoxy, cycloalkylthio, heterocyclic alkylthio, carboxyl, or carboxylate group.

The term “partially unsaturated bicyclic carbocyclic” refers to a bicyclic group including only C atoms as ring members, the bicyclic group is partially unsaturated and includes at least one C—C double bond, a maximum unsaturated carbon ring includes a largest number of conjugated C—C double bonds allowed by a ring size, and a partially unsaturated bicyclic carbon ring includes less than a maximum number of C—C double bonds allowed by a ring size.

The term “partially unsaturated bicyclic heterocyclic” refers to a bicyclic group including at least one of C atoms and N, O, or S heteroatoms that jointly serve as ring members, the bicyclic group is partially unsaturated and includes at least one C—C double bond, a maximum unsaturated heterocycle includes a maximum number of C—C double bonds allowed by a ring size and double bonds between C atoms and heteroatoms, and a partially unsaturated bicyclic heterocycle includes less than a number of double bonds allowed by a ring size.

The term “benzocycloalkyl” refers to a portion of one or more aromatic rings fused to a cycloalkyl ring, such as benzo derivatives of cyclopropane, cyclobutane, cyclopentane, and cyclohexane. Specific examples include dihydroindene, indene, and hydronaphthalene.

The term “alkoxy” refers to —O-(alkyl) and —O-(unsubstituted cycloalkyl), wherein the definition of alkyl is as described above. Non-limiting examples of the alkoxy include: methoxy, ethoxy, propanoxy, butoxy, cyclopropyloxy, cyclobutoxy, cyclopentoxy, and cyclohexoxy. The alkoxy may be optionally substituted or unsubstituted. When the alkoxy is substituted, the substituent is preferably one or more of the following groups, independently selected from alkyl, alkenyl, alkynyl, alkoxy, alkylthio, alkylamino, halogen, sulfydryl, hydrogen, nitro, chlorine group, cycloalkyl, heterocyclic alkyl, aryl, heteroaryl, cycloalkoxy, heterocyclic alkoxy, cycloalkylthio, heterocyclic alkylthio, carboxyl, or carboxylate group.

In the present disclosure, “hydroxyl” refers to an —OH group; “halogen” refers to fluorine, chlorine, bromine, or iodine; “amino” refers to —$NH_2$; “cyano” refers to —CN; “nitro” refers to —$NO_2$; “carbonyl” refers to —C(O)—; “carboxyl” refers to —C(O)OH; “THF” refers to tetrahydrofuran; “EtOAc” refers to ethyl acetate; “MeOH” refers to methanol; “DMF” refers to N,N-dimethylformamide; “DIPEA” refers to diisopropylethylamine; “TFA” refers to trifluoroacetic acid; “MeCN” refers to acetonitrile; “DMA” refers to N,N-dimethylacetamide; “DCE” refers to 1,2-dichloroethane; “NBS” refers to N-bromosuccinimide; “NIS” refers to N-iodosuccinimide; “cbz-cr” refers to benzyl chloroformate; “Pd2(dba)3” refers to tris(dibenzynylacetone)dipalladium; “Dppf” refers to 1,1'-biphenylphosphine ferrocene; “HATU” refers to 2-(7-oxobenzotriazole)-N,N,N,N'-tetramethylurea hexafluorophosphate; “KHNDS” refers to potassium hexamethyldisilicylamine; “LiHMDS” refers to lithium bis(trimethylsilylamine); “MeLi” refers to methyl lithium; “n-BuLi” refers to n-butyl lithium; “$NaBH(OAc)_3$” refers to sodium triacetoxyborohydride; and “—NHAc” refers to acetamido.

In the present disclosure, different expressions such as “X is selected from A, B, or C”, “X is selected from A, B, and C", "X is A, B, or C", and "X is A, B, and C" all express the same meaning, that is, X may be any one or several of A, B, and C.

The hydrogen atoms described in the present disclosure may be substituted by isotope deuterium.

The term "substituted" indicates that one or more, preferably up to 5, or more preferably 1-3 hydrogen atoms in a group are independently substituted by a corresponding number of substituents. The substituents are only in their possible chemical positions, and those skilled in the art can determine (through experiments or theory) possible or impossible substitutions without excessive efforts.

In the present disclosure,

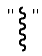

refers to a chemical bond connection point.

Drug or Pharmaceutical Composition

The term "pharmaceutically acceptable" refers to compounds, materials, compositions, and/or formulations that are suitable for use in contact with human and animal tissues within reasonable medical determination ranges, without excessive toxicity, irritation, anaphylaxis, or other problems or complications that are commensurate with reasonable benefit/risk ratios.

The term "pharmaceutically acceptable salt" refers to a salt that retains the biological efficacy of free acids and bases of a specific compound without any biological adverse effects, such as acid (including organic and inorganic acids) addition salts or base addition salts (including organic and inorganic bases).

The pharmaceutically acceptable salt of the present disclosure may be synthesized by a conventional chemical method from a parent compound containing acid or base groups. Generally, a preparation method for such salts includes reaction of these compounds in a form of free acids or bases with stoichiometric appropriate bases or acids in water, organic solvents, or a mixture of both.

The drug or pharmaceutical composition of the present disclosure may be applied orally, locally, parenterally or mucosally (for example, orally, by inhalation, or rectally) in dosage units containing conventional non-toxic pharmaceutically acceptable carriers. Usually, an oral route is preferred. The active reagent may be applied orally in a form of capsules, tablets, or the like (see Remington: The Science and Practice of Pharmacy, 20th Edition).

For oral administration in a tablet or capsule form, active drug ingredients may be combined with non-toxic, pharmaceutically acceptable excipients such as binders (such as pre-gelatinized corn starch, polyvinyl pyrrolidone, or hydroxypropyl methylcellulose); fillers (such as lactose, sucrose, glucose, mannitol, sorbitol and other reducing and non-reducing saccharides, microcrystalline cellulose, calcium sulfate or calcium hydrogen phosphate); lubricants (such as magnesium stearate, talc powder or silica, stearic acid, sodium stearate fumarate, glyceryl dodecanoate, and calcium stearate); disintegrants (such as potato starch or sodium hydroxyacetate starch); or humectants (such as sodium lauryl sulfate), coloring and seasoning agents, gelatin, sweeteners, natural and synthetic gums (such as arabic gum, tragacanth gum or alginate), buffer salts, carboxymethyl cellulose, polyethylene glycol, wax, etc. For oral administration in a liquid form, the drug ingredients may be combined with non-toxic, pharmaceutically acceptable inert carriers (such as ethanol, glycerol, or water), anti-settling agents (such as sorbitol syrup, cellulose derivatives, or hydrogenated edible fats), emulsifiers (such as lecithin or arabic gum), non-aqueous carriers (such as almond oil, oil esters, ethanol, or fractionated vegetable oils), preservatives (such as methyl p-hydroxybenzoate or propyl p-hydroxybenzoate or sorbic acid), etc. Stabilizers such as antioxidants (BHA, BHT, propyl citrate, sodium ascorbate, and citric acid) may also be added to stabilize the dosage form.

Tablets containing active compounds may be coated by well-known methods in the art. The composition of the present disclosure, which includes the compound of formula I as an active compound, may also introduce small beads, microspheres, or microcapsules, such as those constructed from polyglycolic acid/lactic acid (PGLA). Formulations of liquids used for oral administration may be in a form of, for example, solutions, syrups, lotion or suspensions, or they may appear as dry products reconstituted with water or other suitable excipients before use. Formulations used for oral administration may be appropriately prepared to achieve controlled or delayed release of active compounds.

The drug or pharmaceutical composition of the present disclosure may be delivered parenterally, namely, through intravenous (i.v.), intraventricular (i.e.v.), subcutaneous (s.c.), intraperitoneal (i.p.), intramuscular (i.m.) or intradermal (i.d.) administration, by direct injection, such as rapid concentrated injection or continuous infusion. A formulations used for injection may be presented in a unit dosage form, such as in an ampoule or multi-dose container with added preservative. The composition may be in a shape of an excipient, in a form of suspension, solution, or lotion in oil or aqueous carrier, and may include preparation reagents such as anti-settling agent, stabilizer, and/or dispersant. Alternatively, the active ingredient may be reconstituted in a powder form with a suitable carrier (such as sterile and heatless raw water) before use.

The drug or pharmaceutical composition of the present disclosure may further be formulated for rectal administration, such as suppositories or retention enemas (for example, containing conventional suppository matrices such as cocoa butter or other glycerides).

The term "treating" includes inhibiting, alleviating, preventing, or eliminating one or more symptoms or side effects related to the treated disease, condition, or disorder.

The use of the term "reduce", "inhibit", "alleviate", or "decrease" is relative to controls. Those skilled in the art will easily determine appropriate controls for each experiment. For example, a reduction reaction in subjects or cells treated with a compound is compared with a reaction in subjects or cells not treated with the compound.

As used herein, the term "effective dose" or "therapeutic effective dose" refers to a dose that is sufficient to treat, inhibit, or alleviate one or more symptoms of the treated disease or provide desired pharmacological and/or physiological effects in other ways. A precise dose varies based on many factors, such as subject dependent variables (such as age and immune system health), disease or condition, and administered treatment. Effects of effective doses may be compared with those of controls. These controls are known in the art and discussed herein, and may be used for comparing combination effects with effects of only one drug in conditions of subjects before a drug or pharmaceutical composition is administrated or when the drug or pharmaceutical composition is not administrated or in a case of a pharmaceutical composition.

The term "patient in need" refers to a patient who is at risk of or suffers from a disease, condition, or symptom, which may be treated or improved, for example, with the compounds provided herein or pharmaceutically acceptable salts thereof or pharmaceutical compositions. For example, the patient in need may be diagnosed with an AhR mediated disease.

The term “excipient” used herein includes any other compound that may be included in or on microparticles and is not a therapeutic or bioactive compound. Therefore, the excipient should be pharmaceutically or biologically acceptable or relevant, for example, the excipient is usually non-toxic to subjects. The “excipient” includes a single compound and is also intended to include many compounds.

The term “pharmaceutical composition” refers to a composition including the compound or pharmaceutically acceptable salt thereof as disclosed in the present disclosure, as well as at least one of the following pharmaceutically acceptable ingredient selected based on properties of an application method and a dosage form, including but not limited to: carriers, diluents, adjuvants, excipients, preservatives, fillers, disintegrants, wetting agents, emulsifiers, suspensions, sweeteners, correctives, fragrances, antibacterial agents, anti-fungal agents, lubricants, dispersants, temperature-sensitive materials, temperature regulators, adhesives, stabilizers, suspension aids, and the like.

II. Examples

The present disclosure will be further explained below with reference to examples. Descriptions of specific exemplary embodiments of the present disclosure are for the purpose of explanation and illustration. These descriptions are not intended to limit the present disclosure to the precise form disclosed, and it is evident that many changes and variations may be made according to the teachings of the specification of the present disclosure. The purpose of selecting and describing the exemplary embodiments is to explain the specific principle of the present disclosure and its practical application, so that a person skilled in the art can implement and use various exemplary embodiments of the present disclosure and various different choices and changes.

Experimental methods used in the following examples are all conventional methods, unless otherwise specified.

Materials, reagents, etc. used in the following examples may be all obtained from commercial sources, unless otherwise specified.

Experimental Instruments and Methods:

Determination of NMR used a BRUKER 400MR DD2 nuclear magnetic instrument, determination solvents were deuterated dimethyl sulfoxide (DMSO-$d_6$), deuterated methanol ($CD_3OD$) and deuterated chloroform ($CDCl_3$), and an internal standard was tetramethylsilane (TMS). Determination of liquid chromatography-mass spectrometry (LC-MS) used an Agilent 1200 Infinity II-InfinityLab LC/MSD mass spectrometer. Determination of HPLC used an Agilent 1200 Infinity II high-pressure liquid chromatograph (Sunfire C185 μm 150×4.6 mm chromatographic column). Thin layer chromatography silica gel plates were HSGF254 silica gel plates from Yantai Jiangyou Silicone Development Co., Ltd., with a specification of 0.9 mm-1 mm. TLC silica gel plates were GF254 silica gel plates from Cheng Chemical (Shanghai) Co., Ltd., with a specification of 0.2 mm-0.25 mm. Column chromatography used 300-400 mesh silica gel from Qingdao Hailang Silicone Desiccant Co., Ltd. as a carrier. Flash columns were Claricep Flash amorphous silica gel purification columns from Agela & Phenomenex. Reagents 1-propylphosphoanhydride and grade A magnesium bromide in the examples of the present disclosure were purchased from Shanghai McLean Biochemical Technology Co., Ltd.; 4N hydrochloric acid dioxane solution was purchased from Panjin Yanfeng Technology Co., Ltd.; 1M borane tetrahydrofuran solution, N,N-diisopropylethylamine, and (S)-tert-butylsulfinamide were purchased from Adamas Reagent; and other reagents and starting materials were purchased from Shanghai Haohong Biomedical Technology Co., Ltd.; or the reagents may be synthesized by known methods in the art. Unless otherwise specified, all reactions of the present disclosure were carried out under continuous magnetic stirring in dry nitrogen or argon gas, with dry solvents and reaction temperatures in degrees Celsius.

Example 1: Synthesis of (S)-6-(4-chlorophenyl)-N-(1-(3,4-difluorophenyl)ethyl)-2-(1-methyl-1H-pyrazol-4-yl)pyrimidine-4-formamide (Compound 1)

Synthesis steps were as follows:

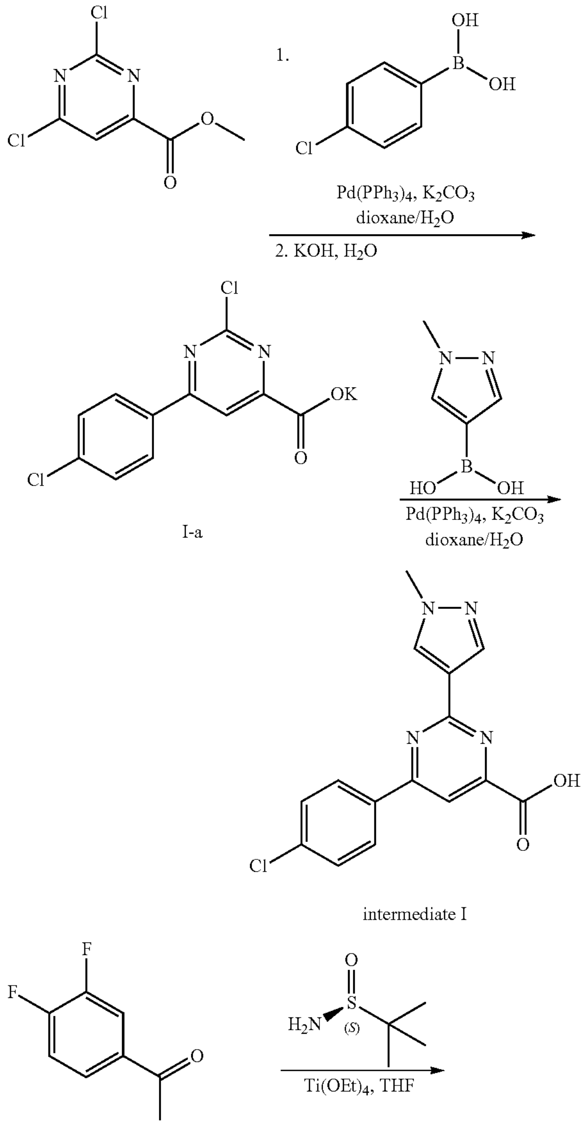

I-a
intermediate I

-continued

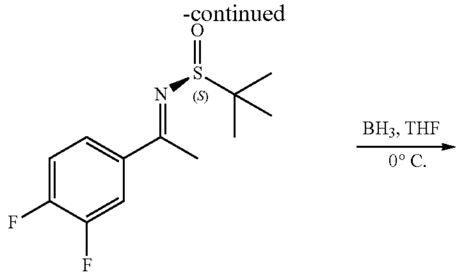

1-a

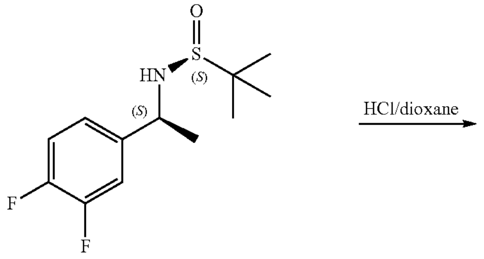

1-b

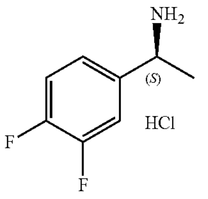

1-c

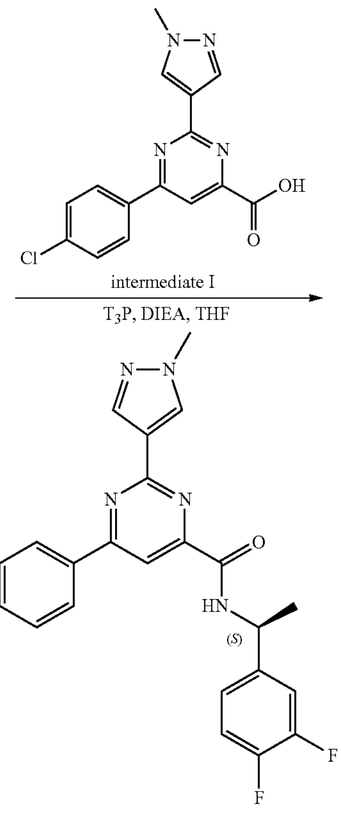

1

Step 1: Synthesis of potassium 2-chloro-6-(4-chlorophenyl)pyrimidine-4-carboxylate (I-a)

P-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 2.01 g of gray solid potassium 2-chloro-6-(4-chlorophenyl)pyrimidine-4-carboxylate (I-a), with a yield of 75%. $^1$H NMR (400 MHz, DMSO-d) δ 11.32 (s, 1H), 8.23-8.16 (m, 2H), 8.14 (s, 1H), 7.65-7.55 (m, 2H). ESI[M+H]$^+$=269.2

Step 2: Synthesis of 6-(4-chlorophenyl)-2-(1-methyl-1H-pyrazol-4-yl)pyrimidine-4-carboxylic acid (intermediate I)

(1-methyl-1H-pyrazol-4-yl) boronic acid (940 mg, 7.5 mmol) and the potassium 2-chloro-6-(4-chlorophenyl)pyrimidine-4-carboxylate (2.01 g, 7.5 mmol) were dissolved in dioxane/water (100 mL/15 mL), tetra(triphenylphosphine) palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 1.71 g of gray solid 6-(4-chlorophenyl)-2-(1-methyl-1H-pyrazol-4-yl)pyrimidine-4-carboxylic acid (intermediate I), with a yield of 74%. $^1$H NMR (400 MHz, DMSO-$d_6$) δ 13.88 (s, 1H), 8.55 (s, 1H), 8.38 (d, J=8.3 Hz, 2H), 8.19 (d, J=16.4 Hz, 2H), 7.63 (d, J=8.4 Hz, 2H), 3.94 (s, 3H). ESI[M+H]$^+$=315.2

Step 3: Synthesis of (S)-N-(1-(3,4-difluorophenyl)ethyl)-2-tert-butylsulfinylimine (1-a)

1-(3,4-difluorophenyl)ethanone (1.54 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.01 g of white solid (S)-N-(1-(3,4-difluorophenyl)ethyl)-2-tert-butylsulfinylimine (1-a), with a yield of 90%. ESI [M+H]$^+$=260.1

Step 4: Synthesis of (S)-N-(1-(3,4-difluorophenyl)ethyl)-2-tert-butylsulfinamide (1-b)

The (S)-N-(1-(3,4-difluorophenyl)ethyl)-2-tert-butylsulfinylimine (2.01 g, 8.0 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.86 g of white solid (S)-N-(1-(3,4-difluorophenyl)ethyl)-2-tert-butylsulfinamide (1-b), with a yield of 81%. ESI [M+H]$^+$=262.2

Step 5: Synthesis of (S)-1-(3,4-difluorophenyl)ethan-1-amine hydrochloride (1-c)

The (S)-N-(1-(3,4-difluorophenyl)ethyl)-2-tert-butylsulfinamide (1.86 g, 7.3 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 1.06 g of white solid (S)-1-(3,4-difluorophenyl)ethan-1-amine hydrochloride (1-c), with a yield of 78%. ESI $[M+H]^+$=158.2

Step 6: Synthesis of(S)-6-(4-chlorophenyl)-N-(1-(3,4-difluorophenyl)ethyl)-2-(1-methyl-1H-pyrazol-4-yl)pyrimidine-4-formamide (Compound 1)

The 6-(4-chlorophenyl)-2-(1-methyl-1H-pyrazol-4-yl)pyrimidine-4-carboxylic acid (intermediate I, 100 mg, 0.32 mmol) and the (S)-1-(3,4-difluorophenyl)ethan-1-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 120 mg of white solid (S)-6-(4-chlorophenyl)-N-(1-(3,4-difluorophenyl)ethyl)-2-(1-methyl-1H-pyrazol-4-yl)pyrimidine-4-formamide (compound 1), with a yield of 83%. $^1H$ NMR (400 MHz, DMSO-$d_6$) δ 9.25 (d, J=8.6 Hz, 1H), 8.68 (s, 1H), 8.44-8.34 (m, 3H), 8.20 (s, 1H), 7.70-7.62 (m, 2H), 7.55 (m, 1H), 7.42 (m, 1H), 7.32 (d, J=5.1 Hz, 1H), 5.27 (m, 1H), 3.97 (s, 3H), 1.60 (d, J=7.0 Hz, 3H). ESI $[M+H]^+$=454.2

Example 2: Synthesis of (S)-6-(4-chlorophenyl)-N-((S)-6,7-dihydro-5H-cyclopentano[B]pyridin-5-yl)-2-(1-methyl-1H-pyrazol-4-yl)pyrimidine-4-formamide (Compound 2)

Step 1: Synthesis of (S)-N-(6,7-dihydro-5H-cyclopentano[B]pyridine)-5-tert-butylsulfinylimine (2-a)

6,7-dihydro-5H-cyclopentano[B]pyridin-5-one (1.33 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.12 g of gray solid (S)-N-(6,7-dihydro-5H-cyclopentano[B]pyridine)-5-tert-butylsulfinylimine (2-a), with a yield of 90%. ESI $[M+H]^+$=237.2

Step 2: Synthesis of (S)-N-(6,7-dihydro-5H-cyclopentano[B]pyridine)-5-tert-butylsulfinamide (2-b)

The (S)-N-(6,7-dihydro-5H-cyclopentano[B]pyridine)-5-tert-butylsulfinylimine (2.12 g, 8.9 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.82 g of gray solid (S)-N-(6,7-dihydro-5H-cyclopentano[B]pyridine)-5-tert-butylsulfinamide (2-b), with a yield of 86%. ESI $[M+H]^+$=239.1

Step 3: Synthesis of (S)-(6,7-dihydro-5H-cyclopentano[B]pyridine)-5-amine hydrochloride (2-c)

The (S)-N-(6,7-dihydro-5H-cyclopentano[B]pyridine)-5-tert-butylsulfinamide (1.82 g, 7.6 mmol) was dissolved in 30

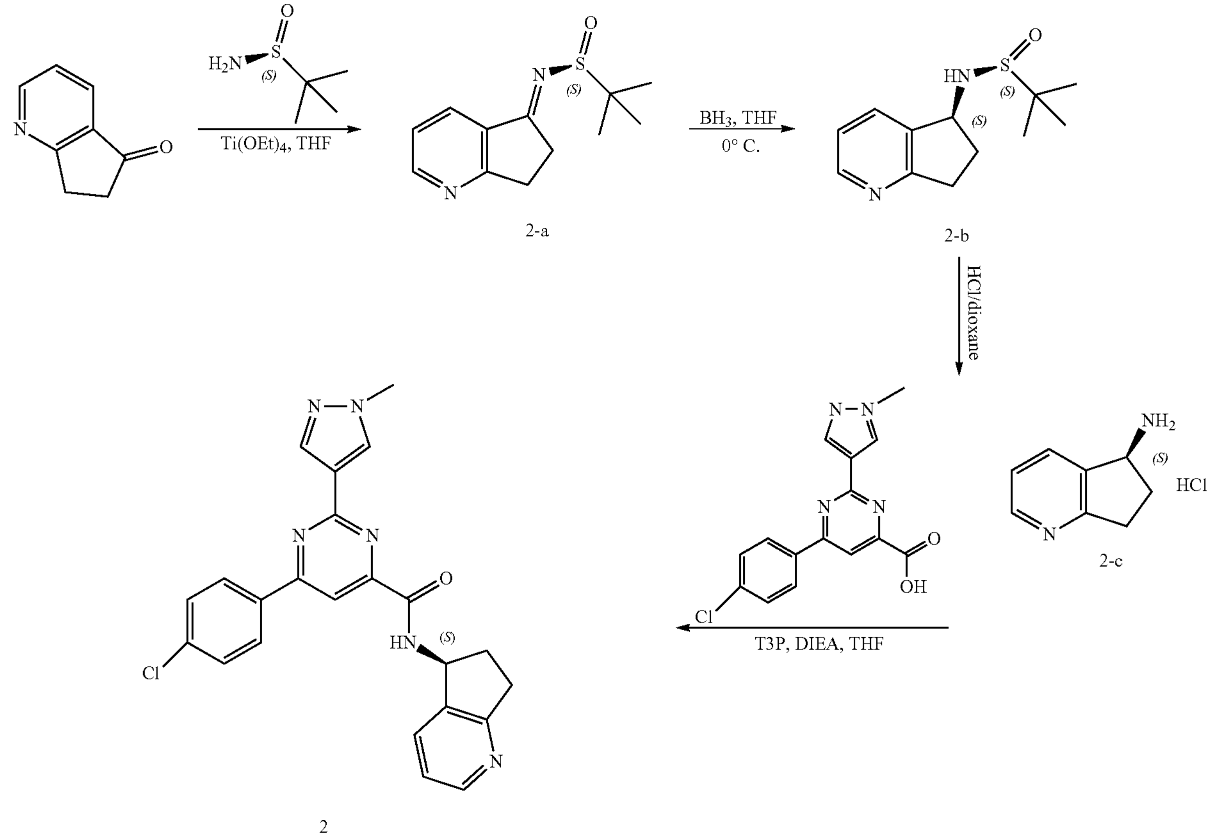

2-a
2-b
2-c
2 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.75 g of gray solid (S)-(6,7-dihydro-5H-cyclopentano[B]pyridine)-5-amine hydrochloride (2-c), with a yield of 73%. ESI $[M+H]^+$ =135.2

Step 4: Synthesis of (S)-6-(4-chlorophenyl)-N-((S)-6,7-dihydro-5H-cyclopentano[B]pyridin-5-yl)-2-(1-methyl-1H-pyrazol-4-yl)pyrimidine-4-formamide (compound 2)

The intermediate 6-(4-chlorophenyl)-2-(1-methyl-1H-pyrazol-4-yl)pyrimidine-4-carboxylic acid (intermediate I, 100 mg, 0.32 mmol) prepared in Example 1 and the (S)-(6,7-dihydro-5H-cyclopentano[B]pyridine)-5-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 120 mg of white solid (S)-6-(4-chlorophenyl)-N-((S)-6,7-dihydro-5H-cyclopentano[B]pyridin-5-yl)-2-(1-methyl-1H-pyrazol-4-yl)pyrimidine-4-formamide (compound 2), with a yield of 83%. $^1H$ NMR (400 MHz, DMSO-$d_6$) δ 9.40 (d, J=8.8 Hz, 1H), 8.66 (s, 1H), 8.45-8.35 (m, 4H), 8.29 (s, 1H), 7.66 (d, J=2.0 Hz, 1H), 7.65-7.58 (m, 2H), 7.20 (dd, J=7.7, 4.9 Hz, 1H), 5.70 (q, J=8.5 Hz, 1H), 3.93 (s, 3H), 3.13-2.94 (m, 2H), 2.56 (m, 1H), 2.32-2.16 (m, 1H). ESI $[M+H]^+$=431.1

Example 3: Synthesis of (S)-6-(4-chlorophenyl)-N-((1S, 2R)-(−)-1-yl-2-indanol)-2-(1-methyl-1H-pyrazol-4-yl)pyrimidine-4-formamide (compound 3)

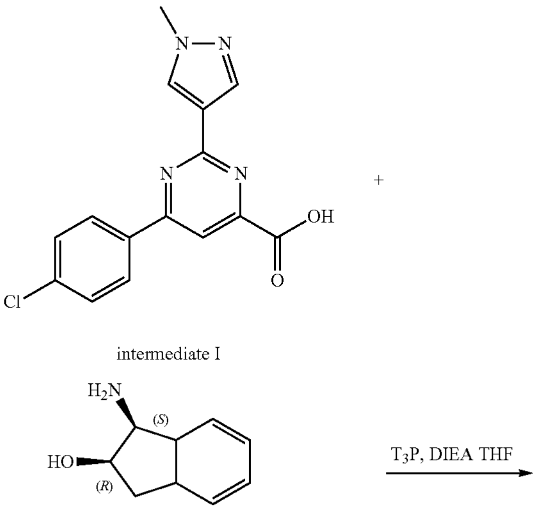

-continued

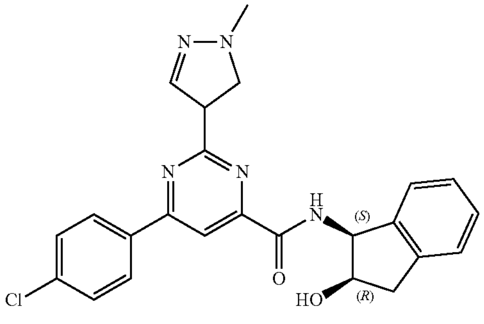

3

Step 1: Synthesis of (S)-6-(4-chlorophenyl)-N-((1S, 2R)-(−)-1-yl-2-indanol)-2-(1-methyl-1H-pyrazol-4-yl)pyrimidine-4-formamide (compound 3)

The 6-(4-chlorophenyl)-2-(1-methyl-1H-pyrazol-4-yl)pyrimidine-4-carboxylic acid (intermediate I, 100 mg, 0.32 mmol) and (1S, 2R)-(−)-1-yl-2-indanol (62 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 117 mg of white solid (S)-6-(4-chlorophenyl)-N-((1S, 2R)-(−)-1-yl-2-indanol)-2-(1-methyl-1H-pyrazol-4-yl)pyrimidine-4-formamide (compound 3), with a yield of 82%. $^1H$ NMR (400 MHz, DMSO-$d_6$) δ 8.95 (d, J=8.8 Hz, 1H), 8.55 (s, 1H), 8.48-8.40 (m, 2H), 8.36 (s, 1H), 8.19 (d, J=0.7 Hz, 1H), 7.71-7.63 (m, 2H), 7.34-7.16 (m, 4H), 5.58 (d, J=5.0 Hz, 1H), 5.47 (dd, J=8.8, 5.1 Hz, 1H), 4.63-4.55 (m, 1H), 3.93 (s, 3H), 3.20 (dd, J=16.4, 5.0 Hz, 1H), 2.93 (d, J=16.3 Hz, 1H). ESI $[M+H]^+$=446.2

Example 4: Synthesis of (S)-6-(4-chlorophenyl)-N-(1-(4-pyridine)ethyl)-2-(1-methyl-1H-pyrazol-4-yl) pyrimidine-4-formamide (Compound 4)

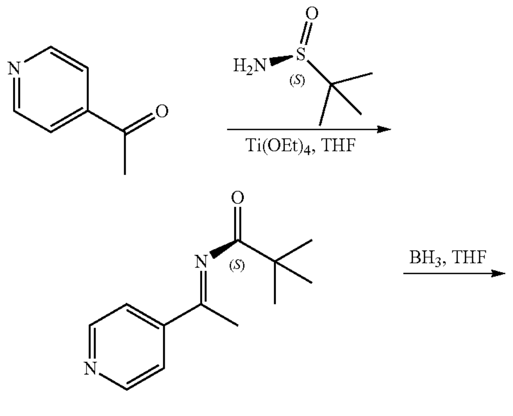

4-a

-continued

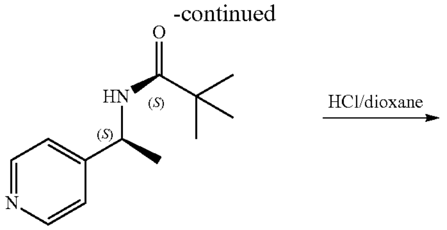

4-b

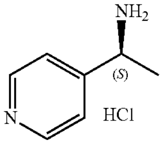

4-c

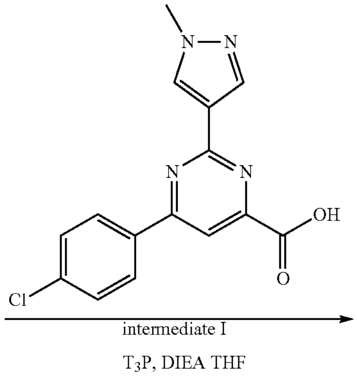

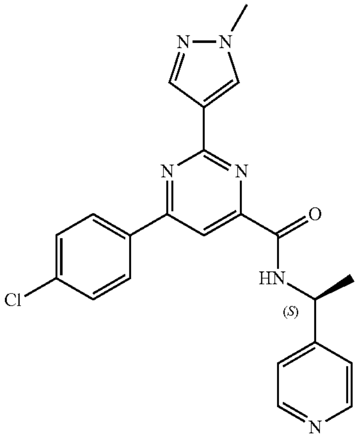

4

Step 1: Synthesis of (S)-1-(4-pyridine)ethyl-2-sulfinylimine (4-a)

4-acetylpyridine (1.21 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.85 g of light yellow liquid (S)-1-(4-pyridine)ethyl-2-sulfinylimine (4-a), with a yield of 82%. ESI $[M+H]^+$=225.2

Step 2: Synthesis of (S)-1-(4-pyridine)ethyl-2-sulfinamide (4-b)

The (S)-1-(4-pyridine)ethyl-2-sulfinylimine (1.85 g, 8.2 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanal was added for quenching after reaction was completed, and the organic phase was purified by a straight-phase column chromatography to obtain 1.64 g of white solid (S)-1-(4-pyridine)ethyl-2-sulfinamide (4-b), with a yield of 86%. ESI $[M+H]^+$=227.1

Step 3: Synthesis of (S)-1-(4-pyridine)ethan-1-amine hydrochloride (4-c)

The (S)-1-(4-pyridine)ethyl-2-sulfinamide (1.64 g, 7.2 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.73 g of white solid (S)-1-(4-pyridine)ethan-1-amine hydrochloride (4-c), with a yield of 81%. ESI [M+H]=123.2

Step 4: Synthesis of (S)-6-(4-chlorophenyl)-N-(1-(4-pyridine)ethyl)-2-(1-methyl-1H-pyrazol-4-yl)pyrimidine-4-formamide (Compound 4)

The 6-(4-chlorophenyl)-2-(1-methyl-1H-pyrazol-4-yl)pyrimidine-4-carboxylic acid (intermediate I, 100 mg, 0.32 mmol) and the (S)-1-(4-pyridine)ethan-1-amine hydrochloride (66 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 110 mg of white solid (S)-6-(4-chlorophenyl)-N-(1-(4-pyridine)ethyl)-2-(1-methyl-1H-pyrazol-4-yl)pyrimidine-4-formamide (compound 4), with a yield of 82%. $^1H$ NMR (400 MHz, DMSO-$d_6$) δ 9.34 (d, J=8.4 Hz, 1H), 8.70 (s, 1H), 8.54 (d, J=4.9 Hz, 2H), 8.42 (s, 1H), 8.38 (d, J=8.3 Hz, 2H), 8.21 (s, 1H), 7.64 (d, J=8.3 Hz, 2H), 7.45 (d, J=5.1 Hz, 2H), 5.26 (t, J=7.6 Hz, 1H), 3.97 (s, 3H), 1.62 (d, J=7.1 Hz, 3H). ESI $[M+H]^+$=419.2

Example 5: Synthesis of (S)-6-(4-chlorophenyl)-N-(1-(2-trifluoromethyl-4-pyridine)ethyl)-2-(1-methyl-1H-pyrazol-4-yl)pyrimidine-4-formamide (Compound 5)

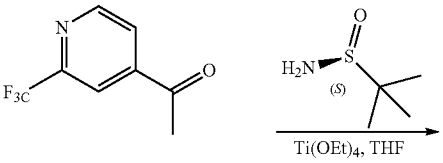

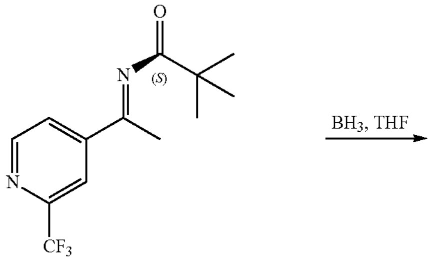

5-a

-continued

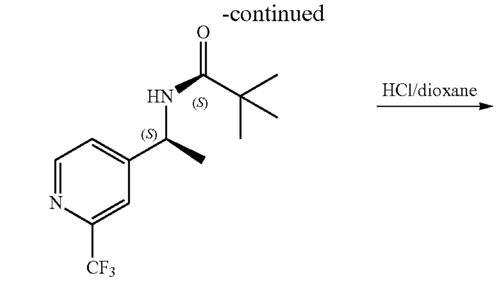

5-b

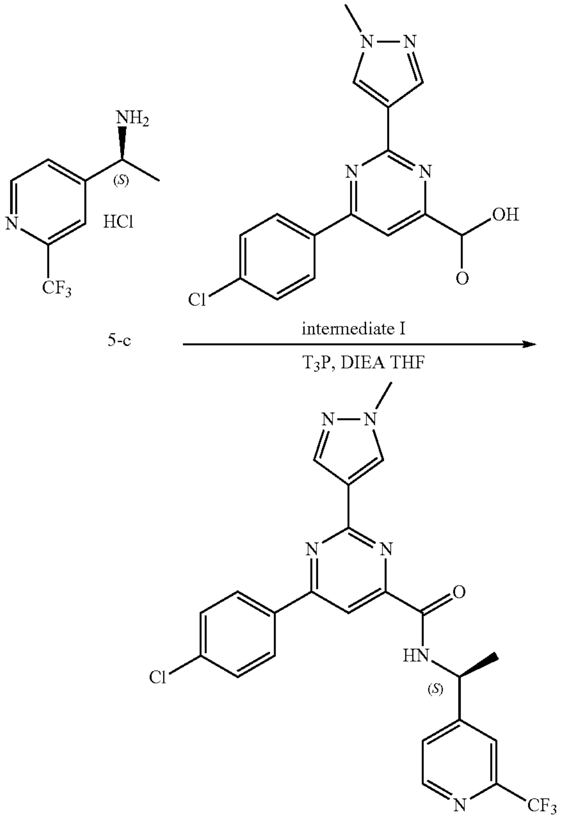

5-c

5

Step 2: Synthesis of (S)-1-(2-trifluoromethyl-4-pyridine)ethyl-2-sulfinamide (5-b)

The (S)-1-(2-trifluoromethyl-4-pyridine)ethyl-2-sulfinylimine (2.43 g, 8.3 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 2.10 g of white solid (S)-1-(2-trifluoromethyl-4-pyridine)ethyl-2-sulfinamide (5-b), with a yield of 86%. ESI $[M+H]^+$=295.1

Step 3: Synthesis of (S)-1-(2-trifluoromethyl-4-pyridine)ethan-1-amine hydrochloride (5-c)

The (S)-1-(2-trifluoromethyl-4-pyridine)ethyl-2-sulfinamide (2.10 g, 7.1 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 1.05 g of white solid (S)-1-(2-trifluoromethyl-4-pyridine)ethan-1-amine hydrochloride (5-c), with a yield of 77%. ESI $[M+H]^+$=191.2

Step 4: Synthesis of (S)-6-(4-chlorophenyl)-N-(1-(2-trifluoromethyl-4-pyridine)ethyl)-2-(1-methyl-1H-pyrazol-4-yl)pyrimidine-4-formamide (Compound 5)

The 6-(4-chlorophenyl)-2-(1-methyl-1H-pyrazol-4-yl)pyrimidine-4-carboxylic acid (intermediate I, 100 mg, 0.32 mmol) and the (S)-1-(2-trifluoromethyl-4-pyridine)ethan-1-amine hydrochloride (95 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 121 mg of white solid (S)-6-(4-chlorophenyl)-N-(1-(2-trifluoromethyl-4-pyridine)ethyl)-2-(1-methyl-1H-pyrazol-4-yl)pyrimidine-4-formamide (compound 5), with a yield of 78%. $^1H$ NMR (400 MHz, DMSO-$d_6$) δ 9.37 (d, J=8.3 Hz, 1H), 8.69 (s, 1H), 8.45-8.30 (m, 4H), 8.20 (s, 1H), 7.72 (d, J=8.3 Hz, 2H), 7.53 (s, 1H), 7.49-7.39 (m, 1H), 5.27 (q, J=7.4 Hz, 1H), 3.97 (s, 3H), 1.61 (d, J=7.1 Hz, 3H). ESI $[M+H]^+$=487.1

Example 6: Synthesis of (S)-6-(4-chlorophenyl)-N-(2-(1H-indol-3-yl)ethyl)-2-(1-methyl-1H-pyrazol-4-yl)pyrimidine-4-formamide (compound 6)

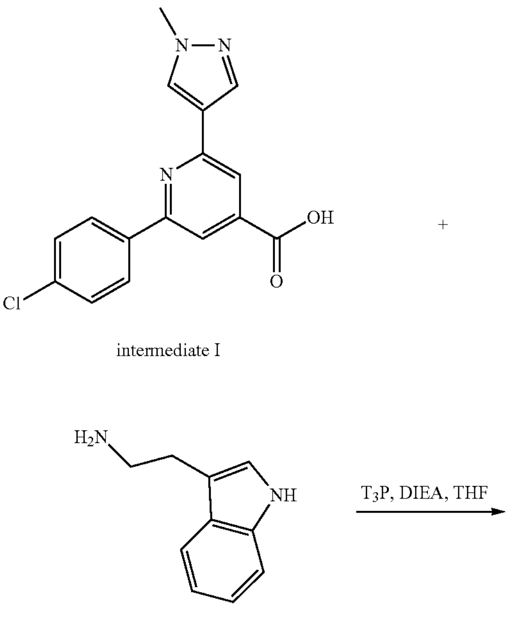

-continued

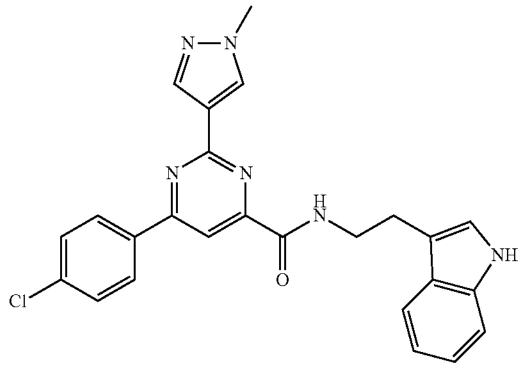

6

Step 1: Synthesis of (S)-6-(4-chlorophenyl)-N-(2-(1H-indol-3-yl)ethyl)-2-(1-methyl-1H-pyrazol-4-yl)pyrimidine-4-formamide (Compound 6)

The 6-(4-chlorophenyl)-2-(1-methyl-1H-pyrazol-4-yl)pyrimidine-4-carboxylic acid (intermediate I, 100 mg, 0.32 mmol) and tryptamine (86 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 129 mg of white solid (S)-6-(4-chlorophenyl)-N-(2-(1H-indol-3-yl)ethyl)-2-(1-methyl-1H-pyrazol-4-yl)pyrimidine-4-formamide (compound 6), with a yield of 86%. $^1H$ NMR (400 MHz, DMSO-$d_6$) δ 10.87 (s, 1H), 9.20 (t, J=6.0 Hz, 1H), 8.62 (s, 1H), 8.42-8.32 (m, 3H), 8.23 (s, 1H), 7.65 (dd, J=7.8, 5.2 Hz, 3H), 7.35 (dt, J=8.1, 1.0 Hz, 1H), 7.25 (d, J=2.3 Hz, 1H), 7.08 (m, 1H), 6.99 (m, 1H), 3.96 (s, 3H), 3.67 (q, J=7.1 Hz, 2H), 3.04 (t, J=7.6 Hz, 2H). ESI $[M+H]^+$=457.2

Example 7: Synthesis of (S)-6-(4-chlorophenyl)-N-(1-(3,4-difluorophenyl)cyclopropyl)-2-(1-methyl-1H-pyrazol-4-yl)pyrimidine-4-formamide (Compound 7)

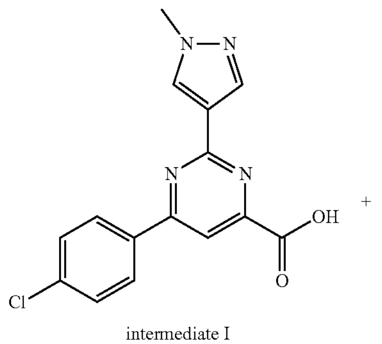

intermediate I

-continued

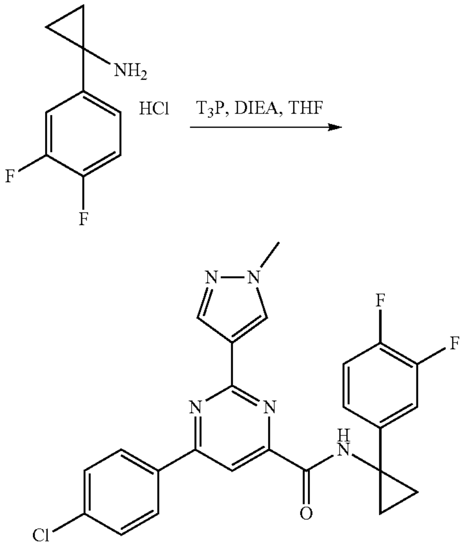

7

Step 1: Synthesis of (S)-6-(4-chlorophenyl)-N-(1-(3,4-difluorophenyl)cyclopropyl)-2-(1-methyl-1H-pyrazol-4-yl)pyrimidine-4-formamide (Compound 7)

The 6-(4-chlorophenyl)-2-(1-methyl-1H-pyrazol-4-yl)pyrimidine-4-carboxylic acid (intermediate I, 100 mg, 0.32 mmol) and 1-(3,4-difluorophenyl)cyclopropylamine hydrochloride (86 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 119 mg of white solid (S)-6-(4-chlorophenyl)-N-(1-(3,4-difluorophenyl)cyclopropyl)-2-(1-methyl-1H-pyrazol-4-yl)pyrimidine-4-formamide (compound 7), with a yield of 80%. $^1H$ NMR (400 MHz, DMSO-$d_6$) δ 9.79 (s, 1H), 8.73 (s, 1H), 8.42 (s, 1H), 8.41-8.34 (m, 2H), 8.20 (s, 1H), 7.68-7.60 (m, 2H), 7.39-7.28 (m, 2H), 7.17-7.10 (m, 1H), 3.96 (s, 3H), 1.36-1.24 (m, 4H). ESI $[M+H]^+$=466.2

Example 8: Synthesis of (S)-6-(4-chlorophenyl)-N-(1-(3-fluoro-4-methoxyphenyl)ethyl)-2-(1-methyl-1H-pyrazol-4-yl)pyrimidine-4-formamide (Compound 8)

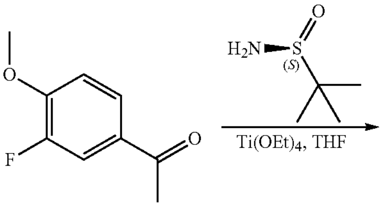

-continued

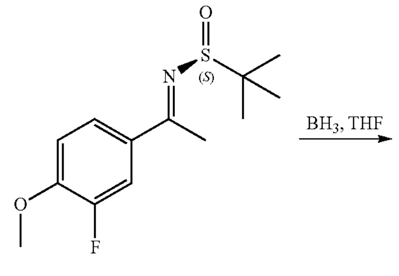

8-a

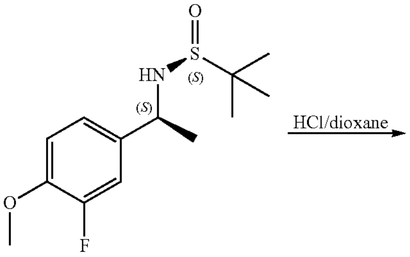

8-b

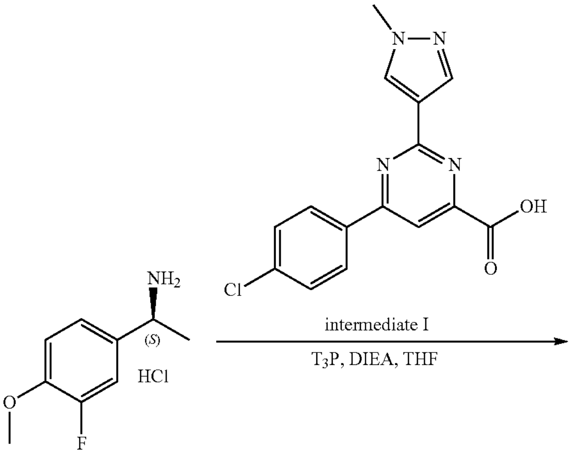

8-c

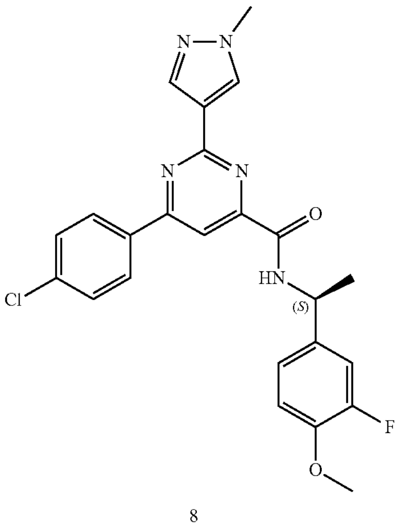

8

Step 1: Synthesis of (S)-N-(1-(3-fluoro-4-methoxyphenyl)ethyl)-2-tert-butylsulfinylimine (8-a)

1-(3-fluoro-4-methoxyphenyl)ethanone (1.68 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 100° C. with stirring for 8 h, then the solution was extracted with ethyl acetate/water, and the organic phase was purified by a straight-phase column chromatography to obtain 2.01 g of white solid (S)-N-(1-(3-fluoro-4-methoxyphenyl)ethyl)-2-tert-butylsulfinylimine (8-a), with a yield of 74%. ESI $[M+H]^+$=272.2

Step 2: Synthesis of (S)-N-(1-(3-fluoro-4-methoxyphenyl)ethyl)-2-tert-butylsulfinamide (8-b)

The (S)-N-(1-(3-fluoro-4-methoxyphenyl)ethyl)-2-tert-butylsulfinylimine (2.01 g, 7.3 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.62 g of white solid (S)-N-(1-(3-fluoro-4-methoxyphenyl)ethyl)-2-tert-butylsulfinamide (8-b), with a yield of 80%. ESI $[M+H]^+$=274.1

Step 3: Synthesis of (S)-1-(3-fluoro-4-methoxyphenyl)ethan-1-amine hydrochloride (8-c)

The (S)-N-(1-(3-fluoro-4-methoxyphenyl)ethyl)-2-tert-butylsulfinamide (1.62 g, 5.9 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.69 g of white solid (S)-1-(3-fluoro-4-methoxyphenyl)ethan-1-amine hydrochloride (8-c), with a yield of 69%. ESI $[M+H]^+$=170.2

Step 4: Synthesis of (S)-6-(4-chlorophenyl)-N-(1-(3-fluoro-4-methoxyphenyl)ethyl)-2-(1-methyl-1H-pyrazol-4-yl)pyrimidine-4-formamide (Compound 8)

The 6-(4-chlorophenyl)-2-(1-methyl-1H-pyrazol-4-yl)pyrimidine-4-carboxylic acid (100 mg, 0.32 mmol) and the (S)-1-(3-fluoro-4-methoxyphenyl)ethan-1-amine hydrochloride (86 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 129 mg of white solid (S)-6-(4-chlorophenyl)-N-(1-(3-fluoro-4-methoxyphenyl)ethyl)-2-(1-methyl-1H-pyrazol-4-yl)pyrimidine-4-formamide (compound 8), with a yield of 86%. $^1$H NMR (400 MHz, DMSO-$d_6$) δ 9.17 (d, J=8.7 Hz, 1H), 8.68 (s, 1H), 8.43-8.33 (m, 3H), 8.20 (s, 1H), 7.68-7.60 (m, 2H), 7.43-7.29 (m, 1H), 7.22 (dd, J=8.6, 2.1 Hz, 1H), 7.14 (t, J=8.7 Hz, 1H), 5.29-5.17 (m, 1H), 3.96 (s, 3H), 3.81 (s, 3H), 1.58 (d, J=7.0 Hz, 3H). ESI $[M+H]^+$=466.1

Example 9: Synthesis of (S)-6-(4-chlorophenyl)-N-(1-(2-chloro-4-pyridine)ethyl)-2-(1-methyl-1H-pyrazol-4-yl)pyrimidine-4-formamide (Compound 9)

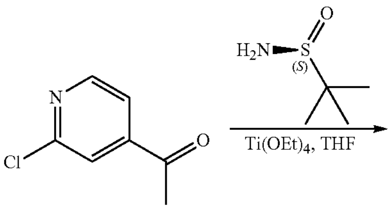

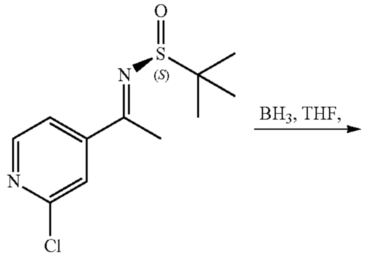

9-a

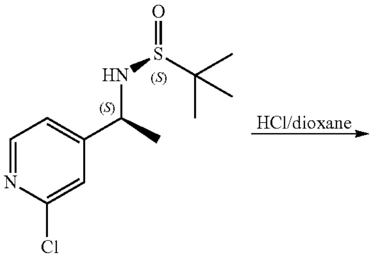

9-b

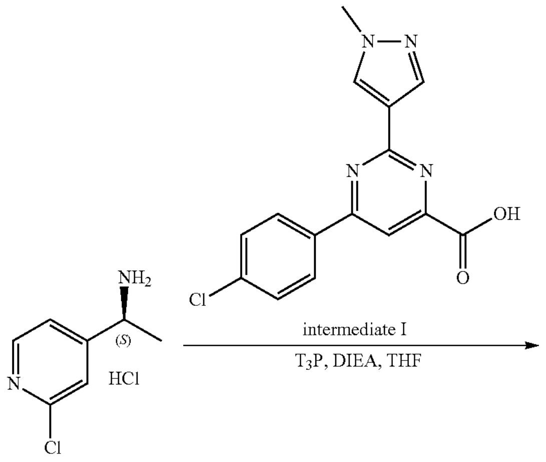

9-c

-continued

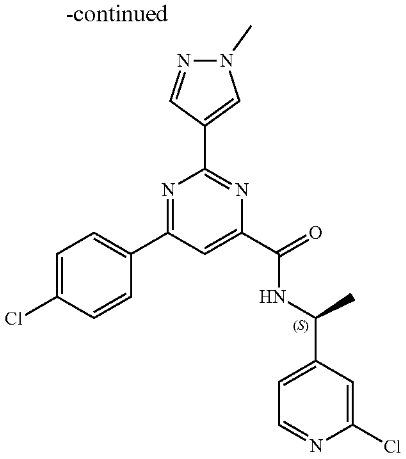

9

Step 1: Synthesis of (S)-1-(2-chloro-4-pyridine)ethyl-2-sulfinylimine (9-a)

2-chloro-4-acetylpyridine (1.55 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.18 g of light yellow liquid (S)-1-(2-chloro-4-pyridine)ethyl-2-sulfinylimine (9-a), with a yield of 85%. ESI $[M+H]^+$=259.1

Step 2: Synthesis of (S)-1-(2-chloro-4-pyridine)ethyl-2-sulfinamide (9-b)

The (S)-1-(2-chloro-4-pyridine)ethyl-2-sulfinylimine (2.18 g, 8.5 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.95 g of white solid (S)-1-(2-chloro-4-pyridine)ethyl-2-sulfinamide (9-b), with a yield of 89%. ESI $[M+H]^+$=261.2

Step 3: Synthesis of (S)-1-(2-chloro-4-pyridine)ethan-1-amine hydrochloride (9-c)

The (S)-1-(2-chloro-4-pyridine)ethyl-2-sulfinamide (1.95 g, 7.2 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.86 g of white solid (S)-1-(2-chloro-4-pyridine)ethan-1-amine hydrochloride (9-c), with a yield of 73%. ESI $[M+H]^+$ =157.3

Step 4: Synthesis of (S)-6-(4-chlorophenyl)-N-(1-(2-chloro-4-pyridine)ethyl)-2-(1-methyl-1H-pyrazol-4-yl)pyrimidine-4-formamide (Compound 9)

The 6-(4-chlorophenyl)-2-(1-methyl-1H-pyrazol-4-yl)pyrimidine-4-carboxylic acid (100 mg, 0.32 mmol) and the (S)-1-(2-chloro-4-pyridine)ethan-1-amine hydrochloride (80 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 114 mg of white solid (S)-6-(4-chlorophenyl)-N-(1-(2-chloro-4-pyridine)ethyl)-2-(1-methyl-1H-pyrazol-4-yl)pyrimidine-4-formamide (compound 9), with a yield of 79%. $^1$H NMR (400 MHz, DMSO-$d_6$) δ 9.37 (d, J=8.3 Hz, 1H), 8.69 (s, 1H), 8.45-8.35 (m, 4H), 8.20 (s, 1H), 7.64 (d, J=8.3 Hz, 2H), 7.58 (s, 1H), 7.56-7.42 (m, 1H), 5.27 (q, J=7.4 Hz, 1H), 3.97 (s, 3H), 1.61 (d, J=7.1 Hz, 3H). ESI [M+H]$^+$=453.1

Example 10: Synthesis of (S)-6-(4-chlorophenyl)-N-(1-(4-pyrimidine)ethyl)-2-(1-methyl-1H-pyrazol-4-yl)pyrimidine-4-formamide (Compound 10)

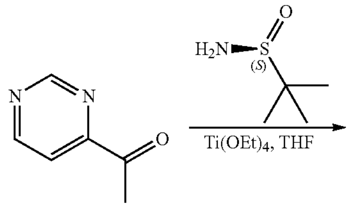

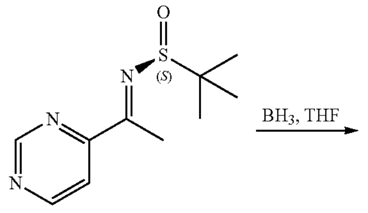

10-a

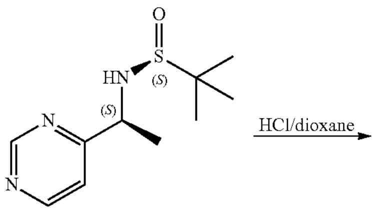

10-b

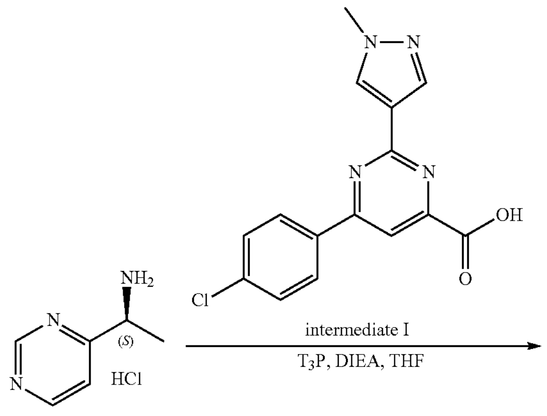

10-c

-continued

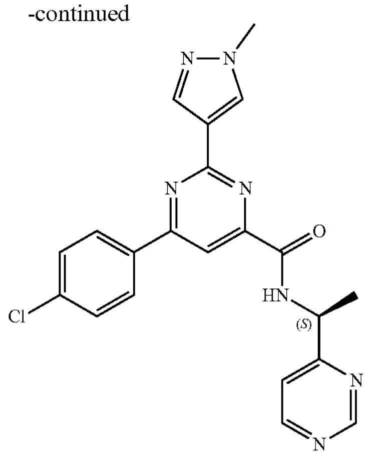

10

Step 1: Synthesis of (S)-N-(1-(4-pyrimidine)ethyl)-2-tert-butylsulfinylimine (10-a)

1-(4-pyrimidine)ethanone (1.22 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.84 g of white solid (S)-N-(1-(4-pyrimidine)ethyl)-2-tert-butylsulfinylimine (10-a), with a yield of 82%. ESI [M+H]$^+$=225.1

Step 2: Synthesis of (S)-N-(1-(4-pyrimidine)ethyl)-2-tert-butylsulfinamide (10-b)

The (S)-N-(1-(4-pyrimidine)ethyl)-2-tert-butylsulfinylimine (1.84 g, 8.2 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.52 g of white solid (S)-N-(1-(4-pyrimidine)ethyl)-2-tert-butylsulfinamide (10-b), with a yield of 82%. ESI [M+H]$^+$=227.1

Step 3: Synthesis of (S)-1-(4-pyrimidine)ethan-1-amine hydrochloride (10-c)

The (S)-N-(1-(4-pyrimidine)ethyl)-2-tert-butylsulfinamide (1.52 g, 6.7 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.61 g of white solid (S)-1-(4-pyrimidine)ethan-1-amine hydrochloride (10-c), with a yield of 73%. ESI [M+H]$^+$=124.2

Step 4: Synthesis of (S)-6-(4-chlorophenyl)-N-(1-(4-pyrimidine)ethyl)-2-(1-methyl-1H-pyrazol-4-yl) pyrimidine-4-formamide (Compound 10)

The 6-(4-chlorophenyl)-2-(1-methyl-1H-pyrazol-4-yl)pyrimidine-4-carboxylic acid (100 mg, 0.32 mmol) and the (S)-1-(4-pyrimidine)ethan-1-amine hydrochloride (67 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 91 mg of white solid (S)-6-(4-chlorophenyl)-N-(1-(4-pyrimidine)ethyl)-2-(1-methyl-1H-pyrazol-4-yl) pyrimidine-4-formamide (compound 10), with a yield of 68%. $^1$H NMR (400 MHz, DMSO-$d_6$) δ 9.37 (d, J=8.3 Hz, 1H), 9.11 (s, 1H), 8.92 (s, 2H), 8.67 (s, 1H), 8.42-8.34 (m, 3H), 8.21 (s, 1H), 7.68-7.60 (m, 2H), 5.34 (p, J=7.2 Hz, 1H), 3.96 (s, 3H), 1.68 (d, J=7.1 Hz, 3H). ESI $[M+H]^+$=420.1

Example 11: Synthesis of (S)-6-(4-chlorophenyl)-N-(1-(3-fluoro-4-hydroxyphenyl)ethyl)-2-(1-methyl-1H-pyrazol-4-yl)pyrimidine-4-formamide (Compound 11)

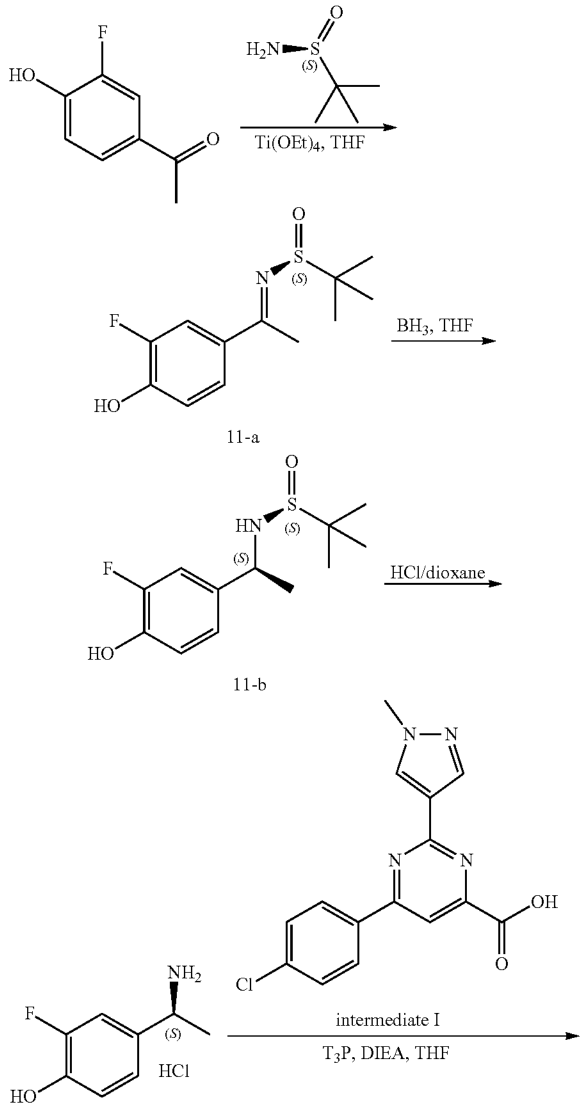

11-a 11-b 11-c

-continued

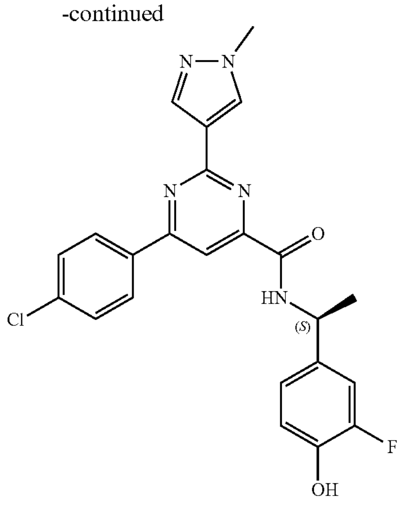

11

Step 1: Synthesis of (S)-N-(1-(3-fluoro-4-phenol) ethyl)-2-tert-butylsulfinylimine (11-a)

1-(3-fluoro-4-hydroxyphenyl)ethanone (1.54 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.11 g of white solid (S)-N-(1-(3-fluoro-4-phenol)ethyl)-2-tert-butylsulfinylimine (11-a), with a yield of 91%. ESI $[M+H]^+$=258.1

Step 2: Synthesis of (S)-N-((S)1-(3-fluoro-4-phenol)ethyl)-2-tert-butylsulfinamide (11-b)

The (S)-N-(1-(3-fluoro-4-phenol)ethyl)-2-tert-butylsulfinylimine (2.11 g, 8.1 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.93 g of white solid (S)-N-((S)1-(3-fluoro-4-phenol)ethyl)-2-tert-butylsulfinamide (11-b), with a yield of 81%. ESI $[M+H]^+$=260.2

Step 3: Synthesis of (S)-4-(1-aminoethyl)-2-fluorophenol hydrochloride (11-c)

The (S)-N-((S)1-(3-fluoro-4-phenol)ethyl)-2-tert-butylsulfinamide (1.93 g, 7.4 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 1.1 g of white solid (S)-4-(1-aminoethyl)-2-fluorophenol hydrochloride (11-c), with a yield of 78%. ESI $[M+H]^+$=156.1

Step 4: Synthesis of (S)-6-(4-chlorophenyl)-N-(1-(3-fluoro-4-hydroxyphenyl)ethyl)-2-(1-methyl-1H-pyrazol-4-yl)pyrimidine-4-formamide (Compound 11)

The 6-(4-chlorophenyl)-2-(1-methyl-1H-pyrazol-4-yl)pyrimidine-4-carboxylic acid (100 mg, 0.32 mmol) and the (S)-4-(1-aminoethyl)-2-fluorophenol hydrochloride (80 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 85 mg of white solid (S)-6-(4-chlorophenyl)-N-(1-(3-fluoro-4-hydroxyphenyl)ethyl)-2-(1-methyl-1H-pyrazol-4-yl)pyrimidine-4-formamide (compound 11), with a yield of 59%. $^1$H NMR (400 MHz, DMSO-$d_6$) δ 9.73 (s, 1H), 9.13 (d, J=8.8 Hz, 1H), 8.69 (s, 1H), 8.43-8.34 (m, 3H), 8.21 (s, 1H), 7.67-7.61 (m, 2H), 7.25 (m, 1H), 7.07 (d, J=8.7 Hz, 1H), 6.95-6.87 (m, 1H), 5.24-5.15 (m, 1H), 3.96 (s, 3H), 1.56 (d, J=7.0 Hz, 3H). ESI $[M+H]^+$=452.1

Example 12: Synthesis of (S)-6-(4-chlorophenyl)-N-(1-(2-cyano-4-pyridine)ethyl)-2-(1-methyl-1H-pyrazol-4-yl)pyrimidine-4-formamide (Compound 12)

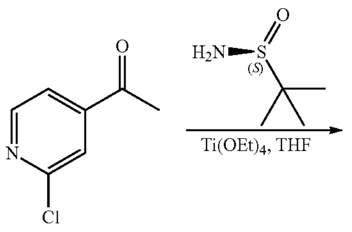

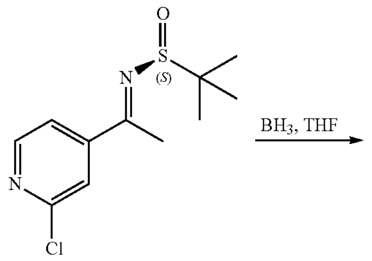

12-a

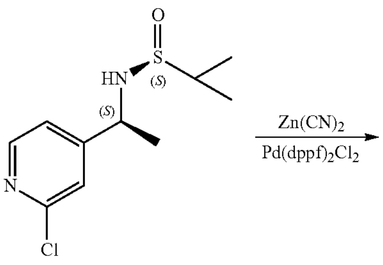

12-b

-continued

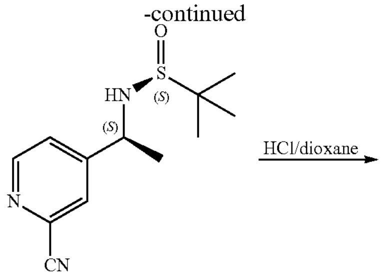

12-c

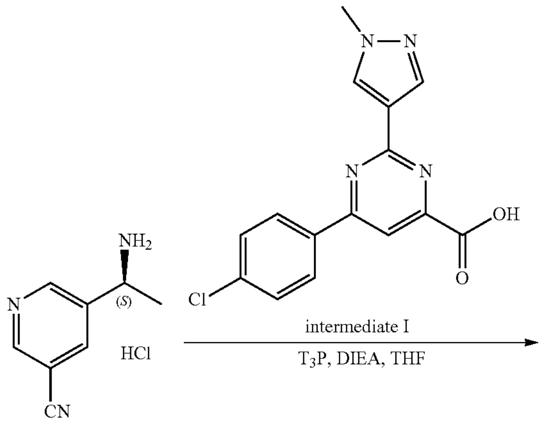

12-d

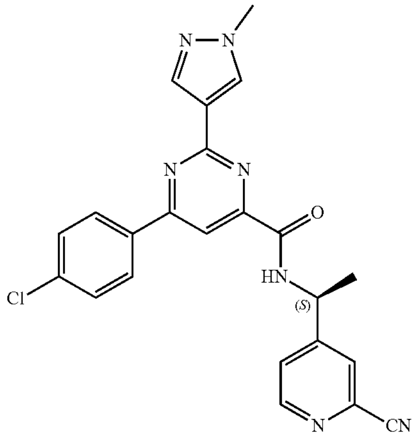

12

Step 1: Synthesis of (S)-1-(2-chloro-4-pyridine)ethyl-2-sulfinylimine (12-a)

2-chloro-4-acetylpyridine (1.55 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 100° C. with stirring for 8 h, then the solution was extracted with ethyl acetate/water, and the organic phase was purified by a straight-phase column chromatography to obtain 2.18 g of light yellow liquid (S)-1-(2-chloro-4-pyridine)ethyl-2-sulfinylimine (12-a), with a yield of 85%. ESI $[M+H]^+$=259.1

Step 2: Synthesis of (S)-1-(2-chloro-4-pyridine)ethyl-2-sulfinamide (12-b)

The (S)-1-(2-chloro-4-pyridine)ethyl-2-sulfinylimine (2.18 g, 8.5 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.95 g of white solid (S)-1-(2-chloro-4-pyridine)ethyl-2-sulfinamide (12-b), with a yield of 89%. ESI $[M+H]^+$=260.2

Step 3: Synthesis of (S)-1-(2-cyano-4-pyridine) ethyl-2-sulfinamide (12-c)

The (S)-1-(2-chloro-4-pyridine)ethyl-2-sulfinamide (1.95 g, 7.5 mmol) was dissolved in 80 mL of dry N,N-dimethylformamide; zinc cyanide (546 mg, 6.0 mmol), zinc powder (247 mg, 3.8 mmol), and [1,1'-bis(diphenylphosphine) ferrocene]palladium dichloride (55 mg, 0.075 mmol) were sequentially added; the solution was stirred at 120° C. for 4 h and extracted with ethyl acetate/water after reaction was completed, and the organic phase was purified by a straight-phase column chromatography to obtain 0.86 g of white solid (S)-1-(2-cyano-4-pyridine)ethyl-2-sulfinamide (12-c), with a yield of 44%. ESI $[M+H]^+$=251.1

Step 4: Synthesis of (S)-1-(2-cyano-4-pyridine) ethan-1-amine hydrochloride (12-d)

The (S)-1-(2-cyano-4-pyridine)ethyl-2-sulfinamide (0.86 g, 3.4 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.32 g of white solid (S)-1-(2-cyano-4-pyridine)ethan-1-amine hydrochloride (12-d), with a yield of 64%. ESI $[M+H]^+$=147.3

Step 5: Synthesis of (S)-6-(4-chlorophenyl)-N-(1-(2-cyano-4-pyridine)ethyl)-2-(1-methyl-1H-pyrazol-4-yl)pyrimidine-4-formamide (Compound 12)

The 6-(4-chlorophenyl)-2-(1-methyl-1H-pyrazol-4-yl)pyrimidine-4-carboxylic acid (100 mg, 0.32 mmol) and the (S)-1-(2-cyano-4-pyridine)ethan-1-amine hydrochloride (77 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 105 mg of white solid (S)-6-(4-chlorophenyl)-N-(1-(2-cyano-4-pyridine)ethyl)-2-(1-methyl-1H-pyrazol-4-yl)pyrimidine-4-formamide (compound 12), with a yield of 74%. $^1H$ NMR (400 MHz, DMSO-$d_6$) δ 9.37 (d, J=8.3 Hz, 1H), 8.69 (s, 1H), 8.45-8.35 (m, 4H), 8.20 (s, 1H), 7.81 (d, J=8.3 Hz, 2H), 7.58 (s, 1H), 7.52-7.42 (m, 1H), 5.27 (q, J=7.4 Hz, 1H), 3.97 (s, 3H), 1.61 (d, J=7.1 Hz, 3H). ESI $[M+H]^+$=443.1

Example 13: Synthesis of (S)-6-(4-chlorophenyl)-N-(1-(3-fluoro-4-chlorophenyl)ethyl)-2-(1-methyl-1H-pyrazol-4-yl)pyrimidine-4-formamide (Compound 13)

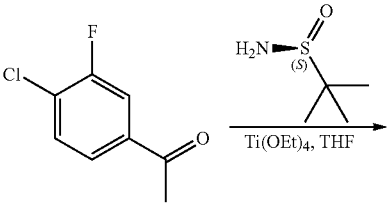

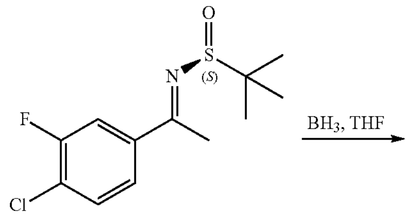

13-a

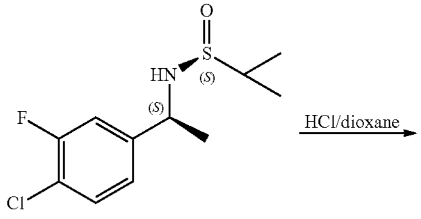

13-b

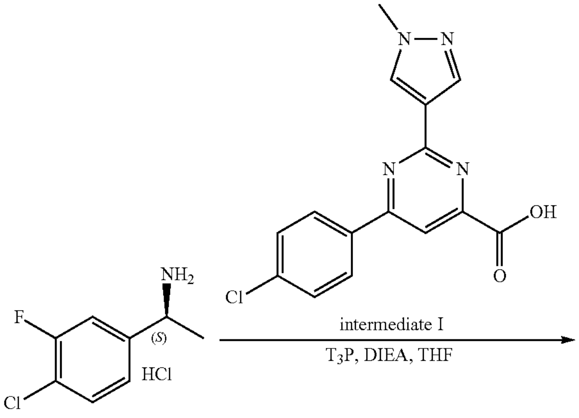

13-c

-continued

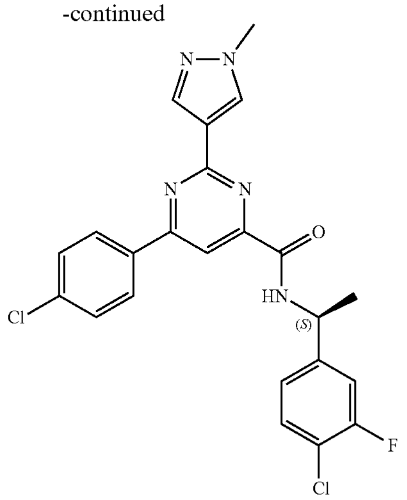

13

Step 1: Synthesis of (S)-N-(1-(3-fluoro-4-chlorophenyl)ethyl)-2-tert-butylsulfinylimine (13-a)

1-(3-fluoro-4-chlorophenyl)ethanone (1.72 g, 10 mmol) was dissolved in 50 mL of dry tetrahydrofuran, (0)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.03 g of white solid (S)-N-(1-(3-fluoro-4-chlorophenyl)ethyl)-2-tert-butylsulfinylimine (13-a), with a yield of 74%. ESI $[M+H]^+=276.1$ Step 2: Synthesis of (S)-N-(1-(3-fluoro-4-chlorophenyl)ethyl)-2-tert-butylsulfinamide (13-b)

The (S)-N-(1-(3-fluoro-4-chlorophenyl)ethyl)-2-tert-butylsulfinylimine (2.03 g, 7.3 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.65 g of white solid (S)-N-(1-(3-fluoro-4-chlorophenyl)ethyl)-2-tert-butylsulfinamide (13-b), with a yield of 80%. ESI $[M+H]^+=278.2$ Step 3: Synthesis of(S)-1-(3-fluoro-4-chlorophenyl) ethan-1-amine hydrochloride (13-c)

The (S)-N-(1-(3-fluoro-4-chlorophenyl)ethyl)-2-tert-butylsulfinamide (1.65 g, 5.9 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.71 g of white solid (S)-1-(3-fluoro-4-chlorophenyl)ethan-1-amine hydrochloride (13-c), with a yield of 69%. ESI $[M+H]^+=174.1$ Step 4: Synthesis of (S)-6-(4-chlorophenyl)-N-(1-(3-fluoro-4-chlorophenyl)ethyl)-2-(1-methyl-1H-pyrazol-4-yl)pyrimidine-4-formamide (Compound 13)

The 6-(4-chlorophenyl)-2-(1-methyl-1H-pyrazol-4-yl)pyrimidine-4-carboxylic acid (100 mg, 0.32 mmol) and the (S)-1-(3-fluoro-4-chlorophenyl)ethan-1-amine hydrochloride (88 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 124 mg of white solid (S)-6-(4-chlorophenyl)-N-(1-(3-fluoro-4-chlorophenyl)ethyl)-2-(1-methyl-1H-pyrazol-4-yl)pyrimidine-4-formamide (compound 13), with a yield of 83%. $^1H$ NMR (400 MHz, DMSO-$d_6$) δ 9.25 (d, J=8.6 Hz, 1H), 8.68 (s, 1H), 8.44-8.34 (m, 3H), 8.20 (s, 1H), 7.70-7.62 (m, 2H), 7.55 (m, 1H), 7.42 (m, 1H), 7.32 (d, J=5.1 Hz, 1H), 5.27 (m, 1H), 3.97 (s, 3H), 1.60 (d, J=7.0 Hz, 3H). ESI $[M+H]^+=470.1$ Example 14: Synthesis of(S)-6-(4-chlorophenyl)-N-(1-(1-methyl-1H-pyrazol-4-yl)ethyl)-2-(1-methyl-1H-pyrazol-4-yl)pyrimidine-4-formamide (Compound 14)

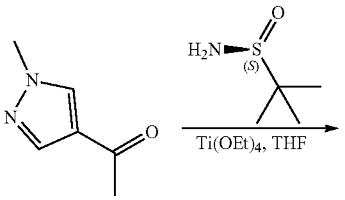

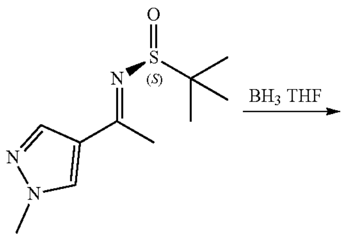

14-a

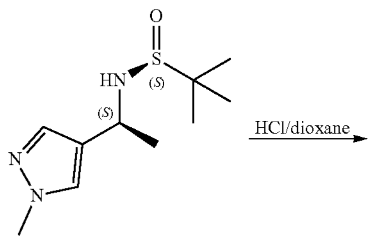

14-b

-continued

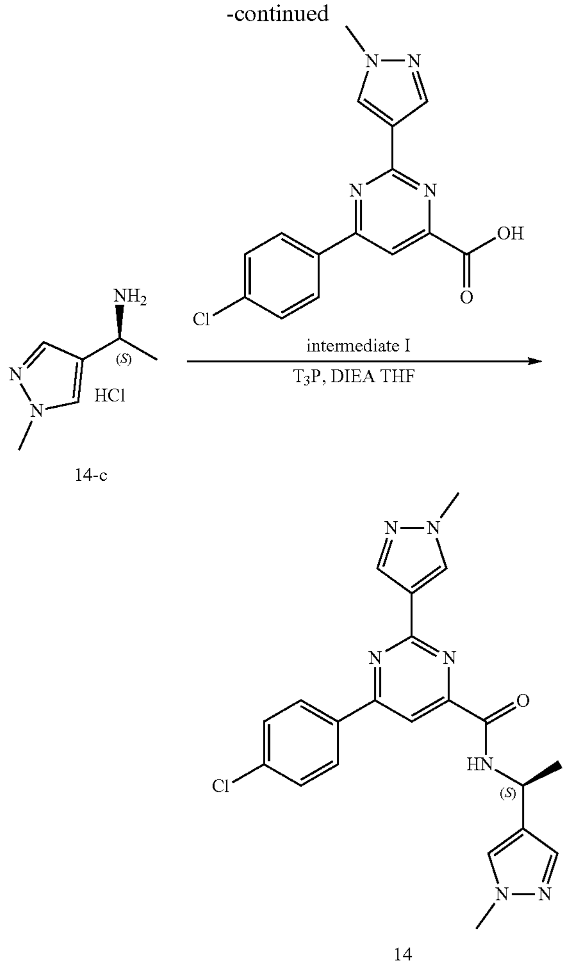

14-c

14

Step 1: Synthesis of (S)-1-(1-methyl-1H-pyrazol-4-yl)ethyl-2-sulfinylimine (14-a)

1-(1-methyl-1H-pyrazol-4-yl)ethanone (1.24 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.83 g of white solid (S)-1-(1-methyl-1H-pyrazol-4-yl)ethyl-2-sulfinylimine (14-a), with a yield of 80%. ESI $[M+H]^+=228.1$ Step 2: Synthesis of (S)-1-(1-methyl-1H-pyrazol-4-yl)ethyl-2-sulfinamide (14-b)

The (S)-1-(1-methyl-1H-pyrazol-4-yl)ethyl-2-sulfinylimine (1.83 g, 8.0 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.59 g of white solid (S)-1-(1-methyl-1H-pyrazol-4-yl)ethyl-2-sulfinamide (14-b), with a yield of 87%. ESI $[M+H]^+=230.2$ Step 3: Synthesis of (S)-1-(1-methyl-1H-pyrazol-4-yl)ethan-1-amine hydrochloride (14-c)

The (S)-1-(1-methyl-1H-pyrazol-4-yl)ethyl-2-sulfinamide (1.59 g, 6.9 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.61 g of white solid (S)-1-(1-methyl-1H-pyrazol-4-yl)ethan-1-amine hydrochloride (14-c), with a yield of 70%. ESI $[M+H]^+=126.1$ Step 4: Synthesis of (S)-6-(4-chlorophenyl)-N-(1-(1-methyl-1H-pyrazol-4-yl)ethyl)-2-(1-methyl-1H-pyrazol-4-yl)pyrimidine-4-formamide (Compound 14)

The 6-(4-chlorophenyl)-2-(1-methyl-1H-pyrazol-4-yl)pyrimidine-4-carboxylic acid (100 mg, 0.32 mmol) and the (S)-1-(1-methyl-1H-pyrazol-4-yl)ethan-1-amine hydrochloride (67 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 102 mg of white solid (S)-6-(4-chlorophenyl)-N-(1-(1-methyl-1H-pyrazol-4-yl)ethyl)-2-(1-methyl-1H-pyrazol-4-yl)pyrimidine-4-formamide (compound 14), with a yield of 76%. $^1H$ NMR (400 MHz, DMSO-$d_6$) δ 9.01 (d, J=8.8 Hz, 1H), 8.68 (s, 1H), 8.39 (d, J=9.4 Hz, 3H), 8.24 (s, 1H), 7.65 (d, J=8.9 Hz, 3H), 7.42 (s, 1H), 5.25 (q, J=7.6, 7.2 Hz, 1H), 3.95 (s, 3H), 3.79 (s, 3H), 1.56 (d, J=6.9 Hz, 3H). ESI $[M+H]^+=421.1$ Example 15: Synthesis of (S)-6-(4-chlorophenyl)-N-(1-(2-fluoro-4-pyridine)ethyl)-2-(1-methyl-1H-pyrazol-4-yl)pyrimidine-4-formamide (Compound 15)

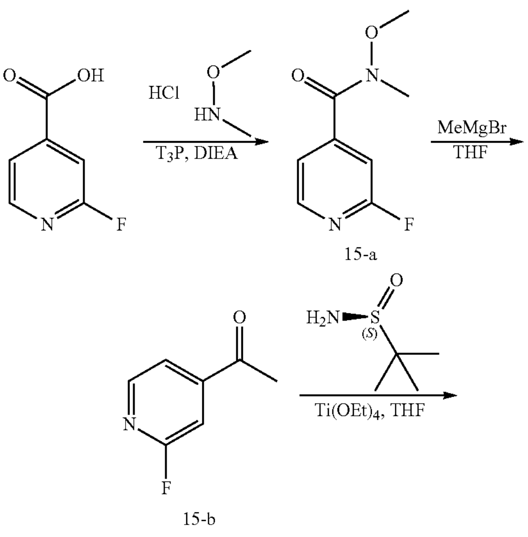

15-a 15-b

-continued

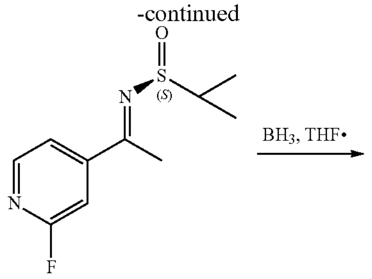

15c

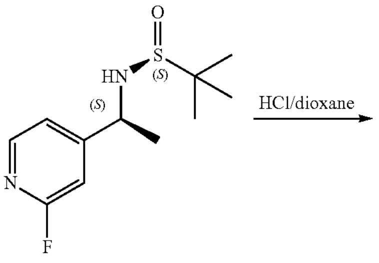

15d

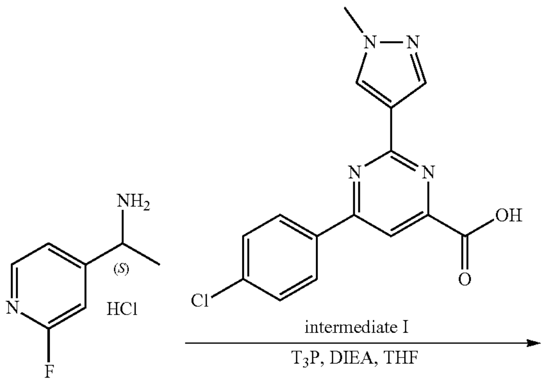

15e

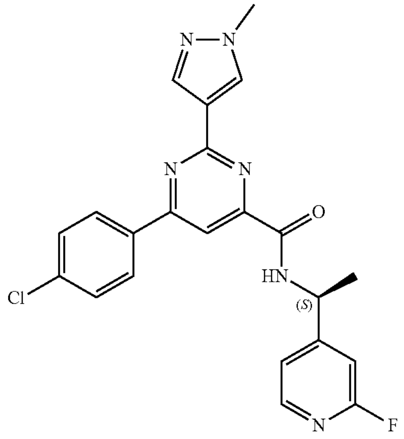

15

Step 1: Synthesis of 2-fluoro-N-methoxy-N-methylisonicotinamide (15-a)

2-fluoroisonicotinic acid (2.42 g, 20 mmol) was dissolved in 100 mL of dry tetrahydrofuran; N,O-dimethylhydroxylamine hydrochloride (2.42 g, 25 mmol), N,N-diisopropylethylamine (6.45 g, 50 mmol), and 1-propylphosphonic anhydride (12.7 g, 20 mmol) were sequentially added at room temperature; reaction occurred at 0° C. with stirring for 2 h, then the solution was extracted with an aqueous solution of ethyl acetate/ammonium chloride, and the organic phase was purified by a straight-phase column chromatography to obtain 2.76 g of white solid 2-fluoro-N-methoxy-N-methylisonicotinamide (15-a), with a yield of 75%. ESI $[M+H]^+$=184.1

Step 2: Synthesis of 2-fluoro-4-acetylpyridine (15-b)

The 2-fluoro-N-methoxy-N-methylisonicotinamide (2.76 g, 15 mmol) was dissolved in 50 mL of dry tetrahydrofuran, methyl magnesium bromide (20 mL, 20 mmol) was added dropwise at 0° C., reaction occurred at 0° C. with stirring for 2 h, then the solution was extracted with an aqueous solution of ethyl acetate/ammonium chloride, and the organic phase was purified by a straight-phase column chromatography to obtain 1.39 g of colorless liquid 2-fluoro-4-acetylpyridine (15-b), with a yield of 66%. ESI $[M+H]^+$=139.2

Step 3: Synthesis of (S)-1-(2-fluoro-4-pyridine)ethyl-2-sulfinylimine (15-c)

The 2-fluoro-4-acetylpyridine (1.39 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.01 g of light yellow liquid (S)-1-(2-fluoro-4-pyridine)ethyl-2-sulfinylimine (15-c), with a yield of 83%. ESI $[M+H]^+$=243.1

Step 4: Synthesis of (S)-1-(2-fluoro-4-pyridine)ethyl-2-sulfinamide (15-d)

The (S)-1-(2-fluoro-4-pyridine)ethyl-2-sulfinylimine (2.01 g, 8.3 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.75 g of white solid (S)-1-(2-fluoro-4-pyridine)ethyl-2-sulfinamide (15-d), with a yield of 86%. ESI $[M+H]^+$=245.1

Step 5: Synthesis of (S)-1-(2-fluoro-4-pyridine)ethan-1-amine hydrochloride (15-e)

The (S)-1-(2-fluoro-4-pyridine)ethyl-2-sulfinamide (1.75 g, 7.2 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.68 g of white solid (S)-1-(2-fluoro-4-pyridine)ethan-1-amine hydrochloride (15-e), with a yield of 67%. ESI $[M+H]^+$=140.1

Step 6: Synthesis of (S)-6-(4-chlorophenyl)-N-(1-(2-fluoro-4-pyridine)ethyl)-2-(1-methyl-1H-pyrazol-4-yl)pyrimidine-4-formamide (Compound 15)

The 6-(4-chlorophenyl)-2-(1-methyl-1H-pyrazol-4-yl)pyrimidine-4-carboxylic acid (100 mg, 0.32 mmol) and the (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 113 mg of white solid (S)-6-(4-chlorophenyl)-N-(1-(2-fluoro-4-pyridine)ethyl)-2-(1-methyl-1H-pyrazol-4-yl)pyrimidine-4-formamide (compound 15), with a yield of 81%. $^1H$ NMR (400 MHz, DMSO-$d_6$) δ 9.37 (d, J=8.3 Hz, 1H), 8.69 (s, 1H), 8.45-8.35 (m, 4H), 8.20 (s, 1H), 7.77 (d, J=8.3 Hz, 2H), 7.51 (s, 1H), 7.46-7.40 (m, 1H), 5.27 (q, J=7.4 Hz, 1H), 3.97 (s, 3H), 1.61 (d, J=7.1 Hz, 3H). ESI $[M+H]^+$=436.2

Example 16: Synthesis of (S)-6-(4-chlorophenyl)-N-(1-[5(2H-1,3-benzodioxomethylene)]ethyl)-2-(1-methyl-1H-pyrazol-4-yl)pyrimidine-4-formamide (Compound 16)

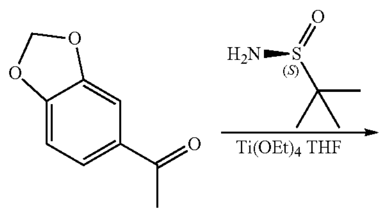

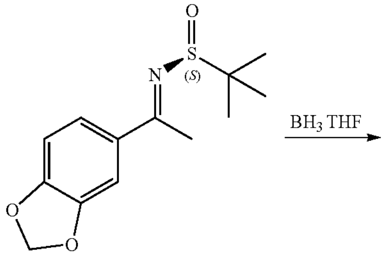

16-a

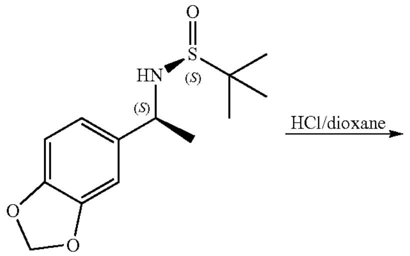

16-b

-continued

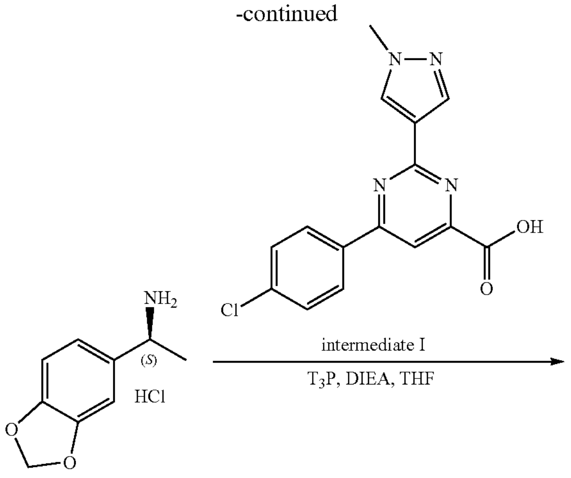

16-c

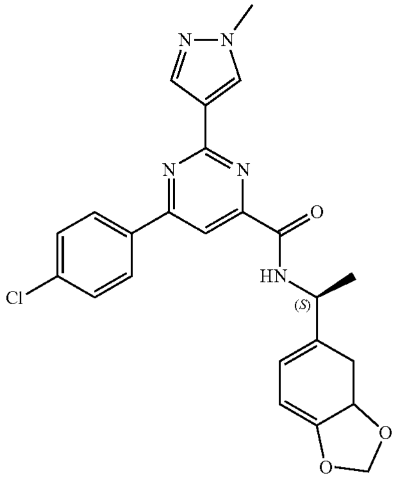

16

Step 1: Synthesis of (S)-N-(1-[5(2H-1,3-benzodioxomethylene)]ethyl)-2-tert-butylsulfinylimine (16-a)

1-[5(2H-1,3-benzodioxomethylene)]ethanone (1.72 g, 10 mmol) was dissolved in 50 mL of dry tetrahydrofuran, (S)-tert-butylsulfinamide (1.45 g, 12 mmol) and tetraethyl titanate (3.42 g 15 mmol) were sequentially added at room temperature, reaction occurred at 80° C. with stirring for 8 h, then the solution was extracted with ethyl acetate/water, and the organic phase was purified by a straight-phase column chromatography to obtain 2.03 g of white solid (S)-N-(1-[5(2H-1,3-benzodioxomethylene)]ethyl)-2-tert-butylsulfinylimine (16-a), with a yield of 74%. ESI $[M+H]^+$ =268.1

Step 2: Synthesis of (S)-N-(1-[5(2H-1,3-benzodioxomethylene)]ethyl)-2-tert-butylsulfinamide (16-b)

The (S)-N-(1-[5(2H-1,3-benzodioxomethylene)]ethyl)-2-tert-butylsulfinylimine (2.03 g, 7.3 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.65 g of white solid (S)-N-(1-[5

(2H-1,3-benzodioxomethylene)]ethyl)-2-tert-butylsulfinamide (16-b), with a yield of 80%. ESI $[M+H]^+$=270.2

Step 3: Synthesis of (S)-1-[5(2H-1,3-benzodioxomethylene)]ethan-1-amine hydrochloride (16-c)

The (S)-N-(1-[5(2H-1,3-benzodioxomethylene)]ethyl)-2-tert-butylsulfinamide (1.65 g, 5.9 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.71 g of white solid (S)-1-[5(2H-1,3-benzodioxomethylene)]ethan-1-amine hydrochloride (16-c), with a yield of 69%. ESI $[M+H]^+$ =166.2

Step 4: Synthesis of(S)-6-(4-chlorophenyl)-N-(1-[5 (2H-1,3-benzodioxomethylene)]ethyl)-2-(1-methyl-1H-pyrazol-4-yl)pyrimidine-4-formamide (compound 16)

The 6-(4-chlorophenyl)-2-(1-methyl-1H-pyrazol-4-yl)pyrimidine-4-carboxylic acid (100 mg, 0.32 mmol) and the (S)-1-[5(2H-1,3-benzodioxomethylene)]ethan-1-amine hydrochloride (86 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 119 mg of white solid (S)-6-(4-chlorophenyl)-N-(1-[5(2H-1,3-benzodioxomethylene)]ethyl)-2-(1-methyl-1H-pyrazol-4-yl)pyrimidine-4-formamide (compound 16), with a yield of 81%. $^1H$ NMR (400 MHz, DMSO-$d_6$) δ 9.12 (d, J=8.7 Hz, 1H), 8.69 (s, 1H), 8.43-8.33 (m, 3H), 8.20 (s, 1H), 7.68-7.60 (m, 2H), 7.09 (d, J=1.7 Hz, 1H), 6.92 (dd, J=8.1, 1.8 Hz, 1H), 6.87 (d, J=8.0 Hz, 1H), 6.01-5.95 (m, 2H), 5.26-5.14 (m, 1H), 3.96 (s, 3H), 1.57 (d, J=7.0 Hz, 3H). ESI $[M+H]^+$=462.2

Example 17: Synthesis of (S)-6-(4-chlorophenyl)-N-(1-([1,2,4-triazolo[1,5-a]pyridin-7-yl)ethyl)-2-(1-methyl-1H-pyrazol-4-yl)pyrimidine-4-formamide (Compound 17)

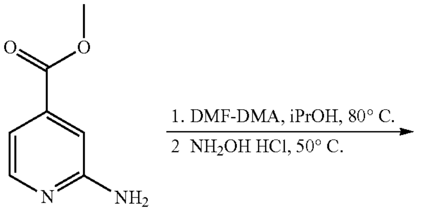

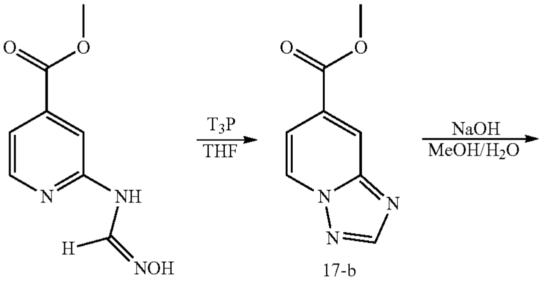

17-a 17-b

-continued

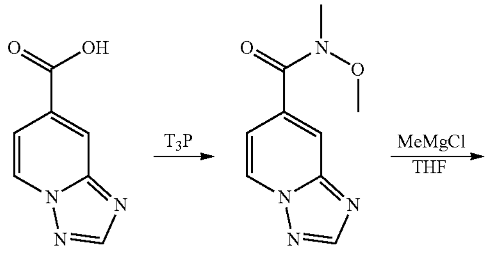

17-c 17-d

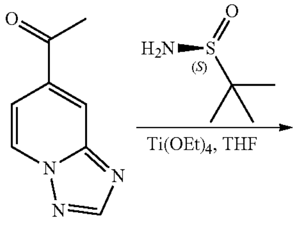

17-e

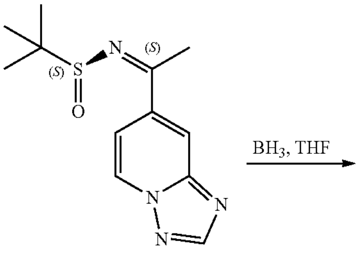

11-f

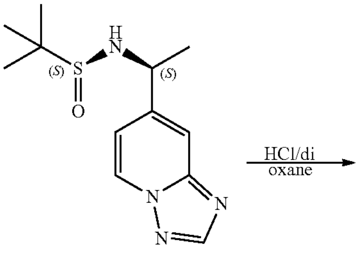

11-g

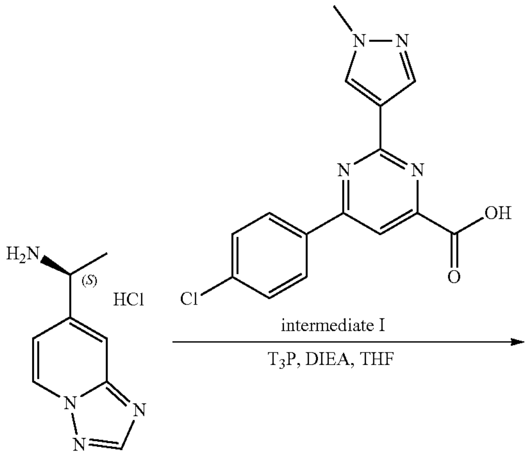

11-h

-continued

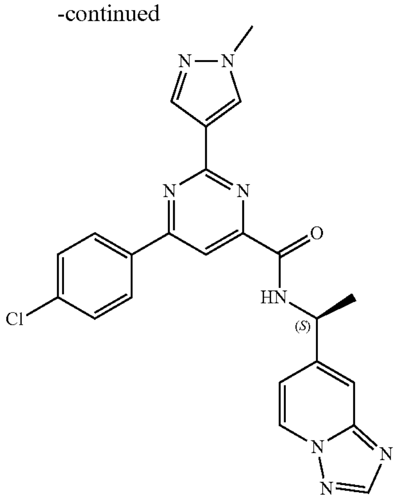

17

Step 1: Synthesis of methyl (Z)-2-(N'-hydroxymethylimido)isonicotinate (17-a)

Methyl 2-aminoisonicotinate (9.12 g, 60 mmol) was dissolved in 100 mL of isopropanol, N,N-dimethylformamide dimethylacetal (7.73 g, 65 mmol) was added at room temperature, reaction occurred at 80° C. with stirring for 4 h, hydroxylamine hydrochloride (5.17 g, 75 mmol) was added after cooling, reaction occurred at 50° C. with stirring for 4 h, then the solution was extracted with an aqueous solution of ethyl acetate/ammonium chloride, and the organic phase was purified by a straight-phase column chromatography to obtain 7.8 g of white solid methyl (Z)-2-(N'-hydroxymethylimido)isonicotinate (17-a), with a yield of 75%. ESI $[M+H]^+$=196.1

Step 2: Synthesis of methyl[1,2,4]triazolo[1,5-a]pyridine-7-carboxylate (17-b)

The methyl (Z)-2-(N'-hydroxymethylimido)isonicotinate (7.8 g, 40 mmol) was dissolved in 100 mL of dry tetrahydrofuran, 1-propylphosphoric anhydride (25.4 g, 40 mmol) was added at room temperature, reaction occurred at 60° C. with stirring for 5 h, then the solution was extracted with an aqueous solution of ethyl acetate/ammonium chloride, and the organic phase was purified by a straight-phase column chromatography to obtain 4.42 g of white solid methyl[1,2,4]triazolo[1,5-a]pyridine-7-carboxylate (17-b), with a yield of 62%. ESI $[M+H]^+$=178.2

Step 3: Synthesis of [1,2,4]triazolo[1,5-a]pyridine-7-carboxylic acid (17-c)

The methyl[1,2,4]triazolo[1,5-a]pyridine-7-carboxylate (4.42 g, 25 mmol) was dissolved in 100 mL of methanol/water (10/1), sodium hydroxide (2.0 g, 50 mmol) was added at room temperature, reaction occurred at 30° C. with stirring for 6 h, then the pH was adjusted to 3-4 with 1N hydrochloric acid, and solid was filtered and dried to obtain 3.26 g of white solid[1,2,4]triazolo[1,5-a]pyridine-7-carboxylic acid (17-c), with a yield of 80%. ESI $[M+H]^+$=164.0

Step 4: Synthesis of N-methoxy-N-methyl-[1,2,4-triazolo[1,5-a]pyridine-7-formamide (17-d)

The [1,2,4]triazolo[1,5-a]pyridine-7-carboxylic acid (3.26 g, 20 mmol) was dissolved in 100 mL of dry tetrahydrofuran; N,O-dimethylhydroxylamine hydrochloride (2.42 g, 25 mmol), N,N-diisopropylethylamine (6.45 g, 50 mmol), and 1-propylphosphonic anhydride (12.7 g, 20 mmol) were sequentially added at room temperature; reaction occurred at 0° C. with stirring for 2 h, then the solution was extracted with an aqueous solution of ethyl acetate/ammonium chloride, and the organic phase was purified by a straight-phase column chromatography to obtain 2.06 g of white solid N-methoxy-N-methyl-[1,2,4-triazolo[1,5-a]pyridine-7-formamide (17-d), with a yield of 75%. ESI $[M+H]^+$=207.1

Step 5: Synthesis of 1-([1,2,4]triazolo[1,5-a]pyridin-7-yl)ethanone (17-e)

The N-methoxy-N-methyl-[1,2,4-triazolo[1,5-a]pyridine-7-formamide (3.09 g, 15 mmol) was dissolved in 50 mL of dry tetrahydrofuran, methyl magnesium bromide (20 mL, 20 mmol) was added dropwise at 0° C., reaction occurred at 0° C. with stirring for 2 h, then the solution was extracted with an aqueous solution of ethyl acetate/ammonium chloride, and the organic phase was purified by a straight-phase column chromatography to obtain 1.61 g of white solid 1-([1,2,4]triazolo[1,5-a]pyridin-7-yl)ethanone (17-e), with a yield of 66%. ESI $[M+H]^+$=162.2

Step 6: Synthesis of (S)-N-(1-([1,2,4]triazolo[1,5-a]pyridin-7-yl)ethyl)-2-tert-butylsulfinylimine (17-f)

The 1-([1,2,4]triazolo[1,5-a]pyridin-7-yl)ethanone (1.61 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 100° C. with stirring for 8 h, then the solution was extracted with ethyl acetate/water, and the organic phase was purified by a straight-phase column chromatography to obtain 2.01 g of white solid (S)-N-(1-([1,2,4]triazolo[1,5-a]pyridin-7-yl)ethyl)-2-tert-butylsulfinylimine (17-f), with a yield of 75%. ESI $[M+H]^+$=265.1

Step 7: Synthesis of (S)-N-(1-([1,2,4]triazolo[1,5-a]pyridin-7-yl)ethyl)-2-tert-butylsulfinamide (17-g)

The (S)-N-(1-([1,2,4]triazolo[1,5-a]pyridin-7-yl)ethyl)-2-tert-butylsulfinylimine (2.01 g, 7.5 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.82 g of white solid (S)-N-(1-([1,2,4]triazolo[1,5-a]pyridin-7-yl)ethyl)-2-tert-butylsulfinamide (17-g), with a yield of 90%. ESI $[M+H]^+$=267.2

Step 8: Synthesis of (S)-1-([1,2,4]triazolo[1,5-a]pyridin-7-yl)ethan-1-amine hydrochloride (17-h)

The (S)-N-(1-([1,2,4]triazolo[1,5-a]pyridin-7-yl)ethyl)-2-tert-butylsulfinamide (1.82 g, 6.8 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.73 g of white solid (S)-1-([1,2,4]triazolo[1,5-a]pyridin-7-yl)ethan-1-amine hydrochloride (17-h), with a yield of 66%. ESI $[M+H]^+$ =163.1

Step 9: Synthesis of (S)-6-(4-chlorophenyl)-N-(1-([1,2,4-triazolo[1,5-a]pyridin-7-yl)ethyl)-2-(1-methyl-1H-pyrazol-4-yl)pyrimidine-4-formamide (Compound 17)

The 6-(4-chlorophenyl)-2-(1-methyl-1H-pyrazol-4-yl)pyrimidine-4-carboxylic acid (100 mg, 0.32 mmol) and the (S)-1-([1,2,4]triazolo[1,5-a]pyridin-7-yl)ethan-1-amine hydrochloride (83 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 95 mg of white solid (S)-6-(4-chlorophenyl)-N-(1-([1,2,4-triazolo[1,5-a]pyridin-7-yl)ethyl)-2-(1-methyl-1H-pyrazol-4-yl)pyrimidine-4-formamide (compound 17), with a yield of 65%. $^1H$ NMR (400 MHz, DMSO-$d_6$) δ 9.40 (d, J=8.4 Hz, 1H), 8.97-8.91 (m, 1H), 8.70 (s, 1H), 8.47 (s, 1H), 8.43 (s, 1H), 8.41-8.34 (m, 2H), 8.21 (s, 1H), 7.85 (d, J=1.7 Hz, 1H), 7.68-7.60 (m, 2H), 7.34 (dd, J=7.1, 1.8 Hz, 1H), 5.44-5.36 (m, 1H), 3.97 (s, 3H), 1.68 (d, J=7.1 Hz, 3H). ESI $[M+H]^+$=459.1

Example 18: Synthesis of (S)-6-(4-chlorophenyl)-N-(1-(4-fluorophenyl)„-propyl)-2-(1-methyl-1H-pyrazol-4-yl)pyrimidine-4-formamide (Compound 18)

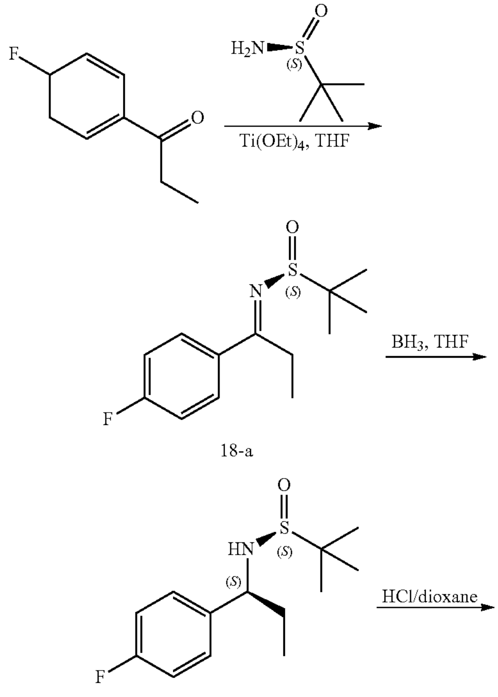

18-a 18-b

-continued

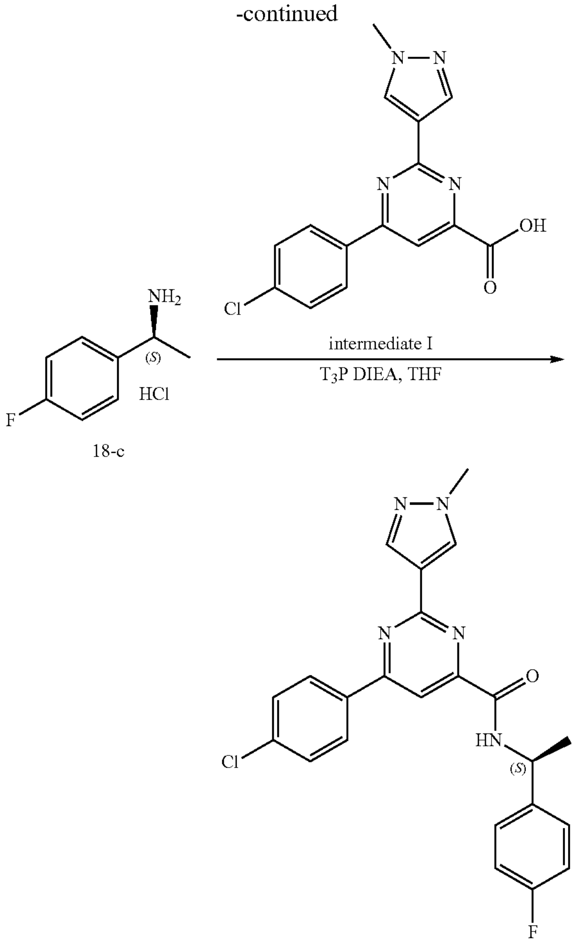

18-c

18

Step 1: Synthesis of (S)-N-(1-(4-fluorophenyl)propyl)-2-tert-butylsulfinylimine (18-a)

1-(4-fluorophenyl)acetone (1.52 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.93 g of white solid (S)-N-(1-(4-fluorophenyl)propyl)-2-tert-butylsulfinylimine (18-a), with a yield of 76%. ESI $[M+H]^+$=256.2

Step 2: Synthesis of (S)-N-(1-(4-fluorophenyl)propyl)-2-tert-butylsulfinamide (18-b)

The (S)-N-(1-(4-fluorophenyl)propyl)-2-tert-butylsulfinylimine (1.93 g, 7.6 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.62 g of white solid (S)-N-(1-(4-fluorophenyl)propyl)-2-tert-butylsulfinamide (18-b), with a yield of 84%. ESI $[M+H]^+$=257.1

Step 3: Synthesis of (S)-1-(4-fluorophenyl)propyl-1-amine hydrochloride (18-c)

The (S)-N-(1-(4-fluorophenyl)propyl)-2-tert-butylsulfinamide (1.62 g, 6.3 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.65 g of white solid (S)-1-(4-fluorophenyl)propyl-1-amine hydrochloride (18-c), with a yield of 67%. ESI $[M+H]^+$=153.1

Step 4: Synthesis of (S)-6-(4-chlorophenyl)-N-(1-(4-fluorophenyl)n-propyl)-2-(1-methyl-1H-pyrazol-4-yl)pyrimidine-4-formamide (Compound 18)

The 6-(4-chlorophenyl)-2-(1-methyl-1H-pyrazol-4-yl)pyrimidine-4-carboxylic acid (100 mg, 0.32 mmol) and the (S)-1-(4-fluorophenyl)propyl-1-amine hydrochloride (79 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 108 mg of white solid (S)-6-(4-chlorophenyl)-N-(1-(4-fluorophenyl)$_n$-propyl)-2-(1-methyl-1H-pyrazol-4-yl)pyrimidine-4-formamide (compound 18), with a yield of 75%. $^1H$ NMR (400 MHz, DMSO-$d_6$) δ 9.14 (d, J=8.7 Hz, 1H), 8.69 (s, 1H), 8.44-8.34 (m, 3H), 8.19 (s, 1H), 7.64 (d, J=8.5 Hz, 2H), 7.52 (dd, J=8.5, 5.6 Hz, 2H), 7.19 (t, J=8.9 Hz, 2H), 5.04-4.97 (m, 1H), 3.98 (s, 3H), 1.92 (m, 2H), 0.93 (t, J=7.3 Hz, 3H). ESI $[M+H]^+$=450.2

Example 19: Synthesis of (S)-6-(4-chlorophenyl)-N-(1-cyclopropyl(4-fluorophenyl))-2-(1-methyl-1H-pyrazol-4-yl)pyrimidine-4-formamide (Compound 19)

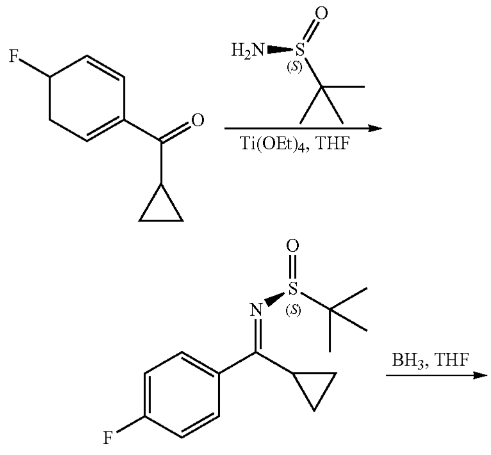

19-a

-continued

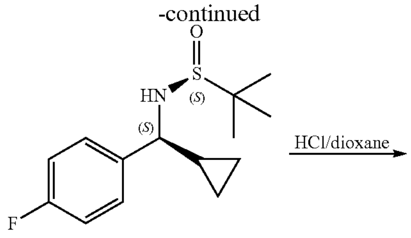

19-b

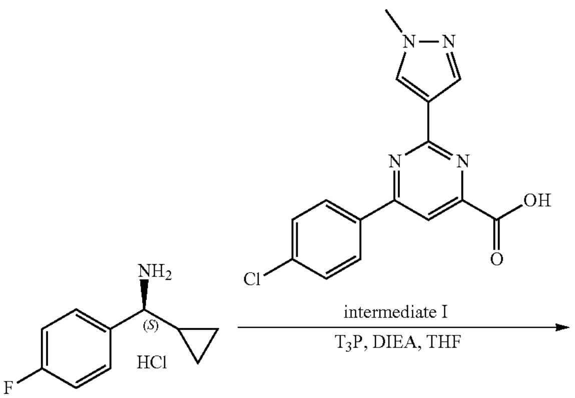

19-c

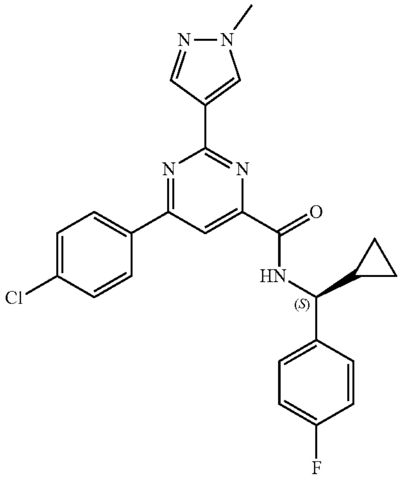
19

Step 1: Synthesis of (S)-N-(1-cyclopropyl(4-fluorophenyl))-2-tert-butylsulfinylimine (19-a)

1-cyclopropyl(4-fluorophenyl)ketone (1.64 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.83 g of white solid (S)-N-(1-cyclopropyl(4-fluorophenyl))-2-tert-butylsulfinylimine (19-a), with a yield of 68%. ESI $[M+H]^+$=268.1

Step 2: Synthesis of (S)-N-(1-cyclopropyl(4-fluorophenyl))-2-tert-butylsulfinamide (19-b)

The (S)-N-(1-cyclopropyl(4-fluorophenyl))-2-tert-butylsulfinylimine (1.83 g, 6.8 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.51 g of white solid (S)-N-(1-cyclopropyl(4-fluorophenyl))-2-tert-butylsulfinamide (19-b), with a yield of 82%. ESI $[M+H]^+=270.2$ Step 3: Synthesis of (S)-1-cyclopropyl(4-fluorophenyl)-1-amine hydrochloride (19-c)

The (S)-N-(1-cyclopropyl(4-fluorophenyl))-2-tert-butylsulfinamide (1.51 g, 5.6 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.65 g of white solid (S)-1-cyclopropyl(4-fluorophenyl)-1-amine hydrochloride (19-c), with a yield of 71%. ESI $[M+H]^+=166.1$ Step 4: Synthesis of (S)-6-(4-chlorophenyl)-N-(1-cyclopropyl(4-fluorophenyl))-2-(1-methyl-1H-pyrazol-4-yl)pyrimidine-4-formamide (Compound 19)

The 6-(4-chlorophenyl)-2-(1-methyl-1H-pyrazol-4-yl)pyrimidine-4-carboxylic acid (100 mg, 0.32 mmol) and the (S)-1-cyclopropyl(4-fluorophenyl)-1-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 104 mg of white solid (S)-6-(4-chlorophenyl)-N-(1-cyclopropyl(4-fluorophenyl))-2-(1-methyl-1H-pyrazol-4-yl)pyrimidine-4-formamide (compound 19), with a yield of 68%. $^1H$ NMR (400 MHz, DMSO-$d_6$) δ 9.44 (d, J=8.8 Hz, 1H), 8.70 (s, 1H), 8.50-8.34 (m, 3H), 8.22 (s, 1H), 7.68-7.61 (m, 2H), 7.61-7.54 (m, 2H), 7.19 (t, J=8.9 Hz, 2H), 4.42 (t, J=9.3 Hz, 1H), 3.97 (s, 3H), 1.58 (m, 1H), 0.63 (m, 2H), 0.54-0.46 (m, 1H), 0.42 (m, 1H). ESI $[M+H]^+=462.2$ Example 20: Synthesis of (S)-6-(4-chlorophenyl)-N-((S)-(5,6-difluoro-2,3-dihydro)-(−)-1-yl-2-indene)-2-(1-methyl-1H-pyrazol-4-yl)pyrimidine-4-formamide (compound 20)

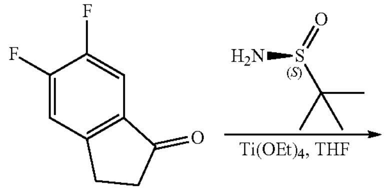

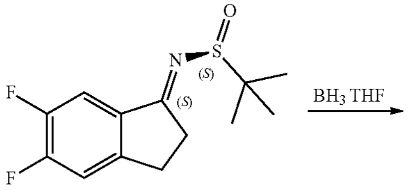

20-a

-continued

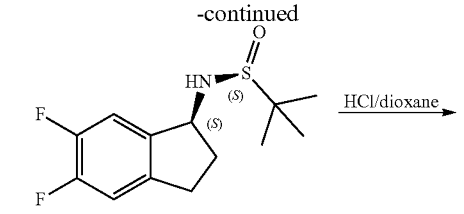

20-b

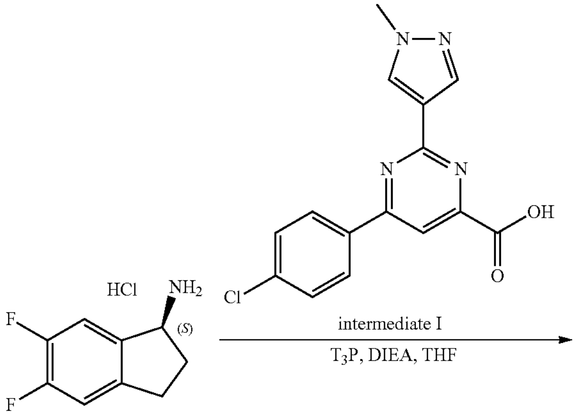

20-c

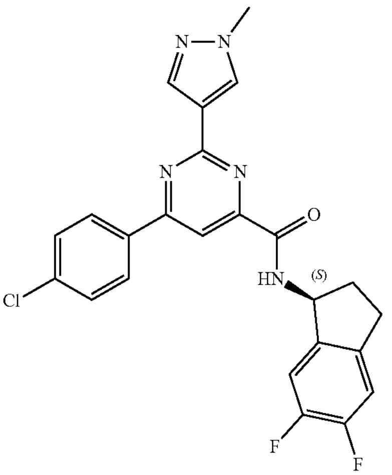

20

Step 1: Synthesis of (S)-N-(5,6-difluoro-2,3-dihydro)-(−)-1-yl-2-indene)-2-tert-butylsulfinylimine (20-a)

(5,6-difluoro-2,3-dihydro)-inden-1-one (1.68 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.12 g of white solid (S)-N-(5,6-difluoro-2,3-dihydro)-(−)-1-yl-2-indene)-2-tert-butylsulfinylimine (20-a), with a yield of 78%. ESI $[M+H]^+=272.1$ Step 2: Synthesis of (S)-N-(5,6-difluoro-2,3-dihydro)-(−)-1-yl-2-indene)-2-tert-butylsulfinamide (20-b)

The (S)-N-(5,6-difluoro-2,3-dihydro)-(−)-1-yl-2-indene)-2-tert-butylsulfinylimine (2.12 g, 7.8 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.78 g of white solid (S)-N-(5,6-difluoro-2,3-dihydro)-(−)-1-yl-2-indene)-2-tert-butylsulfinamide (20-b), with a yield of 84%. ESI $[M+H]^+$=273.2

Step 3: Synthesis of (S)-N-(5,6-difluoro-2,3-dihydro)-(−)-1-yl-2-indene-2-amine hydrochloride (20-c)

The (S)-N-(5,6-difluoro-2,3-dihydro)-(−)-1-yl-2-indene)-2-tert-butylsulfinamide (1.78 g, 6.5 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.71 g of white solid (S)-N-(5,6-difluoro-2,3-dihydro)-(−)-1-yl-2-indene-2-amine hydrochloride (20-c), with a yield of 64%. ESI $[M+H]^+$ =170.1

Step 4: Synthesis of (S)-6-(4-chlorophenyl)-N-((S)-(5,6-difluoro-2,3-dihydro)-(−)-1-yl-2-indene)-2-(1-methyl-1H-pyrazol-4-yl)pyrimidine-4-formamide (Compound 20)

The 6-(4-chlorophenyl)-2-(1-methyl-1H-pyrazol-4-yl)pyrimidine-4-carboxylic acid (100 mg, 0.32 mmol) and the (S)-N-(5,6-difluoro-2,3-dihydro)-(−)-1-yl-2-indene-2-amine hydrochloride (86 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 104 mg of white solid (S)-6-(4-chlorophenyl)-N-((S)-(5,6-difluoro-2,3-dihydro)-(−)-1-yl-2-indene)-2-(1-methyl-1H-pyrazol-4-yl)pyrimidine-4-formamide (compound 20), with a yield of 71%. $^1H$ NMR (400 MHz, DMSO-$d_6$) δ 9.33 (d, J=8.8 Hz, 1H), 8.67 (s, 1H), 8.45-8.36 (m, 3H), 8.29 (s, 1H), 7.69-7.62 (m, 2H), 7.39 (dd, J=10.7, 7.5 Hz, 1H), 7.29-7.20 (m, 1H), 5.62 (q, J=8.4 Hz, 1H), 3.93 (s, 3H), 3.08-2.98 (m, 1H), 2.89 (dt, J=16.1, 8.7 Hz, 1H), 2.32-2.18 (m, 1H), 1.23 (d, J=3.1 Hz, 1H). ESI $[M+H]^+$=466.1

Example 21: Synthesis of (S)-6-(4-chlorophenyl)-N-((S)-(6-fluoro-2,3-dihydro)-(−)-1-yl-2-indene)-2-(1-methyl-1H-pyrazol-4-yl)pyrimidine-4-formamide (Compound 21)

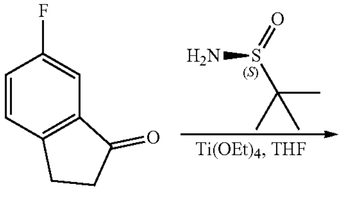

-continued

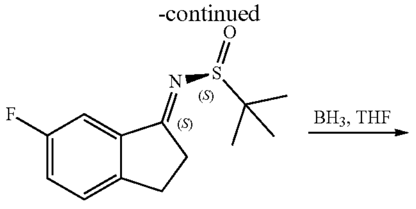

21-a

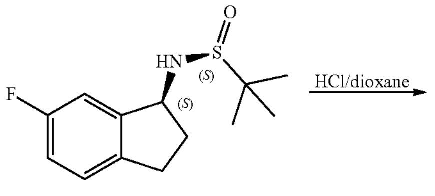

21-b

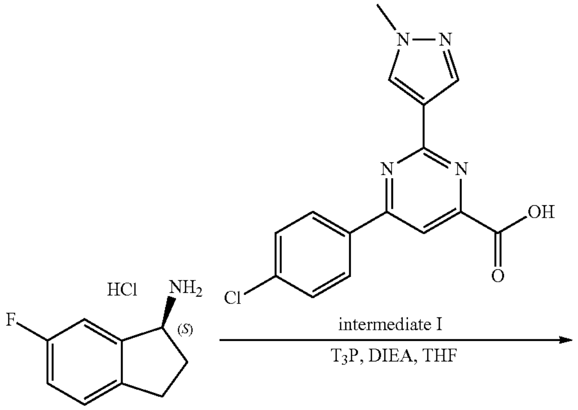

21-c

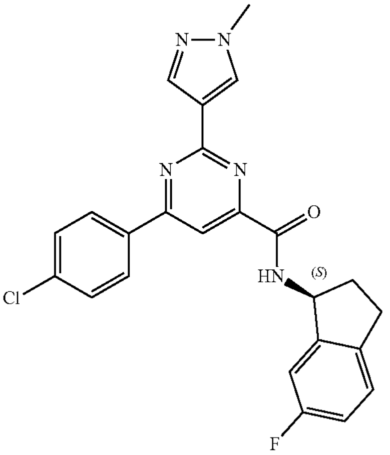

21

Step 1: Synthesis of (S)-N-(6-fluoro-2,3-dihydro)-(−)-1-yl-2-indene)-2-tert-butylsulfinylimine (21-a)

(6-fluoro-2,3-dihydro)-inden-1-one (1.50 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.02 g of white solid (S)-N-(6- fluoro-2,3-dihydro)-(−)-1-yl-2-indene)-2-tert-butylsulfinylimine (21-a), with a yield of 80%. ESI $[M+H]^+$=254.1

Step 2: Synthesis of(S)-N-(6-fluoro-2,3-dihydro)-(−)-1-yl-2-indene)-2-tert-butylsulfinamide (21-b)

The (S)-N-(6-fluoro-2,3-dihydro)-(−)-1-yl-2-indene)-2-tert-butylsulfinylimine (2.02 g, 8.0 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.68 g of white solid (S)-N-(6-fluoro-2,3-dihydro)-(−)-1-yl-2-indene)-2-tert-butylsulfinamide (21-b), with a yield of 83%. ESI $[M+H]^+$=256.2

Step 3: Synthesis of (S)-N-(6-fluoro-2,3-dihydro)-(−)-1-yl-2-indene-2-amine hydrochloride (21-c)

The (S)-N-(6-fluoro-2,3-dihydro)-(−)-1-yl-2-indene)-2-tert-butylsulfinamide (1.68 g, 6.6 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.69 g of white solid (S)-N-(6-fluoro-2,3-dihydro)-(−)-1-yl-2-indene-2-amine hydrochloride (21-c), with a yield of 69%. ESI $[M+H]^+$ =152.1

Step 4: Synthesis of (S)-6-(4-chlorophenyl)-N-((S)-(6-fluoro-2,3-dihydro)-(−)-1-yl-2-indene)-2-(1-methyl-1H-pyrazol-4-yl)pyrimidine-4-formamide (Compound 21)

The 6-(4-chlorophenyl)-2-(1-methyl-1H-pyrazol-4-yl)pyrimidine-4-carboxylic acid (100 mg, 0.32 mmol) and the (S)-N-(6-fluoro-2,3-dihydro)-(−)-1-yl-2-indene-2-amine hydrochloride (86 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 104 mg of white solid (S)-6-(4-chlorophenyl)-N-((S)-(6-fluoro-2,3-dihydro)-(−)-1-yl-2-indene)-2-(1-methyl-1H-pyrazol-4-yl)pyrimidine-4-formamide (compound 21), with a yield of 71%. $^1H$ NMR (400 MHz, DMSO-$d_6$) δ 9.35 (d, J=8.9 Hz, 1H), 8.68 (s, 1H), 8.45-8.36 (m, 3H), 8.29 (s, 1H), 7.69-7.62 (m, 2H), 7.32 (dd, J=8.2, 5.2 Hz, 1H), 7.11-7.03 (m, 1H), 7.01 (d, J=9.0 Hz, 1H), 5.65 (q, J=8.6 Hz, 1H), 3.93 (s, 3H), 3.01 (dd, J=15.8, 8.8 Hz, 1H), 2.88 (dt, J=16.2, 8.5 Hz, 1H), 2.53-2.39 (m, 1H), 2.33-2.19 (m, 1H). ESI $[M+H]^+$=448.1

Example 22: Synthesis of (S)-6-(4-chlorophenyl)-N-(1-[1-(4-chlorophenyl)cyclopropyl]methyl)-2-(1-methyl-1H-pyrazol-4-yl)pyrimidine-4-formamide (Compound 22)

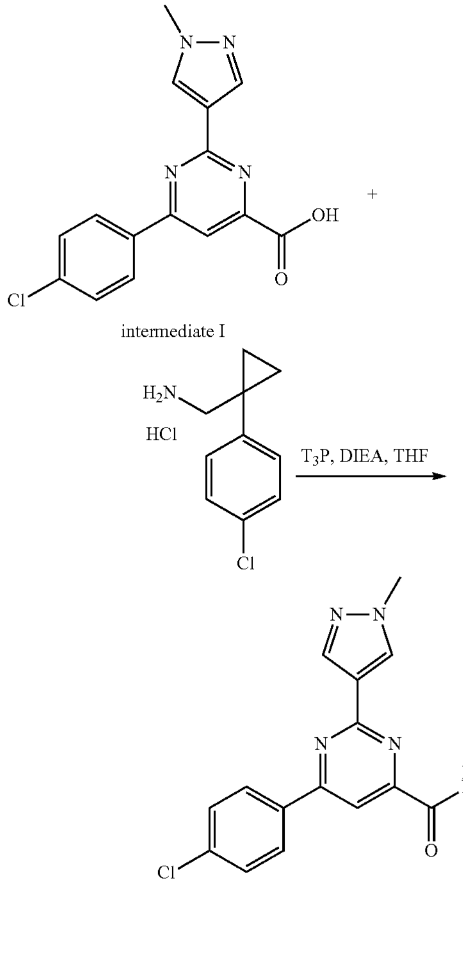

22

Step 1: Synthesis of (S)-6-(4-chlorophenyl)-N-(1-[1-(4-chlorophenyl)cyclopropyl]methyl)-2-(1-methyl-1H-pyrazol-4-yl)pyrimidine-4-formamide (Compound 22)

The 6-(4-chlorophenyl)-2-(1-methyl-1H-pyrazol-4-yl)pyrimidine-4-carboxylic acid (100 mg, 0.32 mmol) and 1-[1-(4-chlorophenyl)cyclopropyl]methylamine hydrochloride (86 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 119 mg of white solid (S)-6-(4-chlorophenyl)-N-(1-[1-(4-chlorophenyl)cyclopropyl]methyl)-2-(1-methyl-1H-pyrazol-4-yl)pyrimidine-4-formamide (compound 22), with a yield of 80%. $^1H$ NMR (400 MHz, DMSO-$d_6$) δ 8.88 (t, J=6.3 Hz, 1H), 8.60 (s, 1H), 8.41-8.33 (m, 2H), 8.29 (s, 1H), 8.17 (s, 1H), 7.67-7.59 (m, 2H), 7.42-7.36 (m, 2H), 7.36-7.29 (m, 2H), 3.96 (s, 3H), 3.64 (d, J=6.3 Hz, 2H), 1.06 (t, J=3.1 Hz, 2H), 0.82 (q, J=4.4 Hz, 2H). ESI $[M+H]^+$=478.1

Example 23: Synthesis of (S)-6-(4-chlorophenyl)-N-((S)-5,6,7,8-tetrahydro-6H-quinol-5-yl)-2-(1-methyl-1H-pyrazol-4-yl)pyrimidine-4-formamide (Compound 23)

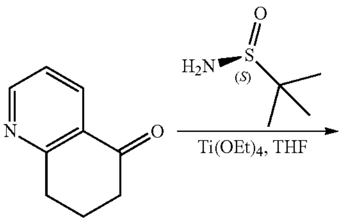

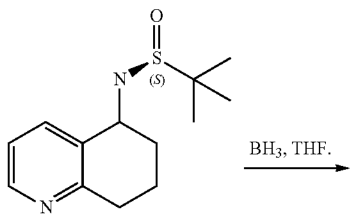

23-a

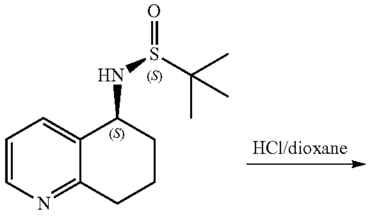

23-b

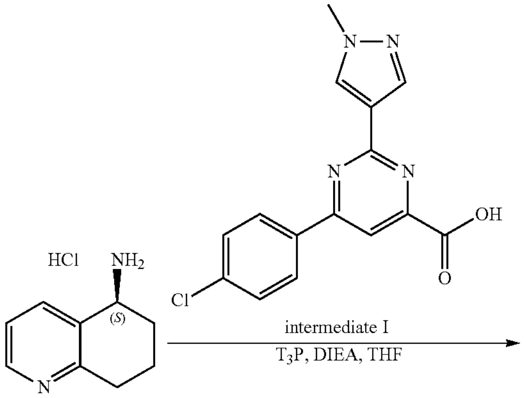

23-c

-continued

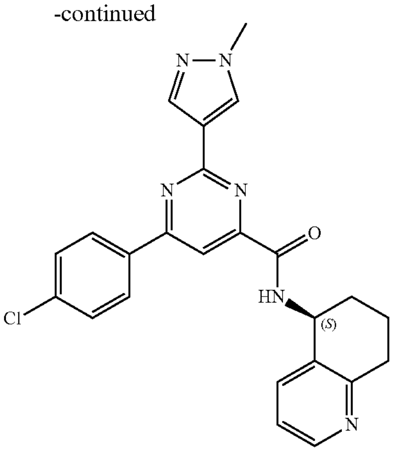

23

Step 1: Synthesis of (S)-N-(7,8-dihydro-6H-quinoline)-5-tert-butylsulfinylimine (23-a)

7,8-dihydro-6H-quinolin-5-one (1.47 g, 10 mmol) was dissolved in 50 mL of dry tetrahydrofuran, (L)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.42 g of gray solid (S)-N-(7,8-dihydro-6H-quinoline)-5-tert-butylsulfinylimine (23-a), with a yield of 57%. ESI $[M+H]^+$=251.1

Step 2: Synthesis of (S)-N-(5,6,7,8-tetrahydro-6H-quinoline)-5-tert-butylsulfinamide (23-b)

The (S)-N-(7,8-dihydro-6H-quinoline)-5-tert-butylsulfinylimine (1.42 g, 5.7 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.03 g of gray solid (S)-N-(5,6,7,8-tetrahydro-6H-quinoline)-5-tert-butylsulfinamide (23-b), with a yield of 72%. ESI $[M+H]^+$=252.2

Step 3: Synthesis of (S)-(5,6,7,8-tetrahydro-6H-quinoline)-5-amine hydrochloride (23-c)

The (S)-N-(5,6,7,8-tetrahydro-6H-quinoline)-5-tert-butylsulfinamide was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.35 g of gray solid (S)-(5,6,7,8-tetrahydro-6H-quinoline)-5-amine hydrochloride (23-c), with a yield of 60%. ESI $[M+H]^+$=149.1

Step 4: Synthesis of (S)-6-(4-chlorophenyl)-N-(S)-5,6,7,8-tetrahydro-6H-quinol-5-yl)-2-(1-methyl-1H-pyrazol-4-yl)pyrimidine-4-formamide (Compound 23)

The 6-(4-chlorophenyl)-2-(1-methyl-1H-pyrazol-4-yl)pyrimidine-4-carboxylic acid (100 mg, 0.32 mmol and the (S)-(5,6,7,8-tetrahydro-6H-quinoline)-5-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 120 mg of white solid (S)-6-(4-chlorophenyl)-N-(S)-5,6,7,8-tetrahydro-6H-quinol-5-yl)-2-(1-methyl-1H-pyrazol-4-yl)pyrimidine-4-formamide (compound 23), with a yield of 83%. $^1$H NMR (400 MHz, DMSO-$d_6$) δ 9.36 (d, J=9.3 Hz, 1H), 8.66 (s, 1H), 8.44-8.35 (m, 4H), 8.30 (s, 1H), 7.74-7.63 (m, 2H), 7.57 (d, J=7.8 Hz, 1H), 7.19 (dd, J=7.8, 4.7 Hz, 1H), 5.38 (q, J=8.4 Hz, 1H), 3.92 (s, 3H), 2.92 (m, 2H), 2.08 (m, 2H), 1.90 (m, 1H), 1.64 (m, 1H). ESI $[M+H]^+$=445.1

Example 24: Synthesis of (S)-6-(4-chlorophenyl)-N-(1-(o-trifluoromethylphenyl)ethyl)-2-(1-methyl-1H-pyrazol-4-yl)pyrimidine-4-formamide (Compound 24)

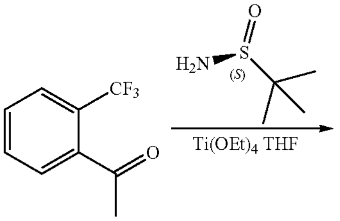

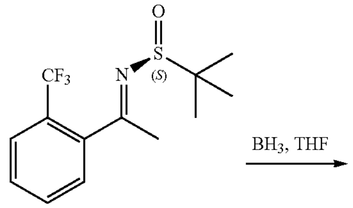

24-a

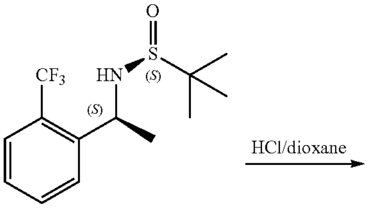

24-b

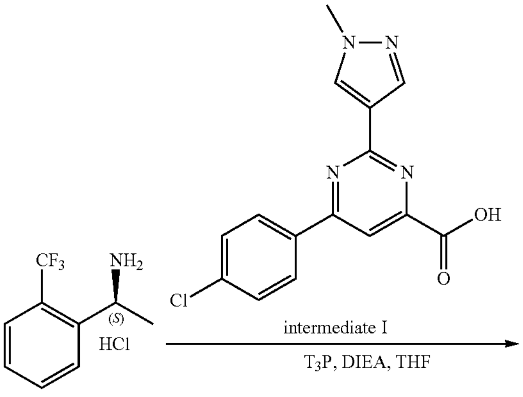

24-c

-continued

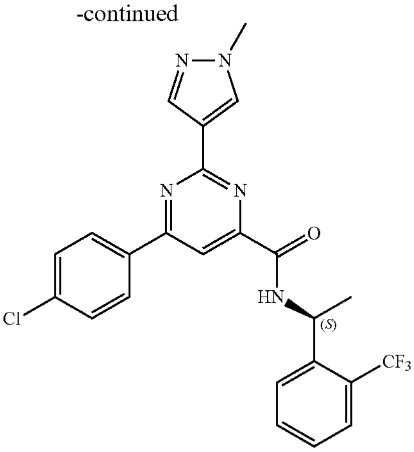

24

Step 1: Synthesis of (S)-N-(1-(o-trifluoromethylphenyl)ethyl)-2-tert-butylsulfinylimine (24-a)

O-trifluoromethylacetophenone (1.88 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 2.01 g of white solid (S)-N-(1-(o-trifluoromethylphenyl)ethyl)-2-tert-butylsulfinylimine (24-a), with a yield of 69%. ESI $[M+H]^+$=292.1

Step 2: Synthesis of (S)-N-(1-(o-trifluoromethylphenyl)ethyl)-2-tert-butylsulfinamide (24-b)

The (S)-N-(1-(o-trifluoromethylphenyl)ethyl)-2-tert-butylsulfinylimine (2.01 g, 6.9 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.53 g of white solid (S)-N-(1-(o-trifluoromethylphenyl)ethyl)-2-tert-butylsulfinamide (24-b), with a yield of 76%. ESI $[M+H]^+$=293.1

Step 3: Synthesis of (S)-1-(o-trifluoromethylphenyl)ethan-1-amine hydrochloride (24-c)

The (S)-N-(1-(o-trifluoromethylphenyl)ethyl)-2-tert-butylsulfinamide (1.53 g, 5.2 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. The solution was concentrated after the reaction, the solid was washed twice with ethyl acetate and twice with petroleum ether, and the solid was dried to obtain 0.65 g of white solid (S)-1-(o-trifluoromethylphenyl)ethan-1-amine hydrochloride (24-c), with a yield of 66%. ESI $[M+H]^+$=190.2

Step 4: Synthesis of(S)-6-(4-chlorophenyl)-N-(1-(o-trifluoromethylphenyl)ethyl)-2-(1-methyl-1H-pyrazol-4-yl)pyrimidine-4-formamide (Compound 24)

The 6-(4-chlorophenyl)-2-(1-methyl-1H-pyrazol-4-yl)pyrimidine-4-carboxylic acid (100 mg, 0.32 mmol) and the (S)-1-(o-trifluoromethylphenyl)ethan-1-amine hydrochloride were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 124 mg of white solid (S)-6-(4-chlorophenyl)-N-(1-(o-trifluoromethylphenyl)ethyl)-2-(1-methyl-1H-pyrazol-4-yl)pyrimidine-4-formamide (compound 24), with a yield of 83%. $^1$H NMR (400 MHz, DMSO-$d_6$) δ 9.26 (d, J=8.6 Hz, 1H), 8.69 (s, 1H), 8.47-8.34 (m, 3H), 8.21 (s, 1H), 7.68-7.58 (m, 2H), 7.40 (m, 1H), 7.35-7.27 (m, 2H), 7.15-7.04 (m, 1H), 5.29 (p, J=7.2 Hz, 1H), 3.97 (s, 3H), 1.61 (d, J=7.0 Hz, 3H). ESI $[M+H]^+$=486.1

Example 25: Synthesis of (S)-6-(4-chlorophenyl)-N-((S)-(3,3-dimethyl-2,3-dihydro)-(−)-1-yl-2-indene)-2-(1-methyl-1H-pyrazol-4-yl)pyrimidine-4-formamide (compound 25)

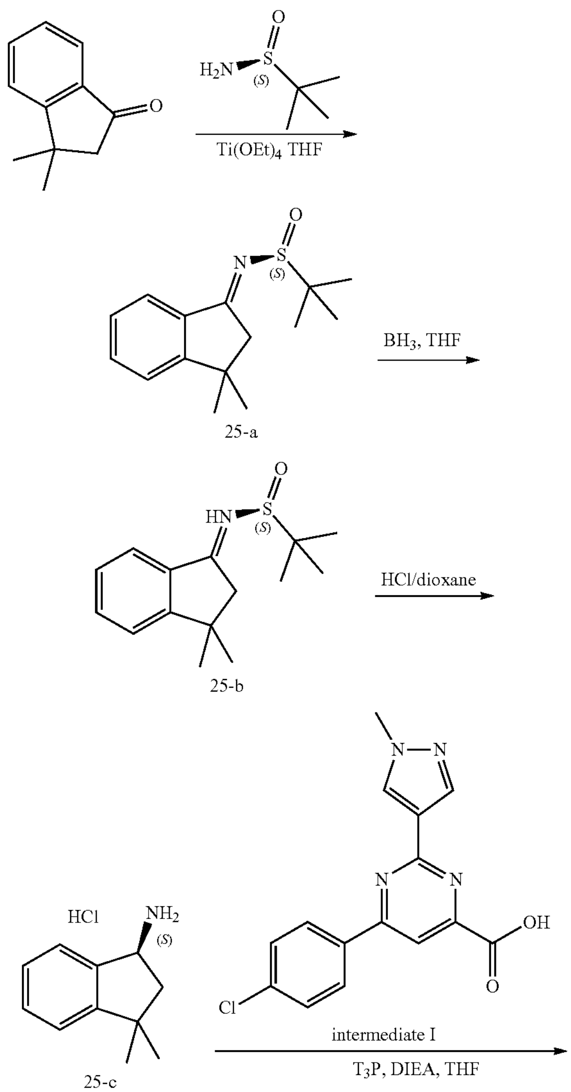

25-a 25-b 25-c

-continued

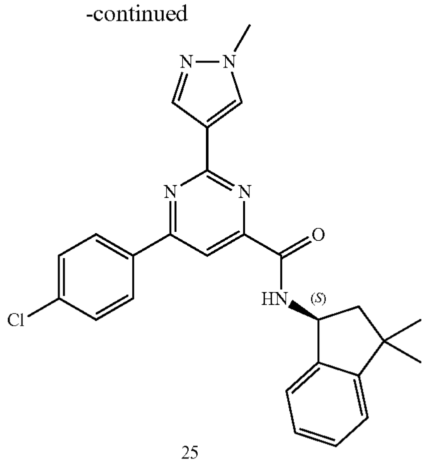

25

Step 1: Synthesis of (S)-N-(3,3-dimethyl-2,3-dihydro)-(−)-1-yl-2-indene)-2-tert-butylsulfinylimine (25-a)

(3,3-dimethyl-2,3-dihydro)-inden-1-one (1.60 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.96 g of white solid (S)-N-(3,3-dimethyl-2,3-dihydro)-(−)-1-yl-2-indene)-2-tert-butylsulfinylimine (25-a), with a yield of 74%. ESI $[M+H]^+$ =263.1

Step 2: Synthesis of(S)-N-(3,3-dimethyl-2,3-dihydro)-(−)-1-yl-2-indene)-2-tert-butylsulfinamide (25-b)

The (S)-N-(3,3-dimethyl-2,3-dihydro)-(−)-1-yl-2-indene)-2-tert-butylsulfinylimine (1.96 g, 7.4 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.52 g of white solid (S)-N-(3,3-dimethyl-2,3-dihydro)-(−)-1-yl-2-indene)-2-tert-butylsulfinamide (25-b), with a yield of 79%. ESI $[M+H]^+$=265.2

Step 3: Synthesis of (S)-N-(3,3-dimethyl-2,3-dihydro)-(−)-1-yl-2-indene-2-amine hydrochloride (25-c)

The (S)-N-(3,3-dimethyl-2,3-dihydro)-(−)-1-yl-2-indene)-2-tert-butylsulfinamide (1.52 g, 5.7 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with methyl acetate and twice with petroleum ether, and the solid was dried to obtain 0.59 g of white solid (S)-N-(3,3-dimethyl-2,3-dihydro)-(−)-1-yl-2-indene-2-amine hydrochloride (25-c), with a yield of 64%. ESI $[M+H]^+$=161.1

Step 4: Synthesis of (S)-6-(4-chlorophenyl)-N-((S)-(3,3-dimethyl-2,3-dihydro)-(−)-1-yl-2-indene)-2-(1-methyl-1H-pyrazol-4-yl)pyrimidine-4-formamide (Compound 25)

The 6-(4-chlorophenyl)-2-(1-methyl-1H-pyrazol-4-yl)pyrimidine-4-carboxylic acid (100 mg, 0.32 mmol) and the (S)-N-(3,3-dimethyl-2,3-dihydro)-(−)-1-yl-2-indene-2-amine hydrochloride (86 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 104 mg of white solid (S)-6-(4-chlorophenyl)-N-((S)-(3,3-dimethyl-2,3-dihydro)-(−)-1-yl-2-indene)-2-(1-methyl-1H-pyrazol-4-yl)pyrimidine-4-formamide (compound 25), with a yield of 71%. $^1$H NMR (400 MHz, DMSO-$d_6$) δ 9.26 (d, J=9.1 Hz, 1H), 8.67 (s, 1H), 8.45-8.36 (m, 3H), 8.31 (s, 1H), 7.69-7.62 (m, 2H), 7.33-7.25 (m, 2H), 7.25-7.13 (m, 2H), 5.73 (q, J=8.8 Hz, 1H), 3.92 (s, 3H), 2.31 (dd, J=12.0, 7.4 Hz, 1H), 2.21 (dd, J=12.0, 9.9 Hz, 1H), 1.45 (s, 3H), 1.23 (s, 3H). ESI $[M+H]^+$ =458.2

Example 26: Synthesis of (S)-6-(4-chlorophenyl)-N-(1-(3-fluorophenyl)ethyl)-2-(1-methyl-1H-pyrazol-4-yl)pyrimidine-4-formamide (Compound 26)

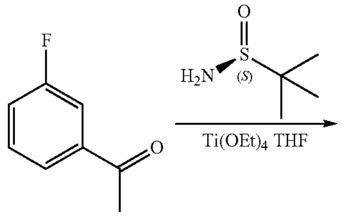

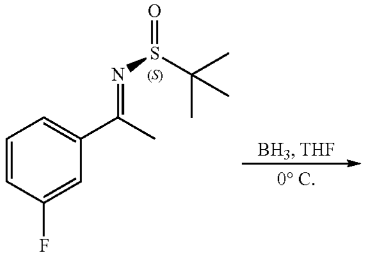

26-a

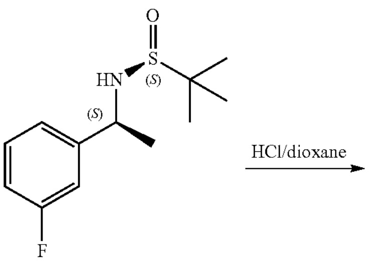

26-b

-continued

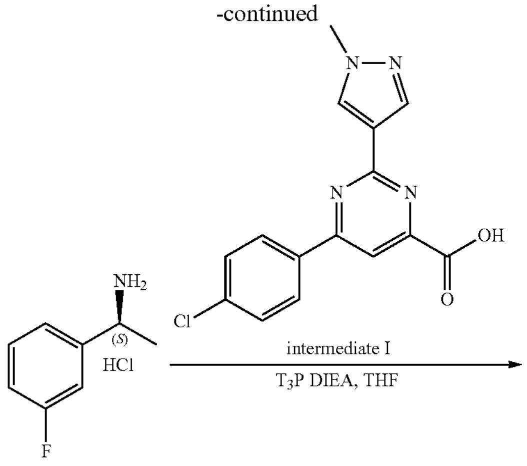

26-c

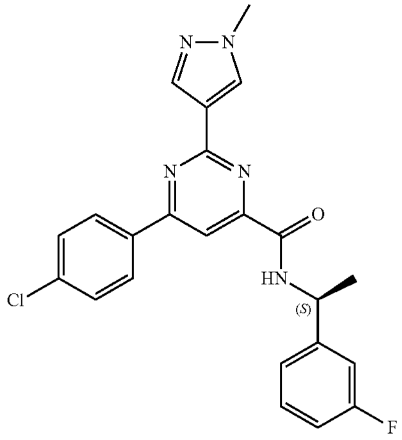

26

Step 1: Synthesis of (S)-N-(1-(3-fluorophenyl)ethyl)-2-tert-butylsulfinylimine (26-a)

1-(3-fluorophenyl)ethanone (1.38 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.62 g of white solid (S)-N-(1-(3-fluorophenyl)ethyl)-2-tert-butylsulfinylimine (26-a), with a yield of 67%. ESI $[M+H]^+$=242.1

Step 2: Synthesis of (S)-N-(1-(3-fluorophenyl)ethyl)-2-tert-butylsulfinamide (26-b)

The (S)-N-(1-(3-fluorophenyl)ethyl)-2-tert-butylsulfinylimine (1.62 g, 6.7 mmol) was dissolved in 80 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was purified by a straight-phase column chromatography to obtain 1.22 g of white solid (S)-N-(1-(3-fluorophenyl)ethyl)-2-tert-butylsulfinamide (26-b), with a yield of 75%. ESI $[M+H]^+$=243.2

Step 3: Synthesis of (S)-1-(3-fluorophenyl)ethan-1-amine hydrochloride (26-c)

The (S)-N-(1-(3-fluorophenyl)ethyl)-2-tert-butylsulfinamide (1.22 g, 5.1 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. The solution was concentrated after the reaction, the solid was washed twice with ethyl acetate and twice with petroleum ether, and the solid was dried to obtain 0.39 g of white solid (S)-1-(3-fluorophenyl)ethan-1-amine hydrochloride (26-c), with a yield of 55%. ESI $[M+H]^+$=140.1

Step 4: Synthesis of (S)-6-(4-chlorophenyl)-N-(1-(3-fluorophenyl)ethyl)-2-(1-methyl-1H-pyrazol-4-yl) pyrimidine-4-formamide (compound 26)

The 6-(4-chlorophenyl)-2-(1-methyl-1H-pyrazol-4-yl)pyrimidine-4-carboxylic acid (100 mg, 0.32 mmol) and the (S)-1-(3-fluorophenyl)ethan-1-amine hydrochloride (88 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The crude product was separated by straight-phase column chromatography to obtain 124 mg of white solid (S)-6-(4-chlorophenyl)-N-(1-(3-fluorophenyl)ethyl)-2-(1-methyl-1H-pyrazol-4-yl)pyrimidine-4-formamide (compound 26), with a yield of 83%. $^1$H NMR (400 MHz, DMSO-$d_6$) δ 9.34 (d, J=7.8 Hz, 1H), 8.71 (s, 1H), 8.45 (s, 1H), 8.41-8.33 (m, 2H), 8.18 (s, 1H), 7.98 (d, J=8.0 Hz, 1H), 7.72 (t, J=8.1 Hz, 2H), 7.67-7.59 (m, 2H), 7.48 (t, J=7.6 Hz, 1H), 5.55 (p, J=7.1 Hz, 1H), 3.98 (s, 3H), 1.60 (d, J=6.9 Hz, 3H). ESI $[M+H]^+$ =436.1

Example 27: Synthesis of (S)-6-(4-trifluoromethoxyphenyl)-N-((S)-6,7-dihydro-5H-cyclopentano[B]pyridin-5-yl)-2-(3-pyridyl)pyrimidine-4-formamide (compound 27)

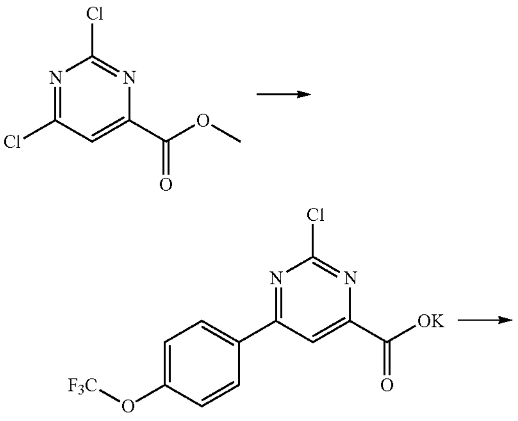

27-a

-continued

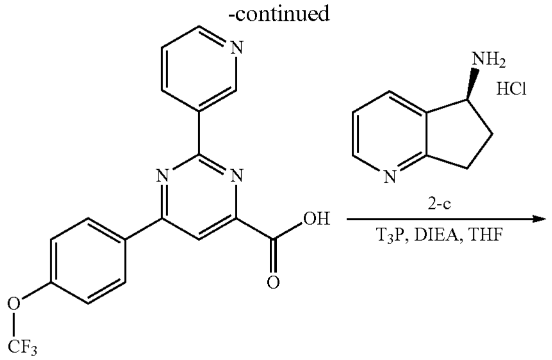

27-b

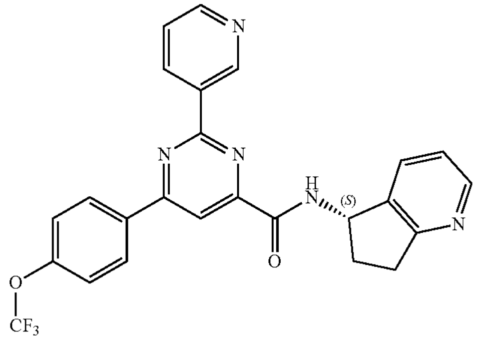

27

Step 1: Synthesis of potassium 2-chloro-6-(4-trifluoromethoxyphenyl)pyrimidine-4-carboxylate (27-a)

4-trifluoromethoxyphenylboronic acid (1.56 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.41 g of gray solid potassium 2-chloro-6-(4-trifluoromethoxyphenyl)pyrimidine-4-carboxylate (27-a), with a yield of 44%. ESI $[M+H]^+$ =319.2

Step 2: Synthesis of 6-(4-trifluoromethoxyphenyl)-2-(3-pyridyl)pyrimidine-4-carboxylic acid (27-b)

3-pyridylboronic acid (738 mg, 6.0 mmol) and potassium 2-chloro-6-(4-trifluoromethoxyphenyl)pyrimidine-4-carboxylate (1.41 g, 4.4 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 420 mg of white solid 6-(4-trifluoromethoxyphenyl)-2-(3-pyridyl)pyrimidine-4-carboxylic acid (27-b), with a yield of 26%. ESI $[M+H]^+$=362.2

Step 3: Synthesis of (S)-6-(4-trifluoromethoxyphenyl)-N-((S)-6,7-dihydro-5H-cyclopentano[B]pyridin-5-yl)-2-(3-pyridyl)pyrimidine-4-formamide (compound 27)

The 6-(4-trifluoromethoxyphenyl)-2-(3-pyridyl)pyrimidine-4-carboxylic acid (116 mg, 0.32 mmol) and (S)-(6,7-dihydro-5H-cyclopentano[B]pyridine)-5-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 51 mg of white solid (S)-6-(4-trifluoromethoxyphenyl)-N-((S)-6,7-dihydro-5H-cyclopentano[B]pyridin-5-yl)-2-(3-pyridyl)pyrimidine-4-formamide (compound 27), with a yield of 33%. $^1$H NMR (400 MHz, DMSO-d6) δ 9.93 (d, J=2.2 Hz, 1H), 9.71 (d, J=8.9 Hz, 1H), 9.06 (dt, J=8.1, 1.9 Hz, 1H), 8.77 (dd, J=4.8, 1.7 Hz, 1H), 8.65-8.57 (m, 2H), 8.56 (s, 1H), 8.45-8.39 (m, 1H), 7.61 (m, 4H), 7.21 (dd, J=7.7, 4.9 Hz, 1H), 5.74 (q, J=8.5 Hz, 1H), 3.14-2.96 (m, 2H), 2.57 (m, 1H), 2.33-2.20 (m, 1H). ESI $[M+H]^+$=478.2

Example 28: Synthesis of (S)-6-(4-chlorophenyl)-N-(5-cyano-(2,3-dihydro)-(−)-1-yl-2-indene)-2-(1-methyl-1H-pyrazol-4-yl)pyrimidine-4-formamide (compound 28)

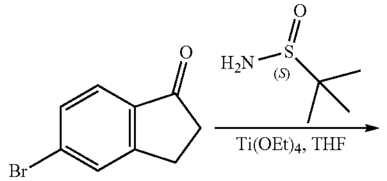

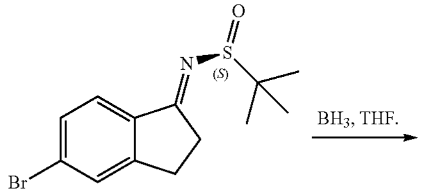

28-a

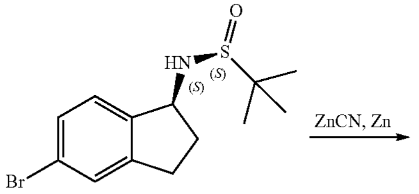

28-b

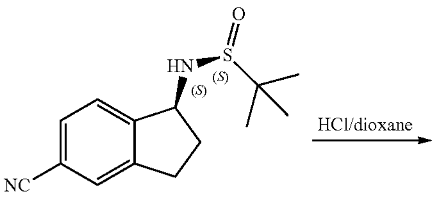

28-c

-continued

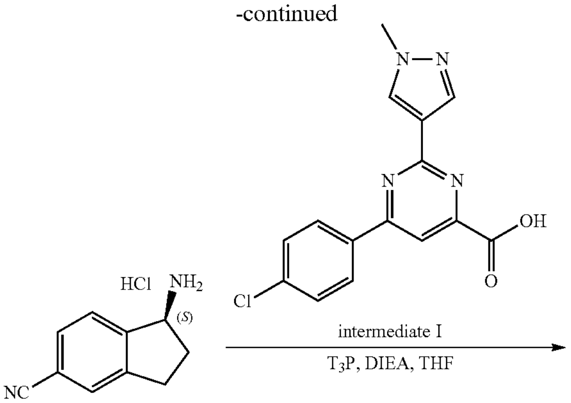

28-d

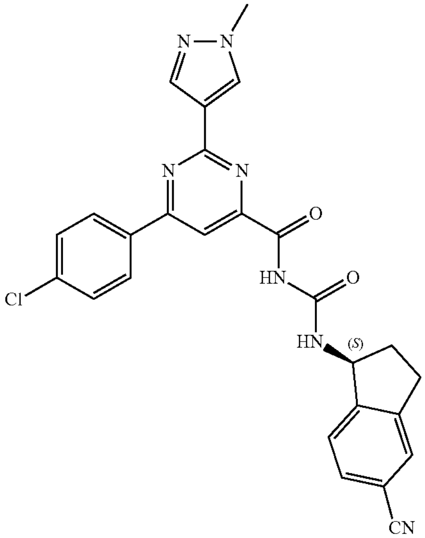

28

Step 1: Synthesis of (S)-N-(5-bromo-2,3-dihydro)-(−)-1-yl-2-indene)-2-tert-butylsulfinylimine (28-a)

(5-bromo-2,3-dihydro)-inden-1-one (2.10 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.10 g of white solid (S)-N-(5-bromo-2,3-dihydro)-(−)-1-yl-2-indene)-2-tert-butylsulfinylimine (28-a), with a yield of 35%. ESI $[M+H]^+$=314.1

Step 2: Synthesis of (S)-N-(5-bromo-2,3-dihydro)-(−)-1-yl-2-indene)-2-tert-butylsulfinamide (28-b)

The (S)-N-(5-bromo-2,3-dihydro)-(−)-1-yl-2-indene)-2-tert-butylsulfinylimine (1.10 g, 3.5 mmol) was dissolved in 80 mL of dry tetrahydrofuran, a tetrahydrofuran solution of 1 M borane (7.0 mL, 7.0 mmol) was added at 0° C., the solution was stirred at room temperature for 2 h, methanol was added for quenching after reaction was completed, and the organic phase was purified by a straight-phase column chromatography to obtain 0.86 g of white solid (S)-N-(5- bromo-2,3-dihydro)-(−)-1-yl-2-indene)-2-tert-butylsulfinamide (28-b), with a yield of 78%. ESI $[M+H]^+$=316.2

Step 3: Synthesis of (S)-N-(5-cyano-2,3-dihydro)-(−)-1-yl-2-indene)-2-tert-butylsulfinamide (28-c)

The (S)-N-(5-bromo-2,3-dihydro)-(−)-1-yl-2-indene)-2-tert-butylsulfinamide (0.86 g, 2.7 mmol) was dissolved in 30 mL of dry DMF; zinc powder (175 mg, 2.7 mmol), zinc cyanide (245 mg, 2.7 mmol), and [1,1'-bis(diphenylphosphine)ferrocene]palladium dichloride (II) dichloromethane complex (243 mg, 0.3 mmol) were sequentially added; the solution was stirred at 120° C. for 4 h, ethyl acetate/water was added for extraction after reaction was completed, and the organic phase was dried in vacuum and then purified by a straight-phase column chromatography to obtain 0.53 g of white solid (S)-N-(5-cyano-2,3-dihydro)-(−)-1-yl-2-indene)-2-tert-butylsulfinamide (28-c), with a yield of 74%. ESI $[M+H]^+$=263.2

Step 4: Synthesis of (S)-N-(5-cyano-2,3-dihydro)-(−)-1-yl-2-indene-2-amine hydrochloride (28-d)

The (S)-N-(5-cyano-2,3-dihydro)-(−)-1-yl-2-indene)-2-tert-butylsulfinamide (0.53 g, 2.0 mmol) was dissolved in 30 mL of tetrahydrofuran, a 1,4-dioxane solution of 4 M hydrochloric acid (2.4 mL, 9.6 mmol) was added, and reaction occurred at room temperature with stirring for 3 h. The solution was concentrated after the reaction, the solid was washed twice with methyl acetate and twice with petroleum ether, and the solid was dried to obtain 0.23 g of white solid (S)-N-(5-cyano-2,3-dihydro)-(−)-1-yl-2-indene-2-amine hydrochloride (28-d), with a yield of 59%. ESI $[M+H]^+$=159.1

Step 5: Synthesis of (S)-6-(4-chlorophenyl)-N-((S)-(5-cyano-2,3-dihydro)-(−)-1-yl-2-indene)-2-(1-methyl-1H-pyrazol-4-yl)pyrimidine-4-formamide (compound 28)

The 6-(4-chlorophenyl)-2-(1-methyl-1H-pyrazol-4-yl)pyrimidine-4-carboxylic acid (100 mg, 0.32 mmol) and the (S)-N-(5-cyano-2,3-dihydro)-(−)-1-yl-2-indene-2-amine hydrochloride (81 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The reaction solution was dried in vacuum and then separated by straight-phase column chromatography to obtain 102 mg of white solid (S)-6-(4-chlorophenyl)-N-((S)-(5-cyano-2,3-dihydro)-(−)-1-yl-2-indene)-2-(1-methyl-1H-pyrazol-4-yl)pyrimidine-4-formamide (compound 28), with a yield of 71%. $^1$H NMR (400 MHz, DMSO-d6) δ 9.43 (d, J=8.9 Hz, 1H), 8.66 (s, 1H), 8.45-8.36 (m, 3H), 8.29 (s, 1H), 7.79 (s, 1H), 7.66 (dq, J=9.4, 2.7, 2.2 Hz, 3H), 7.40 (d, J=7.8 Hz, 1H), 5.71 (q, J=8.8 Hz, 1H), 3.93 (s, 3H), 3.09 (dd, J=16.1, 8.7 Hz, 1H), 3.04-2.87 (m, 1H), 2.57-2.53 (m, 1H), 2.27 (dd, J=12.4, 9.3 Hz, 1H). ESI $[M+H]^+$=455.2

Example 29: Synthesis of (S)-6-(4-chlorophenyl)-N-(1-(3-chloro-4-methoxyphenyl)ethyl)-2-(1-methyl-1H-pyrazol-4-yl)pyrimidine-4-formamide (compound 29)

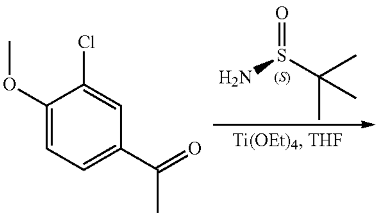

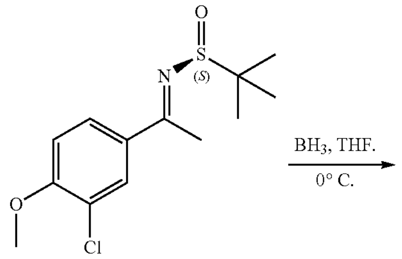

29-a

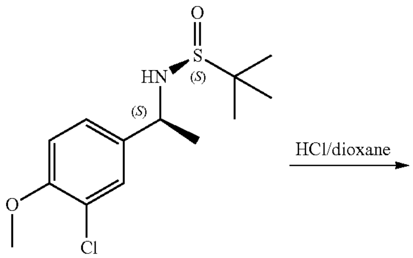

29-b

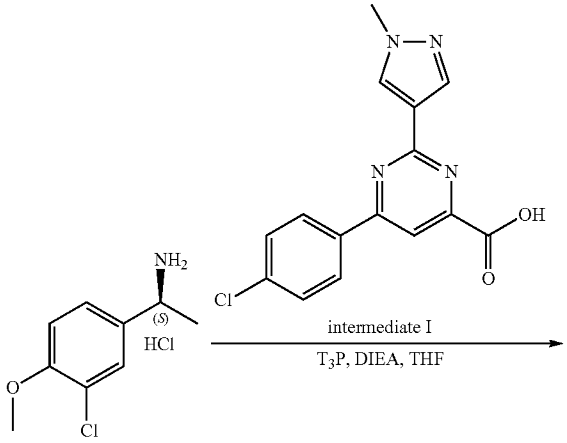

29-c

-continued

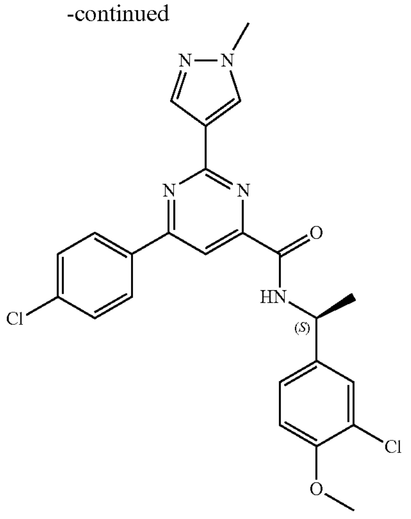

29

Step 1: Synthesis of (S)-N-(1-(3-chloro-4-methoxyphenyl)ethyl)-2-tert-butylsulfinylimine (29-a)

1-(3-chloro-4-methoxyphenyl)ethanone (1.84 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was dried in vacuum and then purified by a straight-phase column chromatography to obtain 1.72 g of white solid (S)-N-(1-(3-chloro-4-methoxyphenyl)ethyl)-2-tert-butylsulfinylimine (29-a), with a yield of 60%. ESI $[M+H]^+$=288.1

Step 2: Synthesis of (S)-N-(1-(3-chloro-4-methoxyphenyl)ethyl)-2-tert-butylsulfinamide (29-b)

The (S)-N-(1-(3-chloro-4-methoxyphenyl)ethyl)-2-tert-butylsulfinylimine (1.72 g, 6.0 mmol) was dissolved in 40 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was dried in vacuum and then purified by a straight-phase column chromatography to obtain 1.32 g of white solid (S)-N-(1-(3-chloro-4-methoxyphenyl)ethyl)-2-tert-butylsulfinamide (29-b), with a yield of 77%. ESI $[M+H]^+$=290.2

Step 3: Synthesis of (S)-1-(3-chloro-4-methoxyphenyl)ethan-1-amine hydrochloride (29-c)

The (S)-N-(1-(3-chloro-4-methoxyphenyl)ethyl)-2-tert-butylsulfinamide (1.32 g, 4.5 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. Pull drying was performed after the reaction, the solid was washed twice with ethyl acetate and twice with petroleum ether, and the solid was dried to obtain 0.34 g of white solid (S)-1-(3-chloro-4-methoxyphenyl)ethan-1-amine hydrochloride (29-c), with a yield of 34%. ESI $[M+H]^+$=186.1

Step 4: Synthesis of (S)-6-(4-chlorophenyl)-N-(1-(3-chloro-4-methoxyphenyl)ethyl)-2-(1-methyl-1H-pyrazol-4-yl)pyrimidine-4-formamide (Compound 29)

The 6-(4-chlorophenyl)-2-(1-methyl-1H-pyrazol-4-yl)pyrimidine-4-carboxylic acid (100 mg, 0.32 mmol) and the (S)-1-(3-chloro-4-methoxyphenyl)ethan-1-amine hydrochloride (93 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 113 mg of white solid (S)-6-(4-chlorophenyl)-N-(1-(3-chloro-4-methoxyphenyl)ethyl)-2-(1-methyl-1H-pyrazol-4-yl)pyrimidine-4-formamide (compound 29), with a yield of 73%. $^1$H NMR (400 MHz, DMSO-d6) δ 9.20 (d, J=8.7 Hz, 1H), 8.69 (s, 1H), 8.41 (s, 1H), 8.40-8.34 (m, 2H), 8.20 (s, 1H), 7.67-7.61 (m, 2H), 7.53 (d, J=2.2 Hz, 1H), 7.40 (dd, J=8.6, 2.3 Hz, 1H), 7.13 (d, J=8.6 Hz, 1H), 5.22 (p, J=7.2 Hz, 1H), 3.97 (s, 3H), 3.83 (s, 3H), 1.59 (d, J=7.1 Hz, 3H). ESI $[M+H]^+$=482.1

Example 30: Synthesis of(S)-6-(4-chlorophenyl)-N-(1-(3-methoxy-4-fluorophenyl)ethyl)-2-(1-methyl-1H-pyrazol-4-yl)pyrimidine-4-formamide (Compound 30)

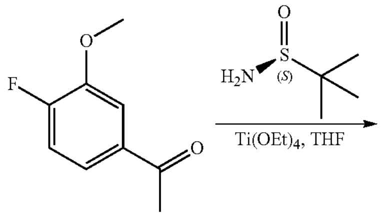

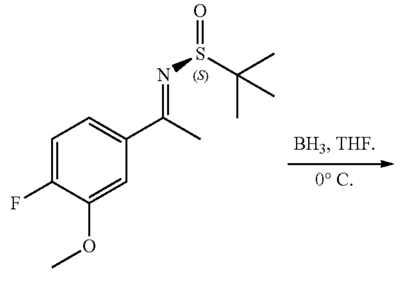

30-a

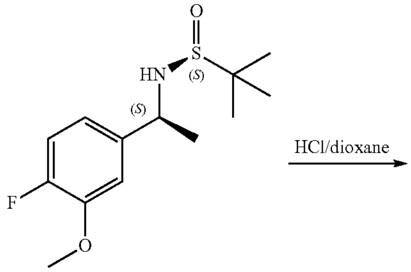

30-b

-continued

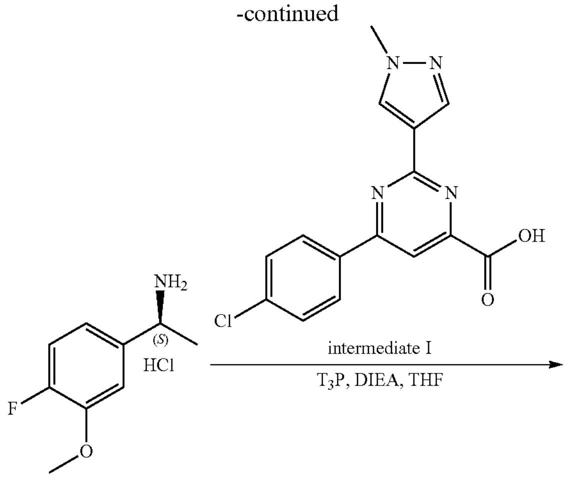

30-c

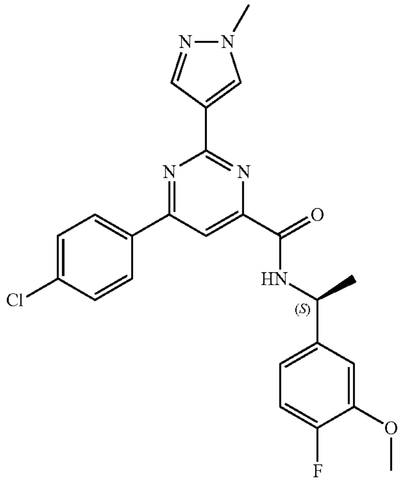

30

Step 1: Synthesis of(S)-N-(1-(3-methoxy-4-fluorophenyl)ethyl)-2-tert-butylsulfinylimine (30-a)

1-(3-methoxy-4-fluorophenyl)ethanone (1.68 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was dried in vacuum and then purified by a straight-phase column chromatography to obtain 1.58 g of white solid (S)-N-(1-(3-methoxy-4-fluorophenyl)ethyl)-2-tert-butylsulfinylimine (30-a), with a yield of 58%. ESI $[M+H]^+$=272.1

Step 2: Synthesis of (S)-N-(1-(3-methoxy-4-fluorophenyl)ethyl)-2-tert-butylsulfinamide (30-b)

The (S)-N-(1-(3-methoxy-4-fluorophenyl)ethyl)-2-tert-butylsulfinylimine (1.58 g, 5.8 mmol) was dissolved in 40 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was dried in vacuum and then purified by a straight-phase column chromatography to obtain 1.22 g of white solid (S)-N-(1-(3-methoxy-4-fluorophenyl)ethyl)-2-tert-butylsulfinamide (30-b), with a yield of 77%. ESI $[M+H]^+$=274.2

Step 3: Synthesis of (S)-1-(3-methoxy-4-fluorophenyl)ethan-1-amine hydrochloride (30-c)

The (S)-N-(1-(3-methoxy-4-fluorophenyl)ethyl)-2-tert-butylsulfinamide (1.22 g, 4.5 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. The solution was concentrated after the reaction, the solid was washed twice with ethyl acetate and twice with petroleum ether, and the solid was dried to obtain 0.36 g of white solid (S)-1-(3-methoxy-4-fluorophenyl)ethan-1-amine hydrochloride (30-c), with a yield of 47%. ESI $[M+H]^+$=170.1

Step 4: Synthesis of(S)-6-(4-chlorophenyl)-N-(1-(3-methoxy-4-fluorophenyl)ethyl)-2-(1-methyl-1H-pyrazol-4-yl)pyrimidine-4-formamide (compound 30)

The 6-(4-chlorophenyl)-2-(1-methyl-1H-pyrazol-4-yl)pyrimidine-4-carboxylic acid (100 mg, 0.32 mmol) and the (S)-1-(3-methoxy-4-fluorophenyl)ethan-1-amine hydrochloride (71 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After the reaction solution was dried in vacuum, the crude product was separated by straight-phase column chromatography to obtain 86 mg of white solid (S)-6-(4-chlorophenyl)-N-(1-(3-methoxy-4-fluorophenyl)ethyl)-2-(1-methyl-1H-pyrazol-4-yl)pyrimidine-4-formamide (compound 30), with a yield of 57%. $^1H$ NMR (400 MHz, DMSO-d6) δ 9.20 (d, J=8.7 Hz, 1H), 8.69 (s, 1H), 8.41 (s, 1H), 8.40-8.34 (m, 2H), 7.90 (s, 1H), 7.67-7.61 (m, 2H), 7.49 (d, J=2.2 Hz, 1H), 7.40 (dd, J=8.6, 2.3 Hz, 1H), 7.11 (d, J=8.6 Hz, 1H), 5.22 (p, J=7.2 Hz, 1H), 3.97 (s, 3H), 3.83 (s, 3H), 1.59 (d, J=7.1 Hz, 3H). ESI $[M+H]^+$=466.1

Example 31: Synthesis of (S)-6-(4-chlorophenyl)-N-(1-(3-chloro-4-fluorophenyl)ethyl)-2-(1-methyl-1H-pyrazol-4-yl)pyrimidine-4-formamide (Compound 31)

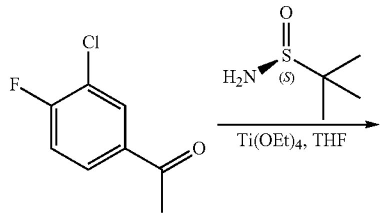

-continued

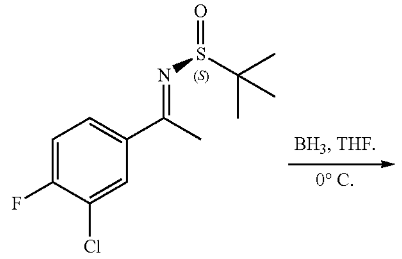

31-a

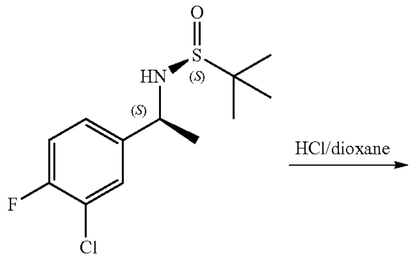

31-b

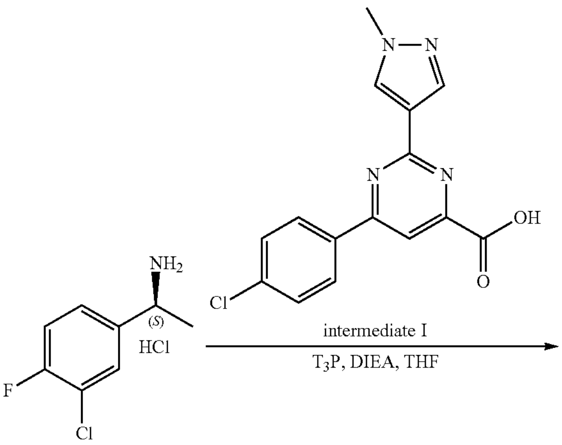

31-c

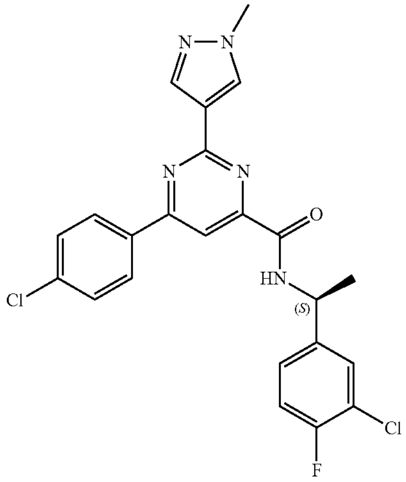

31

Step 1: Synthesis of (S)-N-(1-(3-chloro-4-fluoro-phenyl)ethyl)-2-tert-butylsulfinylimine (31-a)

1-(3-chloro-4-fluorophenyl)ethanone (1.72 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was dried in vacuum and then purified by a straight-phase column chromatography to obtain 1.63 g of white solid (S)-N-(1-(3-chloro-4-fluorophenyl)ethyl)-2-tert-butylsulfinylimine (31-a), with a yield of 59%. ESI $[M+H]^+$= 276.1

Step 2: Synthesis of (S)-N-(1-(3-chloro-4-fluoro-phenyl)ethyl)-2-tert-butylsulfinamide (31-b)

The (S)-N-(1-(3-chloro-4-fluorophenyl)ethyl)-2-tert-butylsulfinylimine (1.63 g, 5.9 mmol) was dissolved in 40 mL of dry tetrahydrofuran, a tetrahydrofuran solution of 1 M borane (12.1 mL, 12.1 mmol) was added at 0° C., the solution was stirred at room temperature for 2 h, methanol was added for quenching after reaction was completed, and the organic phase was dried in vacuum and then purified by a straight-phase column chromatography to obtain 1.26 g of white solid (S)-N-(1-(3-chloro-4-fluorophenyl)ethyl)-2-tert-butylsulfinamide (31-b), with a yield of 77%. ESI $[M+H]^+$= 278.2

Step 3: Synthesis of (S)-1-(3-chloro-4-fluorophenyl) ethan-1-amine hydrochloride (31-c)

The (S)-N-(1-(3-chloro-4-fluorophenyl)ethyl)-2-tert-butylsulfinamide (1.26 g, 4.5 mmol) was dissolved in 30 mL of tetrahydrofuran, a 1,4-dioxane solution of 4 M hydrochloric acid (7.4 mL, 29.6 mmol) was added, and reaction occurred at room temperature with stirring for 3 h. The solution was concentrated after the reaction, the solid was washed twice with ethyl acetate and twice with petroleum ether, and the solid was dried to obtain 0.35 g of white solid (S)-1-(3-chloro-4-fluorophenyl)ethan-1-amine hydrochloride (31-c), with a yield of 34%. ESI $[M+H]^+$=174.1

Step 4: Synthesis of (S)-6-(4-chlorophenyl)-N-(1-(3-chloro-4-fluorophenyl)ethyl)-2-(1-methyl-1H-pyrazol-4-yl)pyrimidine-4-formamide (Compound 31)

The 6-(4-chlorophenyl)-2-(1-methyl-1H-pyrazol-4-yl)pyrimidine-4-carboxylic acid (100 mg, 0.32 mmol) and the (S)-1-(3-chloro-4-fluorophenyl)ethan-1-amine hydrochloride (73 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 64 mg of white solid (S)-6-(4-chlorophenyl)-N-(1-(3-chloro-4-fluorophenyl)ethyl)-2-(1-methyl-1H-pyrazol-4-yl)pyrimidine-4-formamide (compound 31), with a yield of 42%. $^1H$ NMR (400 MHz, DMSO-d6) δ 9.20 (d, J=8.7 Hz, 1H), 8.69 (s, 1H), 8.41 (s, 1H), 8.40-8.34 (m, 2H), 8.20 (s, 1H), 7.67-7.61 (m, 2H), 7.59 (m, 1H), 7.40 (dd, J=8.6, 2.3 Hz, 1H), 7.26 (d, J=8.6 Hz, 1H), 5.22 (p, J=7.2 Hz, 1H), 3.97 (s, 3H), 3.83 (s, 3H), 1.59 (d, J=7.1 Hz, 3H). ESI $[M+H]^+$=470.1

Example 32: Synthesis of (S)-6-(4-trifluoromethylphenyl)-N-(1-(3,4-difluorophenyl)ethyl)-2-(1-methyl-1H-pyrazol-4-yl)pyrimidine-4-formamide (Compound 32)

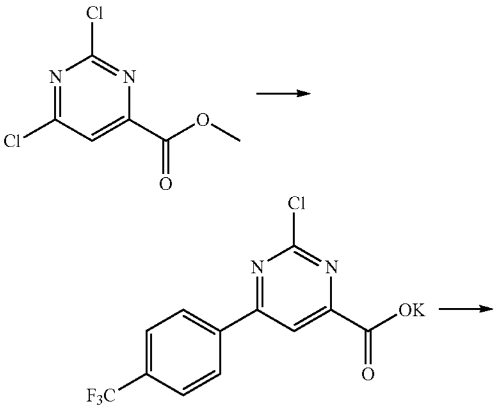

32-a

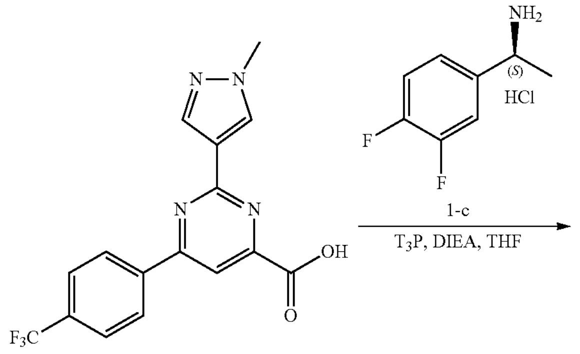

32-b

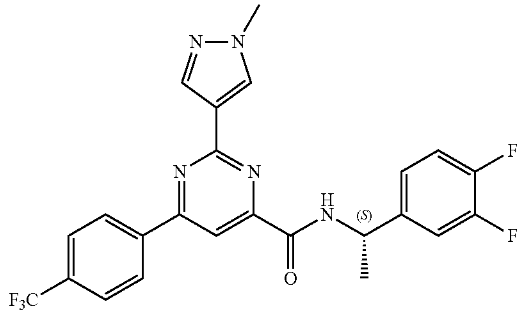

32

Step 1: Synthesis of potassium 2-chloro-6-(4-trifluoromethylphenyl)pyrimidine-4-carboxylate (32-a)

4-trifluoromethylphenylboronic acid (1.90 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.75 g of gray solid potassium 2-chloro-6-(4-trifluoromethylphenyl)pyrimidine-4-carboxylate (32-a), with a yield of 58%. ESI $[M+H]^+$=303.2

Step 2: Synthesis of 6-(4-trifluoromethylphenyl)-2-(1-methyl-1H-pyrazol-4-yl)pyrimidine-4-carboxylic acid (32-b)

(1-methyl-1H-pyrazol-4-yl) boronic acid (940 mg, 7.5 mmol) and the potassium 2-chloro-6-(4-trifluoromethylphenyl)pyrimidine-4-carboxylate (1.75 g, 5.8 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 1.55 g of gray solid 6-(4-trifluoromethylphenyl)-2-(1-methyl-1H-pyrazol-4-yl)pyrimidine-4-carboxylic acid (32-b), with a yield of 76%. ESI $[M+H]^+$=349.2

Step 3: Synthesis of (S)-6-(4-trifluoromethylphenyl)-N-(1-(3,4-difluorophenyl)ethyl)-2-(1-methyl-1H-pyrazol-4-yl)pyrimidine-4-formamide (Compound 32)

The 6-(4-trifluoromethylphenyl)-2-(1-methyl-1H-pyrazol-4-yl)pyrimidine-4-carboxylic acid (100 mg, 0.29 mmol) and (S)-1-(3,4-difluorophenyl)ethan-1-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 96 mg of white solid (S)-6-(4-trifluoromethylphenyl)-N-(1-(3,4-difluorophenyl)ethyl)-2-(1-methyl-1H-pyrazol-4-yl)pyrimidine-4-formamide (compound 32), with a yield of 68%. $^1$H NMR (400 MHz, DMSO-d6) δ 9.28 (d, J=8.6 Hz, 1H), 8.70 (s, 1H), 8.55 (d, J=8.1 Hz, 2H), 8.43 (s, 1H), 8.28 (s, 1H), 7.93 (d, J=8.2 Hz, 2H), 7.56 (ddd, J=12.0, 7.8, 2.2 Hz, 1H), 7.42 (dt, J=10.7, 8.4 Hz, 1H), 7.33 (d, J=5.2 Hz, 1H), 5.28 (p, J=7.3 Hz, 1H), 3.97 (s, 3H), 1.60 (d, J=7.0 Hz, 3H). ESI $[M+H]^+$=488.2

Example 33: Synthesis of (S)-6-(4-trifluoromethylphenyl)-N-(1-(2-fluoro-4-pyridine)ethyl)-2-(1-methyl-1H-pyrazol-4-yl)pyrimidine-4-formamide (Compound 33)

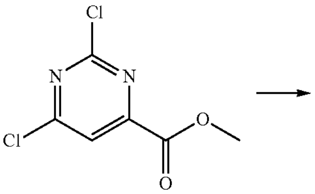

-continued

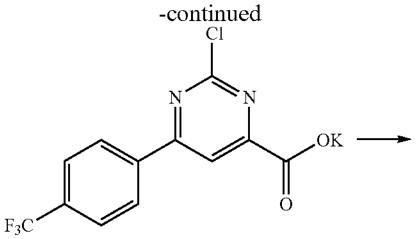

33-a

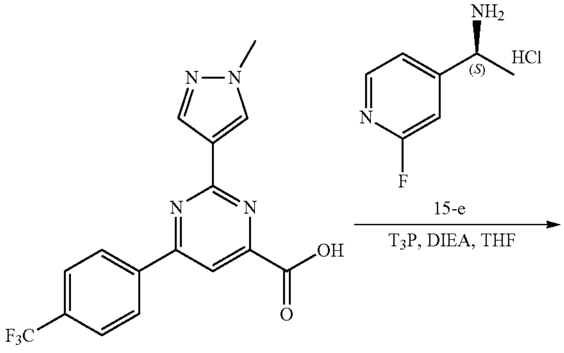

33-b

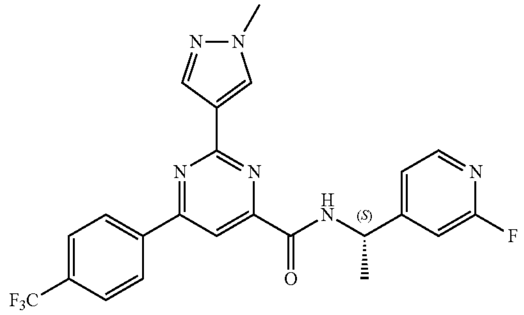

33

Step 1: Synthesis of potassium 2-chloro-6-(4-trifluoromethylphenyl)pyrimidine-4-carboxylate (33-a)

4-trifluoromethylphenylboronic acid (1.90 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.75 g of gray solid potassium 2-chloro-6-(4-trifluoromethylphenyl)pyrimidine-4-carboxylate (33-a), with a yield of 58%. ESI $[M+H]^+$=303.2

Step 2: Synthesis of 6-(4-trifluoromethylphenyl)-2-(1-methyl-1H-pyrazol-4-yl)pyrimidine-4-carboxylic acid (33-b)

(1-methyl-1H-pyrazol-4-yl) boronic acid (940 mg, 7.5 mmol) and potassium 2-chloro-6-(4-trifluoromethylphenyl) pyrimidine-4-carboxylate (1.75 g, 5.8 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 1.55 g of gray solid 6-(4-trifluoromethylphenyl)-2-(1-methyl-1H-pyrazol-4-yl) pyrimidine-4-carboxylic acid (33-b), with a yield of 76%. ESI $[M+H]^+$=349.2

Step 3: Synthesis of (S)-6-(4-trifluoromethylphenyl)-N-(1-(2-fluoro-4-pyridine)ethyl)-2-(1-methyl-1H-pyrazol-4-yl)pyrimidine-4-formamide (Compound 33)

The 6-(4-trifluoromethylphenyl)-2-(1-methyl-1H-pyrazol-4-yl)pyrimidine-4-carboxylic acid (100 mg, 0.29 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 83 mg of white solid (S)-6-(4-trifluoromethylphenyl)-N-(1-(2-fluoro-4-pyridine)ethyl)-2-(1-methyl-1H-pyrazol-4-yl)pyrimidine-4-formamide (compound 33), with a yield of 61%. $^1$H NMR (400 MHz, DMSO-d6) δ 9.39 (d, J=8.4 Hz, 1H), 8.70 (s, 1H), 8.63-8.51 (m, 3H), 8.23 (d, J=5.1 Hz, 2H), 7.60-7.50 (m, 2H), 7.50-7.41 (m, 1H), 7.25 (s, 1H), 5.32 (p, J=7.3 Hz, 1H), 3.98 (s, 3H), 1.63 (d, J=7.1 Hz, 3H). ESI $[M+H]^+$=471.2

Example 34: Synthesis of (S)-6-(4-trifluoromethoxyphenyl)-N-(1-(2-fluoro-4-pyridine)ethyl)-2-(1-methyl-1H-pyrazol-4-yl)pyrimidine-4-formamide (Compound 34)

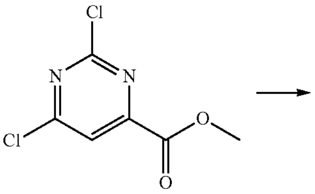

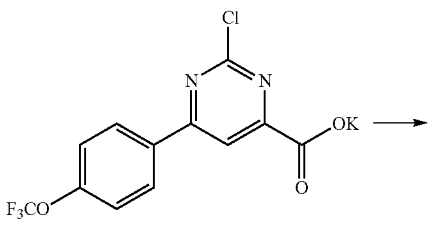

34-a

-continued

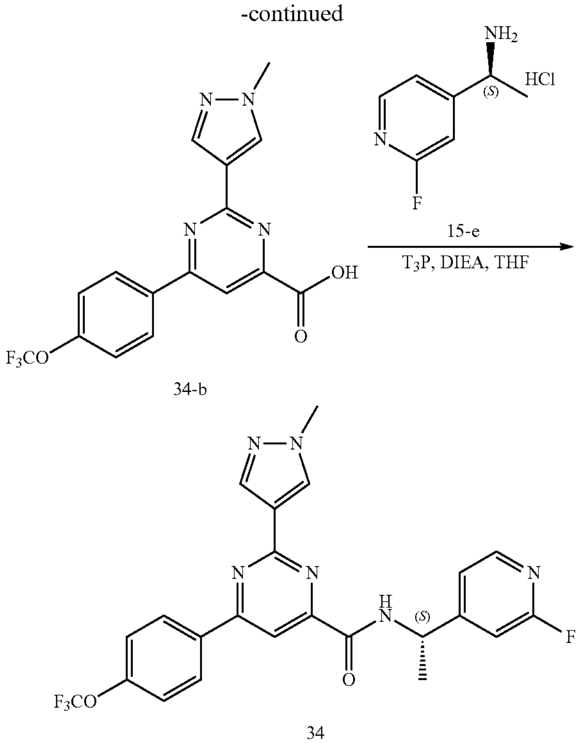

34-b

34

Step 1: Synthesis of potassium 2-chloro-6-(4-trifluoromethoxyphenyl)pyrimidine-4-carboxylate (34-a)

4-trifluoromethoxyphenylboronic acid (2.06 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.62 g of gray solid potassium 2-chloro-6-(4-trifluoromethoxyphenyl)pyrimidine-4-carboxylate (34-a), with a yield of 51%. ESI $[M+H]^+$= 319.2

Step 2: Synthesis of 6-(4-trifluoromethoxyphenyl)-2-(1-methyl-1H-pyrazol-4-yl)pyrimidine-4-carboxylic acid (34-b)

(1-methyl-1H-pyrazol-4-yl) boronic acid (940 mg, 7.5 mmol) and the potassium 2-chloro-6-(4-trifluoromethoxyphenyl)pyrimidine-4-carboxylate (1.62 g, 5.1 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 1.35 g of gray solid 6-(4-trifluoromethoxyphenyl)-2-(1-methyl-1H-pyrazol-4-yl)pyrimidine-4-carboxylic acid (34-b), with a yield of 73%. ESI $[M+H]^+$=365.2

Step 3: Synthesis of (S)-6-(4-trifluoromethoxyphenyl)-N-(1-(2-fluoro-4-pyridine)ethyl)-2-(1-methyl-1H-pyrazol-4-yl)pyrimidine-4-formamide (Compound 34)

The 6-(4-trifluoromethoxyphenyl)-2-(1-methyl-1H-pyrazol-4-yl)pyrimidine-4-carboxylic acid (100 mg, 0.28 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 113 mg of white solid (S)-6-(4-trifluoromethoxyphenyl)-N-(1-(2-fluoro-4-pyridine)ethyl)-2-(1-methyl-1H-pyrazol-4-yl)pyrimidine-4-formamide (compound 34), with a yield of 81%. $^1$H NMR (400 MHz, DMSO-d6) δ 9.39 (d, J=8.4 Hz, 1H), 8.70 (s, 1H), 8.53-8.41 (m, 3H), 8.23 (d, J=5.1 Hz, 2H), 7.60-7.50 (m, 2H), 7.50-7.41 (m, 1H), 7.25 (s, 1H), 5.32 (p, J=7.3 Hz, 1H), 3.98 (s, 3H), 1.63 (d, J=7.1 Hz, 3H). ESI $[M+H]^+$= 487.2

Example 35: Synthesis of (S)-6-(4-chlorophenyl)-N-(1-(3-fluorophenyl)ethyl)-2-(1-methyl-1H-pyrazol-4-yl)pyrimidine-4-formamide (Compound 35)

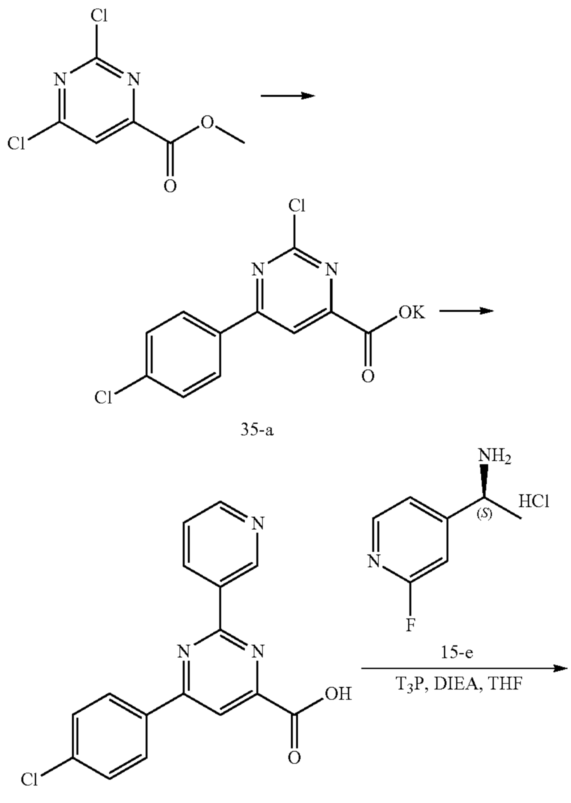

35-a 35-b

-continued

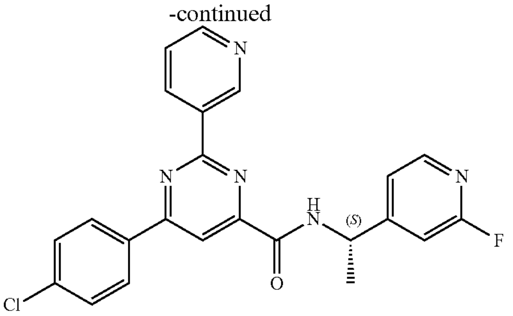

35

Step 1: Synthesis of potassium 2-chloro-6-(4-chlorophenyl)pyrimidine-4-carboxylate (35-a)

4-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra (triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.63 g of gray solid potassium 2-chloro-6-(4-chlorophenyl)pyrimidine-4-carboxylate (35-a), with a yield of 60%. ESI $[M+H]^+$=269.2

Step 2: Synthesis of 6-(4-chlorophenyl)-2-(3-pyridin-4-yl)pyrimidine-4-carboxylic acid (35-b)

Pyridine-3-boronic acid (920 mg, 7.5 mmol) and the potassium 2-chloro-6-(4-chlorophenyl)pyrimidine-4-carboxylate (1.63 g, 6.0 mmol) were dissolved in dioxane/water (100 mL/5 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 750 mg of gray solid 6-(4-chlorophenyl)-2-(3-pyridin-4-yl)pyrimidine-4-carboxylic acid (35-b), with a yield of 52%. ESI $[M+H]^+$=312.2

Step 3: Synthesis of (S)-6-(4-chlorophenyl)-N-(1-(2-fluoro-4-pyridine)ethyl)-2-(3-pyridin-4-yl)pyrimidine-4-formamide (Compound 35)

The 6-(4-chlorophenyl)-2-(3-pyridin-4-yl)pyrimidine-4-carboxylic acid (100 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 63 mg of white solid (S)-6-(4-chlorophenyl)-N-(1-(2-fluoro-4-pyridine)ethyl)-2-(3-pyridin-4-yl)pyrimidine-4-formamide (compound 35), with a yield of 45%. $^1$H NMR (400 MHz, DMSO-d6) δ 9.97 (dd, J=2.3, 0.9 Hz, 1H), 9.64 (d, J=8.4 Hz, 1H), 9.06 (dt, J=8.1, 2.0 Hz, 1H), 8.81 (dd, J=4.8, 1.7 Hz, 1H), 8.52-8.44 (m, 3H), 8.22 (d, J=5.2 Hz, 1H), 7.71-7.62 (m, 3H), 7.49-7.43 (m, 1H), 7.26 (s, 1H), 5.35 (p, J=7.2 Hz, 1H), 1.65 (d, J=7.1 Hz, 3H). ESI $[M+H]^+$=434.2

Example 36: Synthesis of (S)-6-(4-chlorophenyl)-N-(1-(3-fluorophenyl)ethyl)-2-(2-chloropyrimidin-5-yl)pyrimidine-4-formamide (Compound 36)

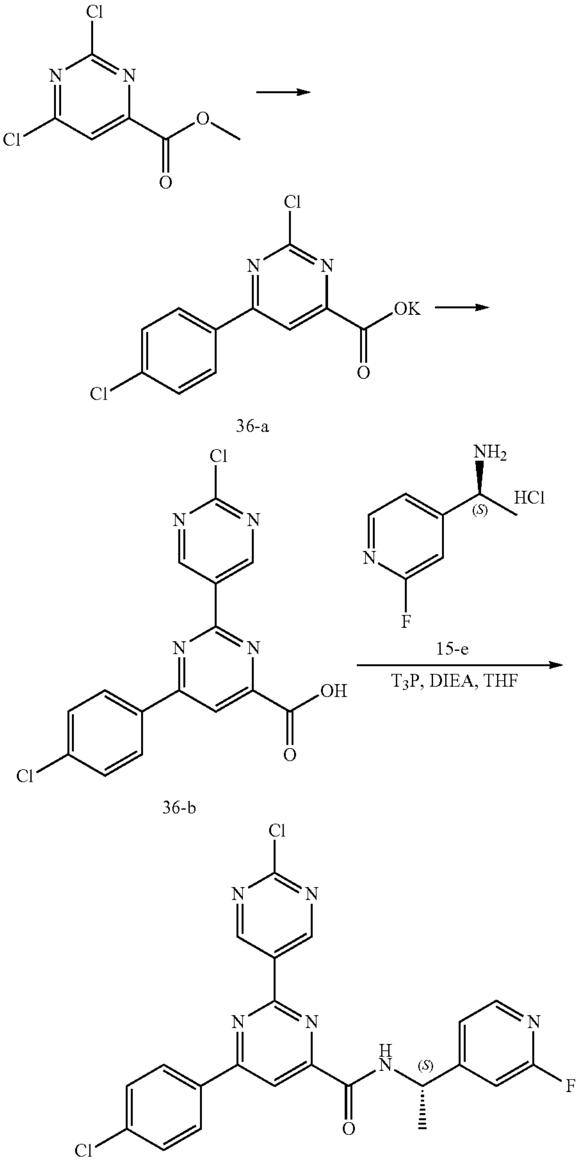

36

Step 1: Synthesis of potassium 2-chloro-6-(4-chlorophenyl)pyrimidine-4-carboxylate (36-a)

4-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra (triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.63 g of gray solid potassium 2-chloro-6-(4-chlorophenyl)pyrimidine-4-carboxylate (36-a), with a yield of 60%. ESI $[M+H]^+$=269.2

Step 2: Synthesis of 6-(4-chlorophenyl)-2-(2-chloropyrimidin-5-yl)pyrimidine-4-carboxylic acid (36-b)

2-chloropyrimidine-5-boronic acid (1.18 g, 7.5 mmol) and the potassium 2-chloro-6-(4-chlorophenyl)pyrimidine-4-carboxylate (1.63 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 760 mg of gray solid 6-(4-chlorophenyl)-2-(2-chloropyrimidin-5-yl)pyrimidine-4-carboxylic acid (36-b), with a yield of 48%. ESI $[M+H]^+$=347.2

Step 3: Synthesis of (S)-6-(4-chlorophenyl)-N-(1-(2-fluoro-4-pyridine)ethyl)-2-(2-chloropyrimidin-5-yl)pyrimidine-4-formamide (Compound 36)

The 6-(4-chlorophenyl)-2-(2-chloropyrimidin-5-yl)pyrimidine-4-carboxylic acid (111 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 45 mg of white solid (S)-6-(4-chlorophenyl)-N-(1-(2-fluoro-4-pyridine)ethyl)-2-(2-chloropyrimidin-5-yl)pyrimidine-4-formamide (HSNC00179), with a yield of 30%. $^1$H NMR (400 MHz, DMSO-d6) δ 9.65 (d, J=8.3 Hz, 1H), 9.12 (s, 2H), 8.63 (dt, J=5.2, 1.7 Hz, 1H), 8.57 (s, 1H), 8.55-8.47 (m, 4H), 7.72-7.64 (m, 1H), 7.49-7.42 (m, 1H), 6.11 (s, 2H), 5.36 (p, J=7.1 Hz, 1H), 1.66 (d, J=7.1 Hz, 3H). ESI $[M+H]^+$=469.2

Example 37: Synthesis of (S)-6-(4-chlorophenyl)-N-(1-(2-fluoro-4-pyridine)ethyl)-2-(2-aminopyridin-4-yl)pyrimidine-4-formamide (Compound 37)

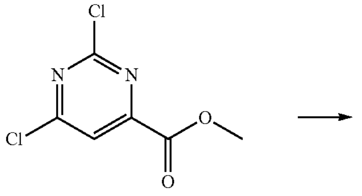

-continued

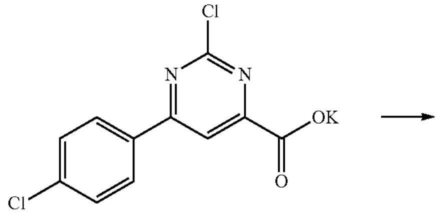

37-a

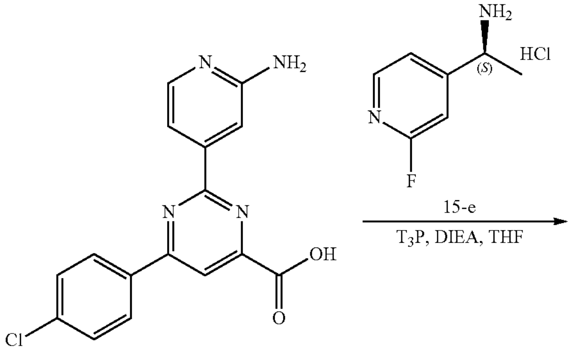

37-b

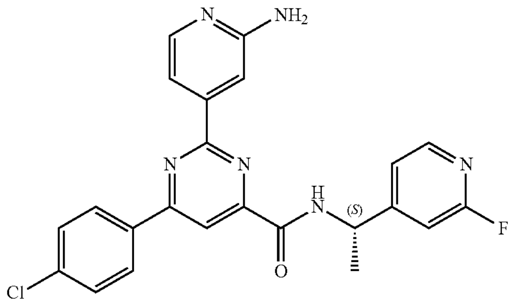

37

Step 1: Synthesis of potassium 2-chloro-6-(4-chlorophenyl)pyrimidine-4-carboxylate (37-a)

4-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.63 g of gray solid potassium 2-chloro-6-(4-chlorophenyl)pyrimidine-4-carboxylate (37-a), with a yield of 60%. ESI $[M+H]^+$=269.2

Step 2: Synthesis of 6-(4-chlorophenyl)-2-(2-aminopyridin-4-yl)pyrimidine-4-carboxylic acid (37-b)

2-aminopyridine-4-boronic acid (1.03 g, 7.5 mmol) and the potassium 2-chloro-6-(4-chlorophenyl)pyrimidine-4-carboxylate (1.63 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 660 mg of gray solid 6-(4-chlorophenyl)-2-(2-aminopyridin-4-yl)pyrimidine-4-carboxylic acid (37-b), with a yield of 27%. ESI $[M+H]^+$=327.2

Step 3: Synthesis of (S)-6-(4-chlorophenyl)-N-(1-(2-fluoro-4-pyridine)ethyl)-2-(2-aminopyridin-4-yl)pyrimidine-4-formamide (Compound 37)

The 6-(4-chlorophenyl)-2-(2-aminopyridin-4-yl)pyrimidine-4-carboxylic acid (104 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 52 mg of white solid (S)-6-(4-chlorophenyl)-N-(1-(2-fluoro-4-pyridine)ethyl)-2-(2-aminopyridin-4-yl)pyrimidine-4-formamide (compound 37), with a yield of 36%. $^1H$ NMR (400 MHz, DMSO-d6) δ 9.65 (d, J=8.3 Hz, 1H), 8.63 (dt, J=5.2, 1.7 Hz, 1H), 8.57 (s, 1H), 8.55-8.47 (m, 4H), 8.23 (d, J=5.2 Hz, 1H), 7.72-7.64 (m, 2H), 7.49-7.42 (m, 1H), 7.26 (s, 1H), 6.11 (s, 2H), 5.36 (p, J=7.1 Hz, 1H), 1.66 (d, J=7.1 Hz, 3H). ESI $[M+H]^+$=449.2

Example 38: Synthesis of (S)-6-(4-chlorophenyl)-N-(1-(2-fluoro-4-pyridine)ethyl)-2-(2-fluoropyridin-4-yl)pyrimidine-4-formamide (Compound 38)

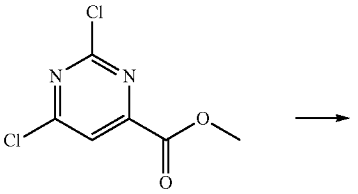

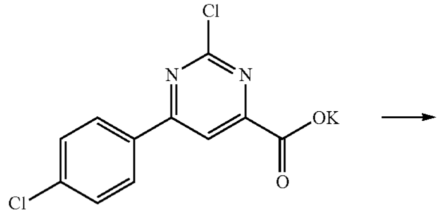

38-a

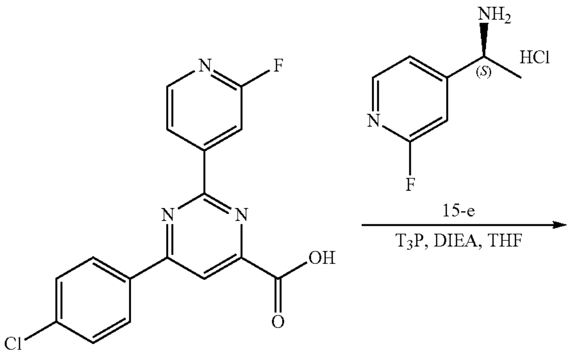

38-b

-continued

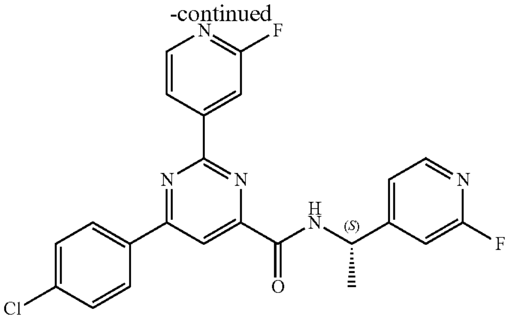

38

Step 1: Synthesis of potassium 2-chloro-6-(4-chlorophenyl)pyrimidine-4-carboxylate (38-a)

4-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.63 g of gray solid potassium 2-chloro-6-(4-chlorophenyl)pyrimidine-4-carboxylate (38-a), with a yield of 60%. ESI $[M+H]^+$=269.2

Step 2: Synthesis of 6-(4-chlorophenyl)-2-(2-fluoropyridin-4-yl)pyrimidine-4-carboxylic acid (38-b)

2-fluoropyridine-4-boronic acid (1.06 g, 7.5 mmol) and the potassium 2-chloro-6-(4-chlorophenyl)pyrimidine-4-carboxylate (1.63 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 710 mg of gray solid 6-(4-chlorophenyl)-2-(2-fluoropyridin-4-yl)pyrimidine-4-carboxylic acid (38-b), with a yield of 29%. ESI $[M+H]^+$=330.2

Step 3: Synthesis of (S)-6-(4-chlorophenyl)-N-(1-(2-fluoro-4-pyridine)ethyl)-2-(2-fluoropyridin-4-yl)pyrimidine-4-formamide (Compound 38)

The 6-(4-chlorophenyl)-2-(2-fluoropyridin-4-yl)pyrimidine-4-carboxylic acid (105 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 72 mg of white solid (S)-6-(4-chlorophenyl)-N-(1-(2-fluoro-4-pyridine)ethyl)-2-(2-fluoropyridin-4-yl)pyrimidine-4-formamide (compound 38), with a yield of 50%. $^1H$ NMR (400 MHz, DMSO-d6) δ 9.65 (d, J=8.3 Hz, 1H), 8.63 (dt, J=5.2, 1.7 Hz, 1H), 8.57 (s, 1H), 8.55-8.47 (m, 4H), 8.23 (d, J=5.2 Hz, 1H), 7.72-7.64 (m, 2H), 7.49-7.42 (m, 1H), 7.26 (s, 1H), 5.36 (p, J=7.1 Hz, 1H), 1.66 (d, J=7.1 Hz, 3H). ESI $[M+H]^+$=452.2

Example 39: Synthesis of (S)-6-(4-chlorophenyl)-N-(1-(2-fluoro-4-pyridine)ethyl)-2-(1-cyclopropylpyrazol-4-yl)pyrimidine-4-formamide (Compound 39)

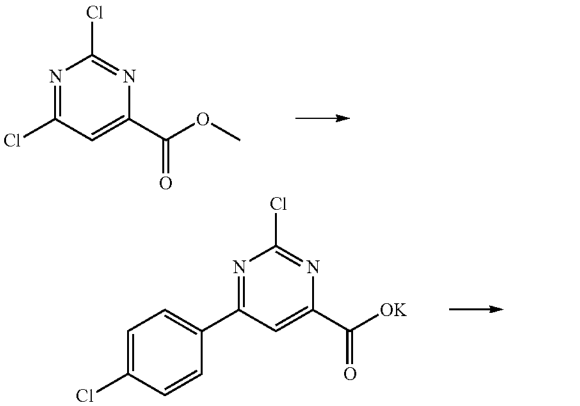

39-a

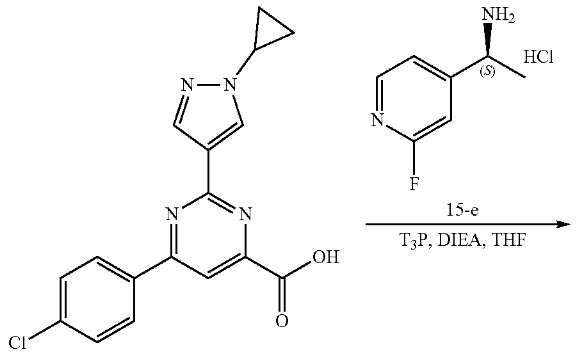

39-b

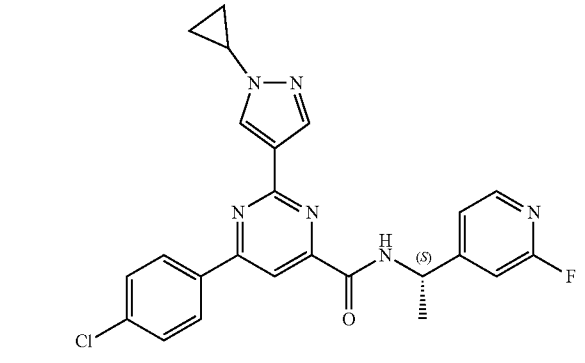

39

Step 1: Synthesis of potassium 2-chloro-6-(4-chlorophenyl)pyrimidine-4-carboxylate (39-a)

4-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.63 g of gray solid potassium 2-chloro-6-(4-chlorophenyl)pyrimidine-4-carboxylate (39-a), with a yield of 60%. ESI $[M+H]^+$=269.2

Step 2: Synthesis of 6-(4-chlorophenyl)-2-(1-cyclopropylpyrazol-4-yl)pyrimidine-4-carboxylic acid (39-b)

1-cyclopropylpyrazole-4-boronic acid (1.14 g, 7.5 mmol) and the potassium 2-chloro-6-(4-chlorophenyl)pyrimidine-4-carboxylate (1.63 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 750 mg of gray solid 6-(4-chlorophenyl)-2-(1-cyclopropylpyrazol-4-yl)pyrimidine-4-carboxylic acid (39-b), with a yield of 29%. ESI $[M+H]^+$=341.2

Step 3: Synthesis of (S)-6-(4-chlorophenyl)-N-(1-(2-fluoro-4-pyridine)ethyl)-2-(1-cyclopropylpyrazol-4-yl)pyrimidine-4-formamide (Compound 39)

The 6-(4-chlorophenyl)-2-(1-cyclopropylpyrazol-4-yl) pyrimidine-4-carboxylic acid (109 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 52 mg of white solid (S)-6-(4-chlorophenyl)-N-(1-(2-fluoro-4-pyridine)ethyl)-2-(1-cyclopropylpyrazol-4-yl)pyrimidine-4-formamide (compound 39), with a yield of 35%. $^1H$ NMR (400 MHz, DMSO-d6) δ 9.37 (d, J=8.4 Hz, 1H), 8.76 (s, 1H), 8.40 (dq, J=4.7, 2.7, 2.3 Hz, 3H), 8.22 (t, J=2.6 Hz, 2H), 7.70-7.60 (m, 2H), 7.43 (dt, J=5.4, 1.8 Hz, 1H), 7.24 (s, 1H), 5.31 (p, J=7.1 Hz, 1H), 3.88 (tt, J=7.4, 3.8 Hz, 1H), 1.63 (d, J=7.1 Hz, 3H), 1.17 (dt, J=7.6, 3.8 Hz, 2H), 1.05 (m, 2H). ESI $[M+H]^+$=463.2

Example 40: Synthesis of (S)-6-(4-chlorophenyl)-N-(1-(3-cyano-4-fluorophenyl)ethyl)-2-(1-methyl-1H-pyrazol-4-yl)pyrimidine-4-formamide (Compound 40)

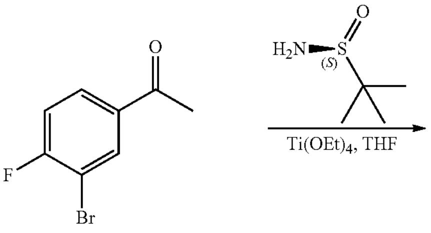

-continued

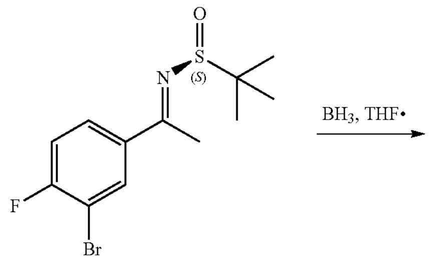

40-a

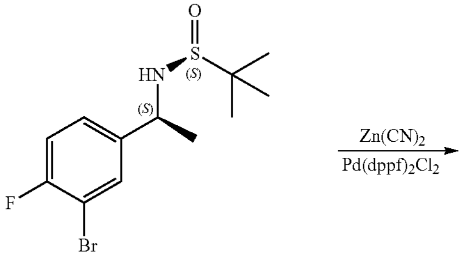

40-b

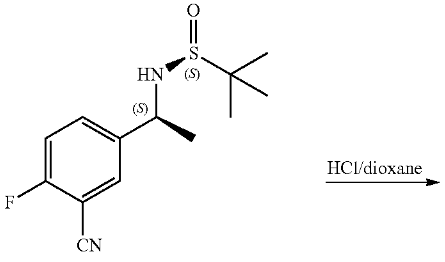

40-c

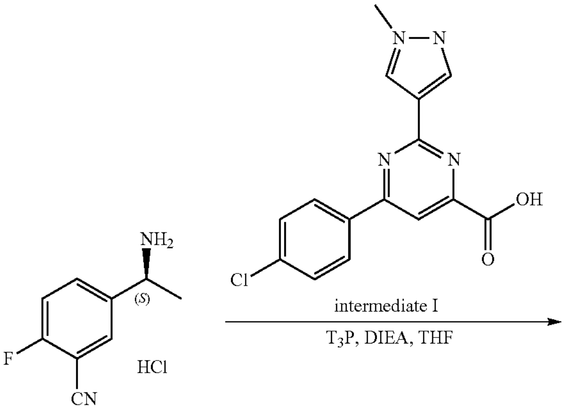

40-d

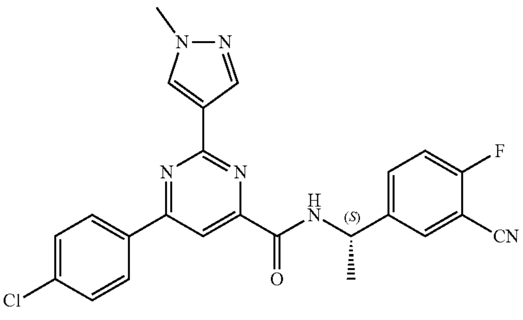

40

Step 1: Synthesis of (S)-N-(1-(3-bromo-4-fluorophenyl)ethyl)-2-tert-butylsulfinylimine (40-a)

1-(3-bromo-4-fluorophenyl)ethanone (2.16 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was purified by a straight-phase column chromatography to obtain 1.20 g of white solid (S)-N-(1-(3-bromo-4-fluorophenyl)ethyl)-2-tert-butylsulfinylimine (40-a), with a yield of 38%. ESI $[M+H]^+$=320.1

Step 2: Synthesis of (S)-N-(1-(3-bromo-4-fluorophenyl)ethyl)-2-tert-butylsulfinamide (40-b)

The (S)-N-(1-(3-bromo-4-fluorophenyl)ethyl)-2-tert-butylsulfinylimine (1.11 g, 3.5 mmol) was dissolved in 80 mL of dry tetrahydrofuran, a tetrahydrofuran solution of 1 M borane (7.0 mL, 7.0 mmol) was added at 0° C., the solution was stirred at room temperature for 2 h, methanol was added for quenching after reaction was completed, and the organic phase was purified by a straight-phase column chromatography to obtain 0.87 g of white solid (S)-N-(1-(3-bromo-4-fluorophenyl)ethyl)-2-tert-butylsulfinamide (40-b), with a yield of 78%. ESI $[M+H]^+$=322.2

Step 3: Synthesis of (S)-N-(1-(3-cyano-4-fluorophenyl)ethyl)-2-tert-butylsulfinamide (40-c)

The (S)-N-(1-(3-bromo-4-fluorophenyl)ethyl)-2-tert-butylsulfinamide (0.87 g, 2.7 mmol) was dissolved in 30 mL of dry DMF; zinc powder (175 mg, 2.7 mmol), zinc cyanide (245 mg, 2.7 mmol), and [1,1'-bis(diphenylphosphine)ferrocene]palladium dichloride (II) dichloromethane complex (243 mg, 0.3 mmol) were sequentially added; the solution was stirred at 120° C. for 4 h, ethyl acetate/water was added for extraction after reaction was completed, and the organic phase was dried in vacuum and then purified by a straight-phase column chromatography to obtain 0.50 g of white solid (S)-N-(1-(3-cyano-4-fluorophenyl)ethyl)-2-tert-butylsulfinamide (40-c), with a yield of 69%. ESI $[M+H]^+$=269.2

Step 4: Synthesis of (S)-N-(1-(3-cyano-4-fluorophenyl)ethyl)-2-amine hydrochloride (40-d)

The (S)-N-(1-(3-cyano-4-fluorophenyl)ethyl)-2-tert-butylsulfinamide (0.53 g, 2.0 mmol) was dissolved in 30 mL of tetrahydrofuran, a 1,4-dioxane solution of 4 M hydrochloric acid (2.4 mL, 9.6 mmol) was added, and reaction occurred at room temperature with stirring for 3 h. The solution was concentrated after the reaction, the solid was washed twice with ethyl acetate and twice with petroleum ether, and the solid was dried to obtain 0.20 g of white solid (S)-N-(1-(3-cyano-4-fluorophenyl)ethyl)-2-amine hydrochloride (40-d), with a yield of 61%. ESI $[M+H]^+$=165.1

Step 5: Synthesis of (S)-6-(4-chlorophenyl)-N-(1-(3-cyano-4-fluorophenyl)ethyl)-2-(1-methyl-1H-pyrazol-4-yl)pyrimidine-4-formamide (Compound 40)

The 6-(4-chlorophenyl)-2-(1-methyl-1H-pyrazol-4-yl)pyrimidine-4-carboxylic acid (100 mg, 0.32 mmol) and the (S)-N-(1-(3-cyano-4-fluorophenyl)ethyl)-2-amine hydrochloride (69 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 65 mg of white solid (S)-6-(4-chlorophenyl)-N-(1-(3-cyano-4-fluorophenyl)ethyl)-2-(1-methyl-1H-pyrazol-4-yl)pyrimidine-4-formamide (HSNC00184), with a yield of 44%. $^1H$ NMR (400 MHz, DMSO-d6) δ 9.29 (d, J=8.4 Hz, 1H), 8.68 (s, 1H), 8.45-8.34 (m, 3H), 8.20 (s, 1H), 8.03 (dd, J=6.2, 2.3 Hz, 1H), 7.89 (ddd, J=8.1, 5.4, 2.4 Hz, 1H), 7.68-7.60 (m, 2H), 7.53 (t, J=9.1 Hz, 1H), 5.29 (q, J=7.3 Hz, 1H), 3.97 (s, 3H), 1.62 (d, J=7.1 Hz, 3H). ESI $[M+H]^+$=461.2

Example 41: Synthesis of 6-(4-chlorophenyl)-N-(1H-indazol-3-yl)-2-(1-methyl-1H-pyrazol-4-yl) pyrimidine-4-formamide (Compound 41)

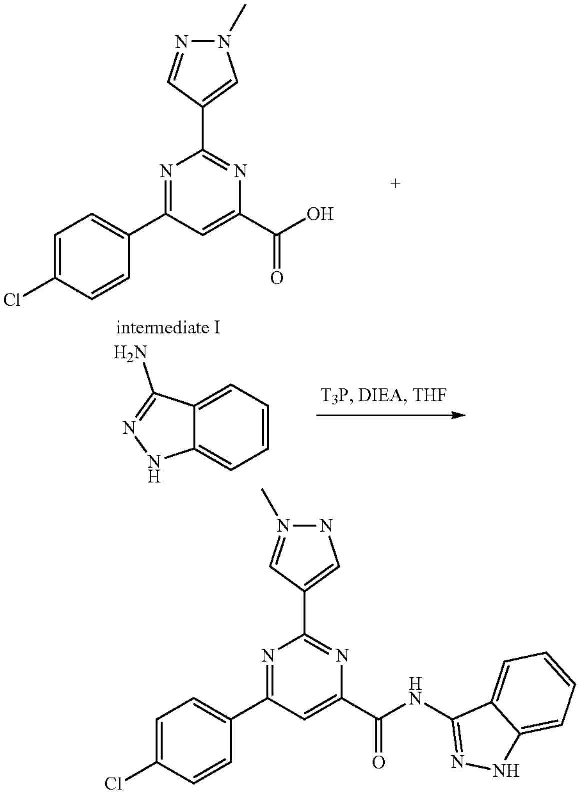

41

Step 1: Synthesis of 6-(4-chlorophenyl)-N-(1H-indazol-3-yl)-2-(1-methyl-1H-pyrazol-4-yl)pyrimidine-4-formamide (Compound 41)

6-(4-chlorophenyl)-2-(1-methyl-1H-pyrazol-4-yl)pyrimidine-4-carboxylic acid (100 mg, 0.32 mmol) and 3-aminoindole (56 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 66 mg of white solid 6-(4-chlorophenyl)-N-(1H-indazol-3-yl)-2-(1-methyl-1H-pyrazol-4-yl)pyrimidine-4-formamide (compound 41), with a yield of 48%. $^1H$ NMR (400 MHz, DMSO-d6) δ 8.55 (s, 1H), 8.39 (dq, J=9.0, 2.4 Hz, 3H), 8.17 (d, J=15.2 Hz, 2H), 7.96 (d, J=7.9 Hz, 1H), 7.77-7.62 (m, 3H), 7.48 (t, J=7.6 Hz, 1H), 6.69 (s, 2H), 3.93 (s, 3H). ESI $[M+H]^+$=430.2

Example 42: Synthesis of 6-(4-chlorophenyl)-N-(1-methyl-1H-indazol-3-yl)-2-(1-methyl-1H-pyrazol-4-yl)pyrimidine-4-formamide (Compound 42)

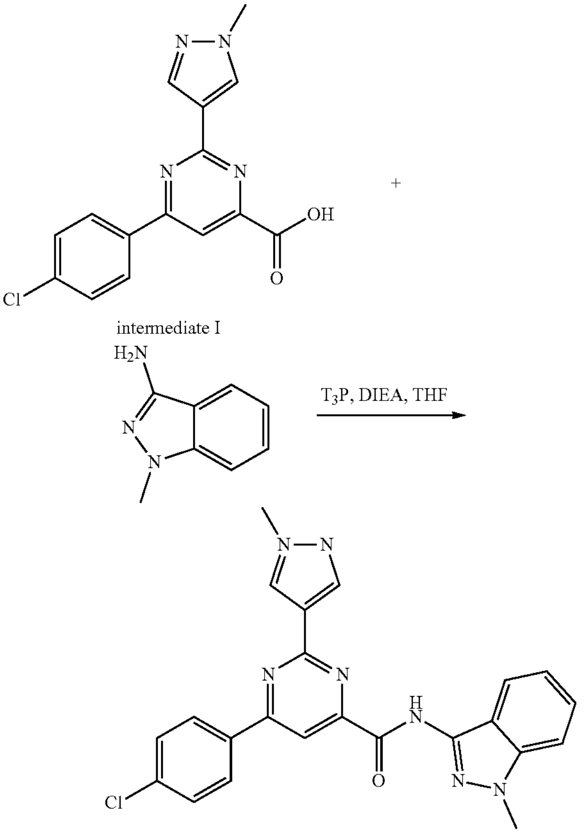

42

Step 1: Synthesis of 6-(4-chlorophenyl)-N-(1-methyl-1H-indazol-3-yl)-2-(1-methyl-1H-pyrazol-4-yl)pyrimidine-4-formamide (compound 42)

6-(4-chlorophenyl)-2-(1-methyl-1H-pyrazol-4-yl)pyrimidine-4-carboxylic acid (100 mg, 0.32 mmol) and 1-methyl-1H-indole-3-amine (62 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 66 mg of white solid 6-(4-chlorophenyl)-N-(1-methyl-1H-indazol-3-yl)-2-(1-methyl-1H-pyrazol-4-yl)pyrimidine-4-formamide (compound 42), with a yield of 48%. $^1H$ NMR (400

MHz, DMSO-d6) δ 11.22 (s, 1H), 8.83 (s, 1H), 8.50-8.40 (m, 3H), 8.36 (s, 1H), 7.81 (dd, J=8.3, 1.2 Hz, 1H), 7.70-7.62 (m, 3H), 7.45 (ddd, J=8.1, 6.8, 1.1 Hz, 1H), 7.19-7.11 (m, 1H), 4.01 (d, J=40.7 Hz, 6H). ESI $[M+H]^+$=444.2

Example 43: Synthesis of 6-(4-chlorophenyl)-N-((4-yl-4-methylpiperidin-1-yl)(cyclopropyl)ketone)-2-(1-methyl-1H-pyrazol-4-yl)pyrimidine-4-formamide (Compound 43)

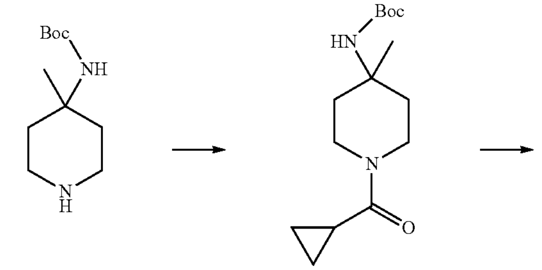

43-a

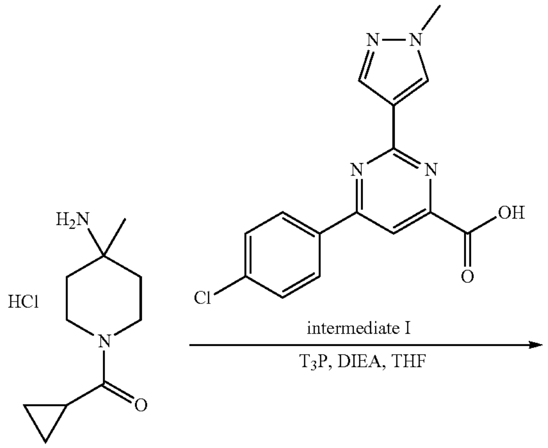

43-b

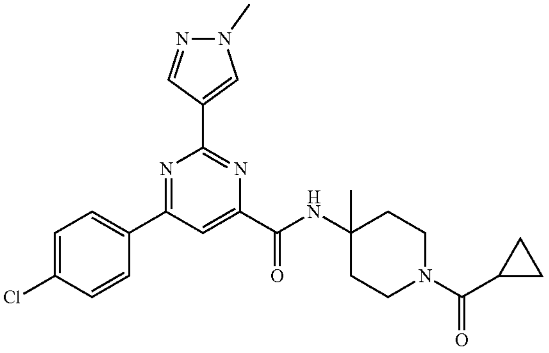

43

Step 1: Synthesis of (1-(cyclopropanecarbonyl)-4-methylpiperidin-4-yl)tert-butylcarbamate (43-a)

(4-methylpiperidin-4-yl)tert-butylcarbamate (214 mg, 1.00 mmol) was dissolved in 20 ml of dry dichloromethane, N,N-diisopropylethylamine (192 mg, 1.50 mmol) and cyclopropanecarbonyl chloride (125 mg, 1.20 mmol) were sequentially added at room temperature, and reaction occurred at room temperature with stirring for 2 h. Vacuum drying was performed after the reaction, and the crude product was separated by straight-phase column chromatography to obtain 200 mg of white solid (1-(cyclopropanecarbonyl)-4-methylpiperidin-4-yl)tert-butylcarbamate (43-a), with a yield of 71%. ESI $[M+H]^+$=283.2

Step 2: Synthesis of (4-amino-4-methylpiperidin-1-yl)(cyclopropyl)ketone hydrochloride (43-b)

The (1-(cyclopropanecarbonyl)-4-methylpiperidin-4-yl) tert-butylcarbamate (200 mg, 0.71 mmol) was dissolved in 10 ml of dichloromethane, a dioxane solution of hydrochloric acid (1 mL, 4.00 mmol) was added at room temperature, and reaction occurred at room temperature with stirring for 2 h. After the reaction, vacuum drying was directly performed to obtain 100 mg of white solid (4-amino-4-methylpiperidin-1-yl)(cyclopropyl)ketone hydrochloride (43-b), with a yield of 64%. ESI $[M+H]^+$=183.2

Step 3: Synthesis of 6-(4-chlorophenyl)-N-((4-yl-4-methylpiperidin-1-yl)(cyclopropyl)ketone)-2-(1-methyl-1H-pyrazol-4-yl)pyrimidine-4-formamide (Compound 43)

The 6-(4-chlorophenyl)-2-(1-methyl-1H-pyrazol-4-yl)pyrimidine-4-carboxylic acid (100 mg, 0.32 mmol) and the (4-amino-4-methylpiperidin-1-yl)(cyclopropyl)ketone hydrochloride (91 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. The reaction solution was dried in vacuum, and the crude product was separated by straight-phase column chromatography to obtain 51 mg of white solid 6-(4-chlorophenyl)-N-((4-yl-4-methylpiperidin-1-yl)(cyclopropyl)ketone)-2-(1-methyl-1H-pyrazol-4-yl)pyrimidine-4-formamide (compound 43), with a yield of 33%. $^1$H NMR (400 MHz, DMSO-d6) δ 8.64 (s, 1H), 8.39 (d, J=8.1 Hz, 2H), 8.31 (s, 1H), 8.19 (d, J=10.1 Hz, 2H), 7.64 (d, J=8.1 Hz, 2H), 3.95 (s, 3H), 3.73 (s, 2H), 2.61 (d, J=11.0 Hz, 2H), 2.45 (s, 2H), 2.37 (t, J=8.1 Hz, 2H), 1.48 (m, 1H), 0.87-0.68 (m, 4H). ESI $[M+H]^+$=479.2

Example 44: Synthesis of 6-(4-chlorophenyl)-N-((4-yl-4-methylpiperidin-1-yl)trifluoroethyl)-2-(1-methyl-1H-pyrazol-4-yl)pyrimidine-4-formamide (Compound 44)

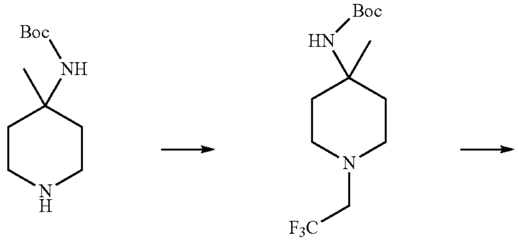

44-a

-continued

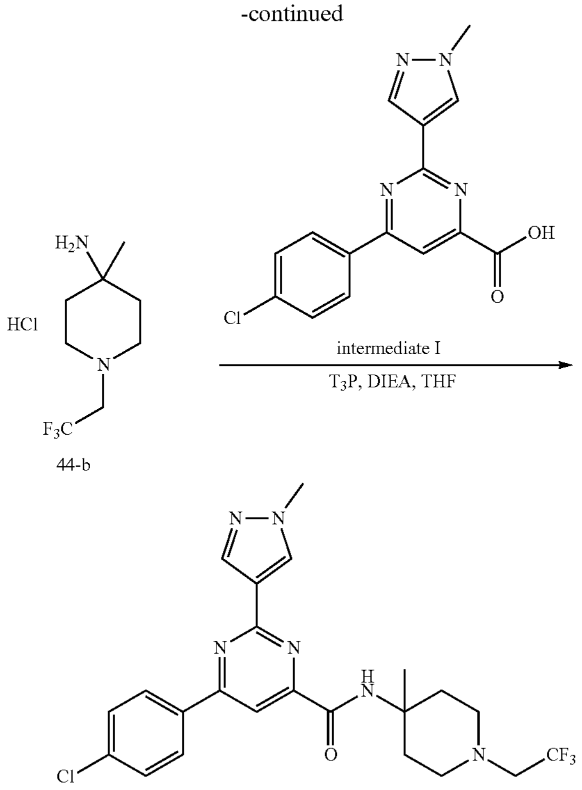

44-b

44

Step 1: Synthesis of (1-(trifluoroethyl)-4-methylpiperidin-4-yl)tert-butylcarbamate (44-a)

(4-methylpiperidin-4-yl)tert-butylcarbamate (214 mg, 1.00 mmol) was dissolved in 20 ml of dry dichloromethane, N,N-diisopropylethylamine (192 mg, 1.50 mmol) and 2,2,2-trifluoroethyltrifluoromethane sulfonate (278 mg, 1.20 mmol) were sequentially added at room temperature, and reaction occurred at room temperature with stirring for 2 h. Vacuum drying was performed after the reaction, and the crude product was separated by straight-phase column chromatography to obtain 205 mg of white solid (1-(trifluoroethyl)-4-methylpiperidin-4-yl)tert-butylcarbamate (44-a), with a yield of 69%. ESI $[M+H]^+$=296.2+

Step 2: Synthesis of (4-amino-4-methylpiperidin-1-yl)trifluoroethyl hydrochloride (44-b)

The (1-(trifluoroethyl)-4-methylpiperidin-4-yl)tert-butylcarbamate (205 mg, 0.69 mmol) was dissolved in 10 ml of dichloromethane, a dioxane solution of hydrochloric acid (1 mL, 4.00 mmol) was added at room temperature, and reaction occurred at room temperature with stirring for 2 h. After the reaction, vacuum drying was directly performed to obtain 100 mg of white solid (4-amino-4-methylpiperidin-1-yl)trifluoroethyl hydrochloride (44-b), with a yield of 74%. ESI $[M+H]^+$=196.2

Step 3: Synthesis of 6-(4-chlorophenyl)-N-((4-yl-4-methylpiperidin-1-yl)trifluoroethyl)-2-(1-methyl-1H-pyrazol-4-yl)pyrimidine-4-formamide (Compound 44)

The 6-(4-chlorophenyl)-2-(1-methyl-1H-pyrazol-4-yl)pyrimidine-4-carboxylic acid (100 mg, 0.32 mmol) and the (4-amino-4-methylpiperidin-1-yl)trifluoroethyl hydrochloride (97 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 46 mg of white solid 6-(4-chlorophenyl)-N-((4-yl-4-methylpiperidin-1-yl)trifluoroethyl)-2-(1-methyl-1H-pyrazol-4-yl)pyrimidine-4-formamide (compound 44), with a yield of 29%. $^1H$ NMR (400 MHz, DMSO-d6) δ 8.64 (s, 1H), 8.43-8.35 (m, 2H), 8.31 (s, 1H), 8.22 (s, 1H), 8.14 (s, 1H), 7.69-7.61 (m, 2H), 3.96 (s, 3H), 3.16 (q, J=10.2 Hz, 2H), 2.73 (s, 1H), 2.57 (t, J=11.0 Hz, 3H), 2.33 (d, J=13.2 Hz, 2H), 1.67 (dd, J=12.9, 9.3 Hz, 2H), 1.45 (s, 3H). ESI $[M+H]^+$=493.2

Example 45: Synthesis of 6-(4-chlorophenyl)-N-(2-(4-yl-4-methylpiperidin-1-yl)acetamide)-2-(1-methyl-1H-pyrazol-4-yl)pyrimidine-4-formamide (Compound 45)

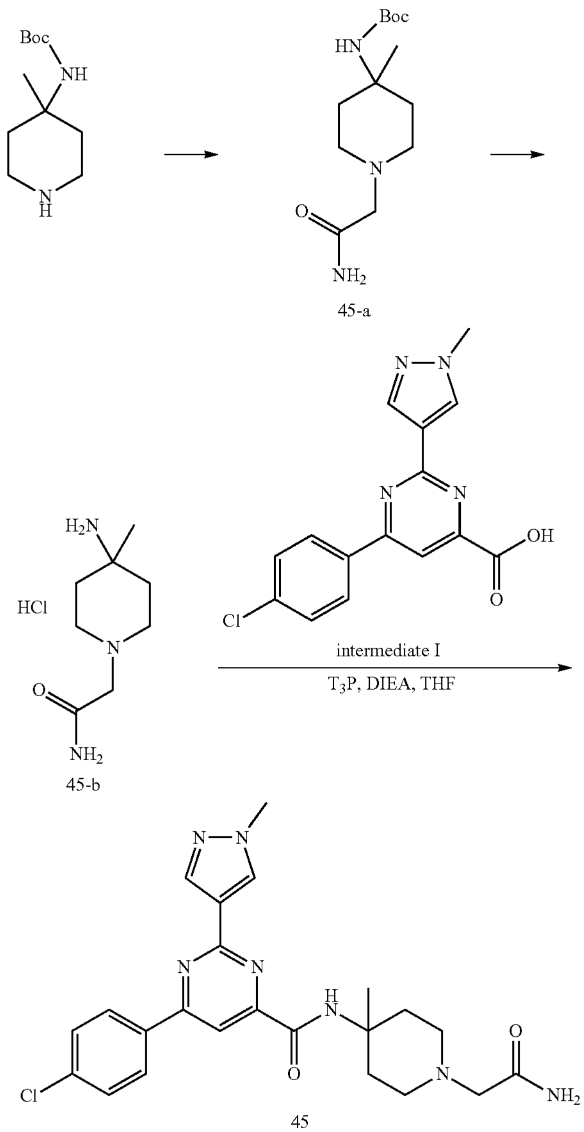 [SMILES: CC1(NC(=O)OC(C)(C)C)CCNCC1 ; CC1(NC(=O)OC(C)(C)C)CCN(CC(N)=O)CC1 ; Cl ; CC1(N)CCN(CC(N)=O)CC1 ; Cn1cc(-c2nc(C(=O)O)cc(-c3ccc(Cl)cc3)n2)cn1 ; Cn1cc(-c2nc(C(=O)NC3(C)CCN(CC(N)=O)CC3)cc(-c3ccc(Cl)cc3)n2)cn1]

45-a 45-b

45

Step 1: Synthesis of (1-(2-amino-2-oxoethyl)-4-methylpiperidin-4-yl)tert-butylcarbamate (45-a)

(4-methylpiperidin-4-yl)tert-butylcarbamate (214 mg, 1.00 mmol) was dissolved in 20 ml of dry dichloromethane, N,N-diisopropylethylamine (192 mg, 1.50 mmol) and bromoacetamide (165 mg, 1.20 mmol) were sequentially added at room temperature, and reaction occurred at room temperature with stirring for 2 h. Vacuum drying was performed after the reaction, and the crude product was separated by straight-phase column chromatography to obtain 185 mg of white solid (1-(2-amino-2-oxoethyl)-4-methylpiperidin-4-yl)tert-butylcarbamate (45-a), with a yield of 68%. ESI $[M+H]^+$=272.2

Step 2: Synthesis of 2-(4-amino-4-methylpiperidin-1-yl)acetamide hydrochloride (45-b)

The (1-(2-amino-2-oxoethyl)-4-methylpiperidin-4-yl) tert-butylcarbamate (205 mg, 0.69 mmol) was dissolved in 10 ml of dichloromethane, a dioxane solution of hydrochloric acid (1 mL, 4.00 mmol) was added at room temperature, and reaction occurred at room temperature with stirring for 2 h. After the reaction, vacuum drying was directly performed to obtain 100 mg of white solid 2-(4-amino-4-methylpiperidin-1-yl)acetamide hydrochloride (45-b), with a yield of 74%. ESI $[M+H]^+$=172.2

Step 3: Synthesis of 6-(4-chlorophenyl)-N-(2-(4-yl-4-methylpiperidin-1-yl)acetamide)-2-(1-methyl-1H-pyrazol-4-yl)pyrimidine-4-formamide (Compound 45)

The 6-(4-chlorophenyl)-2-(1-methyl-1H-pyrazol-4-yl)pyrimidine-4-carboxylic acid (100 mg, 0.32 mmol) and the 2-(4-amino-4-methylpiperidin-1-yl)acetamide hydrochloride (87 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 65 mg of white solid 6-(4-chlorophenyl)-N-(2-(4-yl-4-methylpiperidin-1-yl)acetamide)-2-(1-methyl-1H-pyrazol-4-yl)pyrimidine-4-formamide (compound 45), with a yield of 43%. $^1$H NMR (400 MHz, DMSO-d6) δ 8.64 (s, 1H), 8.43-8.35 (m, 2H), 8.33 (s, 1H), 8.21 (d, J=4.0 Hz, 2H), 7.69-7.61 (m, 2H), 4.32 (s, 2H), 3.95 (s, 3H), 3.91 (s, 2H), 2.78 (s, 2H), 2.62 (s, 3H), 2.43 (s, 3H), 1.73 (t, J=12.1 Hz, 2H), 1.46 (s, 3H). ESI $[M+H]^+$=468.2

Example 46: Synthesis of 6-(4-chlorophenyl)-N-(1-(cyanomethyl)-4-methylpiperidin-4-yl)-2-(1-methyl-1H-pyrazol-4-yl)pyrimidine-4-formamide (Compound 46)

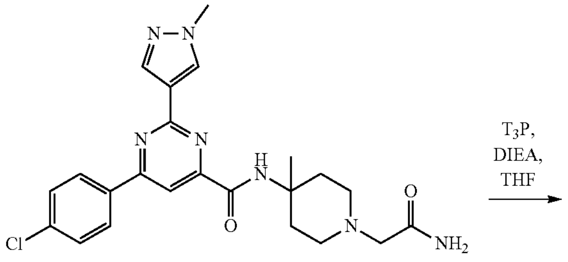

45

-continued

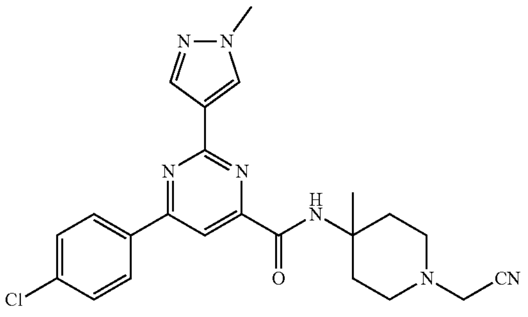

46

Step 1: Synthesis of(S)-6-(4-chlorophenyl)-N-(1-(cyanomethyl)-4-methylpiperidin-4-yl)-2-(1-methyl-1H-pyrazol-4-yl)pyrimidine-4-formamide (Compound 46)

6-(4-chlorophenyl)-N-(2-(4-amino-4-methylpiperidin-1-yl)acetamide)-2-(1-methyl-1H-pyrazol-4-yl)pyrimidine-4-formamide (30 mg, 0.06 mmol) was dissolved in 2 ml of tetrahydrofuran, N,N-diisopropylethylamine (21.6 mg, 0.17 mmol) and 1-propylphosphonic anhydride (100 mg, 0.16 mmol) were sequentially added at room temperature, and reaction occurred at room temperature with stirring for 2 h. After vacuum drying, the crude product was separated by straight-phase column chromatography to obtain 16 mg of white solid (S)-6-(4-chlorophenyl)-N-(1-(cyanomethyl)-4-methylpiperidin-4-yl)-2-(1-methyl-1H-pyrazol-4-yl)pyrimidine-4-formamide (compound 46), with a yield of 55%. $^1$H NMR (400 MHz, DMSO-d6) δ 8.64 (s, 1H), 8.39 (d, J=8.1 Hz, 2H), 8.31 (s, 1H), 8.19 (d, J=10.1 Hz, 2H), 7.64 (d, J=8.1 Hz, 2H), 3.95 (s, 3H), 3.73 (s, 2H), 2.61 (d, J=11.0 Hz, 2H), 2.45 (s, 2H), 2.37 (t, J=8.1 Hz, 2H), 1.68 (t, J=11.1 Hz, 2H), 1.46 (s, 3H). ESI $[M+H]^+$=450.2

Example 47: Synthesis of (S)-6-(4-fluorophenyl)-N-(1-(2-fluoro-4-pyridine)ethyl)-2-(1-methylpyrazol-4-yl)pyrimidine-4-formamide (Compound 47)

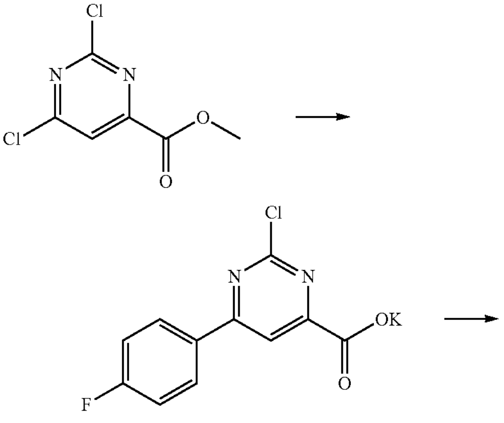

47-a

-continued

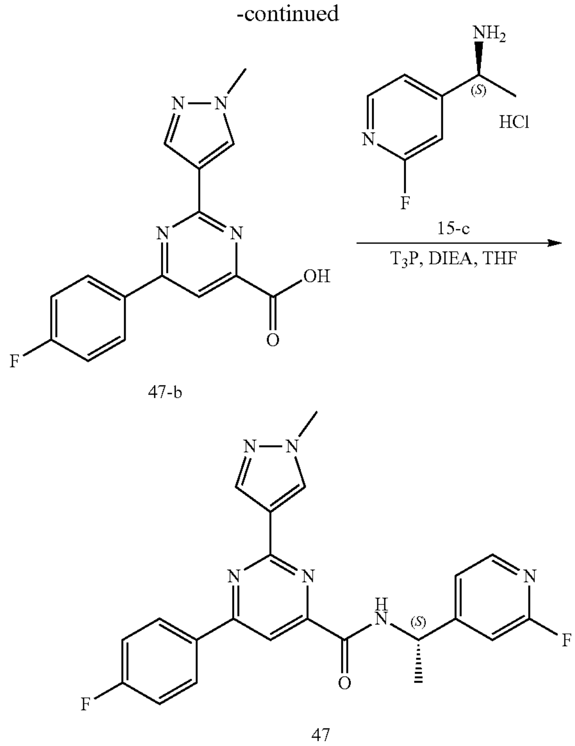

47-b

47

Step 1: Synthesis of potassium 2-chloro-6-(4-fluorophenyl)pyrimidine-4-carboxylate (47-a)

4-fluorophenylboronic acid (1.40 g, 10 mmol) and methyl 2,6-dichloropyrimidine-4-carboxylate (2.06 g, 10 mmol) were dissolved in dioxane/water (100 mL/15 mL), tetra (triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.60 g of gray solid potassium 2-chloro-6-(4-fluorophenyl)pyrimidine-4-carboxylate (47-a), with a yield of 63%. ESI $[M+H]^+$=253.2

Step 2: Synthesis of 6-(4-fluorophenyl)-2-(1-methylpyrazol-4-yl)pyrimidine-4-carboxylic acid (47-b)

1-methylpyrazol-4-boronic acid (945 mg, 7.5 mmol) and the potassium 2-chloro-6-(4-fluorophenyl)pyrimidine-4-carboxylate (1.51 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 680 mg of gray solid 6-(4-fluorophenyl)-2-(1-methylpyrazol-4-yl)pyrimidine-4-carboxylic acid (47-b), with a yield of 38%. ESI $[M+H]^+$=298.2

Step 3: Synthesis of (S)-6-(4-fluorophenyl)-N-(1-(2-fluoro-4-pyridine)ethyl)-2-(1-methyl-1H-pyrazol-4-yl)pyrimidine-4-formamide (Compound 47)

The 6-(4-fluorophenyl)-2-(1-methylpyrazol-4-yl)pyrimidine-4-carboxylic acid (95 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 54 mg of white solid (S)-6-(4-fluorophenyl)-N-(1-(2-fluoro-4-pyridine)ethyl)-2-(1-methyl-1H-pyrazol-4-yl)pyrimidine-4-formamide (compound 47), with a yield of 40%. $^1$H NMR (400 MHz, DMSO-d6) δ 9.36 (d, J=8.3 Hz, 1H), 8.69 (s, 1H), 8.46-8.39 (m, 3H), 8.24-8.18 (m, 2H), 7.45-7.38 (m, 3H), 7.24 (s, 1H), 5.31 (p, J=7.2 Hz, 1H), 3.97 (s, 3H), 1.63 (d, J=7.1 Hz, 3H). ESI $[M+H]^+$=421.2

Example 48: Synthesis of (S)-6-(1-methyl-1H-pyrazol-4-yl)-N-(1-(3-fluorophenyl)ethyl)-2-(1-methyl-1H-pyrazol-4-yl)pyrimidine-4-formamide (Compound 48)

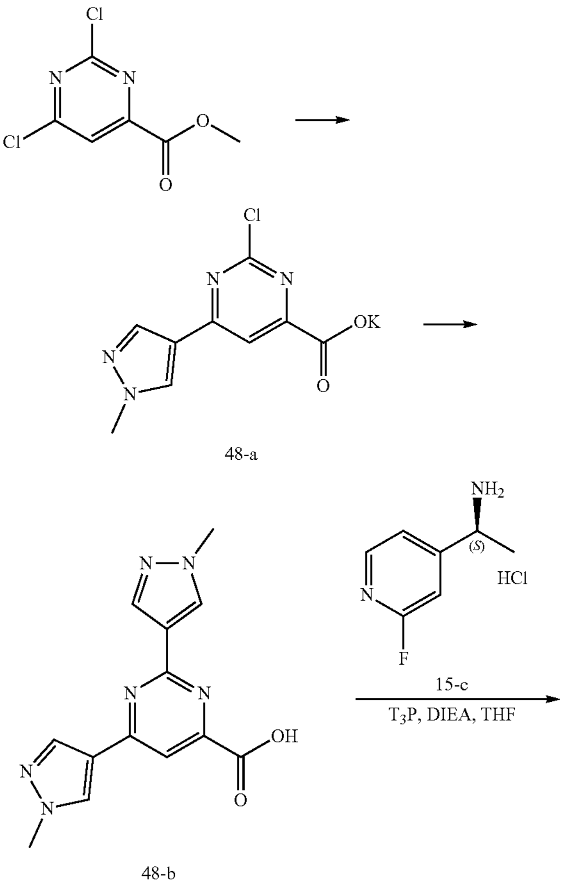

48-a 48-b

-continued

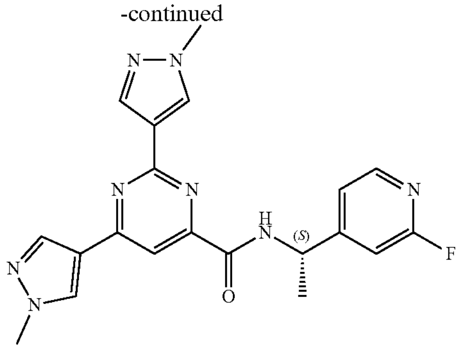

48

Step 1: Synthesis of potassium 2-chloro-6-(1-methyl-1H-pyrazol-4-yl)pyrimidine-4-carboxylate (48-a)

1-methylpyrazol-4-boronic acid (1.26 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.49 g of gray solid potassium 2-chloro-6-(1-methyl-1H-pyrazol-4-yl)pyrimidine-4-carboxylate (48-a), with a yield of 62%. ESI $[M+H]^+$= 239.2

Step 2: Synthesis of 6-(1-methyl-1H-pyrazol-4-yl)-2-(1-methyl-1H-pyrazol-4-yl)pyrimidine-4-carboxylic acid (48-b)

1-methylpyrazol-4-boronic acid (945 mg, 7.5 mmol) and the potassium 2-chloro-6-(1-methyl-1H-pyrazol-4-yl)pyrimidine-4-carboxylate (1.51 g, 6.0 mmol) were dissolved in dioxane/water (100 mL/15 mL), tetra(triphenylphosphine) palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 680 mg of gray solid 6-(1-methyl-1H-pyrazol-4-yl)-2-(1-methyl-1H-pyrazol-4-yl)pyrimidine-4-carboxylic acid (48-b), with a yield of 40%. ESI $[M+H]^+$=285.2

Step 3: Synthesis of (S)-6-(1-methyl-1H-pyrazol-4-yl)-N-(1-(2-fluoro-4-pyridine)ethyl)-2-(1-methyl-1H-pyrazol-4-yl)pyrimidine-4-formamide (Compound 48)

The 6-(1-methyl-1H-pyrazol-4-yl)-2-(1-methyl-1H-pyrazol-4-yl)pyrimidine-4-carboxylic acid (91 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 58 mg of white solid (S)-6-(1-methyl-1H-pyrazol-4-yl)-N-(1-(2-fluoro-4-pyridine)ethyl)-2-(1-methyl-1H-pyrazol-4-yl)pyrimidine-4-formamide (compound 48), with a yield of 45%. $^1H$ NMR (400 MHz, DMSO-d6) δ 9.27 (d, J=8.4 Hz, 1H), 8.65 (s, 1H), 8.60 (s, 1H), 8.35 (d, J=0.7 Hz, 1H), 8.33-8.26 (m, 1H), 8.21 (d, J=5.2 Hz, 1H), 7.88 (s, 1H), 7.42 (d, J=5.1 Hz, 1H), 7.22 (d, J=8.8 Hz, 1H), 5.33-5.23 (m, 1H), 3.98-3.86 (m, 6H), 1.60 (dd, J=7.2, 5.1 Hz, 3H). ESI $[M+H]^+$=407.2

Example 49: Synthesis of (S)-6-(2-fluoro-4-pyridine)-N-(1-(2-fluoro-4-pyridine)ethyl)-2-(1-methyl-1H-pyrazol-4-yl)pyrimidine-4-formamide (Compound 49)

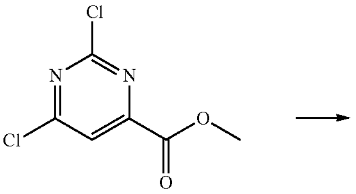

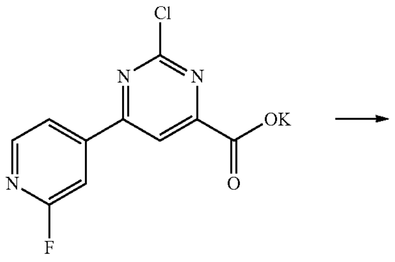

49-a

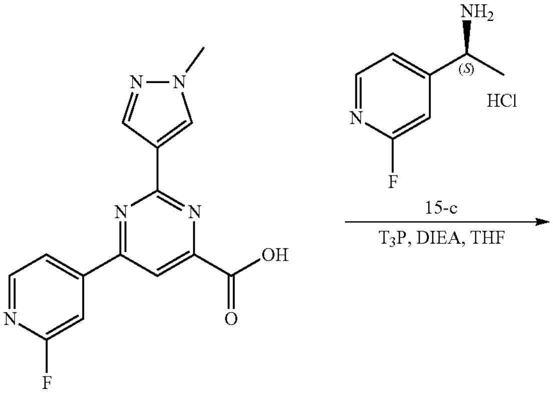

49-b

-continued

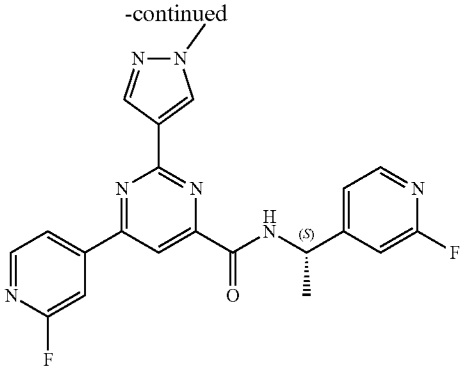

49

Step 1: Synthesis of potassium 2-chloro-6-(2-fluoro-4-pyridine)pyrimidine-4-carboxylate (49-a)

2-fluoropyridine-4-boronic acid (1.41 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.55 g of gray solid potassium 2-chloro-6-(2-fluoro-4-pyridine)pyrimidine-4-carboxylate (49-a), with a yield of 61%. ESI $[M+H]^+=254.2$ Step 2: Synthesis of 6-(2-fluoro-4-pyridine)-2-(1-methyl-1H-pyrazol-4-yl)pyrimidine-4-carboxylic acid (49-b)

1-methylpyrazol-4-boronic acid (945 mg, 7.5 mmol) and the potassium 2-chloro-6-(2-fluoro-4-pyridine)pyrimidine-4-carboxylate (1.52 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 680 mg of gray solid 6-(2-fluoro-4-pyridine)-2-(1-methyl-1H-pyrazol-4-yl)pyrimidine-4-carboxylic acid (49-b), with a yield of 38%. ESI $[M+H]^+=300.2$ Step 3: Synthesis of (S)-6-(2-fluoro-4-pyridine)-N-(1-(2-fluoro-4-pyridine)ethyl)-2-(1-methyl-1H-pyrazol-4-yl)pyrimidine-4-formamide (Compound 49)

The 6-(2-fluoro-4-pyridine)-2-(1-methyl-1H-pyrazol-4-yl)pyrimidine-4-carboxylic acid (96 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 59 mg of white solid (S)-6-(2-fluoro-4-pyridine)-N-(1-(2-fluoro-4-pyridine)ethyl)-2-(1-methyl-1H-pyrazol-4-yl)pyrimidine-4-formamide (compound 49), with a yield of 43%. $^1$H NMR (400 MHz, DMSO-d6) δ 9.43 (d, J=8.2 Hz, 1H), 8.76 (s, 1H), 8.53-8.41 (m, 2H), 8.37 (s, 1H), 8.28 (dt, J=5.2, 1.7 Hz, 1H), 8.25-8.19 (m, 1H), 8.14 (d, J=8.3 Hz, 1H), 7.47-7.37 (m, 1H), 7.25 (s, 1H), 5.32 (p, J=7.5 Hz, 1H), 3.97 (s, 3H), 1.64 (dd, J=7.2, 4.4 Hz, 3H). ESI $[M+H]^+=422.2$ Example 50: Synthesis of (S)-6-(4-chlorophenyl)-N-(1-(2-fluoro-4-pyridine)ethyl)-2-(p-methoxyphenyl)pyrimidine-4-formamide (Compound 50)

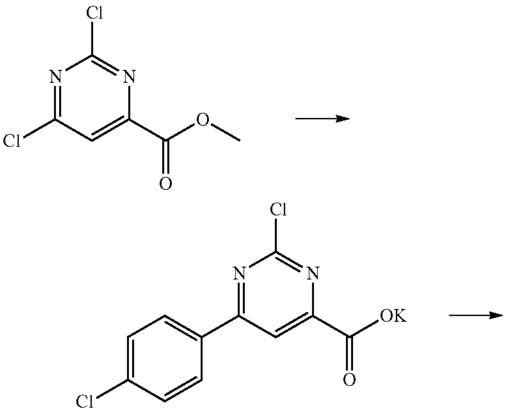

50-a

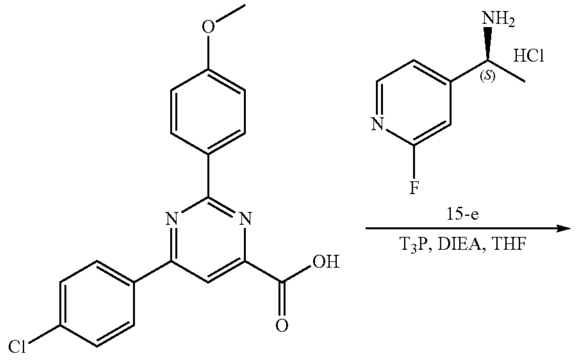

50-b

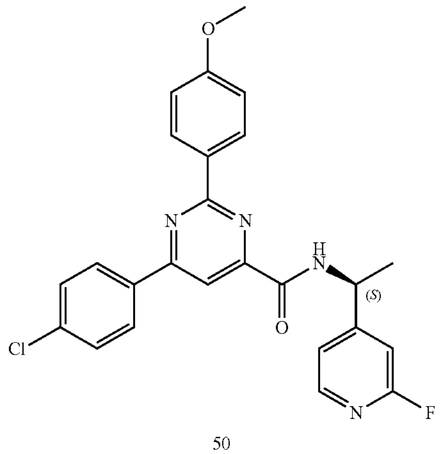

50

Step 1: Synthesis of potassium 2-chloro-6-(4-chlorophenyl)pyrimidine-4-carboxylate (50-a)

4-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.61 g of gray solid potassium 2-chloro-6-(4-chlorophenyl)pyrimidine-4-carboxylate (50-a), with a yield of 60%. ESI $[M+H]^+$=268.2

Step 2: Synthesis of 6-(4-chlorophenyl)-2-(p-methoxyphenyl)pyrimidine-4-carboxylic acid (50-b)

P-methoxyphenylboronic acid (1.14 g, 7.5 mmol) and the potassium 2-chloro-6-(4-chlorophenyl)pyrimidine-4-carboxylate (1.61 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 620 mg of gray solid 6-(4-chlorophenyl)-2-(p-methoxyphenyl)pyrimidine-4-carboxylic acid (50-b), with a yield of 31%. ESI $[M+H]^+$=341.2

Step 3: Synthesis of(S)-6-(4-chlorophenyl)-N-(1-(2-fluoro-4-pyridine)ethyl)-2-(p-methoxyphenyl)pyrimidine-4-formamide (Compound 50)

The 6-(4-chlorophenyl)-2-(p-methoxyphenyl)pyrimidine-4-carboxylic acid (95 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 44 mg of white solid (S)-6-(4-chlorophenyl)-N-(1-(2-fluoro-4-pyridine)ethyl)-2-(p-methoxyphenyl)pyrimidine-4-formamide (compound 50), with a yield of 30%. $^1H$ NMR (400 MHz, DMSO-d6) δ 9.62 (d, J=2.5 Hz, 1H), 9.57 (d, J=8.4 Hz, 1H), 8.94 (dd, J=8.7, 2.4 Hz, 1H), 8.48-8.40 (m, 2H), 8.36 (s, 1H), 8.22 (d, J=5.2 Hz, 1H), 7.68-7.60 (m, 2H), 7.45 (dt, J=5.3, 1.8 Hz, 1H), 7.26 (s, 1H), 7.03 (d, J=8.7 Hz, 1H), 5.34 (p, J=7.2 Hz, 1H), 3.98 (s, 3H), 1.64 (d, J=7.1 Hz, 3H). ESI $[M+H]^+$=463.2

Example 51: Synthesis of (S)-6-(4-chlorophenyl)-N-(1-(4-chlorophenyl)cyclopropylamine)-2-(1-methyl-1H-pyrazol-4-yl)pyrimidine-4-formamide (Compound 51)

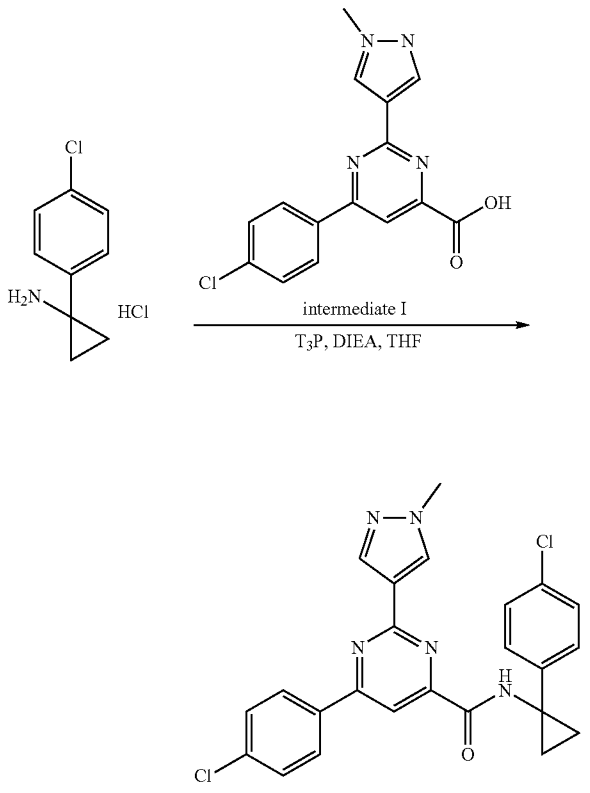

51

Step 1: Synthesis of 6-(4-chlorophenyl)-N-(1-(4-chlorophenyl)cyclopropylamine)-2-(1-methyl-1H-pyrazol-4-yl)pyrimidine-4-formamide (Compound 51)

The 6-(4-chlorophenyl)-2-(1-methyl-1H-pyrazol-4-yl)pyrimidine-4-carboxylic acid (100 mg, 0.32 mmol) and 1-(4-chlorophenyl)cyclopropylamine hydrochloride (85 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 54 mg of white solid 6-(4-chlorophenyl)-N-(1-(4-chlorophenyl)cyclopropylamine)-2-(1-methyl-1H-pyrazol-4-yl)pyrimidine-4-formamide (compound 51), with a yield of 36%. $^1H$ NMR (400 MHz, DMSO-d6) δ 9.80 (s, 1H), 8.74 (s, 1H), 8.43 (s, 1H), 8.40-8.34 (m, 2H), 8.19 (s, 1H), 7.67-7.60 (m, 2H), 7.39-7.31 (m, 2H), 7.32-7.24 (m, 2H), 3.95 (s, 3H), 1.42-1.36 (m, 4H). ESI $[M+H]^+$=464.2

Example 52: Synthesis of (S)-6-(4-chlorophenyl)-N-(1-(3-fluoro-4-(methylaminoformyl)phenyl)ethyl)-2-(1-methyl-1H-pyrazol-4-yl)pyrimidine-4-formamide (Compound 52)

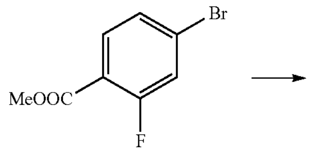

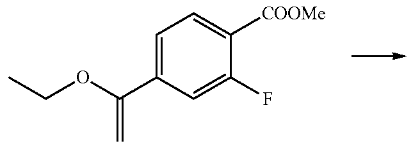

52-a

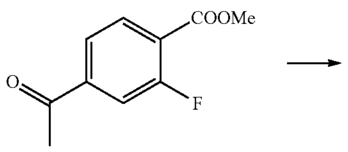

52-b

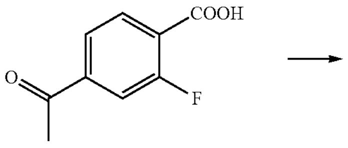

52-c

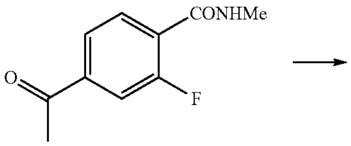

52-d

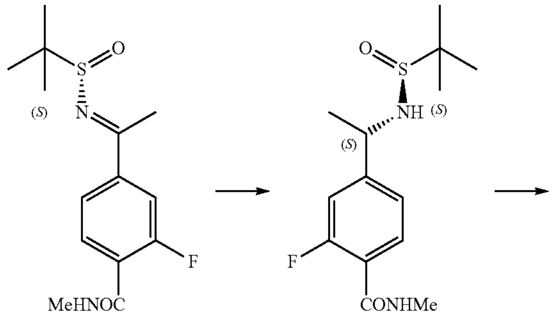

52-e 52-f

-continued

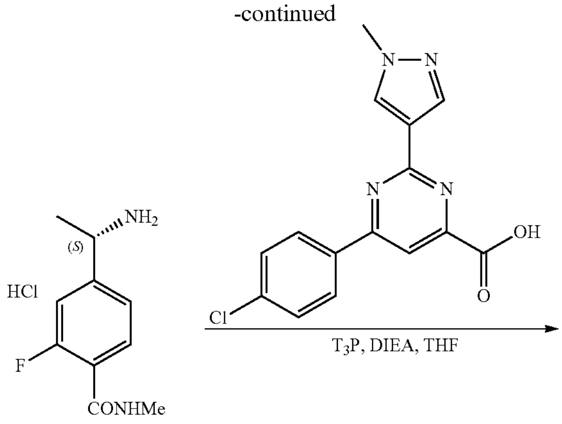

52-g

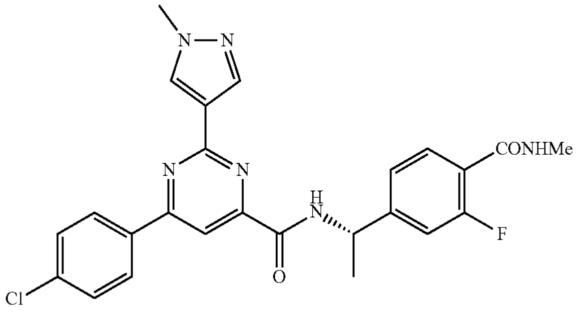

52

Step 1: Synthesis of methyl 4-(1-ethoxyvinyl)-2-fluorobenzoate (52-a)

Methyl 4-bromo-2-fluorobenzoate (464 mg, 2.0 mmol) was dissolved in 20 mL of dry DMF; tributyl(1-ethoxyethylene) tin (902 mg, 2.5 mmol), cuprous iodide (38 mg, 0.2 mmol), tetra(triphenylphosphine)palladium (23 mg, 0.02 mmol), and cesium fluoride (608 mg, 4.0 mmol) were sequentially added at room temperature; reaction occurred at 100° C. with stirring for 8 h, then the solution was extracted with dichloromethane/water, and the organic phase was dried in vacuum and then purified by a straight-phase column chromatography to obtain 261 mg of white solid methyl 4-(1-ethoxyvinyl)-2-fluorobenzoate (52-a), with a yield of 58%. ESI $[M+H]^+=225.1$

Step 2: Synthesis of methyl 4-acetyl-2-fluorobenzoate (52-b)

The methyl 4-(1-ethoxyvinyl)-2-fluorobenzoate (247 mg, 1.1 mmol) was dissolved in 15 mL of dry tetrahydrofuran, a 1,4-dioxane solution of 4 M hydrochloric acid (0.74 mL, 2.96 mmol) was added, and reaction occurred at room temperature with stirring for 3 h. Pull drying was performed after the reaction, the solid was extracted with ethyl acetate/water, and the organic phase was dried in vacuum to obtain 165 mg of light yellow oily methyl 4-acetyl-2-fluorobenzoate (52-b), with a yield of 76%. ESI $[M+H]^+=197.2$

Step 3: Synthesis of 4-acetyl-2-fluorobenzoic acid (52-c)

The methyl 4-acetyl-2-fluorobenzoate (165 mg, 0.84 mmol) was dissolved in 10 mL of methanol/10 mL of water, lithium hydroxide (152 mg, 4.0 mmol) was added, and reaction occurred at room temperature with stirring for 3 h. The solution was extracted with ethyl acetate/water after the reaction, and the organic phase was dried in vacuum to obtain 135 mg of white solid 4-acetyl-2-fluorobenzoic acid (52-c), with a yield of 87%. ESI $[M+H]^+$=183.2

Step 4: Synthesis of 4-acetyl-2-fluorobenzamide (52-d)

The 4-acetyl-2-fluorobenzoic acid (135 mg, 0.74 mmol) and methylamine hydrochloride (100 mg, 1.5 mmol) were dissolved in 10 ml of tetrahydrofuran, N,N-diisopropylethylamine (387 mg, 3.0 mmol) and 1-propylphosphonic anhydride (636 mg, 1.0 mmol) were sequentially added at room temperature, and reaction occurred at room temperature with stirring for 2 h. After vacuum drying, the crude product was separated by straight-phase column chromatography to obtain 130 mg of white solid 4-acetyl-2-fluorobenzamide (52-d), with a yield of 90%. ESI $[M+H]^+$=196.2

Step 5: Synthesis of(S)-4-(1-((tert-butylsulfinyl)imino)ethyl)-2-fluoro-N-methylbenzamide (52-e)

The 4-acetyl-2-fluorobenzamide (130 mg, 0.66 mmol) was dissolved in 15 mL of dry tetrahydrofuran, (S)-tert-butylsulfinamide (145 mg, 1.2 mmol) and tetraethyl titanate (342 g, 1.5 mmol) were sequentially added at room temperature, reaction occurred at 80° C. with stirring for 8 h, then the solution was extracted with ethyl acetate/water, and the organic phase was dried in vacuum and then purified by a straight-phase column chromatography to obtain 121 mg of off-white solid (S)-4-(1-((tert-butylsulfinyl)imino)ethyl)-2-fluoro-N-methylbenzamide (52-e), with a yield of 61%. ESI $[M+H]^+$=299.1

Step 6: Synthesis of 4-((S)-1-(((S)-tert-butylsulfinyl)amino)ethyl)-2-fluoro-N-methylbenzamide (52-f)

The (S)-4-(1-((tert-butylsulfinyl)imino)ethyl)-2-fluoro-N-methylbenzamide (121 mg, 0.40 mmol) was dissolved in 10 mL of dry tetrahydrofuran, a tetrahydrofuran solution of 1 M borane (1.0 mL, 1.0 mmol) was added at 0° C., the solution was stirred at room temperature for 2 h, methanol was added for quenching after reaction was completed, and the organic phase was dried in vacuum and then purified by a straight-phase column chromatography to obtain 103 mg of white solid 4-((S)-1-(((S)-tert-butylsulfinyl)amino)ethyl)-2-fluoro-N-methylbenzamide (52-f), with a yield of 85%. ESI $[M+H]^+$=301.1

Step 7: Synthesis of (S)-4-(1-aminoethyl)-2-fluoro-N-methylbenzamide hydrochloride (52-g)

The 4-((S)-1-(((S)-tert-butylsulfinyl)amino)ethyl)-2-fluoro-N-methylbenzamide (103 mg, 0.34 mmol) was dissolved in 10 mL of tetrahydrofuran, a 1,4-dioxane solution of 4 M hydrochloric acid (0.74 mL, 2.96 mmol) was added, and reaction occurred at room temperature with stirring for 3 h. The solution was concentrated after the reaction, the solid was washed twice with ethyl acetate and twice with petroleum ether, and the solid was dried to obtain 53 mg of white solid (S)-4-(1-aminoethyl)-2-fluoro-N-methylbenzamide hydrochloride (52-g), with a yield of 79%. ESI $[M+H]^+$=197.1

Step 8: Synthesis of (S)-6-(4-chlorophenyl)-N-(1-(3-fluoro-4-(methylaminoformyl)phenyl)ethyl)-2-(1-methyl-1H-pyrazol-4-yl)pyrimidine-4-formamide (Compound 52)

The 6-(4-chlorophenyl)-2-(1-methyl-1H-pyrazol-4-yl)pyrimidine-4-carboxylic acid (100 mg, 0.32 mmol) and the (S)-4-(1-aminoethyl)-2-fluoro-N-methylbenzamide hydrochloride (53 mg, 0.27 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 44 mg of white solid (S)-6-(4-chlorophenyl)-N-(1-(3-fluoro-4-(methylaminoformyl)phenyl)ethyl)-2-(1-methyl-1H-pyrazol-4-yl)pyrimidine-4-formamide (compound 52), with a yield of 33%. $^1H$ NMR (400 MHz, DMSO-d6) δ 9.31 (d, J=8.5 Hz, 1H), 8.70 (s, 1H), 8.43 (s, 1H), 8.41-8.35 (m, 2H), 8.20 (s, 2H), 7.68-7.57 (m, 3H), 7.42-7.32 (m, 2H), 5.33-5.25 (m, 1H), 3.97 (s, 3H), 2.76 (d, J=4.6 Hz, 3H), 1.61 (d, J=7.0 Hz, 3H). ESI $[M+H]^+$=493.2

Example 53: Synthesis of (S)-6-(4-chlorophenyl)-N-(1-(4-(1-aminoethyl)-2-fluorophenyl)ethyl)-2-(1-methyl-1H-pyrazol-4-yl)pyrimidine-4-formamide (Compound 53)

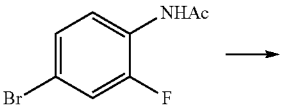

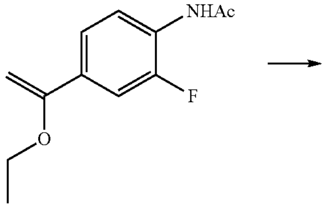

53-a

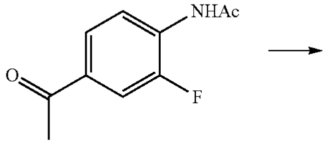

53-b

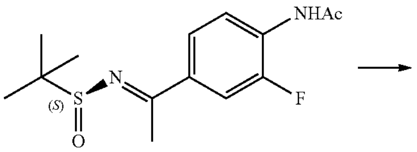

53-c

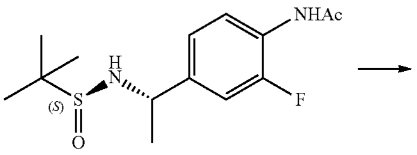

53-d

-continued

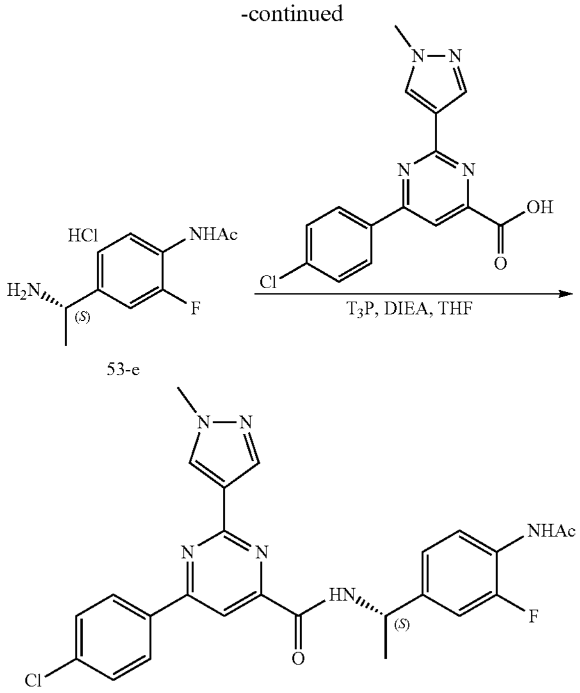

53-e

53

Step 1: Synthesis of N-(4-(1-ethoxyvinyl)-2-fluorophenyl)acetamide (53-a)

N-(4-bromo-2-fluorophenyl)acetamide (462 mg, 2.0 mmol) was dissolved in 20 mL of dry DMF; tributyl(1-ethoxyethylene) tin (902 mg, 2.5 mmol), cuprous iodide (38 mg, 0.2 mmol), tetra(triphenylphosphine)palladium (23 mg, 0.02 mmol), and cesium fluoride (608 mg, 4.0 mmol) were sequentially added at room temperature; reaction occurred at 100° C. with stirring for 8 h, then the solution was extracted with dichloromethane/water, and the organic phase was dried in vacuum and then purified by a straight-phase column chromatography to obtain 260 mg of white solid N-(4-(1-ethoxyvinyl)-2-fluorophenyl)acetamide (53-a), with a yield of 58%. ESI $[M+H]^+$=224.1

Step 2: Synthesis of N-(4-acetyl-2-fluorophenyl)acetamide (53-b)

The N-(4-(1-ethoxyvinyl)-2-fluorophenyl)acetamide (246 mg, 1.1 mmol) was dissolved in 15 mL of dry tetrahydrofuran, a 1,4-dioxane solution of 4 M hydrochloric acid (0.74 mL, 2.96 mmol) was added, and reaction occurred at room temperature with stirring for 3 h. The solution was concentrated after the reaction, the solid was washed twice with ethyl acetate and twice with petroleum ether, and the solid was dried to obtain 164 mg of off-white solid N-(4-acetyl-2-fluorophenyl)acetamide (53-b), with a yield of 76%. ESI $[M+H]^+$=196.2

Step 3: Synthesis of (S)-N-(4-(1-((tert-butylsulfinyl)imino)ethyl)-2-fluorophenyl)acetamide (53-c)

The N-(4-acetyl-2-fluorophenyl)acetamide (164 mg, 0.84 mmol) was dissolved in 20 mL of dry tetrahydrofuran, (S)-tert-butylsulfinamide (145 mg, 1.2 mmol) and tetraethyl titanate (342 g, 1.5 mmol) were sequentially added at room temperature, reaction occurred at 80° C. with stirring for 8 h, then the solution was extracted with ethyl acetate/water, and the organic phase was dried in vacuum and then purified by a straight-phase column chromatography to obtain 160 mg of light yellow solid (S)-N-(4-(1-((tert-butylsulfinyl)imino)ethyl)-2-fluorophenyl)acetamide (53-c), with a yield of 64%. ESI $[M+H]^+$=299.1

Step 4: Synthesis of N-(4-((S)-1-(((S)-tert-butylsulfinyl)amino)ethyl)-2-fluorophenyl)acetamide (53-d)

The (S)-N-(4-(1-((tert-butylsulfinyl)imino)ethyl)-2-fluorophenyl)acetamide (160 mg, 0.53 mmol) was dissolved in 20 mL of dry tetrahydrofuran, a tetrahydrofuran solution of 1 M borane (1.2 mL, 1.2 mmol) was added at 0° C., the solution was stirred at room temperature for 2 h, methanol was added for quenching after reaction was completed, and the organic phase was dried in vacuum and then purified by a straight-phase column chromatography to obtain 133 mg of white solid N-(4-((S)-1-(((S)-tert-butylsulfinyl)amino)ethyl)-2-fluorophenyl)acetamide (53-d), with a yield of 83%. ESI $[M+H]^+$=301.1

Step 5: Synthesis of(S)-N-(4-(1-aminoethyl)-2-fluorophenyl)acetamide hydrochloride (53-e)

The N-(4-(((S)-1-(((S)-tert-butylsulfinyl)amino)ethyl)-2-fluorophenyl)acetamide (133 mg, 0.44 mmol) was dissolved in 15 mL of tetrahydrofuran, a 1,4-dioxane solution of 4 M hydrochloric acid (0.74 mL, 2.96 mmol) was added, and reaction occurred at room temperature with stirring for 3 h. The solution was concentrated after the reaction, the solid was washed twice with ethyl acetate and twice with petroleum ether, and the solid was dried to obtain 54 mg of white solid (S)-N-(4-(1-aminoethyl)-2-fluorophenyl)acetamide hydrochloride (53-e), with a yield of 63%. ESI $[M+H]^+$=197.1

Step 6: Synthesis of(S)-6-(4-chlorophenyl)-N-(1-(4-(1-aminoethyl)-2-fluorophenyl)ethyl)-2-(1-methyl-1H-pyrazol-4-yl)pyrimidine-4-formamide (Compound 53)

The 6-(4-chlorophenyl)-2-(1-methyl-1H-pyrazol-4-yl)pyrimidine-4-carboxylic acid (100 mg, 0.32 mmol) and the (S)-N-(4-(1-aminoethyl)-2-fluorophenyl)acetamide hydrochloride (54 mg, 0.27 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 44 mg of white solid (S)-6-(4-chlorophenyl)-N-(1-(4-(1-aminoethyl)-2-fluorophenyl)ethyl)-2-(1-methyl-1H-pyrazol-4-yl)pyrimidine-4-formamide (compound 53), with a yield of 33%. $^1H$ NMR (400 MHz, DMSO-d6) δ 9.31 (d, J=8.5 Hz, 1H), 8.70 (s, 1H), 8.43 (s, 1H), 8.41-8.35 (m, 2H), 8.20 (s, 2H), 7.68-7.57 (m, 3H), 7.42-7.32 (m, 2H), 5.33-5.25 (m, 1H), 2.76 (d, J=4.6 Hz, 3H), 2.11 (s, 3H), 1.61 (d, J=7.0 Hz, 3H). ESI $[M+H]^+$=493.2

Example 54: Synthesis of(S)-6-(4-chlorophenyl)-N-(1-(1-methyl-1H-benzo[d]imidazol-6-yl)ethyl)-2-(1-methyl-1H-pyrazol-4-yl)pyrimidine-4-formamide (Compound 54)

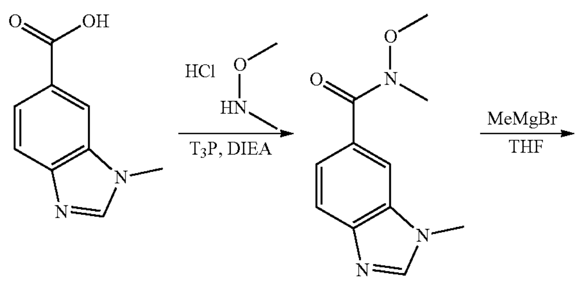

54-a

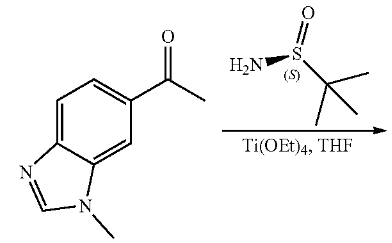

54-b

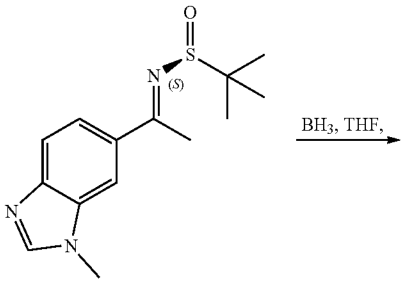

54-c

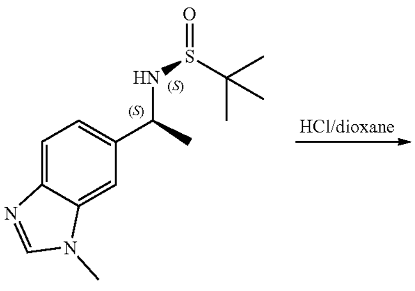

54-d

-continued

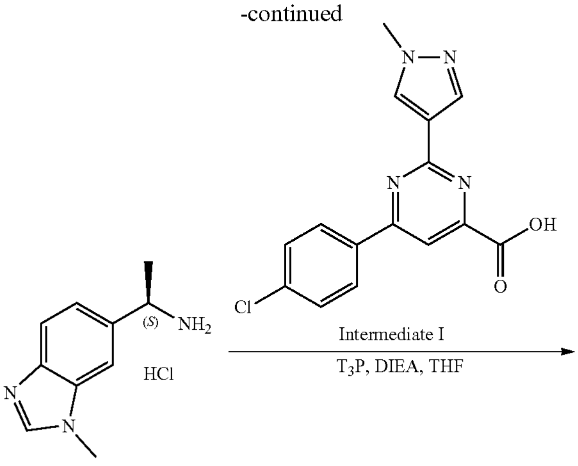

54-e

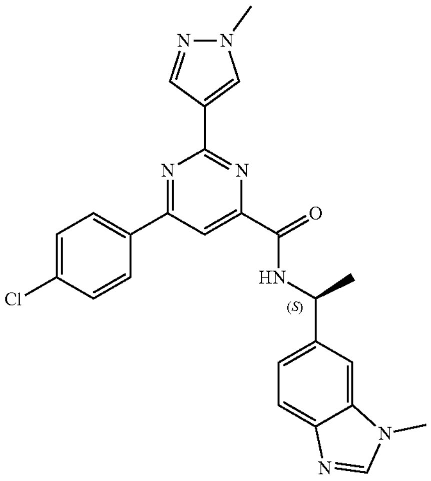

54

Step 1: Synthesis of N-methoxy-N,1-dimethyl-1H-benzo[d]imidazole-6-formamide (54-a)

1-methyl-1H-benzo[d]imidazole-6-carboxylic acid (352 mg, 2.0 mmol) was dissolved in 20 mL of dry tetrahydrofuran; N,O-dimethylhydroxylamine hydrochloride (242 mg, 2.5 mmol), N,N-diisopropylethylamine (645 g, 5.0 mmol), and 1-propylphosphonic anhydride (1.27 g, 2.0 mmol) were sequentially added at room temperature; reaction occurred at 0° C. with stirring for 2 h, then the solution was extracted with an aqueous solution of ethyl acetate/ammonium chloride, and the organic phase was dried in vacuum and then purified by a straight-phase column chromatography to obtain 343 mg of white solid N-methoxy-N,1-dimethyl-1H-benzo[d]imidazole-6-formamide (54-a), with a yield of 78%. ESI $[M+H]^+$=220.1

Step 2: Synthesis of 1-(1-methyl-1H-benzo[d]imidazol-6-yl)ethan-1-one (54-b)

The N-methoxy-N,1-dimethyl-1H-benzo[d]imidazole-6-formamide (330 mg, 1.5 mmol) was dissolved in 50 mL of dry tetrahydrofuran, methyl magnesium bromide (2 mL, 2.0 mmol) was added dropwise at 0° C., reaction occurred at 0° C. with stirring for 2 h, then the solution was extracted with an aqueous solution of ethyl acetate/ammonium chloride, and the organic phase was dried in vacuum and then purified by a straight-phase column chromatography to obtain 175 mg of colorless liquid 1-(1-methyl-1H-benzo[d]imidazol-6-yl)ethan-1-one (54-b), with a yield of 67%. ESI $[M+H]^+$ =175.2

Step 3: Synthesis of (S)-1-(1-methyl-1H-benzo[d] imidazol-6-yl)ethyl-2-sulfinylimine (54-c)

The 1-(1-methyl-1H-benzo[d]imidazol-6-yl)ethan-1-one (175 mg, 1.0 mmol) was dissolved in 30 mL of dry tetrahydrofuran, (S)-tert-butylsulfinamide (145 mg, 1.2 mmol) and tetraethyl titanate (342 g, 1.5 mmol) were sequentially added at room temperature, reaction occurred at 80° C. with stirring for 8 h, then the solution was extracted with ethyl acetate/water, and the organic phase was dried in vacuum and then purified by a straight-phase column chromatography to obtain 200 mg of light yellow liquid (S)-1-(1-methyl-1H-benzo[d]imidazol-6-yl)ethyl-2-sulfinylimine (54-c), with a yield of 72%. ESI $[M+H]^+$=278.1

Step 4: Synthesis of (S)-1-(1-methyl-1H-benzo[d] imidazol-6-yl)ethyl-2-sulfinamide (54-d)

The (S)-1-(1-methyl-1H-benzo[d]imidazol-6-yl)ethyl-2-sulfinylimine (200 mg, 0.72 mmol) was dissolved in 30 mL of dry tetrahydrofuran, a tetrahydrofuran solution of 1 M borane (1.2 mL, 1.2 mmol) was added at 0° C., the solution was stirred at room temperature for 2 h, methanol was added for quenching after reaction was completed, and the organic phase was purified by a straight-phase column chromatography to obtain 175 mg of white solid (S)-1-(1-methyl-1H-benzo[d]imidazol-6-yl)ethyl-2-sulfinamide (54-d), with a yield of 87%. ESI $[M+H]^+$=280.1

Step 5: Synthesis of (S)-1-(1-methyl-1H-benzo[d] imidazol-6-yl)ethan-1-amine hydrochloride (54-e)

The (S)-1-(1-methyl-1H-benzo[d]imidazol-6-yl)ethyl-2-sulfinamide (175 mg, 0.62 mmol) was dissolved in 15 mL of tetrahydrofuran, a 1,4-dioxane solution of 4 M hydrochloric acid (0.74 mL, 2.96 mmol) was added, and reaction occurred at room temperature with stirring for 3 h. The solution was concentrated after the reaction, the solid was washed twice with ethyl acetate and twice with petroleum ether, and the solid was dried to obtain 68 mg of white solid (S)-1-(1-methyl-1H-benzo[d]imidazol-6-yl)ethan-1-amine hydrochloride (54-e), with a yield of 63%. ESI $[M+H]^+$=176.1

Step 6: Synthesis of(S)-6-(4-chlorophenyl)-N-(1-(1-methyl-1H-benzo[d]imidazol-6-yl)ethyl)-2-(1-methyl-1H-pyrazol-4-yl)pyrimidine-4-formamide (Compound 54)

The 6-(4-chlorophenyl)-2-(1-methyl-1H-pyrazol-4-yl)pyrimidine-4-carboxylic acid (100 mg, 0.32 mmol) and the (S)-1-(1-methyl-1H-benzo[d]imidazol-6-yl)ethan-1-amine hydrochloride (68 mg, 0.39 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 43 mg of white solid (S)-6-(4-chlorophenyl)-N-(1-(1-methyl-1H-benzo[d]imidazol-6-yl)ethyl)-2-(1-methyl-1H-pyrazol-4-yl)pyrimidine-4-formamide (compound 54), with a yield of 29%. $^1$H NMR (400 MHz, DMSO-d6) δ 9.23 (d, J=8.7 Hz, 1H), 8.71 (s, 1H), 8.44-8.34 (m, 3H), 8.21 (s, 1H), 8.16 (s, 1H), 7.76 (d, J=1.4 Hz, 1H), 7.67-7.60 (m, 2H), 7.53 (d, J=8.3 Hz, 1H), 7.40 (dd, J=8.5, 1.6 Hz, 1H), 5.45-5.37 (m, 1H), 3.96 (s, 3H), 3.82 (s, 3H), 1.67 (d, J=7.0 Hz, 3H). ESI $[M+H]^+$=471.2

Example 55: Synthesis of (S)-6-(4-trifluoromethylphenyl)-N-((S)-6,7-dihydro-5H-cyclopentano[B] pyridin-5-yl)-2-(pyridin-3-yl)pyrimidine-4-formamide (Compound 55)

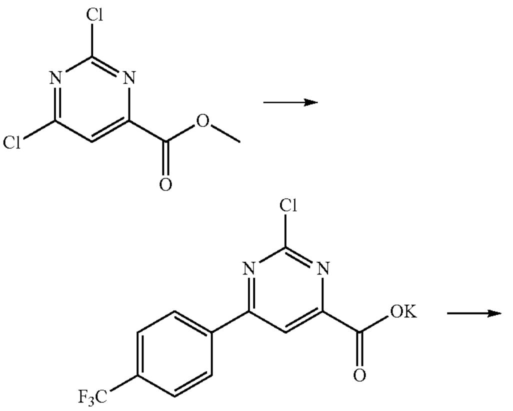

55-a

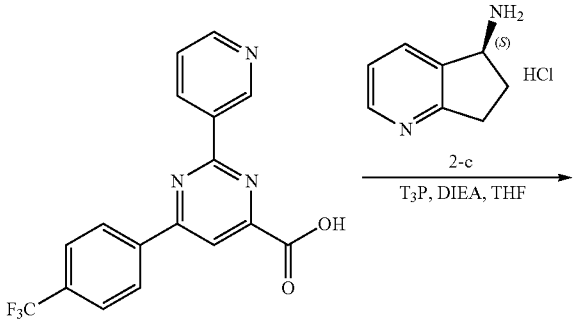

55-b

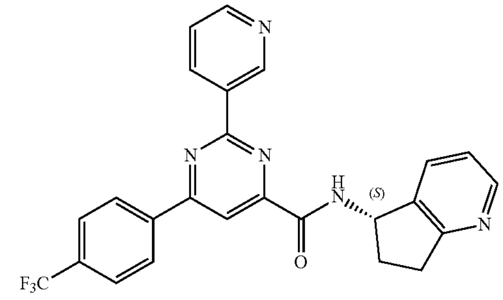

55

Step 1: Synthesis of potassium 2-chloro-6-(4-trifluoromethylphenyl)pyrimidine-4-carboxylate (55-a)

4-trifluoromethylphenylboronic acid (1.90 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.81 g of gray solid potassium 2-chloro-6-(4-trifluoromethylphenyl)pyrimidine-4-carboxylate (55-a), with a yield of 60%. ESI $[M+H]^+$=303.2

Step 2: Synthesis of 6-(4-trifluoromethylphenyl)-2-(pyridin-3-yl)pyrimidine-4-carboxylic acid (55-b)

Pyridine-3-boronic acid (922 mg, 7.5 mmol) and the potassium 2-chloro-6-(4-trifluoromethylphenyl)pyrimidine-4-carboxylate (1.81 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 520 mg of gray solid 6-(4-trifluoromethylphenyl)-2-(pyridin-3-yl)pyrimidine-4-carboxylic acid (55-b), with a yield of 26%. ESI $[M+H]^+$=346.2

Step 3: Synthesis of (S)-6-(4-trifluoromethylphenyl)-N-((S)-6,7-dihydro-5H-cyclopentano[B]pyridin-5-yl)-2-(pyridin-3-yl)pyrimidine-4-formamide (compound 55)

The 6-(4-trifluoromethylphenyl)-2-(pyridin-3-yl)pyrimidine-4-carboxylic acid (111 mg, 0.32 mmol) and (S)-(6,7-dihydro-5H-cyclopentano[B]pyridine)-5-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 54 mg of white solid (S)-6-(4-trifluoromethylphenyl)-N-((S)-6,7-dihydro-5H-cyclopentano[B]pyridin-5-yl)-2-(pyridin-3-yl)pyrimidine-4-formamide (compound 55), with a yield of 36%. $^1$H NMR (400 MHz, DMSO-d6) δ 9.94 (d, J=2.3 Hz, 1H), 9.73 (d, J=8.9 Hz, 1H), 9.07 (dt, J=8.1, 2.0 Hz, 1H),8.78 (dd, J=4.9, 1.7 Hz, 1H), 8.68 (d, J=8.1 Hz, 2H), 8.63 (s, 1H), 8.43 (d, J=4.9 Hz, 1H), 7.99 (d, J=8.3 Hz, 2H), 7.67-7.58 (m, 2H), 7.21 (dd, J=7.6, 4.9 Hz, 1H), 5.75 (q, J=8.5 Hz, 1H), 3.15-2.95 (m, 2H), 2.61-2.54 (m, 1H), 2.27 (dt, J=12.8, 9.0 Hz, 1H). ESI $[M+H]^+$=462.2

Example 56: Synthesis of (S)-6-(4-trifluoromethylphenyl)-N-((S)-6,7-dihydro-5H-cyclopentano[B]pyridin-5-yl)-2-(1-methyl-1H-pyrazol-4-yl)pyrimidine-4-formamide (Compound 56)

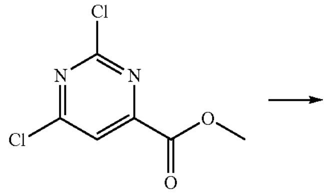

-continued

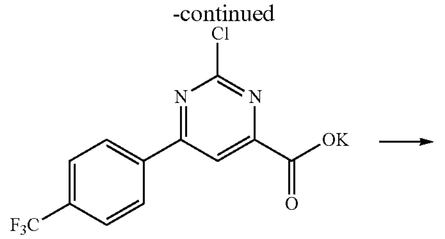

56-a

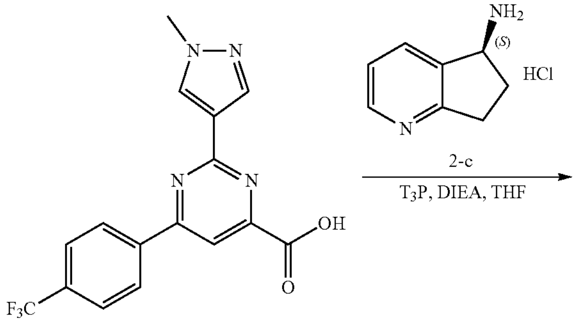

56-b

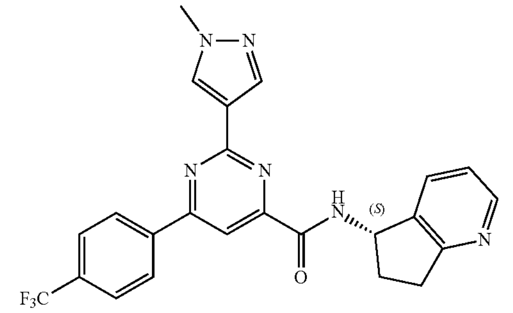

56

Step 1: Synthesis of potassium 2-chloro-6-(4-trifluoromethylphenyl)pyrimidine-4-carboxylate (56-a)

4-trifluoromethylphenylboronic acid (1.90 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.81 g of gray solid potassium 2-chloro-6-(4-trifluoromethylphenyl)pyrimidine-4-carboxylate (56-a), with a yield of 60%. ESI $[M+H]^+$=303.2

Step 2: Synthesis of 6-(4-trifluoromethylphenyl)-2-(1-methyl-1H-pyrazol-4-yl)pyrimidine-4-carboxylic acid (56-b)

1-methyl-1H-pyrazole-4-boronic acid (945 mg, 7.5 mmol) and the potassium 2-chloro-6-(4-trifluoromethylphenyl)pyrimidine-4-carboxylate (1.81 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 520 mg of gray solid 6-(4-trifluoromethylphenyl)-2-(1-methyl-1H-pyrazol-4-yl)pyrimidine-4-carboxylic acid (56-b), with a yield of 25%. ESI $[M+H]^+$=349.2

Step 3: Synthesis of (S)-6-(4-trifluoromethylphenyl)-N-((S)-6,7-dihydro-5H-cyclopentano[B]pyridin-5-yl)-2-(1-methyl-1H-pyrazol-4-yl)pyrimidine-4-formamide (Compound 56)

The 6-(4-trifluoromethylphenyl)-2-(1-methyl-1H-pyrazol-4-yl)pyrimidine-4-carboxylic acid (95 mg, 0.32 mmol) and (S)-(6,7-dihydro-5H-cyclopentano[B]pyridine)-5-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 44 mg of white solid (S)-6-(4-trifluoromethylphenyl)-N-((S)-6,7-dihydro-5H-cyclopentano[B]pyrid-5-yl)-2-(1-methyl-1H-pyrazol-4-yl)pyrimidine-4-formamide (compound 56), with a yield of 30%. $^1$H NMR (400 MHz, DMSO-d6) δ 9.45 (d, J=8.9 Hz, 1H), 8.68 (s, 1H), 8.58 (d, J=8.1 Hz, 2H), 8.38 (d, J=12.6 Hz, 2H), 7.95 (d, J=8.3 Hz, 2H), 7.62 (dt, J=7.6, 1.4 Hz, 1H), 7.45-7.36 (m, 1H), 7.21 (dd, J=7.6, 4.9 Hz, 1H), 5.71 (q, J=8.5 Hz, 1H), 3.93 (s, 3H), 3.05 (qt, J=16.6, 7.7 Hz, 2H), 2.55 (dt, J=7.9, 3.3 Hz, 1H), 2.25 (dq, J=12.6, 9.2 Hz, 1H). ESI $[M+H]^+$=465.2

Example 57: Synthesis of (S)-6-(4-chlorophenyl)-N-(1-(3-fluoro-4-cyanophenyl)ethyl)-2-(1-methyl-1H-pyrazol-4-yl)pyrimidine-4-formamide (Compound 57)

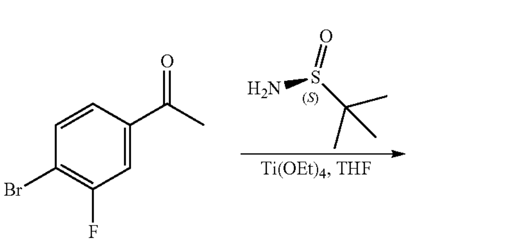

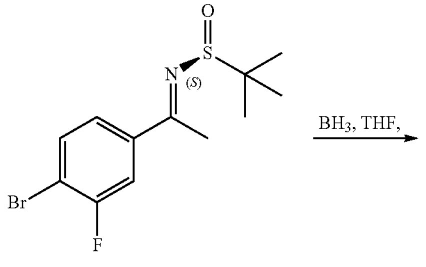

57-a

-continued

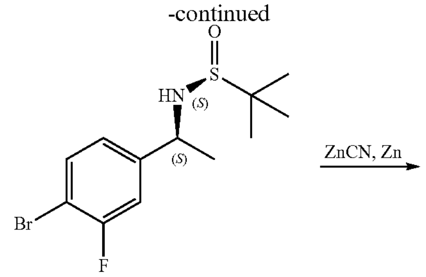

57-b

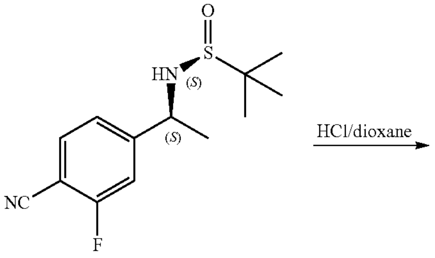

57-c

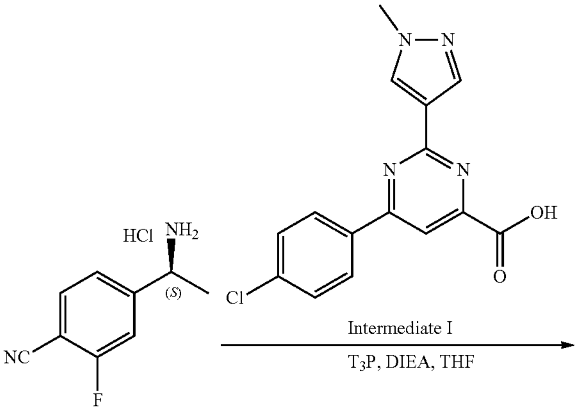

57-d

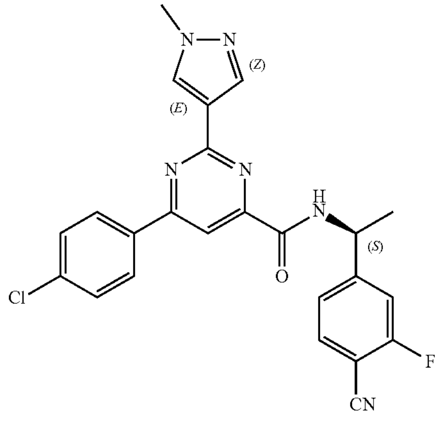

57

Step 1: Synthesis of (S)-N-(1-(3-fluoro-4-bromophenyl)ethyl)-2-tert-butylsulfinylimine (57-a)

1-(3-fluoro-4-bromophenyl)ethanone (2.16 g, 10 mmol) was dissolved in 50 mL of dry tetrahydrofuran, (S)-tert-butylsulfinamide (1.45 g, 12 mmol) and tetraethyl titanate (3.42 g, 15 mmol) were sequentially added at room temperature, reaction occurred at 80° C. with stirring for 8 h, then the solution was extracted with ethyl acetate/water, and the organic phase was dried in vacuum and then purified by a straight-phase column chromatography to obtain 1.20 g of white solid (S)-N-(1-(3-fluoro-4-bromophenyl)ethyl)-2-tert-butylsulfinylimine (57-a), with a yield of 38%. ESI $[M+H]^+$ =320.1

Step 2: Synthesis of (S)-N-(1-(3-fluoro-4-bromophenyl)ethyl)-2-tert-butylsulfinamide (57-b)

The (S)-N-(1-(3-fluoro-4-bromophenyl)ethyl)-2-tert-butylsulfinylimine (1.12 g, 3.5 mmol) was dissolved in 80 mL of dry tetrahydrofuran, a tetrahydrofuran solution of 1 M borane (7.0 mL, 7.0 mmol) was added at 0° C., the solution was stirred at room temperature for 2 h, methanol was added for quenching after reaction was completed, and the organic phase was dried in vacuum and then purified by a straight-phase column chromatography to obtain 0.87 g of white solid (S)-N-(1-(3-fluoro-4-bromophenyl)ethyl)-2-tert-butylsulfinamide (57-b), with a yield of 78%. ESI $[M+H]^+$ =322.2

Step 3: Synthesis of (S)-N-(1-(3-fluoro-4-cyanophenyl)ethyl)-2-tert-butylsulfinamide (57-c)

The (S)-N-(1-(3-fluoro-4-bromophenyl)ethyl)-2-tert-butylsulfinamide (0.87 g, 2.7 mmol) was dissolved in 30 mL of dry DMF; zinc powder (175 mg, 2.7 mmol), zinc cyanide (245 mg, 2.7 mmol), and [1,1'-bis(diphenylphosphine)ferrocene]palladium dichloride (II) dichloromethane complex (243 mg, 0.3 mmol) were sequentially added; the solution was stirred at 120° C. for 4 h, ethyl acetate/water was added for extraction after reaction was completed, and the organic phase was dried in vacuum and purified by a straight-phase column chromatography to obtain 0.50 g of white solid (S)-N-(1-(3-fluoro-4-cyanophenyl)ethyl)-2-tert-butylsulfinamide (57-c), with a yield of 69%. ESI $[M+H]^+$=269.2

Step 4: Synthesis of (S)-N-(1-(3-fluoro-4-cyanophenyl)ethyl)-2-amine hydrochloride (57-d)

The (S)-N-(1-(3-fluoro-4-cyanophenyl)ethyl)-2-tert-butylsulfinamide (0.53 g, 2.0 mmol) was dissolved in 30 mL of tetrahydrofuran, a 1,4-dioxane solution of 4 M hydrochloric acid (2.4 mL, 9.6 mmol) was added, and reaction occurred at room temperature with stirring for 3 h. The solution was concentrated after the reaction, the solid was washed twice with ethyl acetate and twice with petroleum ether, and the solid was dried to obtain 0.20 g of white solid (S)-N-(1-(3-fluoro-4-cyanophenyl)ethyl)-2-amine hydrochloride (57-d), with a yield of 61%. ESI $[M+H]^+$=165.1

Step 5: Synthesis of (S)-6-(4-chlorophenyl)-N-(1-(3-fluoro-4-cyanophenyl)ethyl)-2-(1-methyl-1H-pyrazol-4-yl)pyrimidine-4-formamide (Compound 57)

The 6-(4-chlorophenyl)-2-(1-methyl-1H-pyrazol-4-yl)pyrimidine-4-carboxylic acid (100 mg, 0.32 mmol) and the (S)-N-(1-(3-fluoro-4-cyanophenyl)ethyl)-2-amine hydrochloride (69 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 65 mg of white solid (S)-6-(4-chlorophenyl)-N-(1-(3-fluoro-4-cyanophenyl)ethyl)-2-(1-methyl-1H-pyrazol-4-yl)pyrimidine-4-formamide (compound 57), with a yield of 44%. $^1H$ NMR (400 MHz, DMSO-d6) δ 9.36 (d, J=8.3 Hz, 1H), 8.69 (s, 1H), 8.45-8.34 (m, 3H), 8.20 (s, 1H), 7.93 (dd, J=8.1, 6.9 Hz, 1H), 7.64 (dd, J=9.0, 2.2 Hz, 3H), 7.51 (dd, J=8.1, 1.6 Hz, 1H), 5.33 (p, J=7.1 Hz, 1H), 3.97 (s, 3H), 1.62 (d, J=7.1 Hz, 3H). ESI $[M+H]^+$=461.2

Example 58: Synthesis of(S)-6-(4-cyanophenyl)-N-(1-(2-fluoro-4-pyridine)ethyl)-2-(1-methyl-1H-pyrazol-4-yl)pyrimidine-4-formamide (Compound 58)

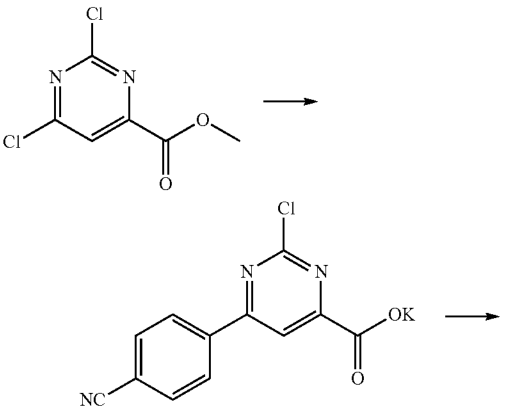

58-a

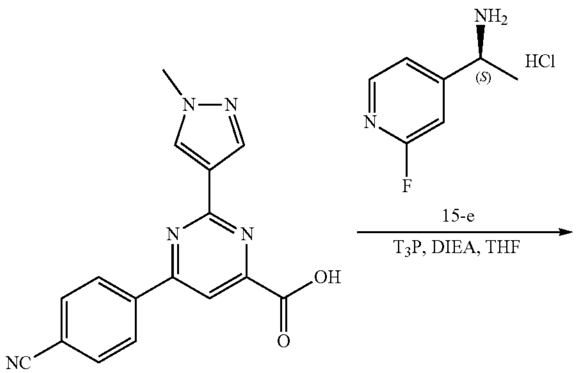

58-b

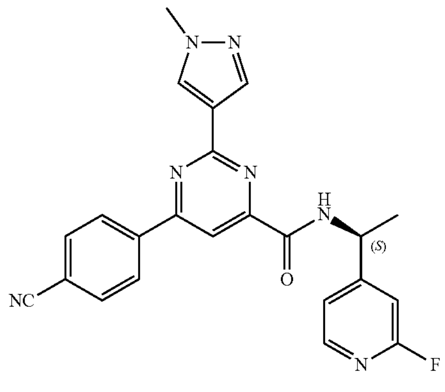

58

Step 1: Synthesis of potassium 2-chloro-6-(4-cyanophenyl)pyrimidine-4-carboxylate (58-a)

4-cyanophenylboronic acid (1.47 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.61 g of gray solid potassium 2-chloro-6-(4-cyanophenyl)pyrimidine-4-carboxylate (58-a), with a yield of 60%. ESI $[M+H]^+$=268.2

Step 2: Synthesis of 6-(4-cyanophenyl)-2-(1-methyl-1H-pyrazol-4-yl)pyrimidine-4-carboxylic acid (58-b)

P-methoxyphenylboronic acid (1.14 g, 7.5 mmol) and the potassium 2-chloro-6-(4-cyanophenyl)pyrimidine-4-carboxylate (1.61 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 620 mg of gray solid 6-(4-cyanophenyl)-2-(1-methyl-1H-pyrazol-4-yl)pyrimidine-4-carboxylic acid (58-b), with a yield of 31%. ESI $[M+H]^+$=341.2

Step 3: Synthesis of (S)-6-(4-cyanophenyl)-N-(1-(2-fluoro-4-pyridine)ethyl)-2-(1-methyl-1H-pyrazol-4-yl)pyrimidine-4-formamide (Compound 58)

The 6-(4-cyanophenyl)-2-(1-methyl-1H-pyrazol-4-yl)pyrimidine-4-carboxylic acid (95 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 44 mg of white solid (S)-6-(4-cyanophenyl)-N-(1-(2-fluoro-4-pyridine)ethyl)-2-(1-methyl-1H-pyrazol-4-yl)pyrimidine-4-formamide (compound 58), with a yield of 30%. $^1H$ NMR (400 MHz, DMSO-d6) δ 9.41 (d, J=8.4 Hz, 1H), 8.72 (s, 1H), 8.54 (d, J=8.5 Hz, 2H), 8.45 (s, 1H), 8.30 (s, 1H), 8.22 (d, J=5.2 Hz, 1H), 8.06 (d, J=8.5 Hz, 2H), 7.44 (d, J=5.3 Hz, 1H), 7.25 (s, 1H), 5.31 (t, J=7.5 Hz, 1H), 3.97 (s, 3H), 1.63 (d, J=7.1 Hz, 3H). ESI $[M+H]^+$=463.2

Example 59: Synthesis of (S)-6-(4-chlorophenyl)-N-(1-(2-fluoro-4-pyridine)ethyl)-2-(3,5-dimethylisoxazol-4-yl)pyrimidine-4-formamide (Compound 59)

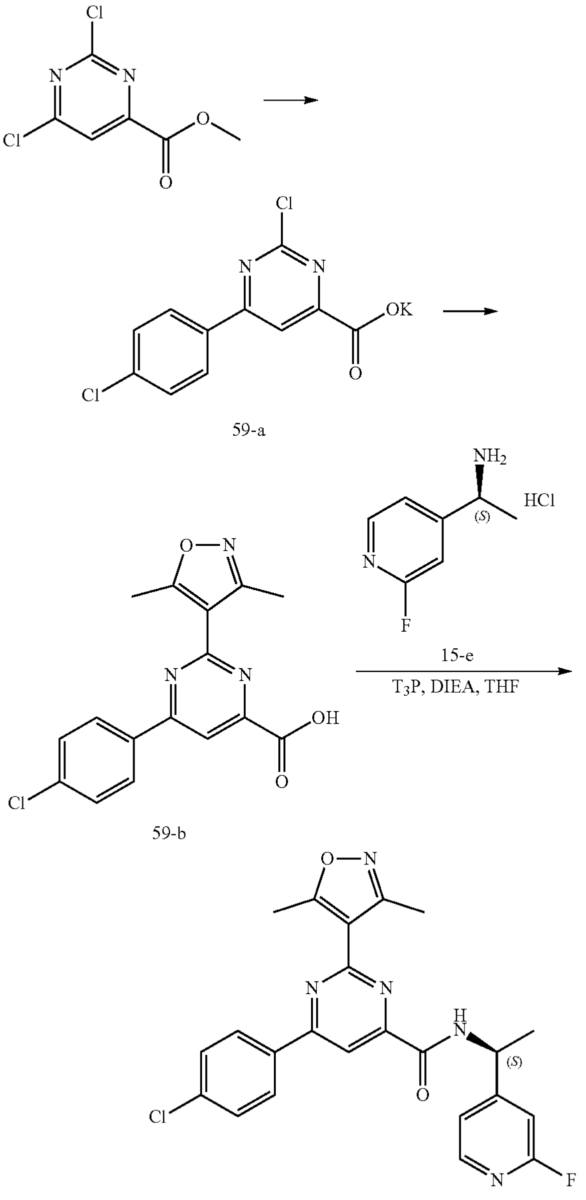

59-a 59-b

59

Step 1: Synthesis of potassium 2-chloro-6-(4-chlorophenyl)pyrimidine-4-carboxylate (59-a)

4-chlorophenylboronic acid (156 mg, 1.0 mmol) and methyl 2,6-dichloropyrimidine-4-carboxylate (206 mg, 1.0 mmol) were dissolved in dioxane/water (10 mL/1 mL), tetra(triphenylphosphine)palladium (23 mg, 0.02 mmol) and potassium carbonate (276 mg, 2.0 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 161 mg of gray solid potassium 2-chloro-6-(4-chlorophenyl)pyrimidine-4-carboxylate (59-a), with a yield of 60%. ESI $[M+H]^+$=268.2

Step 2: Synthesis of 6-(4-chlorophenyl)-2-(3,5-dimethylisoxazol-4-yl)pyrimidine-4-carboxylic acid (59-b)

3,5-dimethylisoxazole-4-boronic acid (106 mg, 0.75 mmol) and the potassium 2-chloro-6-(4-chlorophenyl)pyrimidine-4-carboxylate (161 mg, 0.60 mmol) were dissolved in dioxane/water (100 mL/15 mL), tetra(triphenylphosphine)palladium (23 mg, 0.02 mmol) and potassium carbonate (276 mg, 2.0 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 105 mg of gray solid 6-(4-chlorophenyl)-2-(3,5-dimethylisoxazol-4-yl)pyrimidine-4-carboxylic acid (59-b), with a yield of 53%. ESI $[M+H]^+$=330.2

Step 3: Synthesis of(S)-6-(4-chlorophenyl)-N-(1-(2-fluoro-4-pyridine)ethyl)-2-(3,5-dimethylisoxazol-4-yl)pyrimidine-4-formamide (Compound 59)

The 6-(4-chlorophenyl)-2-(3,5-dimethylisoxazol-4-yl)pyrimidine-4-carboxylic acid (105 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 47 mg of white solid (S)-6-(4-chlorophenyl)-N-(1-(2-fluoro-4-pyridine)ethyl)-2-(3,5-dimethylisoxazol-4-yl)pyrimidine-4-formamide (compound 59), with a yield of 32%. $^1H$ NMR (400 MHz, DMSO-d6) δ 9.16 (d, J=8.1 Hz, 1H), 8.40-8.30 (m, 3H), 8.22 (d, J=5.2 Hz, 1H), 7.71-7.64 (m, 2H), 7.44 (d, J=5.3 Hz, 1H), 7.25 (s, 1H), 5.26 (p, J=7.1 Hz, 1H), 2.90 (s, 3H), 2.67 (s, 3H), 1.57 (d, J=7.1 Hz, 3H). ESI $[M+H]^+$=452.2

Example 60: Synthesis of (S)-6-(4-chlorophenyl)-N-(1-(2-fluoro-4-pyridine)ethyl)-2-(p-cyanophenyl)pyrimidine-4-formamide (Compound 60)

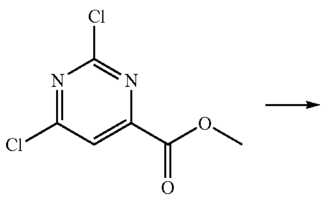

-continued

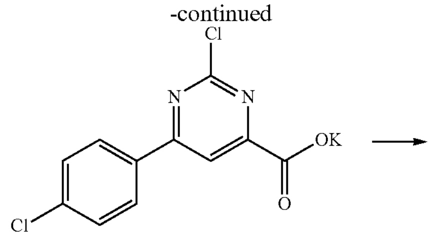

60-a

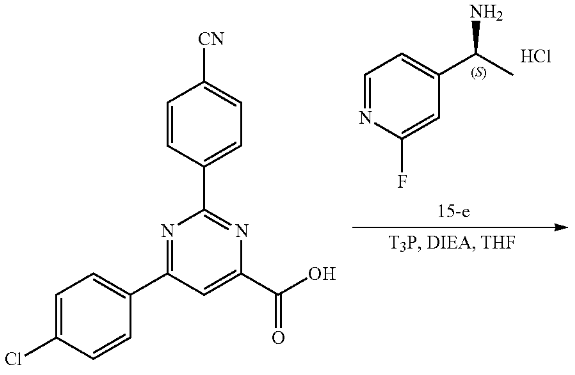

60-b

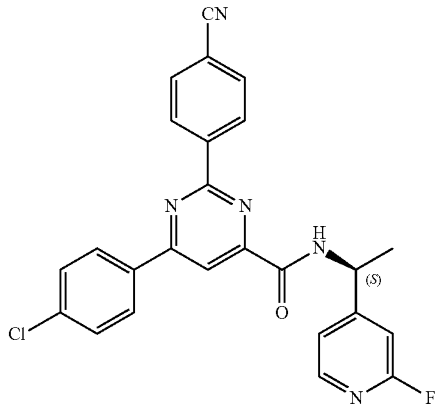

60

Step 1: Synthesis of potassium 2-chloro-6-(4-chlorophenyl)pyrimidine-4-carboxylate (60-a)

4-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra (triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.61 g of gray solid potassium 2-chloro-6-(4-chlorophenyl)pyrimidine-4-carboxylate (60-a), with a yield of 60%. ESI $[M+H]^+$=268.2

Step 2: Synthesis of 6-(4-chlorophenyl)-2-(p-cyanophenyl)pyrimidine-4-carboxylic acid (60-b)

P-cyanophenylboronic acid (1.10 g, 7.5 mmol) and the potassium 2-chloro-6-(4-chlorophenyl)pyrimidine-4-carboxylate (1.61 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 420 mg of gray solid 6-(4-chlorophenyl)-2-(p-cyanophenyl)pyrimidine-4-carboxylic acid (60-b), with a yield of 21%. ESI $[M+H]^+$=336.2

Step 3: Synthesis of (S)-6-(4-chlorophenyl)-N-(1-(2-fluoro-4-pyridine)ethyl)-2-(p-cyanophenyl)pyrimidine-4-formamide (Compound 60)

The 6-(4-chlorophenyl)-2-(p-cyanophenyl)pyrimidine-4-carboxylic acid (107 mg, 0.32 mmol) and (S)-1-(2-fluoro-4-pyridine)ethan-1-amine hydrochloride (74 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 54 mg of white solid (S)-6-(4-chlorophenyl)-N-(1-(2-fluoro-4-pyridine)ethyl)-2-(p-cyanophenyl)pyrimidine-4-formamide (compound 60), with a yield of 37%. $^1$H NMR (400 MHz, DMSO-d6) δ 9.65 (d, J=8.3 Hz, 1H), 9.00-8.93 (m, 2H), 8.48 (d, J=9.0 Hz, 3H), 8.22 (d, J=5.2 Hz, 1H), 8.15-8.09 (m, 2H), 7.68 (d, J=8.6 Hz, 2H), 7.45 (d, J=5.4 Hz, 1H), 7.26 (s, 1H), 5.38-5.32 (m, 1H), 1.65 (d, J=7.1 Hz, 3H). ESI $[M+H]^+$=458.2

Example 61: Synthesis of (S)-6-(4-trifluoromethoxyphenyl)-N-((S)-6,7-dihydro-5H-cyclopentano[B]pyridin-5-yl)-2-(1-methyl-1H-pyrazol-4-yl) pyrimidine-4-formamide (Compound 61)

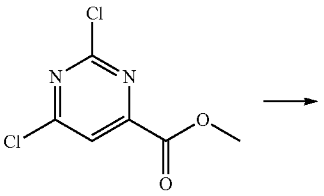

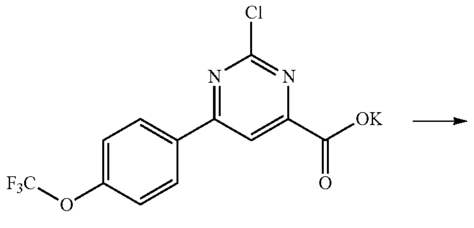

61-a

-continued

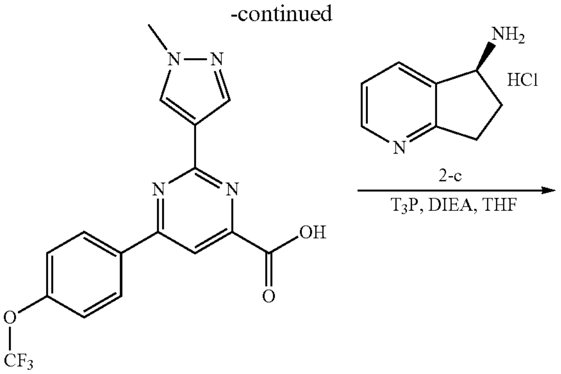

61-b

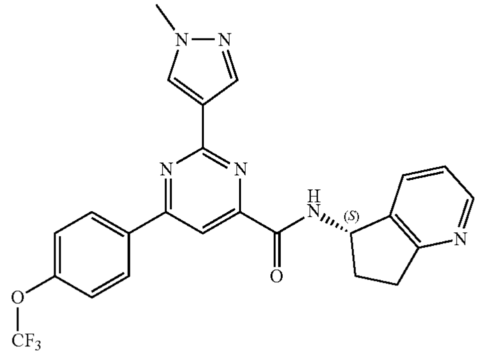

61

Step 1: Synthesis of potassium 2-chloro-6-(4-trifluoromethoxyphenyl)pyrimidine-4-carboxylate (61-a)

4-trifluoromethoxyphenylboronic acid (1.56 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.41 g of gray solid potassium 2-chloro-6-(4-trifluoromethoxyphenyl)pyrimidine-4-carboxylate (61-a), with a yield of 44%. ESI $[M+H]^+$= 319.2

Step 2: Synthesis of 6-(4-trifluoromethoxyphenyl)-2-(1-methyl-1H-pyrazol-4-yl)pyrimidine-4-carboxylic acid (61-b)

1-methylpyrazol-4-boronic acid (756 mg, 6.0 mmol) and the potassium 2-chloro-6-(4-trifluoromethoxyphenyl)pyrimidine-4-carboxylate (1.41 g, 4.4 mmol) were dissolved in dioxane/water (100 mL/15 mL), tetra(triphenylphosphine) palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 460 mg of white solid 6-(4-trifluoromethoxyphenyl)-2-(1-methyl-1H-pyrazol-4-yl)pyrimidine-4-carboxylic acid (61-b), with a yield of 29%. ESI $[M+H]^+$=365.2

Step 3: Synthesis of (S)-6-(4-trifluoromethoxyphenyl)-N-((S)-6,7-dihydro-5H-cyclopentano[B]pyridin-5-yl)-2-(1-methyl-1H-pyrazol-4-yl)pyrimidine-4-formamide (Compound 61)

The 6-(4-trifluoromethoxyphenyl)-2-(1-methyl-1H-pyrazol-4-yl)pyrimidine-4-carboxylic acid (117 mg, 0.32 mmol) and (S)-(6,7-dihydro-5H-cyclopentano[B]pyridine)-5-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 51 mg of white solid (S)-6-(4-trifluoromethoxyphenyl)-N-((S)-6,7-dihydro-5H-cyclopentano[B]pyridin-5-yl)-2-(1-methyl-1H-pyrazol-4-yl)pyrimidine-4-formamide (compound 61), with a yield of 33%. $^1$H NMR (400 MHz, DMSO-d6) δ 9.43 (d, J=8.8 Hz, 1H), 8.67 (s, 1H), 8.51 (d, J=8.8 Hz, 2H), 8.40 (d, J=14.8 Hz, 2H), 8.31 (s, 1H), 7.60 (dd, J=15.9, 7.9 Hz, 3H), 7.20 (dd, J=7.6, 4.8 Hz, 1H), 5.70 (q, J=8.7 Hz, 1H), 3.93 (s, 3H), 3.02 (dq, J=16.3, 8.9 Hz, 3H), 2.28-2.21 (m, 1H). ESI $[M+H]^+$=481.2

Example 62: Synthesis of (S)-6-(4-chlorophenyl)-N-((S)-6,7-dihydro-5H-cyclopentano[B]pyridin-5-yl)-2-(2-fluoro-4-pyridine)pyrimidine-4-formamide (Compound 62)

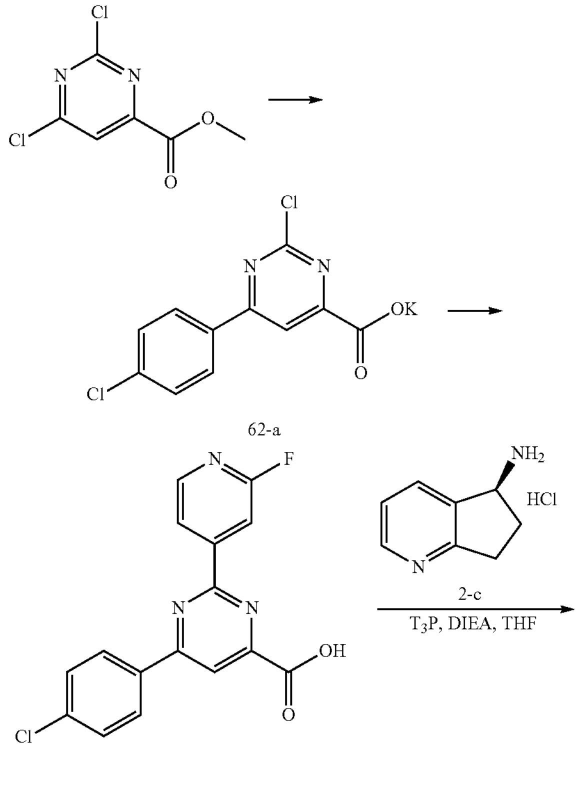

62-a 62-b

-continued

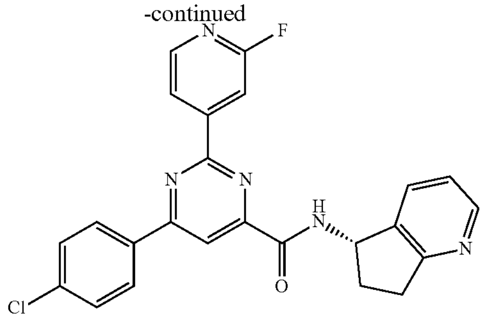

62

Step 1: Synthesis of potassium 2-chloro-6-(4-chlorophenyl)pyrimidine-4-carboxylate (62-a)

4-chlorophenylboronic acid (1.56 g, 10 mmol) and methyl 2,6-dichloropyrimidine-4-carboxylate (2.06 g, 10 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, and an aqueous solution of 6 N potassium hydroxide was added, followed by stirring at room temperature for 8 h. After the reaction, cooling was performed to precipitate a solid, then filtration was performed, and the solid was dried to obtain 1.61 g of gray solid potassium 2-chloro-6-(4-chlorophenyl)pyrimidine-4-carboxylate (62-a), with a yield of 60%. ESI $[M+H]^+$=268.2

Step 2: Synthesis of 6-(4-chlorophenyl)-2-(2-fluoro-4-pyridine)pyrimidine-4-carboxylic acid (62-b)

2-fluoropyridine-4-boronic acid (1.41 g, 7.5 mmol) and the potassium 2-chloro-6-(4-chlorophenyl)pyrimidine-4-carboxylate (1.61 g, 6.0 mmol) were dissolved in dioxane/water (100 mL/15 mL), tetra(triphenylphosphine)palladium (230 mg, 0.2 mmol) and potassium carbonate (2.76 g, 20 mmol) were sequentially added at room temperature, reaction occurred at 100° C. with stirring for 8 h, then the solution was extracted with ethyl acetate, 2N hydrochloric acid was added to the aqueous phase until pH=3-4, filtration was performed after a solid was precipitated, and the solid was dried to obtain 570 mg of white solid 6-(4-chlorophenyl)-2-(2-fluoro-4-pyridine)pyrimidine-4-carboxylic acid (62-b), with a yield of 29%. ESI $[M+H]^+$=330.2

Step 3: Synthesis of (S)-6-(4-chlorophenyl)-N-((S)-6,7-dihydro-5H-cyclopentano[B]pyridin-5-yl)-2-(2-fluoro-4-pyridine)pyrimidine-4-formamide (Compound 62)

The 6-(4-chlorophenyl)-2-(2-fluoro-4-pyridine)pyrimidine-4-carboxylic acid (105 mg, 0.32 mmol) and (S)-(6,7-dihydro-5H-cyclopentano[B]pyridine)-5-amine hydrochloride (84 mg, 0.42 mmol) were dissolved in 10 ml of tetrahydrofuran, N,N-diisopropylethylamine (108 mg, 0.84 mmol) and 1-propylphosphonic anhydride (350 mg, 0.55 mmol) were sequentially added at room temperature, and reaction occurred at room temperature with stirring for 2 h. After vacuum drying, the crude product was separated by straight-phase column chromatography to obtain 54 mg of white solid (S)-6-(4-chlorophenyl)-N-((S)-6,7-dihydro-5H- cyclopentano[B]pyridin-5-yl)-2-(2-fluoro-4-pyridine)pyrimidine-4-formamide (compound 62), with a yield of 38%. $^{1}$H NMR (400 MHz, DMSO-d6) δ 9.72 (d, J=8.9 Hz, 1H), 8.67-8.58 (m, 2H), 8.56-8.51 (m, 2H), 8.48 (d, J=5.9 Hz, 2H), 8.43 (d, J=4.9 Hz, 1H), 7.73-7.65 (m, 2H), 7.62 (d, J=7.5 Hz, 1H), 7.21 (dd, J=7.6, 4.9 Hz, 1H), 5.75 (q, J=8.6 Hz, 1H), 3.15-2.96 (m, 2H), 2.57 (dd, J=8.5, 4.1 Hz, 1H), 2.27 (dd, J=12.6, 8.9 Hz, 1H). ESI $[M+H]^+$=446.2

Test Example: AhR Inhibitory Activity Experiment

In vitro activities of the above compounds were demonstrated in the following assay: HepG2-Lucia™ AhR cells (InvivoGen Company) are modified from human HepG2 liver cancer cell lines, the cells express and secrete Lucia luciferase under the control of a minimum promoter, the promoter is coupled with an entire regulatory sequence of a human Cyp1a1 gene, and the regulatory sequence contains six dioxin response elements (DRE). When QUANTI-Luc™ (InvivoGen Company) testing reagents are used, AhR gene signaling pathways can be studied by monitoring the activity of Lucia luciferase in the cell culture supernatant.

In Vitro Assay 1: Assay on Inhibitory Activity in Human Cell Lines

Adherent cell layers of HepG2-Lucia™ AhR cells in a logarithmic growth phase were washed with PBS, and then the cells were isolated with trypsin. The isolated cells were centrifuged at 1000 RPM for 5 minutes, the supernatant was removed, and the cells were re-suspended with a test medium by 1.25×105 cells/ml.

20,000 cells were added to each well of a 96-well plate, and the 96-well plate was placed in a CO2 incubator to incubate the cells at 37° C. for 24 hours in the absence (negative control) or presence of test compounds with gradient increasing concentrations (typical dilutions: 169 pmol/L, 0.5 nmol/L, 1.5 nmol/L; 4.6 nmol/L, 13.7 nmol/L, 41 nmol/L, 123 nmol/L, 370 nmol/L, 1.1 μmol/L, 3.3 μmol/L and 10 μmol/L, in triplicate).

The 20 μl/well cell supernatant was transferred to a black 96-well plate, a 50 μL/well QUANTI-Luc™ solution was added, and the activity of Lucia luciferase was measured on a multifunctional ELISA reader Spark 10 M (Tecan Company) through a QUANTI-Luc™ luciferase assay system.

Experimental results are shown in Table 1, wherein for $IC_{50}$ values, "++++" represents $IC_{50}$<0.05 μM; "+++" represents $IC_{50}$ between 0.05 μM and 0.2 μM; "++" represents $IC_{50}$ between 0.2 μM and 1.0 μM; and "+" represents $IC_{50}$>1.0 μM.

TABLE 1

$IC_{50}$ values of compounds in the examples in vitro assay 1

| Example | AhR inhibitory activity $C_{50}$ (μM) |
|---|---|
| Compound 1 | ++++ |
| Compound 2 | ++++ |
| Compound 3 | +++ |
| Compound 4 | ++++ |
| Compound 5 | ++++ |
| Compound 6 | + |
| Compound 7 | ++++ |
| Compound 8 | ++++ |
| Compound 9 | ++++ |
| Compound 10 | + |
| Compound 11 | + |
| Compound 12 | ++++ |
| Compound 13 | ++++ |
| Compound 14 | ++++ |

TABLE 1-continued $IC_{50}$ values of compounds in the examples in vitro assay 1

| Example | AhR inhibitory activity $C_{50}$ (μM) |
|---|---|
| Compound 15 | ++++ |
| Compound 16 | +++ |
| Compound 17 | ++++ |
| Compound 18 | ++++ |
| Compound 19 | ++++ |
| Compound 20 | +++ |
| Compound 21 | +++ |
| Compound 22 | + |
| Compound 23 | ++++ |
| Compound 24 | ++ |
| Compound 25 | + |
| Compound 26 | ++++ |
| Compound 27 | ++++ |
| Compound 28 | ++++ |
| Compound 29 | ++++ |
| Compound 30 | ++++ |
| Compound 31 | ++++ |
| Compound 32 | ++++ |
| Compound 33 | ++++ |
| Compound 34 | ++++ |
| Compound 35 | ++++ |
| Compound 36 | + |
| Compound 37 | ++++ |
| Compound 38 | ++++ |
| Compound 39 | + |
| Compound 40 | ++++ |
| Compound 41 | + |
| Compound 42 | + |
| Compound 43 | ++++ |
| Compound 44 | ++++ |
| Compound 45 | ++++ |
| Compound 46 | ++++ |
| Compound 47 | +++ |
| Compound 48 | + |
| Compound 49 | + |
| Compound 50 | + |
| Compound 51 | ++++ |
| Compound 52 | ++++ |
| Compound 53 | ++++ |
| Compound 54 | ++++ |
| Compound 55 | ++++ |
| Compound 56 | ++++ |
| Compound 57 | ++++ |
| Compound 58 | +++ |
| Compound 59 | + |
| Compound 60 | + |
| Compound 61 | + |
| Compound 62 | ++++ |

The foregoing descriptions of specific exemplary embodiments of the present disclosure are for the purpose of explanation and illustration. These descriptions are not intended to limit the present disclosure to the precise form disclosed, and it is obvious that many changes and variations may be made based on the above teachings. The purpose of selecting and describing the exemplary embodiments is to explain the specific principle of the present disclosure and its practical application, so that a person skilled in the art can implement and use various exemplary embodiments of the present disclosure and various different choices and changes. The scope of the present disclosure is intended to be defined by the claims and equivalents thereof.

The invention claimed is:

1. A compound represented by formula (I) or a pharmaceutically acceptable salt thereof, (I)

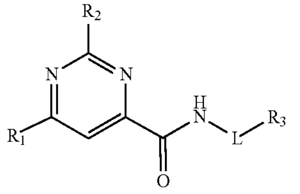

wherein, $R_1$ is selected from phenyl, pyridyl, pyrazolyl, wherein, the phenyl, pyridyl, or pyrazolyl is optionally substituted by one or two $R_{11}$;

$R_{11}$ is selected from fluoro, chloro, cyano, methyl, trifluoromethyl, or trifluoromethoxy;

$R_2$ is selected from phenyl, pyrazolyl, pyridyl, isoxazolyl, or pyrimidinyl, wherein, the phenyl, pyrazolyl, pyridyl, isoxazolyl, or pyrimidinyl is optionally substituted by one or two $R_{21}$;

$R_{21}$ is selected from fluoro, chloro, cyano, amino, methyl, methoxy, or cyclopropyl;

L is selected from single bond, $-CH(CH_3)-$, $-CH_2CH_2-$, $-CH(CH_2CH_3)-$,

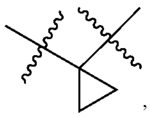, 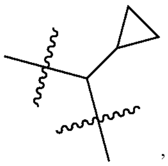, or 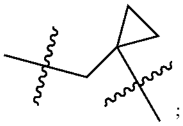;

$R_3$ is selected from

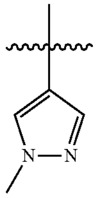, 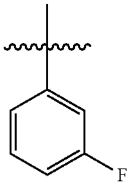, 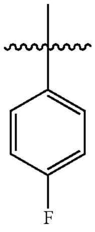, 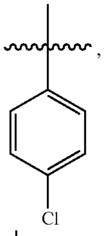,

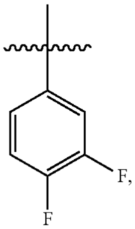 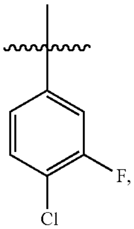 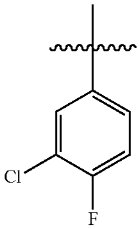,

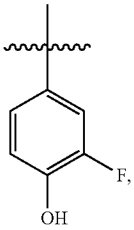 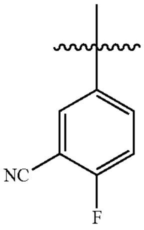, 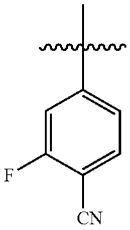,

-continued

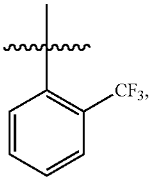 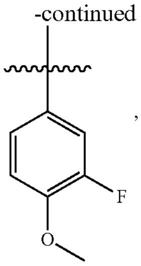, 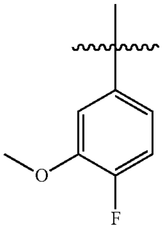,

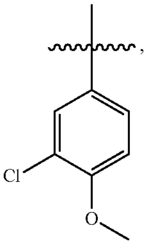, 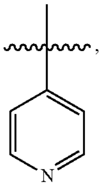, 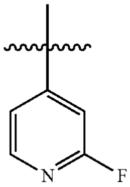, 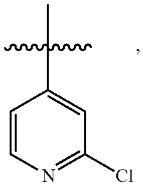,

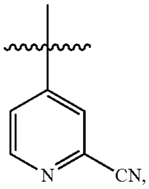 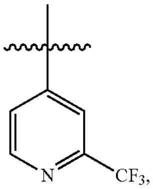 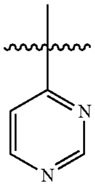,

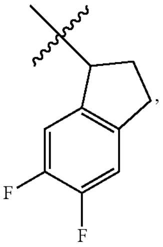 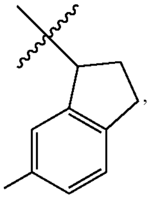 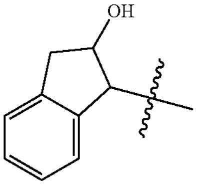,

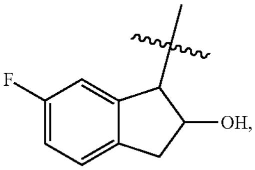 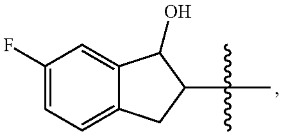,

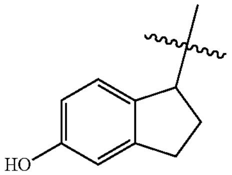 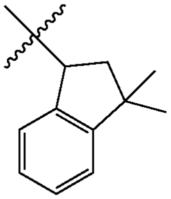, 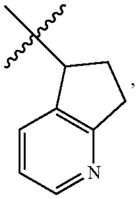,

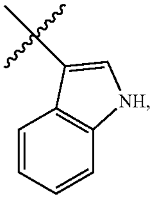 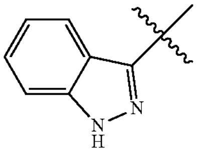, 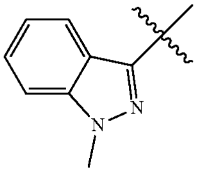,

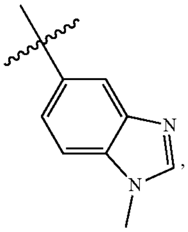 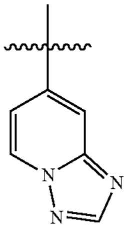 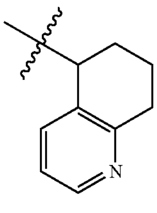,

-continued
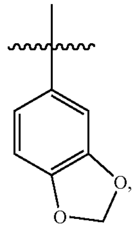 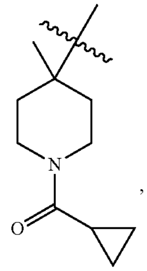, 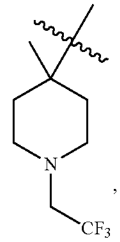,
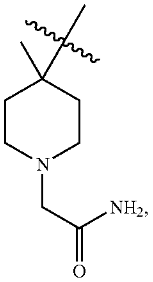 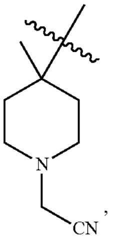 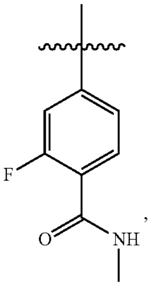
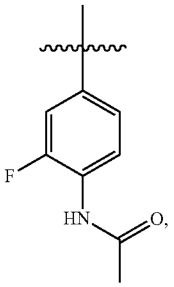 or 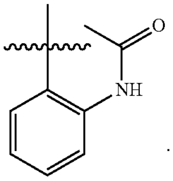.
2. The compound or pharmaceutically acceptable salt thereof according to claim 1, wherein:
-L-$R_3$ is selected from
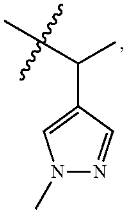 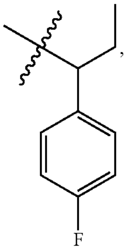 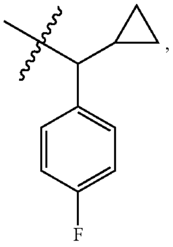
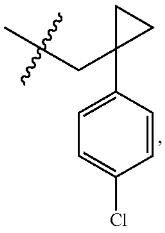 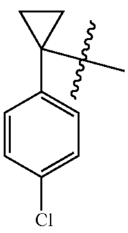, 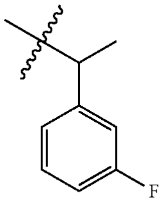,
-continued
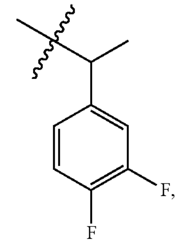 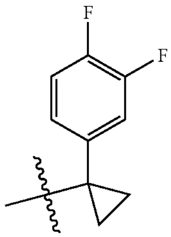, 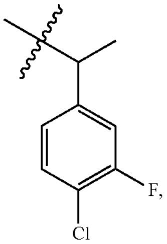
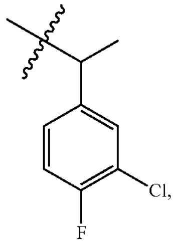 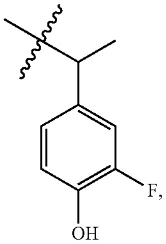 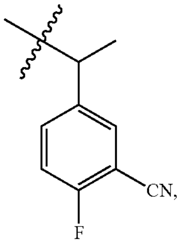
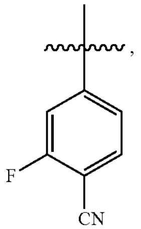 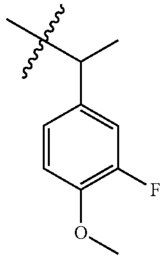, 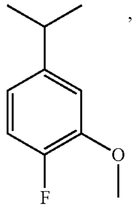,
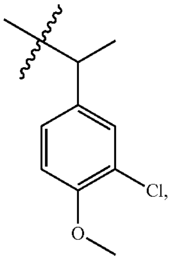 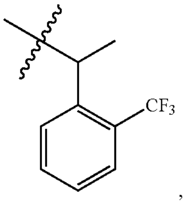, 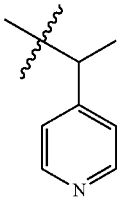,
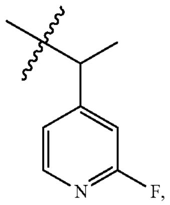 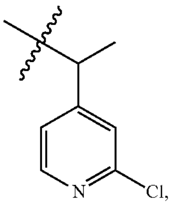 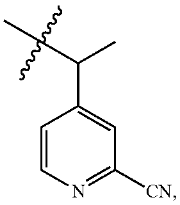
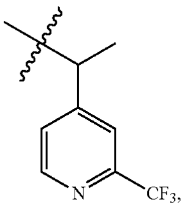 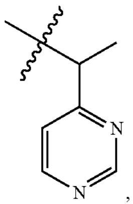, 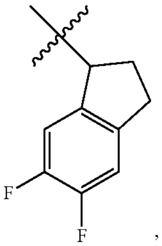,
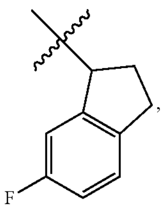 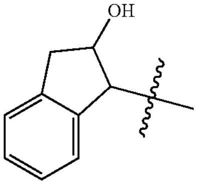, 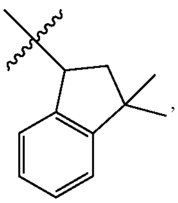

-continued

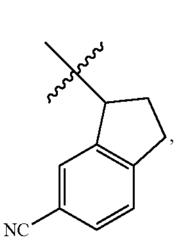, 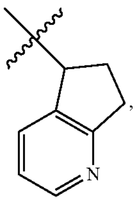, 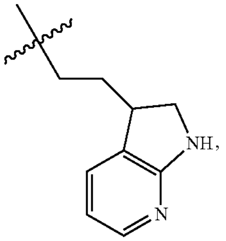,

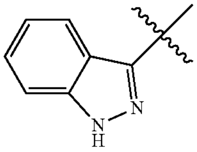, 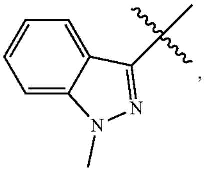,

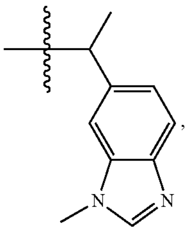, 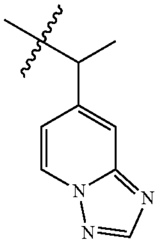, 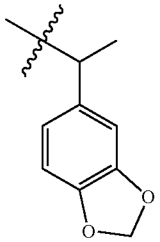,

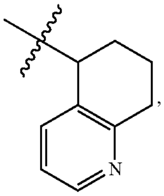, 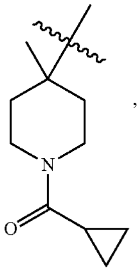, 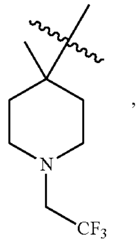,

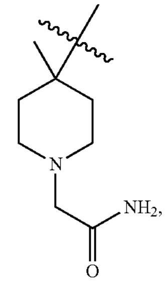, 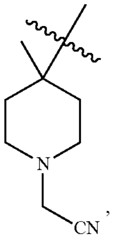, 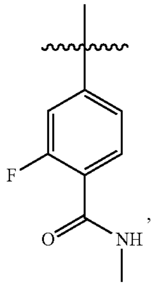, or

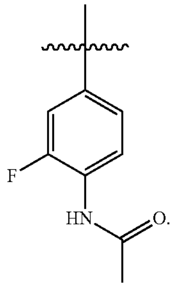

3. The compound or pharmaceutically acceptable salt thereof according to claim 1, wherein $R_1$ is selected from

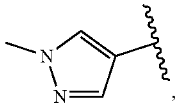, 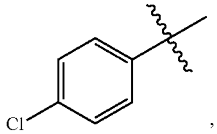,

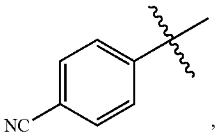, 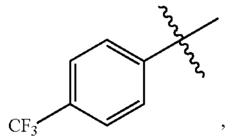,

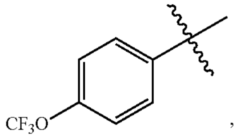, 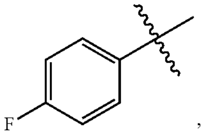, or

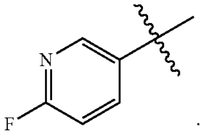.

4. The compound or pharmaceutically acceptable salt thereof according to claim 1, wherein $R_2$ is selected from

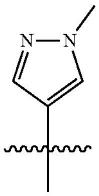, 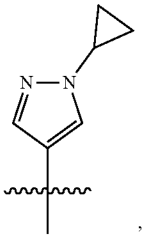, 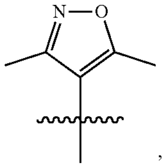,

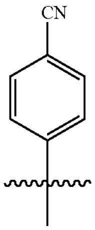, 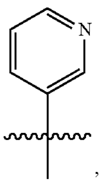, 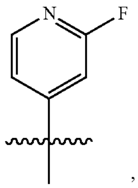, 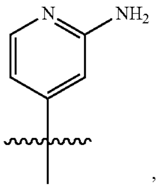,

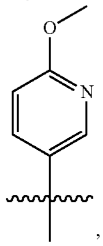, or 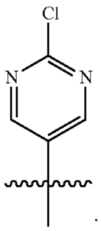.

5. The compound or pharmaceutically acceptable salt thereof according to claim 1, wherein the compound is selected from the group consisting of:

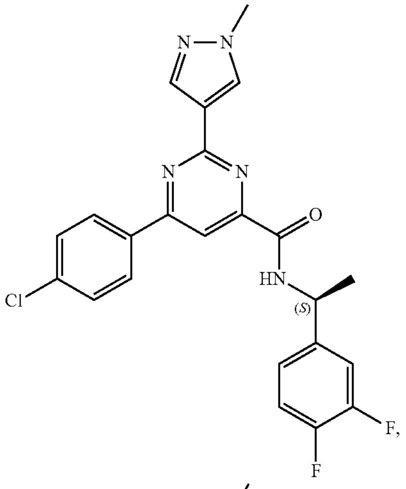
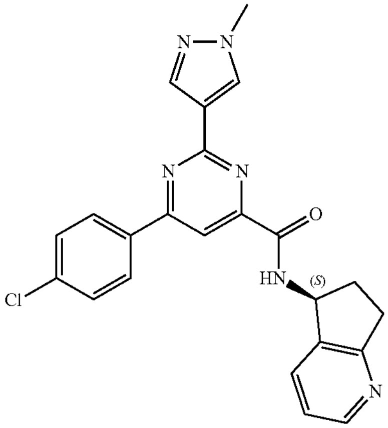
,
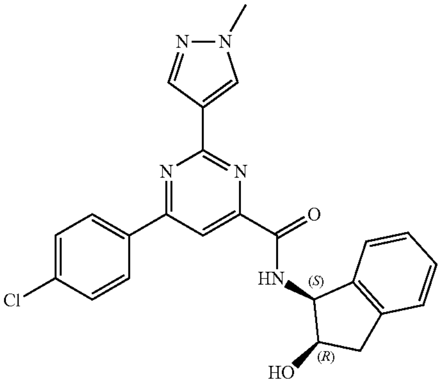
,
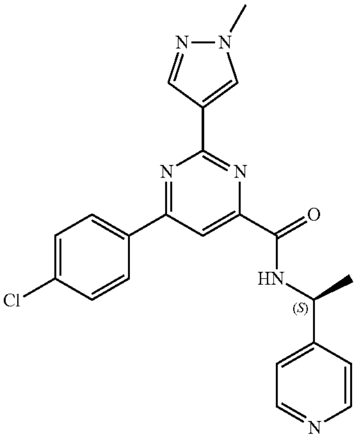
,
-continued
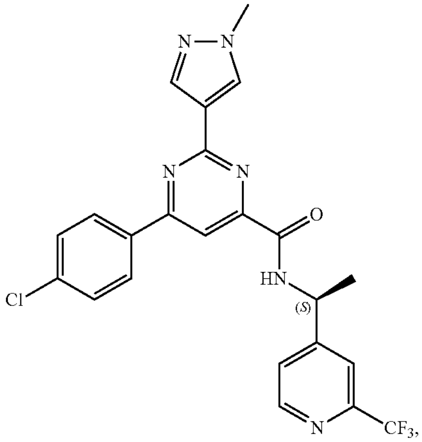
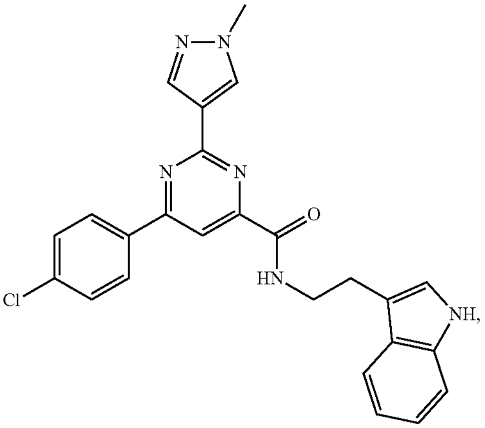
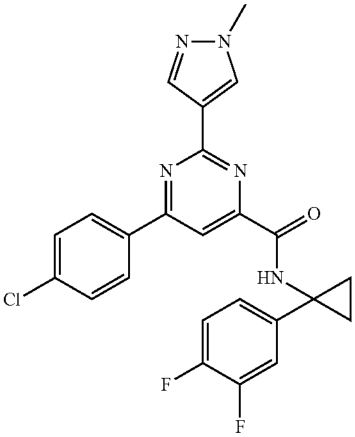
, -continued
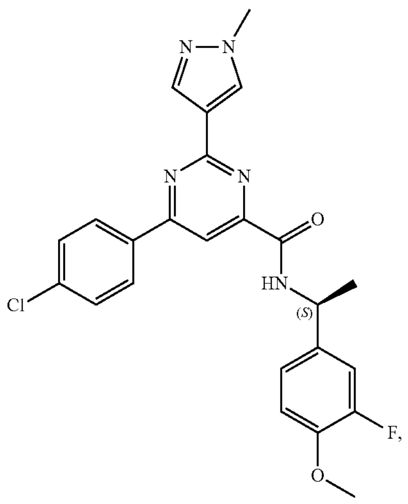
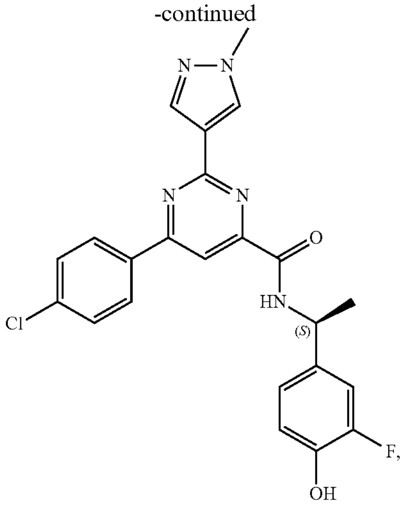
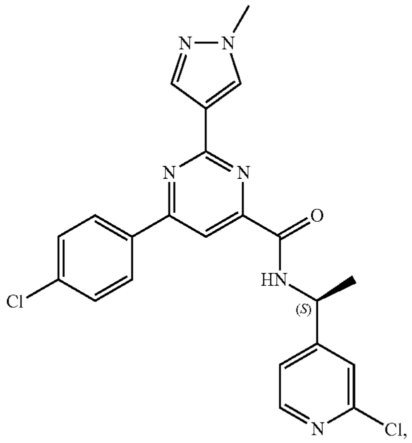
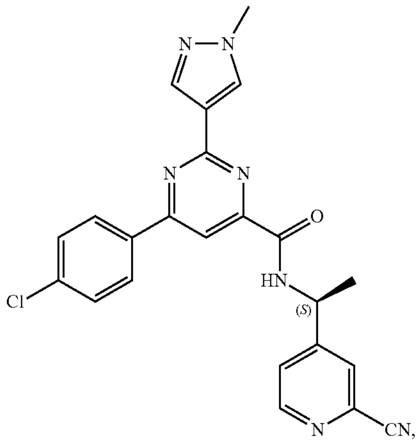
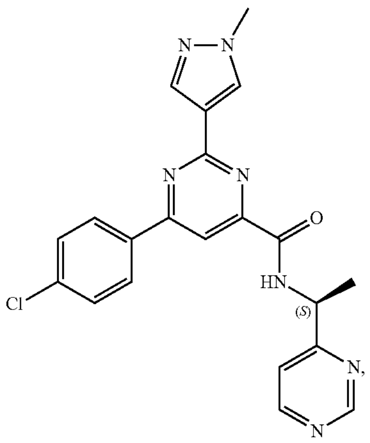
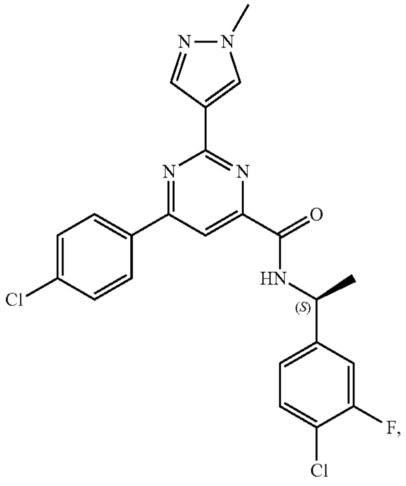

-continued
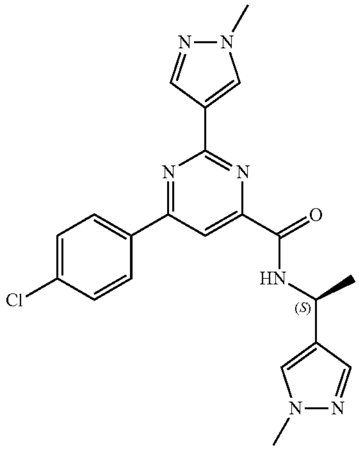
,
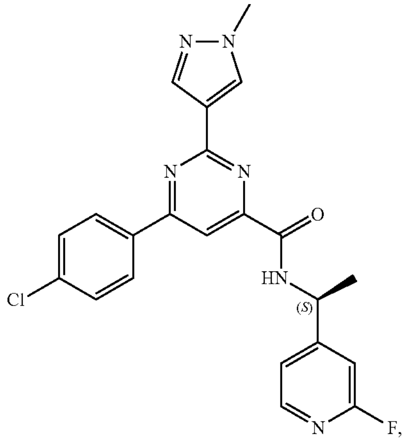
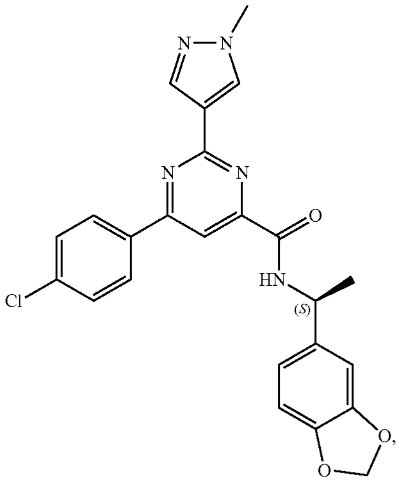
-continued
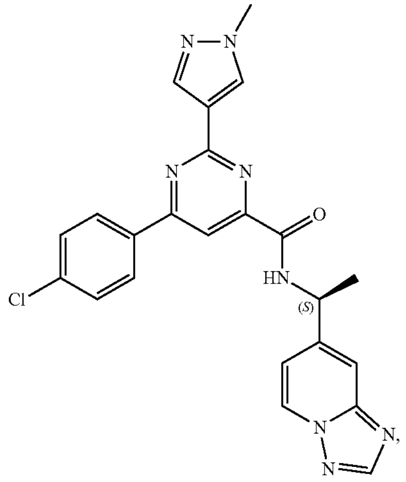
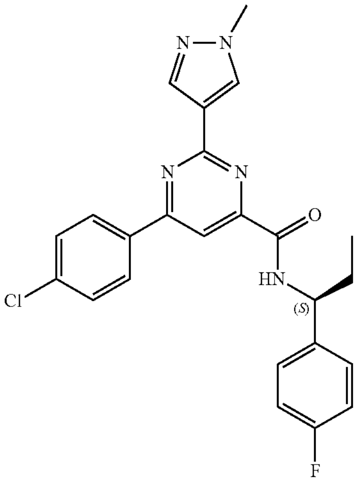
,
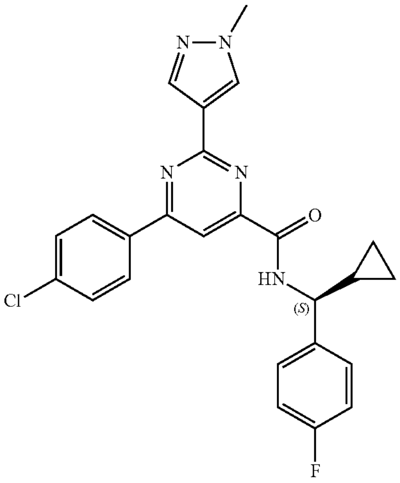
, -continued
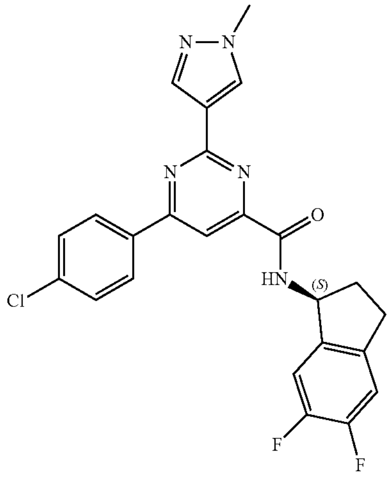
,
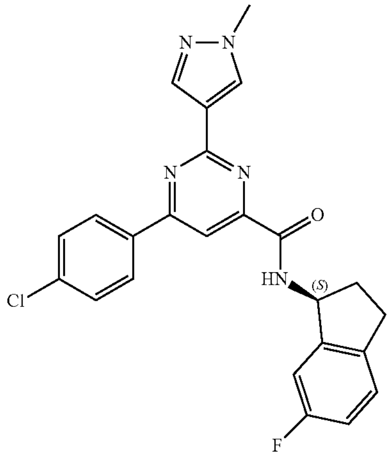
,
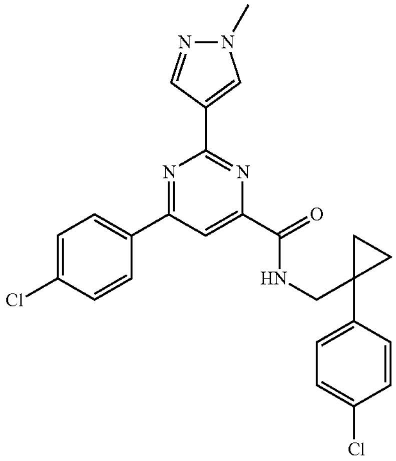
,
-continued
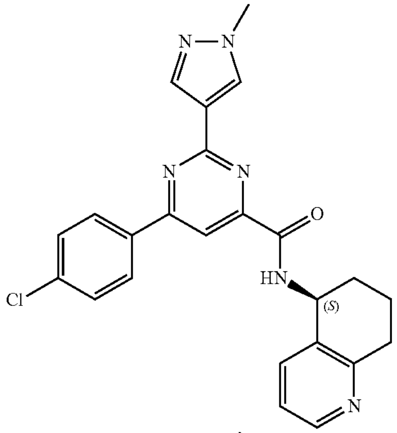
,
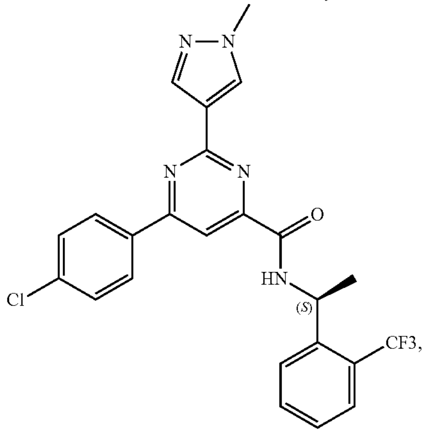
,
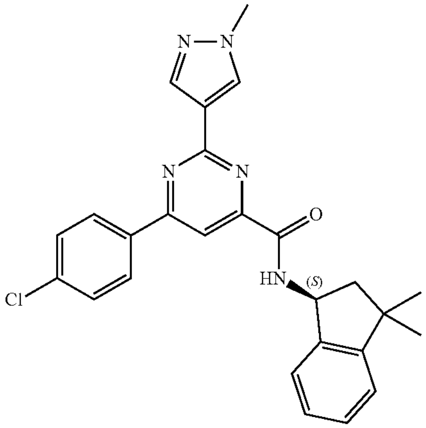
,
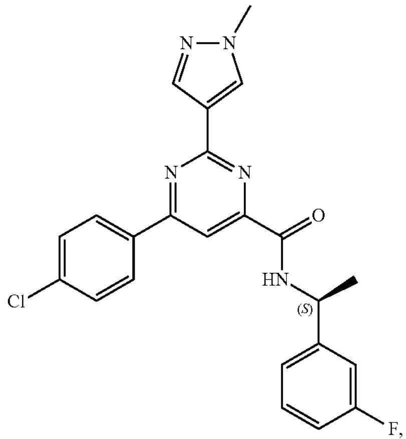
, -continued
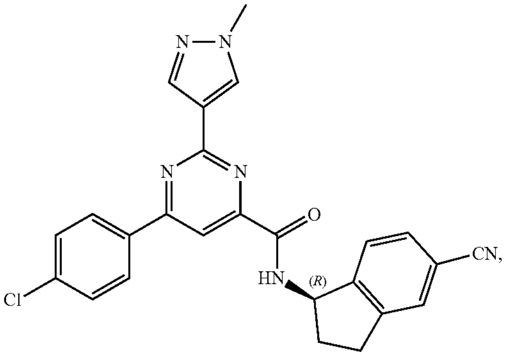
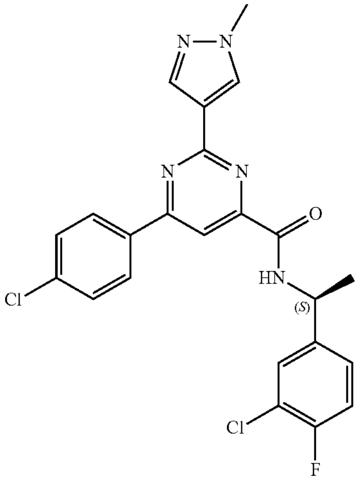
,
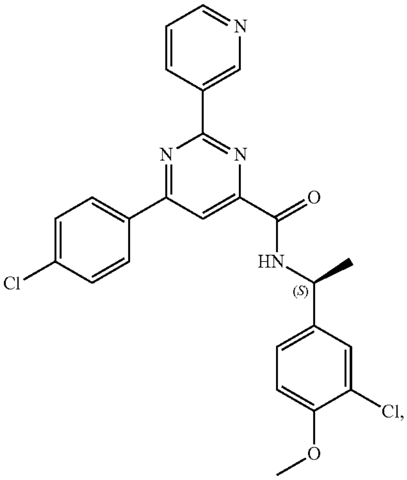
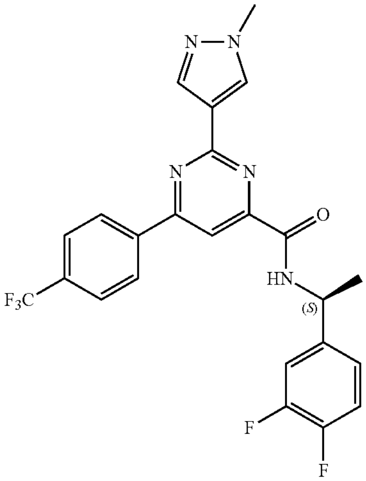
,
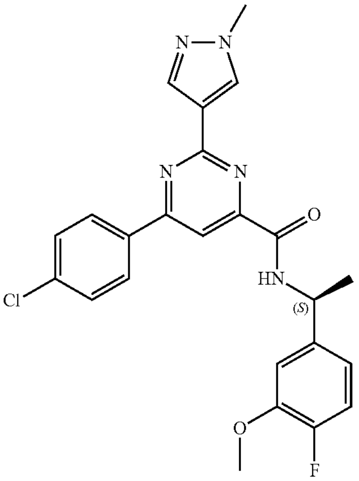
,
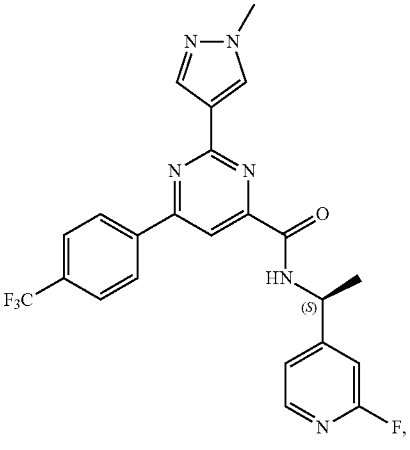
-continued -continued
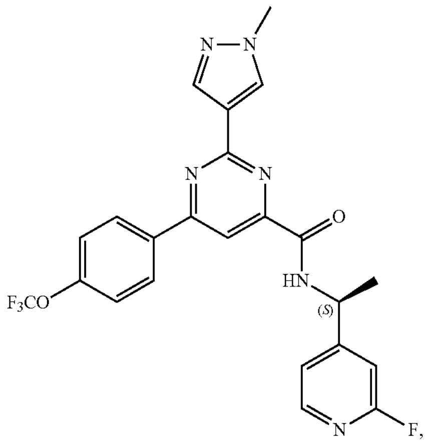
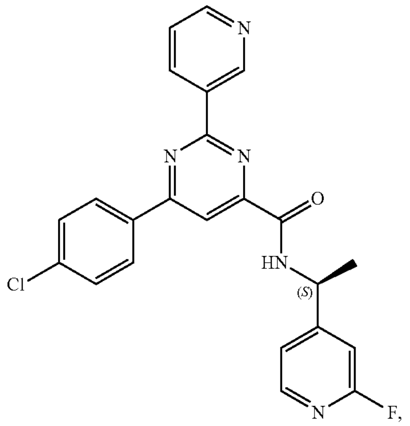
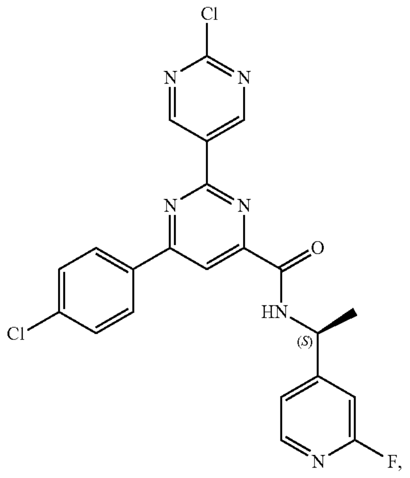
-continued
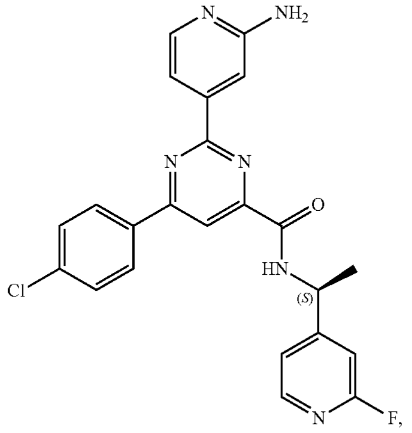
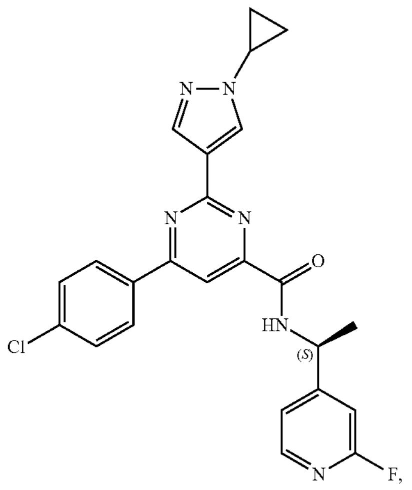
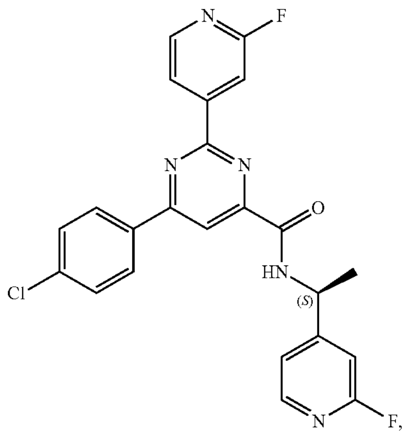

-continued
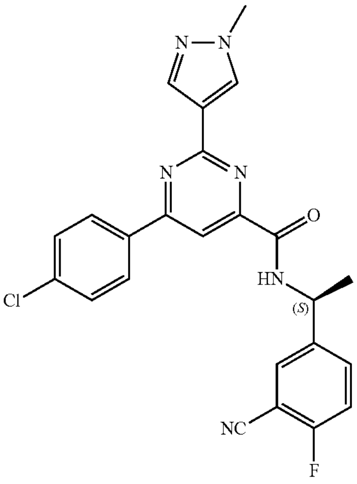
,
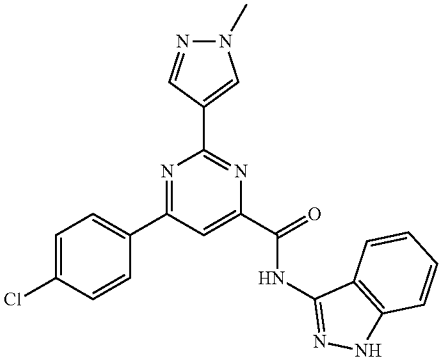
,
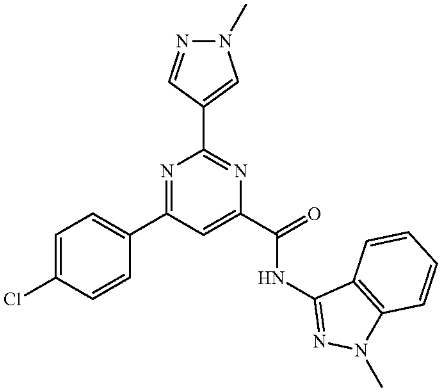
,
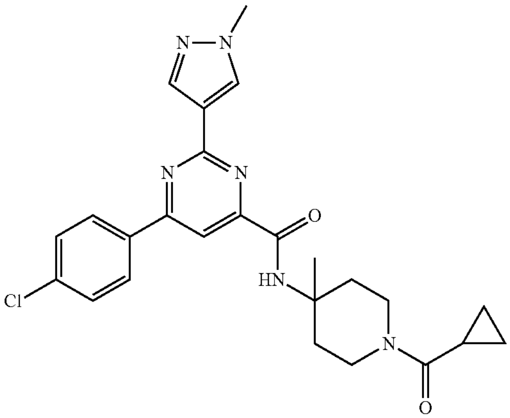
,
-continued
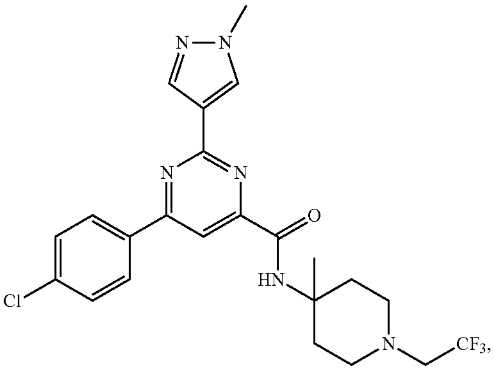
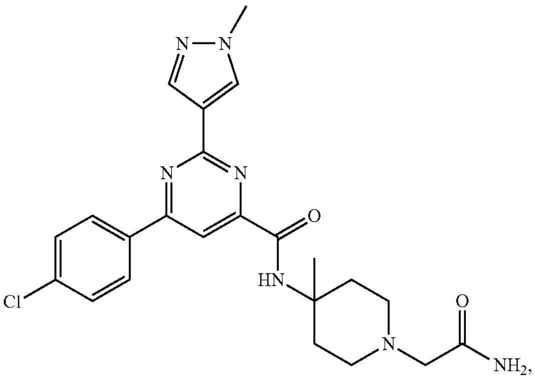
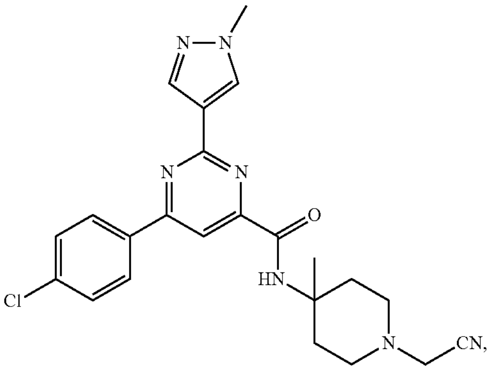
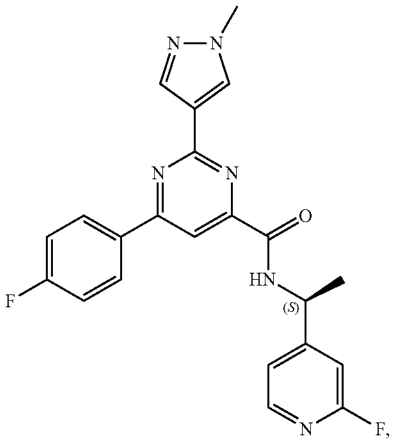

-continued
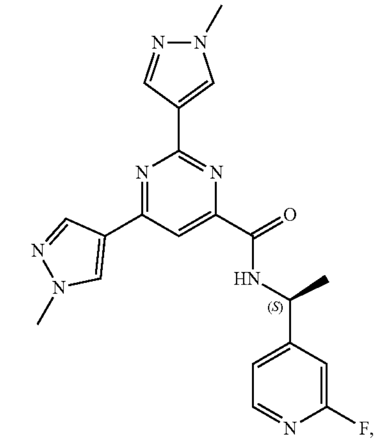
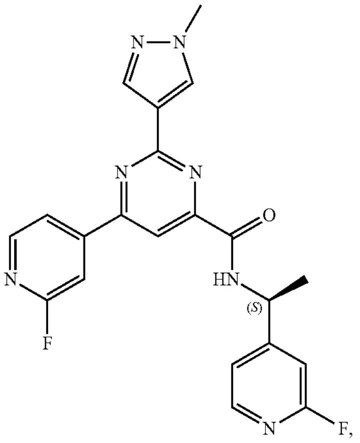
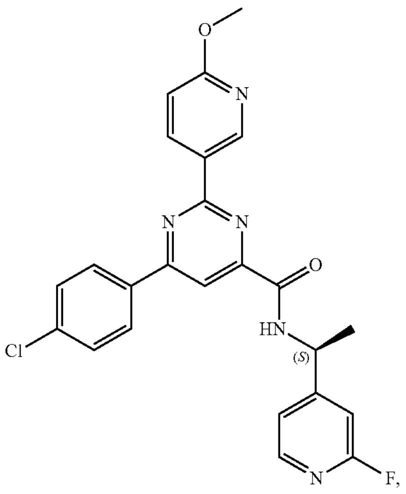
-continued
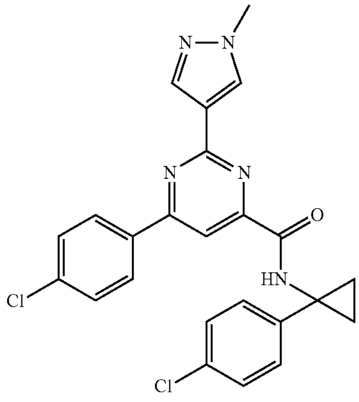
,
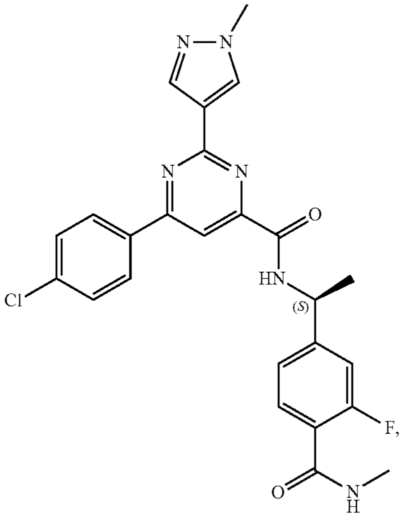
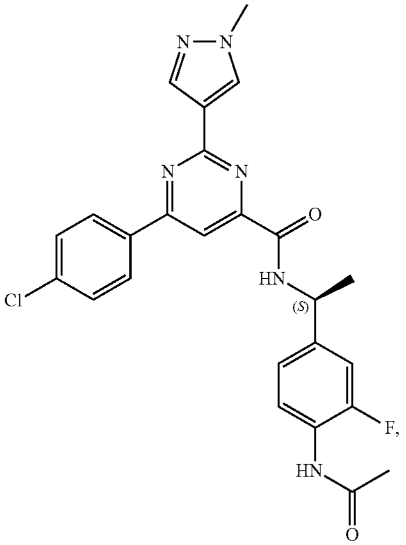

-continued
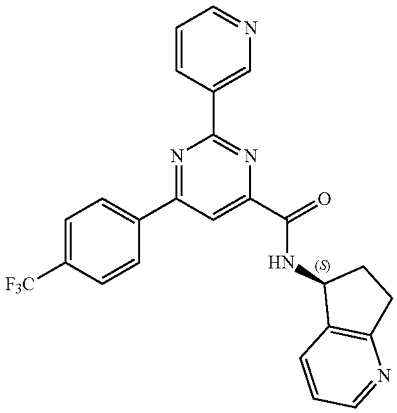
,
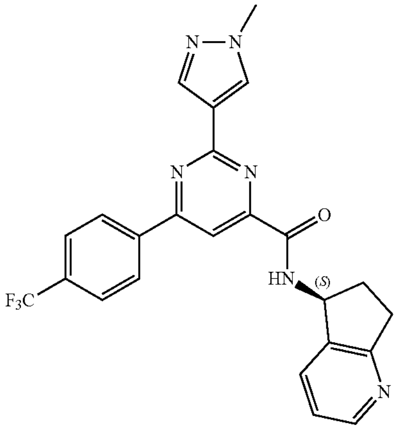
,
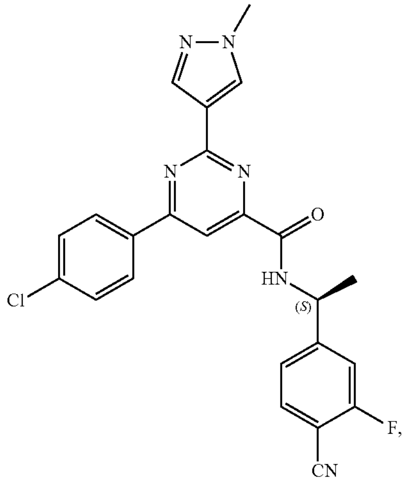
-continued
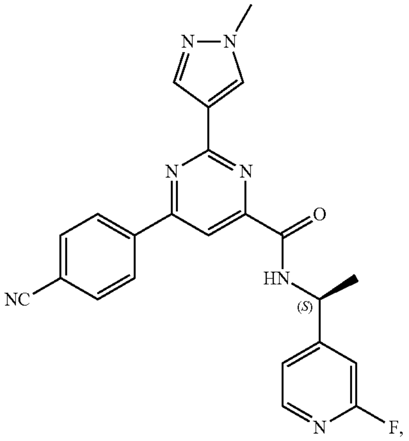
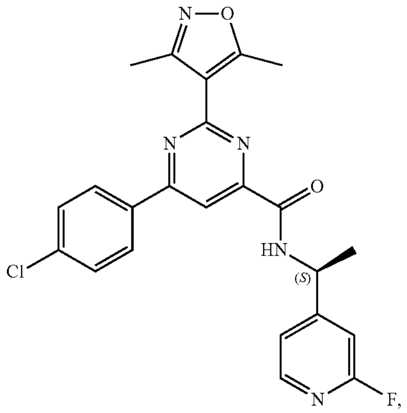
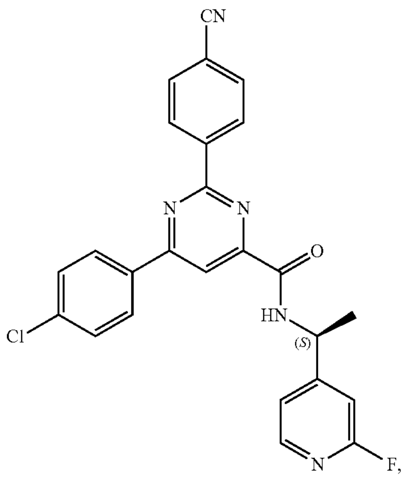

-continued

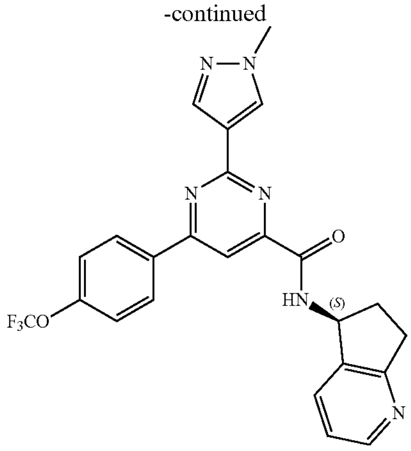

,

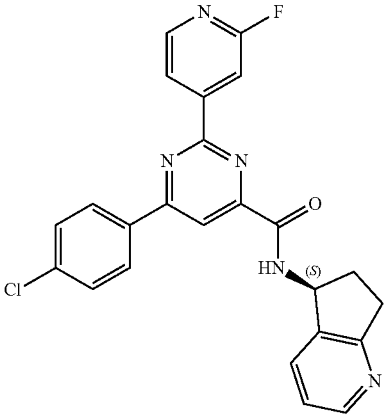

, and

-continued

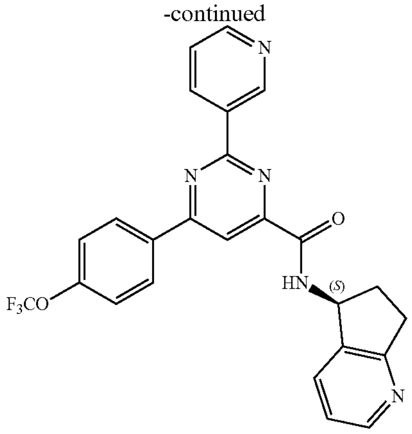

.

6. The compound or pharmaceutically acceptable salt thereof according to claim 1, wherein the pharmaceutically acceptable salt is any or a combination of hydrochloride, hydrobromate, sulfate, phosphate, carbonate, acetate, propionate, methanesulfonate, lactate, benzenesulfonate, p-toluenesulfonate, succinate, maleate, fumarate, tartrate, citrate, or malate.

7. A pharmaceutical composition, wherein the composition comprises the compound or pharmaceutically acceptable salt thereof according to claim 1, or a pharmaceutically acceptable carrier.

* * * * *